US011535630B2

(12) United States Patent
Runyon et al.

(10) Patent No.: US 11,535,630 B2
(45) Date of Patent: *Dec. 27, 2022

(54) APELIN RECEPTOR (APJ) AGONISTS AND USES THEREOF

(71) Applicant: Research Triangle Institute, Research Triangle Park, NC (US)

(72) Inventors: Scott P. Runyon, Hillsborough, NC (US); Rangan Maitra, Cary, NC (US); Sanju Narayanan, Durham, NC (US); James Barnwell Thomas, Efland, NC (US); Kenneth S. Rehder, Durham, NC (US); Srinivas Olepu, Cary, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/082,650

(22) Filed: Oct. 28, 2020

(65) Prior Publication Data

US 2021/0070767 A1 Mar. 11, 2021

Related U.S. Application Data

(63) Continuation of application No. 15/983,519, filed on May 18, 2018, now Pat. No. 10,954,247, which is a continuation of application No. 15/374,386, filed on Dec. 9, 2016, now Pat. No. 10,100,059.

(60) Provisional application No. 62/265,168, filed on Dec. 9, 2015, provisional application No. 62/265,177, filed on Dec. 9, 2015.

(51) Int. Cl.
| | |
|---|---|
| *C07D 491/107* | (2006.01) |
| *C07D 403/12* | (2006.01) |
| *C07D 231/14* | (2006.01) |
| *C07D 403/06* | (2006.01) |
| *C07D 407/12* | (2006.01) |
| *C07D 413/12* | (2006.01) |
| *A61K 31/415* | (2006.01) |
| *A61K 31/4196* | (2006.01) |
| *A61K 31/422* | (2006.01) |
| *A61K 31/4245* | (2006.01) |
| *A61K 31/427* | (2006.01) |
| *A61K 31/439* | (2006.01) |
| *A61K 31/4439* | (2006.01) |
| *A61K 31/454* | (2006.01) |
| *A61K 31/497* | (2006.01) |
| *A61K 31/5377* | (2006.01) |
| *A61K 31/55* | (2006.01) |
| *A61K 45/06* | (2006.01) |
| *C07D 401/12* | (2006.01) |
| *C07D 401/14* | (2006.01) |
| *C07D 405/12* | (2006.01) |
| *C07D 409/04* | (2006.01) |
| *C07D 413/04* | (2006.01) |
| *C07D 417/04* | (2006.01) |
| *C07D 417/12* | (2006.01) |
| *C07D 417/14* | (2006.01) |
| *C07D 471/08* | (2006.01) |
| *C07D 487/08* | (2006.01) |
| *C07D 403/04* | (2006.01) |
| *C07D 403/14* | (2006.01) |

(52) U.S. Cl.
CPC ........ *C07D 491/107* (2013.01); *A61K 31/415* (2013.01); *A61K 31/4196* (2013.01); *A61K 31/422* (2013.01); *A61K 31/427* (2013.01); *A61K 31/4245* (2013.01); *A61K 31/439* (2013.01); *A61K 31/4439* (2013.01); *A61K 31/454* (2013.01); *A61K 31/497* (2013.01); *A61K 31/5377* (2013.01); *A61K 31/55* (2013.01); *A61K 45/06* (2013.01); *C07D 231/14* (2013.01); *C07D 401/12* (2013.01); *C07D 401/14* (2013.01); *C07D 403/04* (2013.01); *C07D 403/06* (2013.01); *C07D 403/12* (2013.01); *C07D 403/14* (2013.01); *C07D 405/12* (2013.01); *C07D 407/12* (2013.01); *C07D 409/04* (2013.01); *C07D 413/04* (2013.01); *C07D 413/12* (2013.01); *C07D 417/04* (2013.01); *C07D 417/12* (2013.01); *C07D 417/14* (2013.01); *C07D 471/08* (2013.01); *C07D 487/08* (2013.01)

(58) Field of Classification Search
None
See application file for complete search history.

(56) References Cited

U.S. PATENT DOCUMENTS

| | | |
|---|---|---|
| 4,795,484 A | 1/1989 | Aoki et al. |
| 5,304,121 A | 4/1994 | Sahatjian |

(Continued)

FOREIGN PATENT DOCUMENTS

| | | |
|---|---|---|
| CA | 2136893 C | 6/2002 |
| CN | 1556703 A | 12/2004 |

(Continued)

OTHER PUBLICATIONS

Zhong et al., Targeting the apelin pathway as a novel therapeutic approach for cardiovascular diseases. Biochimica et Biophysica Acta, 2017, 1863, 1942-1950.*

(Continued)

*Primary Examiner* — Po-Chih Chen
(74) *Attorney, Agent, or Firm* — Barnes & Thornburg LLP

(57) ABSTRACT

This disclosure is directed to agonists of the apelin receptor (APJ) and uses of such agonists.

17 Claims, No Drawings

(56) References Cited

U.S. PATENT DOCUMENTS

| | | |
|---|---|---|
| 5,420,141 A | 5/1995 | Boigegrain et al. |
| 5,502,059 A | 3/1996 | Labeeuw et al. |
| 5,523,455 A | 6/1996 | Labeeuw et al. |
| 5,585,497 A | 12/1996 | Labeeuw et al. |
| 5,624,941 A | 4/1997 | Barth et al. |
| 5,723,483 A | 3/1998 | Labeeuw et al. |
| 5,744,491 A | 4/1998 | Boigegrain et al. |
| 5,886,026 A | 3/1999 | Hunter et al. |
| 5,925,661 A | 7/1999 | Labeeuw et al. |
| 5,936,123 A | 8/1999 | Labeeuw et al. |
| 5,939,449 A | 8/1999 | Labeeuw et al. |
| 5,965,579 A | 10/1999 | Labeeuw et al. |
| 6,028,084 A | 2/2000 | Barth et al. |
| 6,075,121 A | 6/2000 | Simon et al. |
| 6,099,562 A | 8/2000 | Ding et al. |
| 6,172,239 B1 | 1/2001 | Labeeuw et al. |
| 6,803,031 B2 | 10/2004 | Rabinowitz et al. |
| 7,014,866 B2 | 3/2006 | Infeld et al. |
| 7,186,741 B2 | 3/2007 | Feenstra et al. |
| 7,531,592 B2 | 5/2009 | Dubouis et al. |
| 8,252,790 B2 | 8/2012 | Yamagishi et al. |
| 8,354,557 B2 | 1/2013 | Liu et al. |
| 8,513,244 B2 | 8/2013 | Gendron et al. |
| 8,704,001 B2 | 4/2014 | Masse |
| 10,100,059 B2 | 10/2018 | Runyon et al. |
| 10,377,718 B2 | 8/2019 | Runyon et al. |
| 10,954,247 B2 | 3/2021 | Runyon et al. |
| 2004/0063691 A1 | 4/2004 | Smith et al. |
| 2004/0082496 A1 | 4/2004 | Acton et al. |
| 2004/0235854 A1 | 11/2004 | Kruse et al. |
| 2005/0054679 A1 | 3/2005 | Kruse et al. |
| 2006/0014813 A1 | 1/2006 | Connelly et al. |
| 2006/0079502 A1 | 4/2006 | Lang |
| 2006/0094744 A1 | 5/2006 | Maryanoff et al. |
| 2007/0213302 A1 | 9/2007 | McElroy et al. |
| 2007/0219210 A1 | 9/2007 | Kanaya et al. |
| 2008/0125409 A1 | 5/2008 | Kanaya et al. |
| 2010/0160323 A1 | 6/2010 | Bischoff et al. |
| 2010/0331540 A1 | 12/2010 | Shimodaira et al. |
| 2014/0081019 A1 | 3/2014 | Atzrodt et al. |
| 2014/0094450 A1 | 4/2014 | Hachtel et al. |
| 2014/0341994 A1 | 11/2014 | Sommer et al. |
| 2015/0299166 A1 | 10/2015 | Tung |
| 2016/0207889 A1 | 7/2016 | Runyon et al. |
| 2017/0174633 A1 | 6/2017 | Thomas et al. |

FOREIGN PATENT DOCUMENTS

| | | |
|---|---|---|
| CN | 101519430 A | 9/2009 |
| CN | 104640846 A | 5/2015 |
| CN | 106459004 A | 2/2017 |
| CO | NC2016/0004908 | 3/1992 |
| EP | 0477049 A1 | 3/1992 |
| EP | 0576357 B1 | 3/1997 |
| EP | 0477049 B1 | 12/1999 |
| EP | 1903052 A2 | 3/2008 |
| JP | S58194866 A | 11/1983 |
| JP | S5998004 A | 6/1984 |
| JP | H04244065 A | 9/1992 |
| JP | 2005504805 A | 2/2005 |
| JP | 2005508384 A | 3/2005 |
| JP | 2009529540 A | 8/2009 |
| JP | 2010500336 A | 1/2010 |
| JP | 2013231000 A | 11/2013 |
| JP | 2014525912 A | 10/2014 |
| JP | 2015521193 A | 7/2015 |
| JP | 2015524449 A | 8/2015 |
| JP | 2017-523126 A | 8/2018 |
| JP | 2019501899 A | 1/2019 |
| JP | 6767878 B2 | 10/2020 |
| MX | 2016014890 A | 5/2017 |
| RU | 2141479 C1 | 11/1999 |
| RU | 2325382 C2 | 5/2008 |
| WO | 2003027076 A2 | 4/2003 |
| WO | 2003040107 A1 | 5/2003 |
| WO | 2004026301 A1 | 4/2004 |
| WO | 2005063737 A1 | 7/2005 |
| WO | 2005099705 A2 | 10/2005 |
| WO | 2006043594 A1 | 4/2006 |
| WO | 2006133926 A1 | 12/2006 |
| WO | 2007106721 A2 | 9/2007 |
| WO | 2008017932 A2 | 2/2008 |
| WO | 2008098104 A1 | 8/2008 |
| WO | 2010053545 A2 | 5/2010 |
| WO | 2011005052 A2 | 1/2011 |
| WO | 2011012630 A1 | 2/2011 |
| WO | 2011156557 A2 | 12/2011 |
| WO | 2012166387 A1 | 12/2012 |
| WO | 2013014204 A2 | 1/2013 |
| WO | 2013079223 A1 | 6/2013 |
| WO | 2013178362 A1 | 12/2013 |
| WO | 2014023367 A1 | 2/2014 |
| WO | 2014044738 A1 | 3/2014 |
| WO | 2014053533 A1 | 4/2014 |
| WO | 2014152588 A1 | 9/2014 |
| WO | 2014169280 A2 | 10/2014 |
| WO | 2015058067 A1 | 4/2015 |
| WO | 2015184011 A2 | 12/2015 |
| WO | 2015188073 A1 | 12/2015 |
| WO | 2017100558 A1 | 6/2017 |
| WO | 2018010398 A1 | 1/2018 |
| WO | 2018071526 A1 | 4/2018 |
| WO | 2021041791 A1 | 3/2021 |

OTHER PUBLICATIONS

Shafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Anderson et al.; "Apelin and pulmonary hypertension", Pulm. Circ. Jul.-Sep. 2011, 1(3) pp. 334-346.

Carpéné et al.; "Expanding role for the apelin/APJ system in physiopathology" J. Physiol. Biochem., 63 (4), 359-374, 2007.

Charo et al.; "Endogenous regulation of cardiovascular function by apelin-APJ" Am J Physiol Heart Circ Physiol 297:H1904-H1913, 2009.

Cobellis et al.; "Modulation of apelin and APJ receptor in normal and preeclampsia-complicated placentas." Histol Histopathol. Jan. 2007, 22(1) pp. 1-8.

Giddings et al.; "Development of a functional HTS assay for the APJ receptor" International Journal of High Throughput Screening 2010:1 pp. 39-47.

International Search Report and Written Opinion dated Sep. 25, 2015 for International Application No. PCT/US2015/034427.

Iturrioz et al.; "Identification and pharmacological properties of E339-3D6, the first nonpeptidic apelin receptor agonist" The FASEB Journal, May 2010, vol. 24, pp. 1506-1517.

International Search Report and Written Opinion dated Jan. 27, 2017 for International Application No. PCT/US2016/065808.

Kourtis et al.; "Apelin levels in normal pregnancy" Clinical Endocrinology (2011) 75, pp. 367-371.

Lathen et al.; "ERG-APLNR Axis Controls Pulmonary Venule Endothelial Proliferation in Pulmonary Veno-Occlusive Disease" Circulation 2014;130: pp. 1179-1191.

Maloney et al.; "Discovery of 4-oxo-6-((pyrimidin-2-ylthio)methyl)-4H-pyran-3-yl 4-nitrobenzoate (ML221) as a functional antagonist of the apelin (APJ) receptor" Bioorganic & Medicinal Chemistry Letters 22 (2012) pp. 6656-6660.

Narayanan et al.; "141—Discovery of small molecule functional agonist leads of APJ receptor" MEDI: Division of Medical Chemistry.

Sheikh et al.: "In vivo genetic profiling and cellular localization of apelin reveals a hypoxia-sensitive, endothelial-centered pathway activated in ischemic heart failure" Am J Physiol Heart Circ Physiol 294: H88-H98, 2008.

(56) References Cited

OTHER PUBLICATIONS

Tatemoto et al.; "Isolation and Characterization of a Novel Endogenous Peptide Ligand for the Human APJ Receptor" Biochemical and Biophysical Research Communications 251, pp. 471-476 (1998).
Tatemoto et al.; "The novel peptide apelin lowers blood pressure via a nitric oxide-dependent mechanism" Regulatory Peptides 99 Ž2001. pp. 87-92.
Tiemann et al., "Increasing myocardial contraction and blood pressure in C57BL/6 mice during early postnatal development" Am J Physiol Heart Circ Physiol 284:H464-H474, 2003.
Khan et al.; "Probe Report" Molecular Libraries, Jul. 2011, pp. 1-22.
XP-002768454 Database Registry, Chemical Abstracts Service. Oct. 22, 2009.
XP-002768455 Database Registry, Chemical Abstracts Service. Sep. 16, 2009.
XP-002768456 Database Registry, Chemical Abstracts Service. Oct. 23, 2009.
XP-002768457 Database Registry, Chemical Abstracts Service. Oct. 25, 2009.
XP-002768458 Database Registry, Chemical Abstracts Service. Aug. 2, 2009.
XP-002768459 Database Registry, Chemical Abstracts Service. Nov. 20, 2009.
XP-002768460 Database Registry, Chemical Abstracts Service. Nov. 22, 2009.
International Preliminary Report on Patentability dated Jun. 21, 2018 for International Application No. PCT/US2016/065808.
Australian Examination Report for Australian Application No. 2016-366310, dated May 8, 2020.
European Search Report for EP Application No. 16 826 220.2, dated Apr. 29, 2020.
Office Action for Russian Application No. 2018-118568, dated Feb. 20, 2020.
Chemical Abstract Registry No. 1189436-73-4, indexed in the Registry File on STN CAS Online Oct. 22, 2009.
Thomas et al., Identification of 1-({[1-(4-Fluorophenyl)-5-(-methoxyphenyl)-1H-pyrazol-3-yl]carbonyl}amino) cyclohexane carboxylic acid as a selective nonpeptide neurotensin receptor type 2 compound, Journal of Medicinal Chemistry (2014), vol. 57, pp. 5318-5332.
Alvarez et al., "Structure-Activity Study of Bioisosteric Trifluoromethyl and Pentafluorosulfanyl Indole Inhibitors of the AAA ATPase p97", ACS. Med. Chem. Let., 2015, pp. 1225-1230, vol. 6.
Baxendale et al., "The Synthesis of Neurotensin Antagonist SR 48692 for Prostate Cancer Research," Bioorg. Med. Chem., 2013, vol. 21, pp. 4378-4387.
CAS Registry No. 1831835-31-4 which entered STN on Jun. 24, 2016.
CAS Registry No. 1423365-99-4, which entered STN on Mar. 14, 2013.
CAS Registry No. 1569560-23-1, which entered STN on Mar. 18, 2014.
CAS Registry No. 1569675-43-9, which entered STN on Mar. 18, 2014 (Year: 2014).
CAS Registry No. 1580321-28-3, which entered STN on Apr. 4, 2014 (Year: 2014).
CAS Registry No. 1830232-36-4 which entered STN on Jun. 24, 2016.
CAS Registry No. 1938292-99-9 which entered STN on Jun. 24, 2016.
CAS Registry No. 1938533-13-1 which entered STN on Jun. 24, 2016.
CAS Registry No. 931620-33-6, which entered STN on Apr. 22, 2007.
CAS Registry No. 1171327-99-3 which entered STN Aug. 2, 2009.
CAS Registry No. 1185029-85-9 which entered STN Sep. 16, 2009.
CAS Registry No. 1185070-07-8 which entered STN Sep. 16, 2009.
CAS Registry No. 1185080-91-4 which entered STN Sep. 16, 2009.
CAS Registry No. 1185108-25-1 which entered STN on Sep. 16, 2009.
CAS Registry No. 1185123-59-4 which entered STN on Sep. 16, 2009.
CAS Registry No. 1189470-51-6 which entered STN on Oct. 22, 2009.
CAS Registry No. 1189643-98-8 which entered STN Oct. 23, 2009.
CAS Registry No. 1189728-26-4 which entered STN Oct. 23, 2009.
CAS Registry No. 1189885-22-0 which entered STN Oct. 25, 2009.
CAS Registry No. 1190009-39-2 which entered STN Oct. 25, 2009.
CAS Registry No. 1192964-68-3 which entered STN Nov. 20, 2009.
CAS Registry No. 1193235-59-4 which entered STN Nov. 20, 2009.
Cho, K-I, et al., "Targeting the cyclophilin domain of ran-binding protein 2 (Ranbp2) with novel small molecules to control the proteostasis of STAT3, mnRNPA2B1 and M-Opsin", ACS Chemical Neuroscience (Aug. 2015), vol. 6, No. 8, pp. 1476-1485.
Duncton et al., "A one-pot synthesis of tetrazolones from acid chlorides: understanding functional group compatibility, and application to the late-stage functionalization of marketed drugs", Org. Biomol. Chem (2016) vol. 14, pp. 9338-9342.
Dyck, B, et al., "Potent imidazole and triazole CPIreceptor antagonists related to SR141716", Bioorganic & Medicinal Chemistry Letters, (2004), vol. 14, No. 5, pp. 1151-1154.
Fleisher et al., "Improved Review oral drug delivery: solubility limitations of prodrugs", Advanced Drug Delivery Reviews, 1996, p. 115-130, vol. 19.
Freireich et al., "Quantitative comparison of toxicity of anticancer agents in mouse, rat, hamster, dog, monkey, and man," Cancer Chemother. Rep., 1966, 50(4) pp. 219-244.
Geigy Pharmaceuticals, "Scientific Tables Excerpts From the Seventh Edition—Documenta Geigy," Ardsley, New York, 1970, pp. 537.
Gross, TJ et al, "Idiopathic Pulmonary Fibrosis" NEngl J Med, 2001, pp. 517-525, vol. 345, No. 7.
Habata et al., "Apelin, the natural ligand of the orphan receptor APJ, is abundantly secreted in the colostrum," Biochim. Biophys. Acta., 1999,1452(1), pp. 25-35.
Hagihara, M. et al., "Reassignment of stereochemistry and total synthesis of the thrombin inhibitor cyclotheonamide B," J. Amer. Chem. Soc. 1992, 114(16) pp. 6570-6571.
Hershberger et al., "Imidazole-derived agonists for the neurotensin 1 receptor" Bioorg. Med. Chem. Lett. (2014), vol. 247, pp. 262-267.
Hobbs Dewitt et al., "'Diversomers': An approach to nonpeptide, nonoligomeric chemical diversity," Proc. Natl. Acad. Sci. USA, 1993, 90(15) pp. 6909-6913.
Huang, S. et al., "The apelin-APJ axis: A novel potential therapeutic target for organ fibrosis" Clinica Chimica Acta, 2016, p. 81-88, vol. 456.
Laderias-Lopez et al., "The apelinergic system: the role played in human physiology and pathology and pootential therapeutic applications," Arq Bras Cardiol., 2008, 90(5) pp. 343-349.
Lee et al., "Characterization of Apelin, the Ligand for the APJ Receptor," Neurochem., 2000, 74(1), pp. 34-41.
Martinez, FJ et al. "The Clinical Course of Patients with Idiopathic Pulmonary Fibrosis" Ann Intern Med, 2005, p. 963-967, vol. 142.
Medhurst et al., "Pharmacological and immunohistochemical characterization of the APJ receptor and its endogenous ligand apelin," J. Neurochem., 2003, 84(5) pp. 1162-1172.
O'Donnell et al., "Apelin, an endogenous neuronal peptide, protects hippocampal neurons against excitotoxic injury," J. Neurochem., 2007, 102(6) pp. 1905-1917.
Preissl, S. et al., "Development of an Assay for Complex I/Complex III of the Respiratory Chain Using Solid Supported Membranes and Its Application in Mitochondrial Toxicity Screening in Drug Discovery," Assay and Drug Development Technologies, 2011 vol. 9 pp. 147-156.
Rautio et al., "Prodrugs: design and clinical Applications", Nat Rev Drug Dis, 2008 p. 255-270, vol. 7.
Robinson et al., "Discovery of the Hemifumarate and (r-L-Alanyloxy)methyl Ether as Prodrugs of an Antirheumatic Oxindole: Prodrugs for the Enolic OH Group" J Med Chem, 1996, p. 10-18, vol. 39.

(56) References Cited

OTHER PUBLICATIONS

Selman M et al., "Idiopathic Pulmonary Fibrosis: Prevailing and Evolving Hypotheses about Its Pathogenesis and Implications for Therapy", Ami Intern Med, 2001, p. 134-136, vo. 51.
Selman. M., et al., Role of Epithelial Cells in Idiopathic Pulmonary Fibrosis, Am Thorac Soc, 2006, p. 364-372, vol. 4.
Wang et al., "Expanding the genetic code for biological studies," Chem Biol., 2009, 16(3) pp. 323-336.
Xie, "A chemical toolkit for proteins—an expanded genetic code," Nat. Rev. Mol. Cell Biol., 2006, 7(10) pp. 775-782.
Zou, M.X. et al., "Apelin peptides block the entry of human immunodeficiency virus (HIV)," FEBS Lett., 2000, 473(1) pp. 15-18.
CAS Registry No. 1606440-69-0, which entered STN on May 19, 2014.
CAS Registry No. 1584603-48-4, which entered STN on Apr. 15, 2014.
CAS Registry No. 1578083-00-7, which entered STN on Apr. 1, 2014.
CAS Registry No. 1833984-41-0, which entered STN on Dec. 21, 2015.
CAS Nos. 141511-09-9, which entered STN on Dec. 26, 2012.
CAS Nos. 1415511-07-7, which entered STN on Dec. 26, 2012.

* cited by examiner

APELIN RECEPTOR (APJ) AGONISTS AND USES THEREOF

CROSS REFERENCE TO RELATED APPLICATIONS

This application is a Continuation of U.S. application Ser. No. 15/983,519, filed May 18, 2018, now allowed, which is a Continuation application of U.S. application Ser. No. 15/374,386, filed Dec. 9, 2016, now U.S. Pat. No. 10,100,059, which claims the benefit of U.S. Provisional Application No. 62/265,177, filed Dec. 9, 2015 and U.S. Provisional Application No. 62/265,168, filed Dec. 9, 2015, each of which is herein incorporated by reference in its entirety.

1. FIELD

This disclosure relates generally to the discovery of agonists of the apelin receptor (APJ) and uses of such agonists.

2. BACKGROUND 2.1. Introduction: Apelin and the Apelin Receptor (APJ)

The apelin receptor (APJ) was cloned in 1993 as an orphan G-protein coupled receptor (GPCR). The human APJ gene is located on the long arm of chromosome 11 and encodes a 377 amino acid G protein-coupled receptor. The gene for APJ was designated angiotensin-receptor like 1 (AGTRL1) due to sequence similarities between the two receptors. Carpene et al., J Physiol Biochem. 2007; 63(4):359-373. However, none of the known peptidergic ligands for the angiotensin receptors, including angiotensin, activate APJ. APJ remained an orphan GPCR until 1998 when the peptide apelin was identified as its endogenous ligand. Lee et al., J Neurochem. 2000; 74(1):34-41; Habata et al., Biochim Biophys Acta. 1999; 1452(1):25-35.

Over the years, apelin and APJ have emerged as an important regulator of various physiological processes. Both apelin and APJ are expressed in the central nervous system (CNS) and peripherally in a number of tissues. Expression of APJ has been noted within the vasculature of some organs and is a potent regulator of related processes including angiogenesis and vasoconstriction. Cobellis et al. report increased of expression levels of both apelin and APJ receptor in preeclampsia-complicated pregnancies. Cobellis et al., Histol Histopathol. 2007; 22(1):1-8. APJ is also expressed in nonvascular cell types in heart, liver, and CNS where its primary role is currently under investigation. Medhurst et al., J Neurochem. 2003; 84(5):1162-1172. Apelin and APJ are often co-localized within the same organ suggesting an autocrine regulation of the receptor by its ligand. However, apelin has since been detected in blood suggesting that concomitant paracrine regulation of the receptor is also possible. The apelin—APJ system has been implicated as a regulator of various physiological functions and is believed to play an important role in thermoregulation, immunity, glucose metabolism, angiogenesis, fluid homeostasis, cardiac function, hepatic function and renal function. Ladeiras-Lopes et al., Arq Bras Cardiol. 2008; 90(5):343-349. APJ also acts as a co-receptor during HIV infection. O'Donnell et al., J Neurochem. 2007; 102(6):1905-1917; Zou et al., FEBS Lett. 2000; 473(1):15-18.

Expression of apelin and APJ are either up- or down-regulated in various pathophysiological conditions. In particular, the APJ appears to be an emerging target for the treatment of cardiovascular failure, liver fibrosis, cancer, angiopathies, pancreatitis, and as a prophylactic against HIV infection. In 2011 Andersen et al. reviewed apelin and APJ as an opportunity for therapeutic uses for pulmonary hypertension and pulmonary arterial hypertension (PAH). Andersen et al. Pulm. Circ. 2011; 1(3) 334-346.

Unfortunately, small molecule ligands of the APJ having suitable pharmacological properties are lacking. Few non-peptide ligand systems has been reported to date. Iturrioz et al. report compounds that contain polycyclic fluorophores, such as lissamine, which make them ill-suited for pharmaceutical uses. Iturrioz et al., FASEB J. 2010; 24:1506-1517; EP 1903052 (Llorens-Cortes et al.). US Publ. Pat. Appn. 2014/0094450 (Hachtel et al.) discloses benzoimidazole-carboxylic acid amide derivatives as APJ receptor modulators.

Accordingly, there is a need for small molecule agonists of APJ.

3. SUMMARY OF THE DISCLOSURE

This disclosure provides a compound represented by the Formula I:

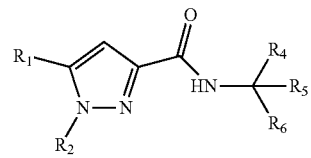

or a pharmaceutically acceptable salt, a prodrug, or a salt of a prodrug, wherein $R_1$ is represented by the formula:

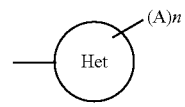

wherein

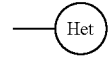

is a monocyclic aryl or heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCO_{1-8}$ alkyl, —$OCO(CH_2)_xNR_7R_8$, —$SF_5$, —$SO_2NR_7R_8$, —$SO_{(1-3)}R_7$, —$SR_7$, or tetrazolone; $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups; n is 1, 2, 3, 4 or 5; $R_2$ is $C_{3-8}$ alkyl, $C_{1-8}$ alkyl ($C_{3-8}$ cycloalkyl), $C_{3-8}$ cycloalkyl, heteroaryl, or substituted aryl; $R_4$, $R_5$ and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)—$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNR_9COR_7$, —$(CH_2)_xNR_9SO_2R_7$, —$(CH_2)_xNR_9CO_2R_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_7R_8$, —$(CH_2)_xCONR_7(CH_2)_yR_9$, —$(CH_2)_xCOR_7$, —$(CH_2)_xCO_2R_7$, —$(CH_2)_xSO_2NR_7(CH_2)_yR_9$, —$CHR_7COR_9$ —$CHR_7CONHCHR_8COR_9$ —$CONR_7R_8$, —$CONR_7(CH_2)_xCO_2R_8$, —$CONR_7CHR_8CO_2R_9$, —$CO_2R_9$, H, or —$NHCO_2R_7$, —$(CH_2)_xSO_2NR_7R_8$; —$SF_5$; or $R_4$ and $R_5$ together make a 4-8 member ring which may be substituted with one or more heteroatoms; or $R_4$ and $R_5$ together make a 5-8 nitrogen containing member ring with one or more carbonyl groups; wherein the group $R_4$ is substituted with one or more fluorine atoms; $R_9$ is aryl, $C_1$-$C_8$ alkoxy, $C_{1-8}$ alkyl, $C_{1-8}$ alkyl(aryl), $C_{3-8}$ cycloalkyl, H, heteroaryl, or hydroxyl; each x is independently 0-8; and each y is independently 1-8.

The disclosure also provides a compound represented by the Formula II:

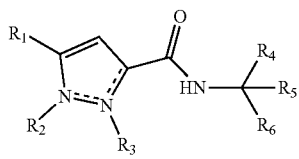

II or a pharmaceutically acceptable salt, a prodrug, or a salt of a prodrug,

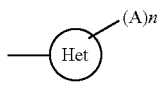

wherein $R_1$ is represented by the formula: wherein

is a monocyclic heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —NHCOR$_7$, —NHSO$_2C_{1-8}$ alkyl, —NHCO$_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_x(NR_7R_8)$, —$SF_5$, —$SO_2NR_7R_8$, —$SO_{(1-3)}R_7$, or —$SR_7$; each $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_x(CO_2R_9$, H, or heteroaryl; or $R_7$ and $R_8$ together make a 3-9 member cycloalkyl or heterocycloalkyl group; n is 1, 2, 3, 4 or 5; each x is independently 0-8;

$R_2$ is present or absent, and if present, is $C_{3-8}$ alkyl, $C_{1-8}$ alkyl ($C_{3-8}$ cycloalkyl), $C_{3-8}$ cycloalkyl, heteroaryl, or substituted aryl;

$R_3$ is present or absent, is absent if $R_2$ is present, and if present is $C_{1-8}$ alkyl, $C_{1-8}$ alkyl ($C_{3-8}$ cycloalkyl), $C_{3-8}$ cycloalkyl or substituted aryl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl $C_6$ heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-9}$ cycloalkyl, $C_{3-8}$ cycloalkyl-$CO_2R_7$, —$(CH_2)_xNR_7R_8$, —$(CH_2)_xOR_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_8R_9$, —$(CH_2)_xCONR_7(CH_2)_yR_9$, —$(CH_2)_xCONR_7(CH_2)_ySO_2R_9$, —$(CH_2)_xCOR_7$, —$(CH_2)_xCO_2R_7$, —$(CH_2)_xSO_2NR_7(CH_2)_yR_9$, —$CHR_7COR_9$ —$CHR_7CONHCHR_8COR_9$, —$CONR_7R_8$, —$CONR_7(CH_2)_xCO_2R_8$, —$CONR_7CHR_8CO_2R_9$, —$CO_2R_9$, H, —$NHCO_2R_7$, —$SF_5$, —$SO_2NR_7R_8$, or $R_4$ and $R_5$ together make a 4-9 member cycloalkyl or heterocycloalkyl group; wherein the group $R_4$ is substituted with one or more fluorine atoms; $R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; and each y is independently 1-8.

Furthermore, the disclosure provides a compound of the present disclosure, represented by Formula III

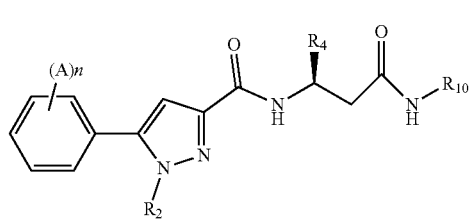

III wherein n is 1, 2 or 3; each A is independently $C_1$-$C_5$ alkoxy, $C_1$-$C_5$ alkyl, $C_{3-8}$ cycloalkyl, halogen, or —$SF_5$; $R_2$ is $C_3$-$C_6$ alkyl, $C_{1-3}$ alkyl ($C_{3-6}$ cycloalkyl) or $C_3$-$C_7$ cycloalkyl;

$R_4$ is aryl, $C_{1-4}$ alkyl, $C_{2-8}$ alkyl(aryl), $C_{1-8}$ alkyl ($C_{3-8}$ cycloalkyl), $C_{1-8}$ alkyl heteroaryl, $C_{2-4}$ alkyl $C_6$ heterocycloalkyl, $C_{2-8}$ alkenyl(aryl), $C_{2-8}$ alkenyl(heteroaryl), or heteroaryl; wherein the group $R_4$ is substituted with one or more fluorine atoms; and $R_{10}$ is aryl, $C_{1-8}$ alkyl, $C_{1-8}$ alkyl(aryl), $C_{1-8}$ alkyl ($C_{3-8}$ cycloalkyl), $C_{1-8}$ alkyl heteroaryl, $C_{1-8}$ alkyl tetrazol-5-one, $C_{3-8}$ cycloalkyl, or heteroaryl.

The disclosure provides the compound of the present disclosure, wherein each A is independently $C_1$-$C_3$ alkoxy, $C_1$-$C_3$ alkyl, chloro, or fluoro. In one embodiment, each A is independently fluoro substituted $C_1$-$C_3$ alkoxy or fluoro substituted $C_1$-$C_3$ alkyl.

The disclosure provides the compound of the present disclosure, wherein $R_2$ is —$C_4H_9$, —$C_5H_{11}$, -$cC_4H_8$ or -$cC_5H_{10}$.

The disclosure provides the compound of the present disclosure, wherein the $R_4$ group contains a nitrogen and two or more fluorine atoms.

The disclosure provides the compound of the present disclosure, wherein $R_4$ is $C_{1-8}$ alkyl(aryl), $C_{1-4}$ alkyl cycloalkyl, $C_{1-8}$ alkyl heteroaryl, $C_{1-4}$ alkyl heterocycloalkyl, $C_{2-8}$ alkenyl(aryl), or $C_{2-8}$ alkenyl(heteroaryl). The cycloalkyl group in the $C_{1-4}$ alkyl cycloalkyl may be a bicycloalkyl or a spiroalkyl group or the heterocycloalkyl group in the $C_{1-4}$ alkyl cycloalkyl may be a heterobicycloalkyl or a heterospiroalkyl group. More specifically, $R_4$ may be $C_{1-8}$ alkyl (difluoroaryl), $C_{1-4}$ alkyl difluorocycloalkyl, $C_{1-8}$ alkyl difluoro heteroaryl, $C_{1-4}$ alkyl difluoroheterocycloalkyl, $C_{2-8}$ alkenyl(difluoro aryl), or $C_{2-8}$ alkenyl(difluoro heteroaryl).

The disclosure also provides the compound of the present disclosure, wherein $R_8$ is heteroaryl. In particular, $R_8$ may be oxadiazole, oxazole, n-methyl thiazole, tetrazole, thiazole, or triazole.

Pharmaceutical compositions are also provided comprising at least one pharmaceutically acceptable excipient and a therapeutically effective amount of the compound of the present disclosure. The therapeutically effective amount may be an amount effective for lowering blood pressure. Alternatively, the therapeutically effective amount is an amount effective for the treatment of asthma, cardiomyopathy, diabetes, dyslipidemia, hypertension, inflammation, liver disease, metabolic disorder, neurodegenerative disease, obesity, preeclampsia, or renal dysfunction.

In another embodiment, the disclosure provides the use in a treatment of an apelin receptor (APJ) related disorder of a compound Formula I:

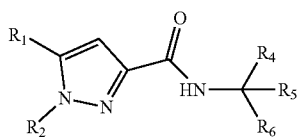

I or a pharmaceutically acceptable salt, a prodrug, or a salt of a prodrug, wherein $R_1$ is represented by the formula:

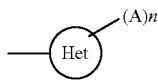

wherein

is a monocyclic aryl or heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCO_{1-8}$ alkyl, —$OCO(CH_2)_xNR_7R_8$, —$SF_5$, —$SO_2NR_7R_8$, —$SO_{(1-3)}R_7$, —$SR_7$, or tetrazolone; $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member ring which may contain one or more heteroatoms; or $R_7$ and $R_8$ together make a 5-8 nitrogen containing member ring with one or more carbonyl groups; n is 1, 2, 3, 4 or 5;

$R_2$ is $C_{3-8}$ alkyl, $C_{1-8}$ alkyl ($C_{3-8}$ cycloalkyl), $C_{3-8}$ cycloalkyl, heteroaryl, or substituted aryl;

$R_4$, $R_5$ and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, —$(CH_2)_xNR_7R_8$, —$(CH_2)_xOR_7$, —$(CH_2)_xNR_9COR_7$, —$(CH_2)_xNR_9SO_2R_7$, —$(CH_2)_xN$ $R_9CO_2R_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7$ $(CH_2)_yCONR_7R_8$, —$(CH_2)_xCONR_7(CH_2)_yR_9$, —$(CH_2)_xCOR_7$, —$(CH_2)_xCO_2R_7$, —$(CH_2)_xSO_2NR_7$ $(CH_2)_yR_9$, —$CHR_7COR_9$, —$CHR_7CONHCHR_8COR_9$— $CONR_7R_8$, —$CONR_7(CH_2)_xCO_2R_8$, —$CONR_7CHR_8CO_2R_9$, —$CO_2R_9$, H, or —$NHCO_2R_7$, —$(CH_2)_xSO_2NR_7R_8$; —$SF_5$; or $R_4$ and $R_5$ together make a 4-8 member ring which may be substituted with one or more heteroatoms; or $R_4$ and $R_5$ together make a 5-8 nitrogen containing member ring with one or more carbonyl groups;

wherein the group $R_4$ is substituted with one or more fluorine atoms;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; each x is independently 0-8; and each y is independently 1-8.

In yet another embodiment, the disclosure provides the use in a treatment of an apelin receptor (APJ) related disorder of a compound represented by the Formula II:

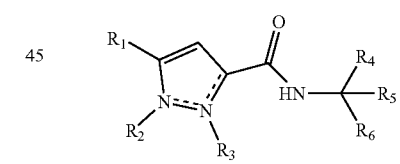

II or a pharmaceutically acceptable salt, a prodrug, or a salt of a prodrug, wherein $R_1$ is represented by the formula:

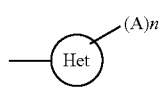

wherein

is a monocyclic heteroaryl group; each A is independently $C_{1-8}$ alkyl, $C_{1-8}$ alkyl(aryl), $C_{1-8}$ alkoxy, $C_{1-8}$ alkoxy aryl, $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —NHCOR_7, —$NHSO_2C_{1-8}$ alkyl, —$NHCO_2C_{1-8}$ alkyl, —$NO_2$, —$NR_7R_8$, —$O(CH_2)_xNR_7R_8$, —$O(CH_2)_xCO_2R_7$, —$OCOC_{1-8}$ alkyl, —$OCO(CH_2)_xNR_7R_8$, —$SF_5$, —$SO_2NR_7R_8$, —$SO_{(1-3)}R_7$, or —$SR_7$; each $R_7$ and $R_8$ are independently $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl; or $R_7$ and $R_8$ together make a 3-9 member cycloalkyl or heterocycloalkyl group; n is 1, 2, 3, 4 or 5; each x is independently 0-8;

$R_2$ is present or absent, and if present, is $C_{3-8}$ alkyl, $C_{1-8}$ alkyl ($C_{3-8}$ cycloalkyl), $C_{3-8}$ cycloalkyl, heteroaryl, or substituted aryl;

$R_3$ is present or absent, is absent if $R_2$ is present, and if present is $C_{1-8}$ alkyl, $C_{1-8}$ alkyl ($C_{3-8}$ cycloalkyl), $C_{3-8}$ cycloalkyl or substituted aryl;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl tetrazol-5-one, $C_{2-4}$ alkyl $C_6$ heterocycloalkyl, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-9}$ cycloalkyl, $C_{3-8}$ cycloalkyl-$CO_2R_7$, —$(CH_2)_xNR_7R_8$, —$(CH_2)_xOR_7$, —$(CH_2)_xNHCOR_7$, —$(CH_2)_xNHSO_2R_7$, —$(CH_2)_xNHCO_2R_7$, —$(CH_2)_xCONR_7R_8$, —$(CH_2)_xCONR_7(CH_2)_yCO_2R_9$, —$(CH_2)_xCONR_7(CH_2)_yCONR_8R_9$, —$(CH_2)_xCONR_7(CH_2)_yR_9$, —$(CH_2)_xCONR_7(CH_2)_ySO_2R_9$, —$(CH_2)_xCOR_7$, —$(CH_2)_xCO_2R_7$, —$(CH_2)_xSO_2NR_7(CH_2)_yR_9$, —$CHR_7COR_9$ —$CHR_7CONHCHR_8COR_9$, —$CONR_7R_8$, —$CONR_7(CH_2)_xCO_2R_8$, —$CONR_7CHR_8COR_9$, —$CO_2R_9$, H, —$NHCO_2R_7$, —$SF_5$, —$SO_2NR_7R_8$, or $R_4$ and $R_5$ together make a 4-9 member cycloalkyl or heterocycloalkyl group;

wherein the group $R_4$ is substituted with one or more fluorine atoms;

$R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl; and each y is independently 1-8.

The use in a treatment of an apelin receptor (APJ) related disorder of a compound represented by the represented by Formula III

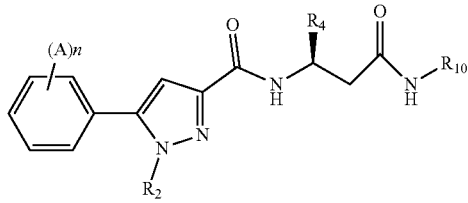

wherein n is 1, 2 or 3; each A is independently $C_1$-$C_5$ alkoxy, $C_1$-$C_5$ alkyl, $C_{3-8}$ cycloalkyl, halogen, or —$SF_5$;

$R_2$ is $C_3$-$C_6$ alkyl, $C_{1-3}$ alkyl ($C_{3-6}$ cycloalkyl) or $C_3$-$C_7$ cycloalkyl;

$R_4$ is aryl, $C_{1-4}$ alkyl, $C_{2-8}$ alkyl(aryl), $C_{1-8}$ alkyl ($C_{3-8}$ cycloalkyl), $C_{1-8}$ alkyl heteroaryl, $C_{2-4}$ alkyl $C_6$ heterocycloalkyl, $C_{2-8}$ alkenyl(aryl), $C_{2-8}$ alkenyl(heteroaryl), or heteroaryl; wherein the group $R_4$ is substituted with one or more fluorine atoms; and $R_{10}$ is aryl, $C_{1-8}$ alkyl, $C_{1-8}$ alkyl(aryl), $C_{1-8}$ alkyl ($C_{3-8}$ cycloalkyl), $C_{1-8}$ alkyl heteroaryl, $C_{1-8}$ alkyl tetrazol-5-one, $C_{3-8}$ cycloalkyl, or heteroaryl.

In another embodiment, the disclosure provides the use of a compound of the present disclosure, wherein the apelin receptor (APJ) related disorder is asthma, cardiomyopathy, diabetes, dyslipidemia, hypertension, inflammation, liver disease, metabolic disorder, neurodegenerative disease, obesity, preeclampsia, or renal dysfunction.

In one embodiment, the disclosure provides the use of a compound of the present disclosure, further comprising an α-blocker, an angiotensin converting enzyme (ACE) inhibitor, an angiotensin-receptor blocker (ARB), a β-blocker, a calcium channel blocker, or a diuretic for the treatment of the apelin receptor (APJ) related disorder.

In another embodiment, the disclosure provides a compound represented by the Formula IV:

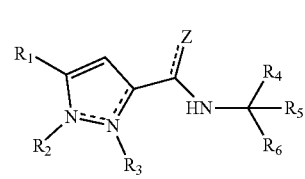

or a pharmaceutically acceptable salt, a prodrug, or a salt of a prodrug, wherein $R_1$ is represented by the formula:

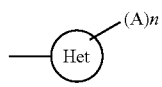

wherein

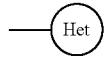

is a monocyclic heteroaryl group; each A is independently $C_{1-8}$ alkyl, $C_{1-8}$ alkyl(aryl), $C_{2-8}$ alkenyl, $C_{3-8}$ alkynyl, $C_{3-8}$ cycloalkyl, —$CF_3$, —$(CH_2)_xNR_7R_8$, —CN, —$CONR_7R_8$, —$COR_7$, —$CO_2(CH_2)_xNR_7R_8$, —$CO_2R_7$, halogen, hydroxyl, —$N_3$, —$NHCOR_7$, —$NHSO_2C_{1-8}$ alkyl, —$NHCO_2C_{1-8}$ alkyl, —$NO_2$, —$NR_7R_8$, —$O(CH_2)_x(NR_7R_8$, —$O(CH_2)_x(CO_2R_7$, —$OCOC_{1-8}$ alkyl, —$OCO(CH_2)_x(NR_7R_8$, —$SF_5$, —$SO_2NR_7R_8$, —$SO_{(1-3)}R_7$, —$SR_7$, or tetrazalone;

$R_7$ and $R_8$ are independently alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, —$(CH_2)_xCONHR_9$, —$(CH_2)_xCOR_9$, —$(CH_2)_xCO_2R_9$, H, or heteroaryl;

or $R_7$ and $R_8$ together make a 3-8 member ring which may be substituted with one or more heteroatoms;

n is 1, 2, 3, 4 or 5;

each x is independently 0-8;

$R_2$ is present or absent, and if present, is $C_{3-8}$ alkyl, $C_{1-8}$ alkyl ($C_{3-8}$ cycloalkyl), $C_{2-8}$ alkyl(aryl), $C_{3-8}$ cycloalkyl, heteroaryl, or substituted aryl;

$R_3$ is present or absent, is absent if $R_2$ is present, and if present is $C_{1-8}$ alkyl, $C_{1-8}$ alkyl ($C_{3-8}$ cycloalkyl), $C_{2-8}$ alkyl(aryl), $C_{3-8}$ cycloalkyl or substituted aryl; provided that if n is two, both A's are not chlorine;

$R_4$, $R_5$, and $R_6$ are independently adamantanyl, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl ($C_{3-8}$ cycloalkyl)-$CO_2R_7$, $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl tetrazol-5-one, $C_{1-8}$ alkyl thioether, $C_{1-8}$ alkyl thiol, $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $-(CH_2)_xNR_7R_8$, $-(CH_2)_xOR_7$, $-(CH_2)_xNH\text{-}COR_7$, $-(CH_2)_xNHSO_2R_7$, $-(CH_2)_xNHCO_2R_7$, $-(CH_2)_xCONR_7R_8$, $-(CH_2)_xCONR_7(CH_2)_yCO_2R_9$, $-(CH_2)_xCONR_7(CH_2)_yCONR_7R_8$, $-(CH_2)_xCONR_7(CH_2)_yR_9$, $-(CH_2)_xCOR_7$, $-(CH_2)_xCO_2R_7$, $-(CH_2)_xSO_2NR_7(CH_2)_yR_9$, $-CHR_7COR_9$, $-CHR_7CONHCHR_8COR_9$, $-CONR_7R_8$, $-CONR_7(CH_2)_xCO_2R_8$, $-CONR_7CHR_8CO_2R_9$, $-CO_2R_9$, H, or $-NHCO_2R_7$, $-SF_5$, $-SO_2NR_7R_8$; or $R_4$ and $R_5$ together make a 4-8 member ring which may be substituted with one or more heteroatoms; $R_9$ is aryl, $C_{1-8}$ alkoxy, $C_{1-8}$ alkyl, $C_{1-8}$ alkyl(aryl), $C_{3-8}$ cycloalkyl, H, heteroaryl, or hydroxyl;

each y is independently 1-8;

and Z is $H_2$ or $=O$.

The composition of the present disclosure Formula IV may incorporate the modifications as described in the present disclosure for Formulas I-III. In addition, compounds of Formula IV may be prepared in pharmaceutical compositions as described in the present disclosure. Moreover, disclosure provides the use in a treatment of apelin receptor (APJ) related disorders, as disclosed herein, of a compound represented by the Formula IV.

In a preferred embodiment of the compositions or uses of the compounds of the present disclosure,

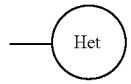

is phenyl or 2- or 3-pyridyl, n is 1, group A is in the ortho position and is $-CF_3$, $-CF_2CH_3$, $-CH_2CH_3$, Cl, $-cC_3H_5$, $-OCF_2H$ or $-OCF_3$. Alternatively, n is 2 and $A_1$ is $-OCH_3$ and $A_2$ is $-OCH_3$ or F. More specifically,

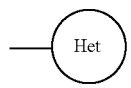

is

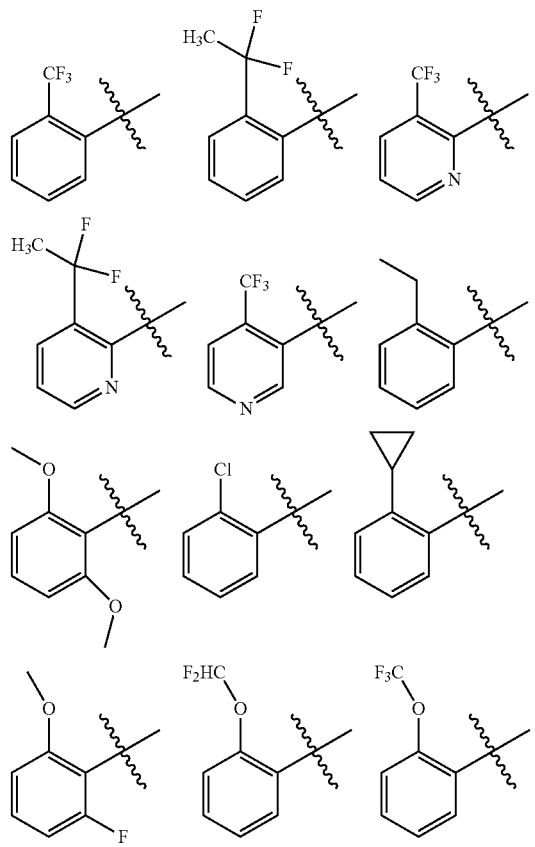

In another preferred embodiment of the compositions or uses of the compound of the present disclosure, $R_2$ is $-CH_2cC_3H_5$, $-C(CH_3)_2CC_3H_5$, $-cC_4H_7$, $-cC_4H_6(CH_3)_2$, $-CH_2cC_4H_7$, $-cC_5H_9$, $cC_5H_8F$, $-cC_5H_8(CH_3)$, $-cC_5H_7(CH_3)_2$, $-CH_2cC_5H_9$, $-CH_2cC_5H_9$, $-cC_6H_{11}$, $-CH_2CH_2CH_3$, $-CH_2CH(CH_3)_2$, or $-C(CH_3)CH(CH_3)_2$. In particular, $R_2$ may be

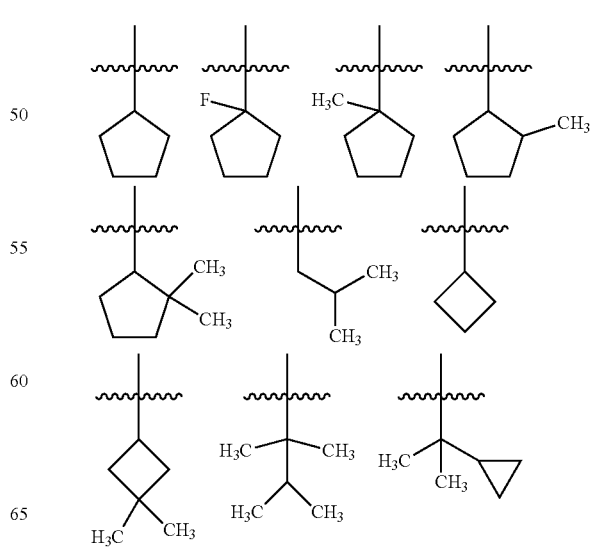

-continued
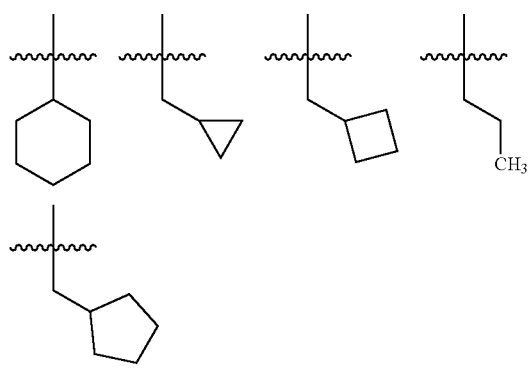
In another preferred embodiment of the compositions or uses of the compounds of the present disclosure, R₄ may be
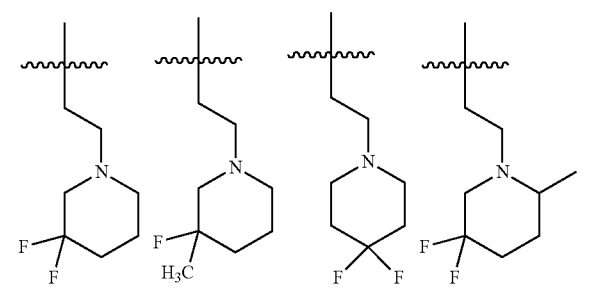
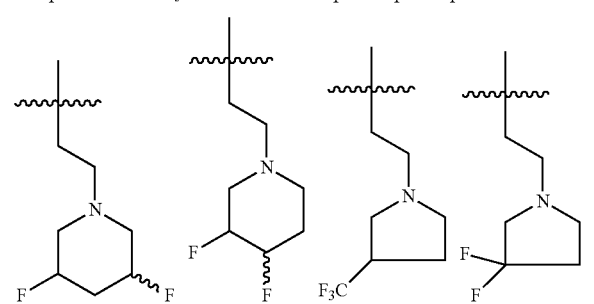
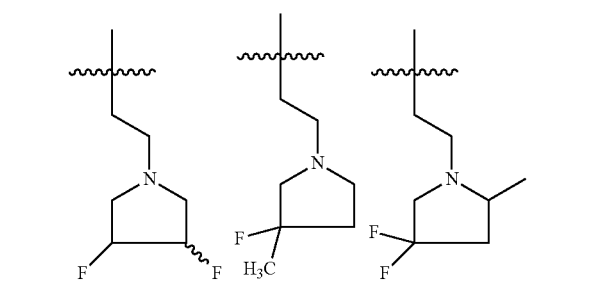
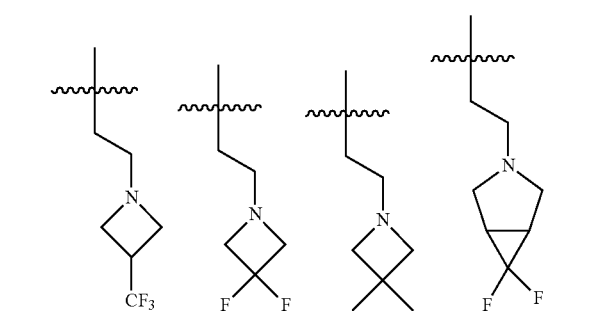
-continued
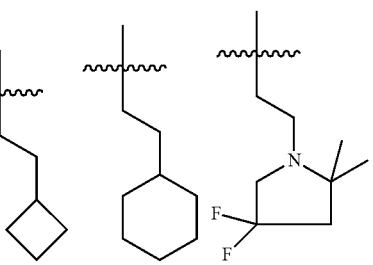
In an additional preferred embodiment, R₄ may be
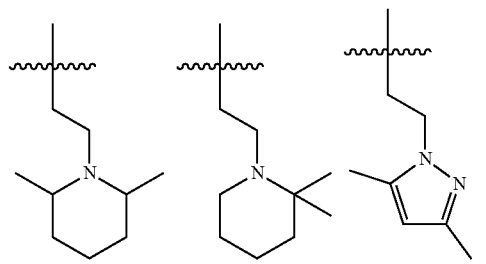
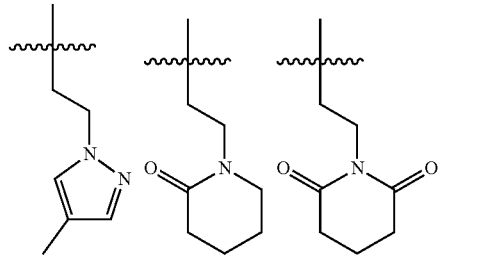
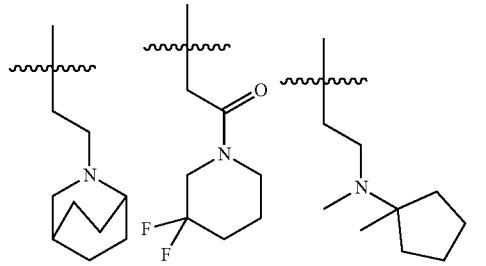
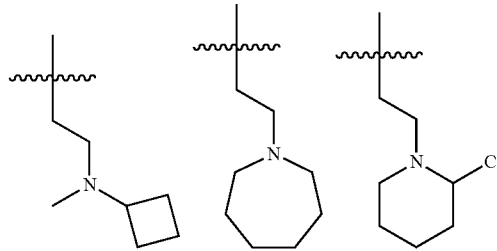
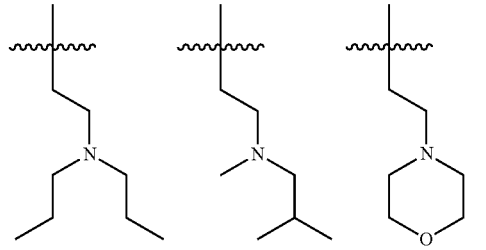

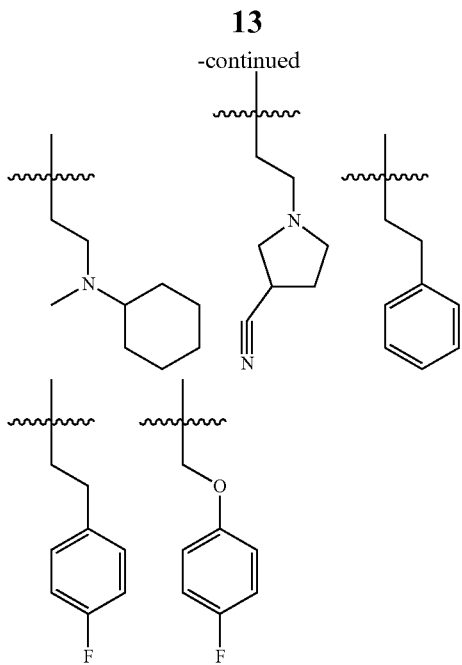

If there are no fluorines in the group, the backbones of the $R_4$ groups in the compounds of the present disclosure may be modified to contain one or more fluorine atoms by the replacement of one or more hydrogens. Alternatively, if the $R_4$ groups in the present disclosure contain fluorines, the backbone may be modified to incorporate additional fluorine substituents by replacement of aliphatic or aromatic hydrogens.

In yet another preferred embodiment, $R_5$ or $R_{10}$ may be

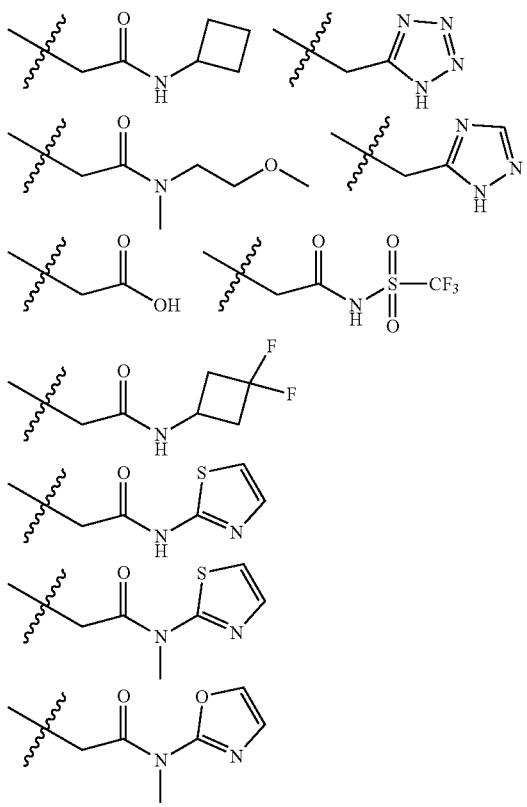

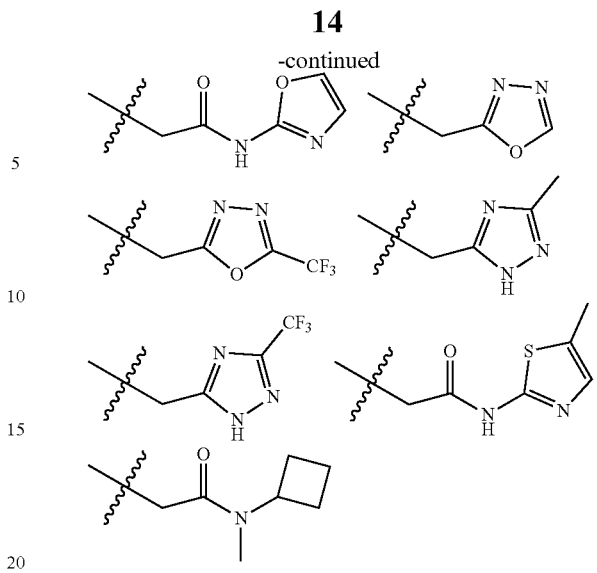

In preferred embodiments, two groups in the set of $R_1$, $R_2$, $R_4$, $R_5$ and $R_{10}$ are selected from the groups shown in the compounds of the present disclosure. In other preferred embodiments, three groups in the set of $R_1$, $R_2$, $R_4$, $R_5$ and $R_{10}$ are selected from the groups in the compounds of present disclosure. In yet another embodiment, four groups in the set of $R_1$, $R_2$, $R_4$, $R_5$ and $R_{10}$ are selected from the groups in the compounds of the present disclosure.

For the compounds and uses above, the disclosure also includes bioisosteres such as tetrazolones and pentafluorosulfanyl. In particular, —$CF_3$, —$CH_3$, —O—$CH_3$, or —O—$CF_3$ or an aryl —$CF_3$, —$CH_3$, —O—$CH_3$, or —O—$CF_3$ may be replaced with —$SF_5$ or aryl-$SF_5$, respectively. See Alvarez et al. 2015 ACS Med Chem Let 6 1225-1230. Alternatively, a —$CO_2H$ may be replaced with a tetrazolone. See Duncton et al. 2016 Org Biomol Chem 14 9338-9342.

4. DETAILED DESCRIPTION OF THE DISCLOSURE

4.1. Definitions

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical —OR where R represents an alkyl, cycloalkyl, aryl, or heteroaryl group as defined herein. Representative examples include, but are not limited to, methoxy, ethoxy, propoxy, butoxy, cyclohexyloxy, and the like. The alkoxy group may be substituted or unsubstituted.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with methyl or a halogen(s) such as difluoro or trifluoro. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$. The alkyl(aryl) group may be substituted or unsubstituted.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen, such as fluorine.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl or $cC_6H_{12}$. The cycloalkyl group may also be a bridged bicyclic cycloalkyl group, a fused cycloalkyl group or a spiro cycloalkyl group. Non-limiting examples of bridged bicyclic cycloalkyl groups are bicyclo [2.2.1]heptane, bicyclo[2.2.1]hexane, bicycle[2.2.2]octane. An example of a fused cycloalkyl group is bicyclo[4.4.0] decane or decalin. Non-limiting examples of spiro cycloalkyl groups are spiro [3.3] heptane, spiro [4.3] octane, or spiro [5.4] decane.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heterocycloalkyl" refers to a non-aromatic monocyclic ring or fused non-aromatic polycyclic rings with one or more heteroatom(s) independently selected from N, S and O, with the remaining ring atoms being carbon and wherein at least one heteroatom is present in each non-aromatic ring. The heterocycle group may be a three-member ring, a four member ring, a five member ring, a six member ring or a seven member ring. In certain embodiments, the heterocycloalkyl group is 1,4-dioxane, 1,3-dioxolane, 1,4-dithiane, imidazolidine, morpholine, piperidine, piperidone, piperazine, pyrolidone, pyrrolidine, or 1,3,5-trithiane. It may contain an imide. The heterocycloalkyl group may be bicyclic such as an heterospiro group, e.g., heterospiro [3.3] heptanyl, heterospiro [3.4] octanyl, or heterospiro [5.5] undecanyls. The heterocycloalkyl group may be substituted or unsubstituted. Thus, heterocycloalkyl group encompasses heterocycloalkyl groups substituted with one or more halogens, such as 3,3-difluoropiperidine, or 4,4-difluoropiperidine. In addition, the heterocycloalkyl group may be substituted with a $C_1$-$C_4$ alkyl or $C_1$-$C_4$ halo alkyl group such as a —$CF_3$ group.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Prodrug" refers to a precursor or derivative form of a pharmaceutically active substance that is less bioactive compared to the parent drug and is capable of being enzymatically activated or converted into the more active parent form. Prodrug forms of the compounds described herein may designed to improve bioavailability or stability or reduce toxicity. For example, compounds of the invention having free amino, amido, carboxylic, hydroxyl, or thiol groups can be converted into prodrugs. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Prodrugs may also include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes beta-alanine, citrulline, demosine, gamma-aminobutyric acid, homocysteine, homoserine, 4-hydroxyproline, hydroxylysine, isodemosine, 3-methylhistidine, norvalin, methionine sulfone, and ornithine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, cyano, difluoro, difluoromethyl, halogen, hydroxyl, keto, methyl, $—N_3$, $—NH_2$, $—SO_{(1-3)}H$, $—SH$, or trifluoromethyl.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Pairs of the functional groups defined herein may be combined in a chemically rational way. For example, $C_1$-$C_8$ alkyl amino means the functional group $C_1$-$C_8$ alkyl, e.g., -$nC_5H_{11}$, is combined with the functional group, amino, e.g., $—NH_2$ to form in this example-$nC_5H_{10}NH_2$. Likewise, $C_1$-$C_8$ alkyl alcohol would mean a group, e.g., $nC_3H_6OH$. Similarly, $C_1$-$C_8$ alkoxy aryl means the functional group $C_1$-$C_8$ alkoxy, e.g., $—CH_2CH_2OCH_2CH_3$ or $—OCH_2CH_3$ combined with an aryl group, e.g., $—C_6H_5F$ to form $—CH_2CH_2OCH_2CH_2—C_6H_5F$ or $—OCH_2CH_3—C_6H_5F$, respectively.

As used herein the substituents $R_4$, $R_5$, $R_6$, $R_7$, or $R_8$ may independently may be single α, β, γ, δ amino acids, or their corresponding side chains, such as the twenty naturally occurring amino acids, e.g., alanine (Ala/A); arginine (Arg/R); asparagine (Asn/N); aspartic acid (Asp/D); cysteine (Cys/C); glutamic acid (Glu/E); glutamine (Gln/Q); glycine (Gly/G); histidine (His/H); isoleucine (Ile/I); leucine (Leu/L); lysine (Lys/K); methionine (Met/M); phenylalanine (Phe/F); proline (Pro/P); Serine (Ser/S); threonine (Thr/T); tryptophan (Trp/W); tyrosine (Tyr/Y); and valine (Val/V). The individual amino acids may of either the R or the S chirality. Alternatively, $R_4$, $R_5$, $R_6$, $R_7$, or $R_8$ independently may be two or three amino acids linked by a peptide bond.

R$_4$, R$_5$, R$_6$, R$_7$, or R$_8$ independently may be dipeptides or tripeptides (Hobbs et al., Proc Nat Acad Sci USA. 1993, 90, 6909-6913); U.S. Pat. No. 6,075,121 (Bartlett et al.) peptoids; or vinylogous polypeptides (Hagihara et al., J Amer Chem Soc. 1992, 114, 6568), the contents of which are hereby incorporated by reference in their entireties. R$_4$, R$_5$, R$_6$, R$_7$, or R$_8$ independently may be part of the extended unnatural amino acids, e.g., Xie and Schultz, Nat Rev Mol Cell Biol. 2006, 7(10):775-82 or Wang et al., Chem Biol. 2009, 16(3):323-36, the contents of which are hereby incorporated by reference in their entireties.

4.2. Deuterated and Other Isotopic Variants

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2$H (deuterium), $^3$H (tritium) $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Substitution with positron emitting isotopes, such as $^{11}$C, $^{18}$F, $^{15}$O and $^{13}$N, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2$H), tritium ($^3$H) or $^{14}$C isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as D$_2$SO$_4$/D$_2$O. Alternatively, deuterium may be also incorporated into a compound using methods such as through reduction such as using LiAlD$_4$ or NaBD$_3$, catalytic hydrogenation or acidic or basic isotopic exchange using appropriate deuterated reagents such as deuterides, D$_2$ and D$_2$O. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

4.3. Pharmaceutical Compositions

The disclosure also provides pharmaceutical compositions comprising an effective amount of a compound Formula I (e.g., any of the formulae and/or structures disclosed herein), or a pharmaceutically acceptable salt of said compound; and a pharmaceutically acceptable carrier.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866 (Infeld et al.); and US Pat. Pubs. 20060094744 (Maryanoff et al.) and 20060079502 (Lang).

The pharmaceutical compositions of the disclosure include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031 (Rabinowitz & Zaffaroni).

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene or polyoxypropylene compounds, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the therapeutics may be local, so as to be administered at the site of interest. Various techniques can be used for providing the compositions at the site of interest, such as injection, use of catheters, trocars, projectiles, pluronic gels, stents, sustained drug release polymers or other devices which provide for internal access. Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. No. 6,099,562 (Ding & Helmus); U.S. Pat. No. 5,886,026 (Hunter et al.); and U.S. Pat. No. 5,304,121 (Sahatjian). The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active. Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

In one embodiment, this disclosure provides a composition comprising a compound of Formula I, or more specific compounds disclosed herein, to treat or prevent asthma, atherosclerosis, cancer, cardiomyopathy, diabetes, dyslipidemia, HIV neurodegeneration, hypertension, inflammation, liver disease, metabolic disorder, neurodegenerative disease, obesity, or preeclampsia. In another embodiment, the disclosure provides a composition comprising a compound of Formula I, or more specific compounds disclosed herein, to treat or prevent cancer, cell proliferation, diabetes, fluid homeostasis, heart diseases (e.g., hypertension and heart failure, such as congestive heart failure), HIV infection, immune function, obesity, stem cell trafficking, metastatic cancer or a vein-related disorder such as an angioma, a venous insufficiency, a stasis, or a thrombosis.

In another embodiment, a composition of this disclosure further comprises a second therapeutic agent. In one embodiment, the second therapeutic agent is one or more additional compounds of the disclosure. In another embodiment, the second therapeutic agent may be selected from any compound or therapeutic agent known to have or that demonstrates advantageous properties when administered with a compound having the same mechanism of action as the APJ receptor compound of Formula I.

In a particular embodiment, the second therapeutic is an agent useful in the treatment or prevention of a disease or condition selected from acute decompensated heart failure (ADHF), amyotrophic lateral sclerosis, arrhythmia, asthma, atherosclerosis, atherosclerosis, atrial fibrillation, Brugada syndrome, burn injuries (including sunburn), cancer, cardiac fibrosis, cardiomyopathy, cerebrovascular accidents, chronic heart failure, diabetes (including gestational diabetes), dyslipidemia, HIV neurodegeneration, hypertension, inflammation, ischemic cardiovascular diseases, liver disease, metabolic disorder, neurodegenerative disease, obesity, peripheral arterial disease, preeclampsia, pulmonary hypertension, restenosis, transient ischemic attacks, traumatic brain injuries, ventricular tachycardia, or water retention. In another embodiment, the second therapeutic is an agent useful in the treatment or prevention of a disease or condition selected from cancer, cell proliferation, diabetes, fluid homeostasis, heart diseases (e.g., hypertension and heart failure, such as congestive heart failure), HIV infection, immune function, obesity, stem cell trafficking, or metastatic cancer.

For example, when the disease or condition is congestive heart failure, the second therapeutic agent can be selected from: ACE inhibitors, beta blockers, vasodilators, calcium channel blockers, loop diuretics, aldosterone antagonists, and angiotensin receptor blockers.

When the disease or condition being treated is hypertension, the second therapeutic agent can be selected from: α-blockers, β-blockers, calcium channel blockers, diuretics, natriuretics, saluretics, centrally acting antihypertensives, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonists.

Non-limiting examples of α-Blockers include doxazosin, prazosin, tamsulosin, and terazosin.

Non-limiting examples of β-Blockers for combination therapy are selected from acebutolol, acetutolol, atenolol, bisoprol, bupranolol, carteolol, carvedilol, celiprolol, esmolol, mepindolol, metoprolol, nadolol, oxprenolol, penbutolol, pindolol, propanolol, taliprolol, and their pharmaceutically acceptable salts.

Non-limiting examples of calcium channel blockers include dihydropyridines (DHPs) and non-DHPs. The preferred DHPs are selected from the group consisting of amlodipine, felodipine, isradipine, lacidipine, nicardipine, nifedipine, nigulpidine, niludipine, nimodiphine, nisoldipine, nitrendipine, nivaldipine, ryosidine, and their pharmaceutically acceptable salts. Non-DHPs are selected from anipamil, diltiazem, fendiline, flunarizine, gallopamil, mibefradil, prenylamine, tiapamil, and verampimil and their pharmaceutically acceptable salts.

Non-limiting examples of thiazide derivative include amiloride, chlorothalidon, chlorothiazide, hydrochlorothiazide, and methylchlorothiazide.

Non-limiting examples of centrally acting antihypertensives include clonidine, guanabenz, guanfacine and methyldopa.

Non-limiting examples of ACE inhibitors include alacepril, benazepril, benazaprilat, captopril, ceronapril, cilazapril, delapril, enalapril, enalaprilat, fosinopril, lisinopril, moexipiril, moveltopril, perindopril, quinapril, quinaprilat, ramipril, ramiprilat, spirapril, temocapril, trandolapril, and zofenopril. Preferred ACE inhibitors are benazepril, enalpril, lisinopril, and ramipril.

Non-limiting examples of dual ACE/NEP inhibitors are, for example, omapatrilat, fasidotril, and fasidotrilat.

Non-limiting examples of preferred ARBs include candesartan, eprosartan, irbesartan, losartan, olmesartan, tasosartan, telmisartan, and valsartan.

Non-limiting examples of preferred aldosterone synthase inhibitors are anastrozole, fadrozole, and exemestane.

Non-limiting examples of preferred aldosterone-receptor antagonists are spironolactone and eplerenone.

Non-limiting examples of preferred endothelin antagonist include, for example, bosentan, enrasentan, atrasentan, darusentan, sitaxentan, and tezosentan and their pharmaceutically acceptable salts.

In one embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to treat (therapeutically or prophylactically) the target disorder. For example, and effective amount is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy. Preferably, the compound is present in the composition in an amount of from 0.1 to 50 wt. %, more preferably from 1 to 30 wt. %, most preferably from 5 to 20 wt. %.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970,537.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

The compounds for use in the method of the disclosure can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily treatment dose or one of multiple daily treatment doses (e.g., about 1 to 4 or more times per day). When multiple daily treatment doses are used, the unit dosage form can be the same or different for each dose.

4.4. Methods of Treatment

The disclosure also includes methods of treating diseases, disorders or pathological conditions which benefit from modulation of the APJ receptor comprising administering an effective amount of an APJ receptor compound of the disclosure to a subject in need thereof. Diseases and conditions which can benefit from modulation (inhibition or activation) of the APJ receptor include, but are not limited to, acute decompensated heart failure (ADHF), amyotrophic lateral sclerosis, arrhythmia, asthma, atherosclerosis, atherosclerosis, atrial fibrillation, Brugada syndrome, burn injuries (including sunburn), cancer, cardiac fibrosis, cardiomyopathy, cerebrovascular accidents, chronic heart failure, diabetes (including gestational diabetes), dyslipidemia, HIV neurodegeneration, hypertension, inflammation, ischemic cardiovascular diseases, liver disease, metabolic disorder, neurodegenerative disease, obesity, peripheral arterial disease, preeclampsia, pulmonary hypertension, restenosis, transient ischemic attacks, traumatic brain injuries, ventricular tachycardia, or water retention. More specifically, the hypertension may be pulmonary arterial hypertension. The liver disease may be alcoholic liver disease, toxicant-induced liver disease or viral-induced liver disease and the renal dysfunction may be polycystic kidney disease. The apelin receptor system is involved in vein-related disorders. See, e.g., Lathen et al., "ERG-APLNR Axis Controls Pulmonary Venule Endothelial Proliferation in Pulmonary Veno-Occlusive Disease" 2014 Circulation 130: 1179-1191. Apelin receptor system has also been implicated in heart failure. See, e.g., Sheikh et al., "In vivo genetic profiling and cellular localization of apelin reveals a hypoxia-sensitive, endothelial-centered pathway activated in ischemic heart failure" 2007 Am J Physiol Heart Circ Physiol 294:H88-H98. The contents of both Lathen et al. and Sheikh et al. are hereby incorporated by reference in their entireties into the present disclosure.

In one non-limiting embodiment, the disclosure provides a method of treating an apelin receptor (APJ) related disorder in a subject which comprises administering to the subject the compound of embodiment 1. The apelin receptor (APJ) related disorder may be asthma, atherosclerosis, cancer, cardiomyopathy, diabetes, dyslipidemia, hypertension, inflammation, liver disease, metabolic disorder, neurodegenerative disease, obesity, or preeclampsia. The disclosure provides methods further comprising treating the subject with an a-blocker, an angiotensin converting enzyme (ACE) inhibitor, an angiotensin-receptor blocker (ARB), a β-blocker, a calcium channel blocker, or a diuretic. Alternatively, the disclosure provides a method to treat or prevent a vein-related disorder such as an angioma, a venous insufficiency, a stasis or a thrombosis.

In addition, the disclosure provides a method of preventing HIV neurodegeneration in a subject which comprises administering to the subject the compound of embodiment 1.

In one embodiment, an effective amount of a compound of this disclosure can range from about 0.005 mg to about 5000 mg per treatment. In more specific embodiments, the range is from about 0.05 mg to about 1000 mg, or from about 0.5 mg to about 500 mg, or from about 5 mg to about 50 mg. Treatment can be administered one or more times per day (for example, once per day, twice per day, three times per day, four times per day, five times per day, etc.). When multiple treatments are used, the amount can be the same or different. It is understood that a treatment can be administered every day, every other day, every 2 days, every 3 days, every 4 days, every 5 days, etc. For example, with every other day administration, a treatment dose can be initiated on Monday with a first subsequent treatment administered on Wednesday, a second subsequent treatment administered on Friday, etc. Treatment is typically administered from one to two times daily. Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Alternatively, the effective amount of a compound of the disclosure is from about 0.01 mg/kg/day to about 1000 mg/kg/day, from about 0.1 mg/kg/day to about 100 mg/kg/day, from about 0.5 mg/kg/day to about 50 mg/kg/day, or from about 1 mg/kg/day to 10 mg/kg/day.

In another embodiment, any of the above methods of treatment comprises the further step of co-administering to said subject one or more second therapeutic agents. The choice of second therapeutic agent may be made from any second therapeutic agent known to be useful for co-administration with a compound that modulates the APJ receptor. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

The term "co-administered" as used herein means that the second therapeutic agent may be administered together with a compound of this disclosure as part of a single dosage form (such as a composition of this disclosure comprising a compound of the disclosure and a second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent or any compound of this disclosure to said subject at another time during a course of treatment.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

4.5. Kits

The present disclosure also provides kits for use to treat the target disease, disorder or condition. These kits comprise (a) a pharmaceutical composition comprising a compound of Formula I, or a salt thereof, wherein said pharmaceutical composition is in a container; and (b) instructions describing a method of using the pharmaceutical composition to treat the target disease, disorder or condition.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this disclosure may also comprise a device to administer or to measure out a unit dose of the pharmaceutical composition. Such a device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiments, the kits of this disclosure may comprise in a separate vessel of container a pharmaceutical composition comprising a second therapeutic agent, such as one of those listed above for use for co-administration with a compound of this disclosure.

Unless defined otherwise, all technical and scientific terms used herein have the same meaning as commonly understood by one of ordinary skill in the art to which this disclosure belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

The following Examples further illustrate the disclosure and are not intended to limit the scope of the disclosure. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

5. EXAMPLES
5.1. Representative Compounds
TABLE 1
| ID # | STRUCTURE | [M + H]+/ [M − H]− |
|---|---|---|
| 253 | 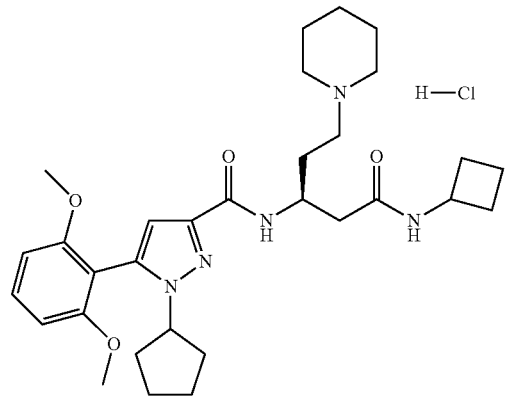 | 587.3 |
| 296 | 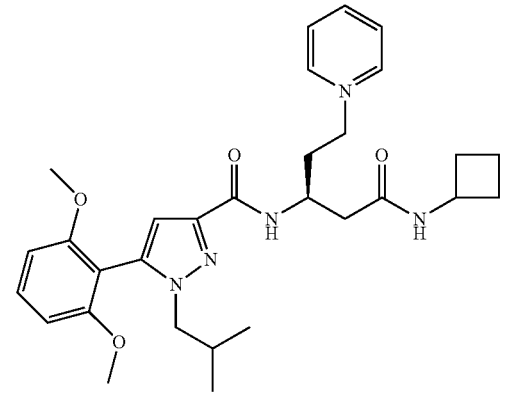 | 533.7 |
| 297 | 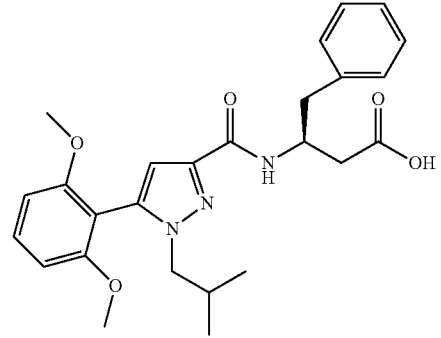 [SMILES: COc1cccc(OC)c1-c1cc(C(=O)N[C@H](CC(=O)O)Cc2ccccc2)nn1CC(C)C] | 464.8 |

TABLE 1-continued
| ID # | STRUCTURE | [M + H]+/ [M − H]− |
|---|---|---|
| 298 | 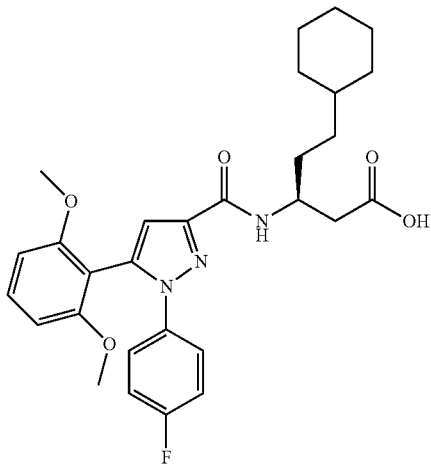 [SMILES: COc1cccc(OC)c1-c1cc(C(=O)N[C@@H](CCC2CCCCC2)CC(=O)O)nn1-c1ccc(F)cc1] | 522.7 |
| 299 | 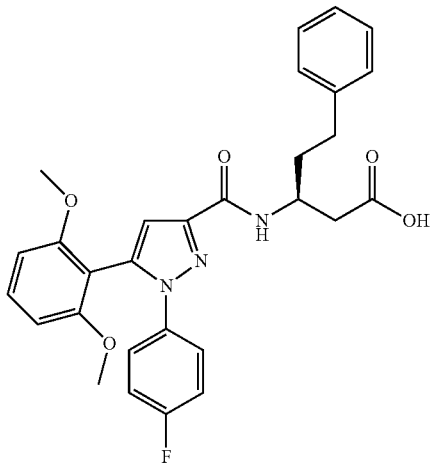 [SMILES: COc1cccc(OC)c1-c1cc(C(=O)N[C@@H](CCc2ccccc2)CC(=O)O)nn1-c1ccc(F)cc1] | 516.8 |
| 300 | 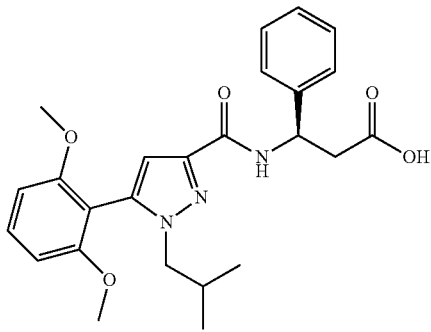 [SMILES: COc1cccc(OC)c1-c1cc(C(=O)N[C@H](CC(=O)O)c2ccccc2)nn1CC(C)C] | 450.8 |

TABLE 1-continued

| ID # | STRUCTURE | [M + H]+/ [M − H]− |
|---|---|---|
| 301 | 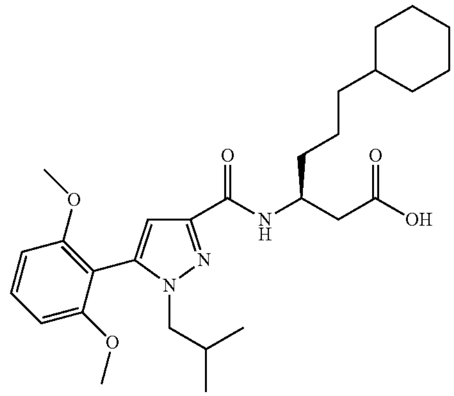 [SMILES: COc1cccc(OC)c1-c1cc(C(=O)N[C@@H](CCCC2CCCCC2)CC(=O)O)nn1CC(C)C] | 498.9 |
| 302 | 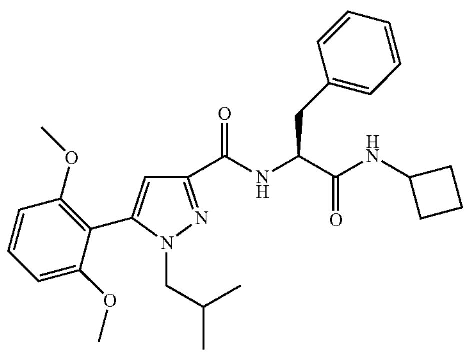 [SMILES: COc1cccc(OC)c1-c1cc(C(=O)N[C@@H](Cc2ccccc2)C(=O)NC2CCC2)nn1CC(C)C] | 505.7 |
| 303 | 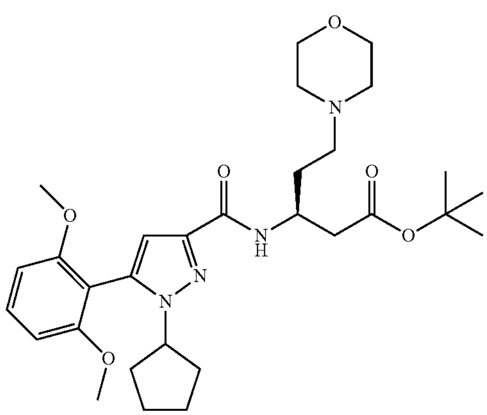 [SMILES: COc1cccc(OC)c1-c1cc(C(=O)N[C@@H](CCN2CCOCC2)CC(=O)OC(C)(C)C)nn1C1CCCC1] | 557.9 |
| 304 | 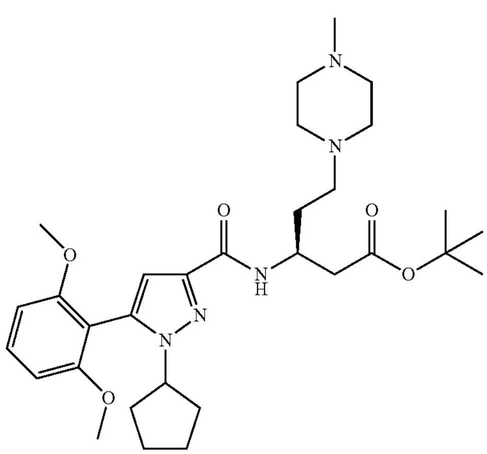 [SMILES: COc1cccc(OC)c1-c1cc(C(=O)N[C@@H](CCN2CCN(C)CC2)CC(=O)OC(C)(C)C)nn1C1CCCC1] | 570.9 |

TABLE 1-continued
| ID # | STRUCTURE | [M + H]+/ [M − H]− |
|---|---|---|
| 305 | 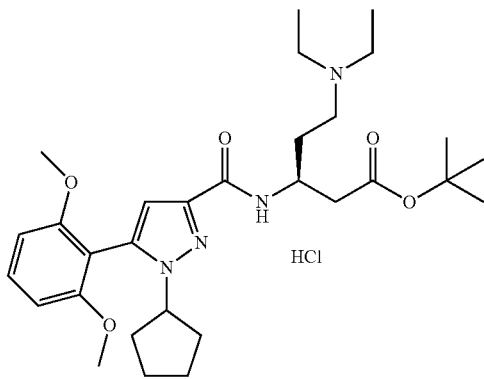 [SMILES: CCN(CC)CC[C@@H](CC(=O)OC(C)(C)C)NC(=O)c1cc(-c2c(OC)cccc2OC)n(C2CCCC2)n1 ; Cl] | 543.9 |
| 306 | 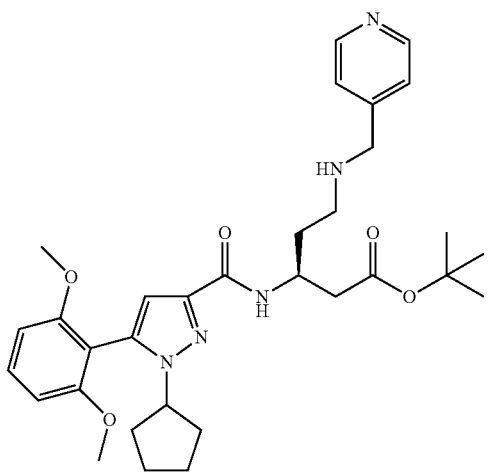 [SMILES: COc1cccc(OC)c1-c1cc(C(=O)N[C@@H](CCNCc2ccncc2)CC(=O)OC(C)(C)C)nn1C1CCCC1] | 578.4 |
| 307 | 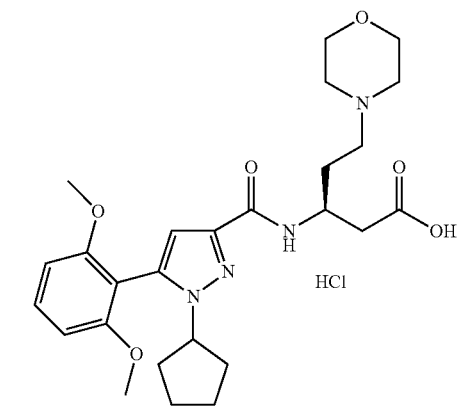 [SMILES: COc1cccc(OC)c1-c1cc(C(=O)N[C@@H](CCN2CCOCC2)CC(=O)O)nn1C1CCCC1 ; Cl] | 499.7 |

TABLE 1-continued
| ID # | STRUCTURE | [M + H]+/ [M − H]− |
|---|---|---|
| 308 | 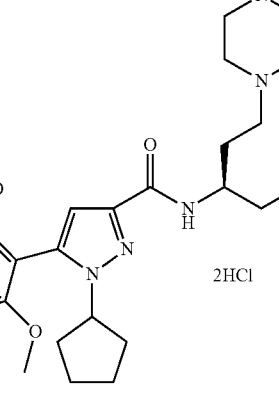 2HCl | 512.3 |
| 309 | 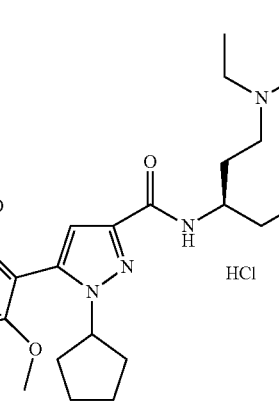 HCl | 485.4 |
| 310 | 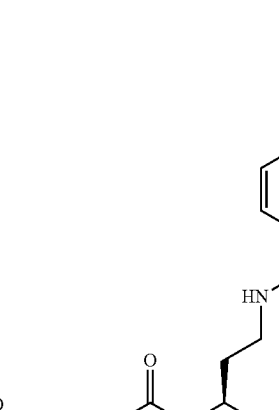 2HCl | 522.6 |

TABLE 1-continued

| ID # | STRUCTURE | [M + H]+/ [M − H]− |
|---|---|---|
| 311 | 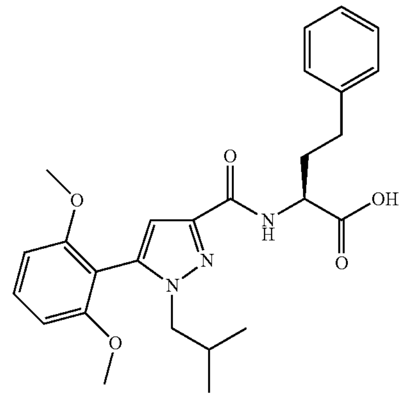 [SMILES: COc1cccc(OC)c1-c1cc(C(=O)N[C@@H](CCc2ccccc2)C(=O)O)nn1CC(C)C] | 464.8 |
| 312 | 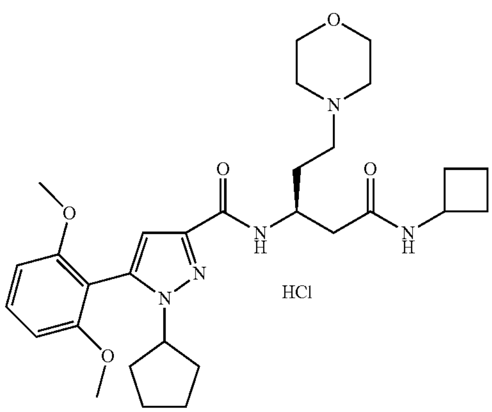 [SMILES: COc1cccc(OC)c1-c1cc(C(=O)N[C@@H](CCN2CCOCC2)CC(=O)NC2CCC2)nn1C1CCCC1 ; Cl] | 555.0 |
| 313 | 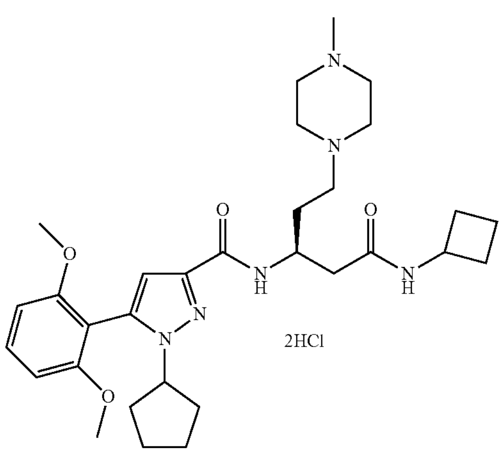 [SMILES: COc1cccc(OC)c1-c1cc(C(=O)N[C@@H](CCN2CCN(C)CC2)CC(=O)NC2CCC2)nn1C1CCCC1] | 567.5 |

TABLE 1-continued
| ID # | STRUCTURE | [M + H]+/ [M − H]− |
|---|---|---|
| 314 | 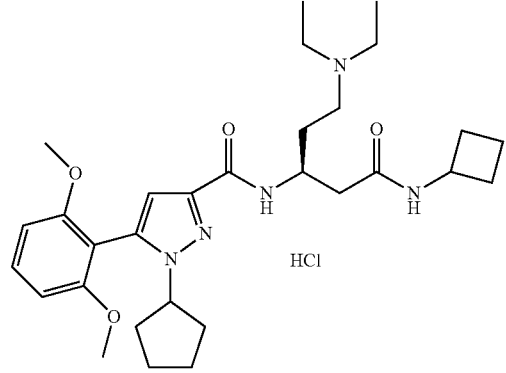 [SMILES: CCN(CC)CC[C@@H](CC(=O)NC1CCC1)NC(=O)c1cc(-c2c(OC)cccc2OC)n(C2CCCC2)n1 ; Cl] | 540.3 |
| 315 | 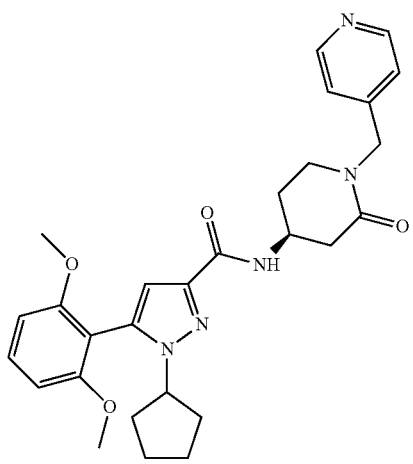 [SMILES: COc1cccc(OC)c1-c1cc(C(=O)N[C@H]2CCN(Cc3ccncc3)C(=O)C2)nn1C1CCCC1] | 504.7 |
| 316 | 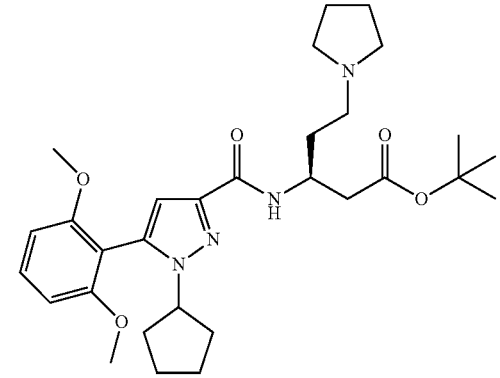 [SMILES: COc1cccc(OC)c1-c1cc(C(=O)N[C@@H](CCN2CCCC2)CC(=O)OC(C)(C)C)nn1C1CCCC1] | 541.7 |
| 317 | 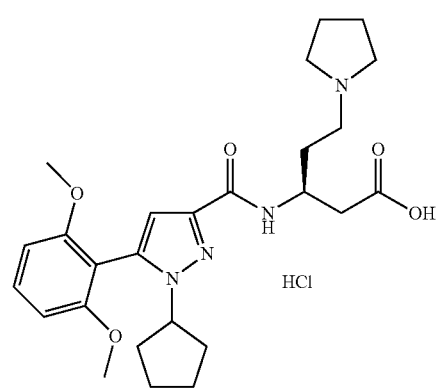 [SMILES: COc1cccc(OC)c1-c1cc(C(=O)N[C@@H](CCN2CCCC2)CC(=O)O)nn1C1CCCC1 ; Cl] | 485.1 |

TABLE 1-continued
| ID # | STRUCTURE | [M + H]+/ [M − H]− |
|---|---|---|
| 318 | 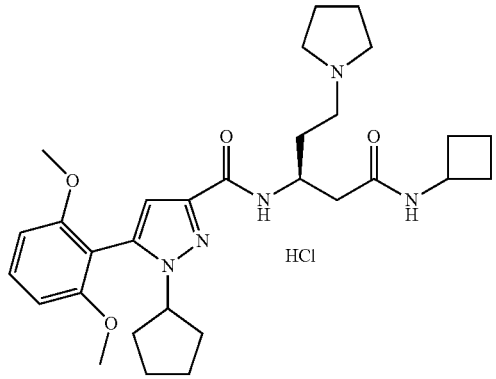 [SMILES: COc1cccc(OC)c1-c1cc(C(=O)N[C@@H](CCN2CCCC2)CC(=O)NC2CCC2)nn1C1CCCC1 ; Cl] | 538.6 |
| 319 | 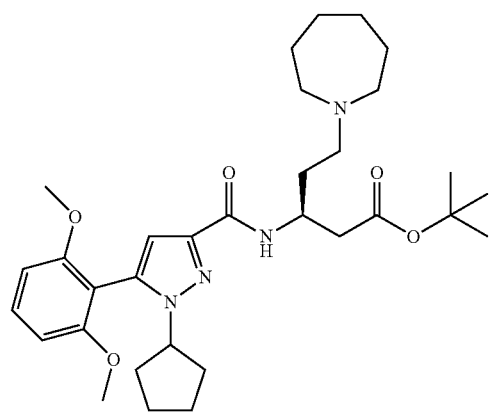 [SMILES: COc1cccc(OC)c1-c1cc(C(=O)N[C@@H](CCN2CCCCCC2)CC(=O)OC(C)(C)C)nn1C1CCCC1] | 569.8 |
| 320 | 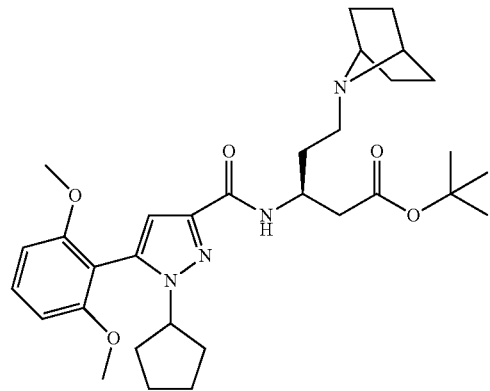 [SMILES: COc1cccc(OC)c1-c1cc(C(=O)N[C@@H](CCN2C3CCC2CC3)CC(=O)OC(C)(C)C)nn1C1CCCC1] | 567.6 |
| 321 | 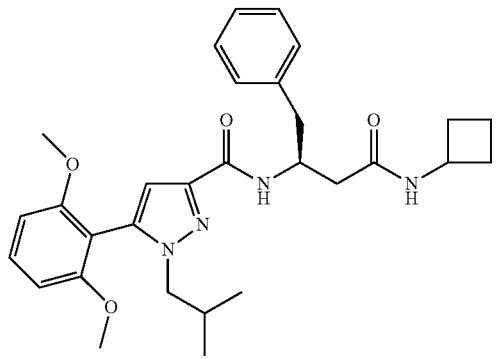 [SMILES: COc1cccc(OC)c1-c1cc(C(=O)N[C@H](CC(=O)NC2CCC2)Cc2ccccc2)nn1CC(C)C] | 519.8 |

TABLE 1-continued
| ID # | STRUCTURE | [M + H]+/ [M − H]− |
|---|---|---|
| 322 | 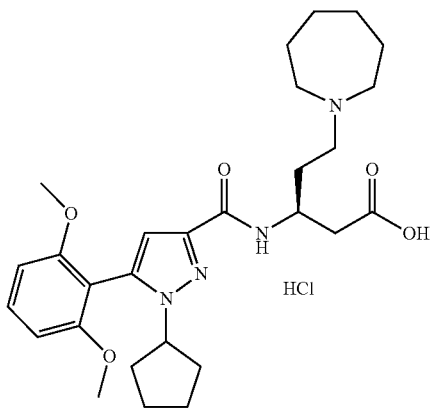 [SMILES: COc1cccc(OC)c1-c1cc(C(=O)N[C@@H](CCN2CCCCCC2)CC(=O)O)nn1C1CCCC1 ; Cl] | 513.7 |
| 323 | 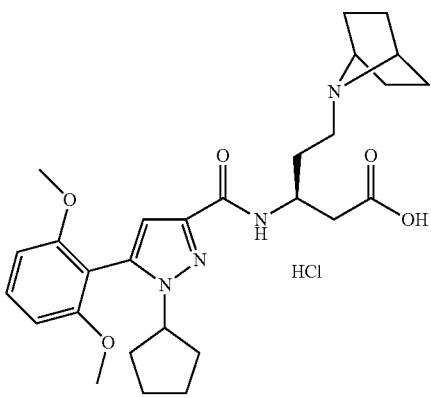 [SMILES: COc1cccc(OC)c1-c1cc(C(=O)N[C@@H](CCN2C3CCC2CC3)CC(=O)O)nn1C1CCCC1 ; Cl] | 511.5 |
| 324 | 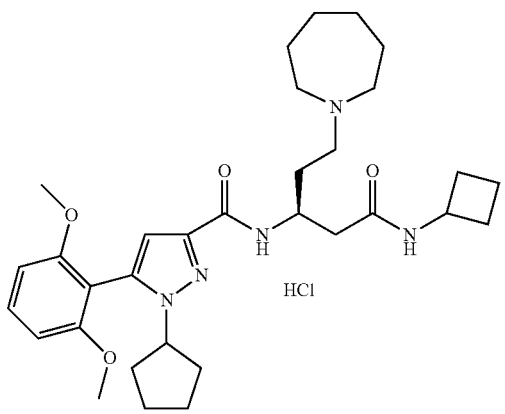 [SMILES: COc1cccc(OC)c1-c1cc(C(=O)N[C@@H](CCN2CCCCCC2)CC(=O)NC2CCC2)nn1C1CCCC1 ; Cl] | 566.5 |

TABLE 1-continued
| ID # | STRUCTURE | [M + H]+/ [M − H]− |
|---|---|---|
| 325 | 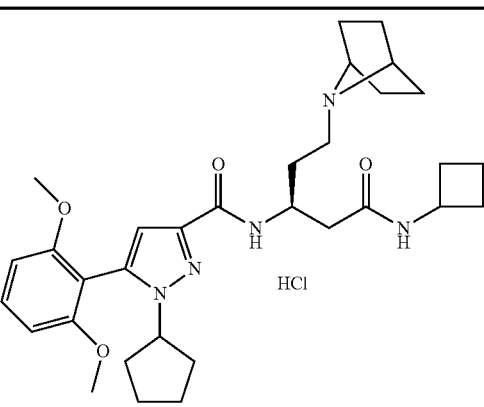 | 564.6 |
| 326 | 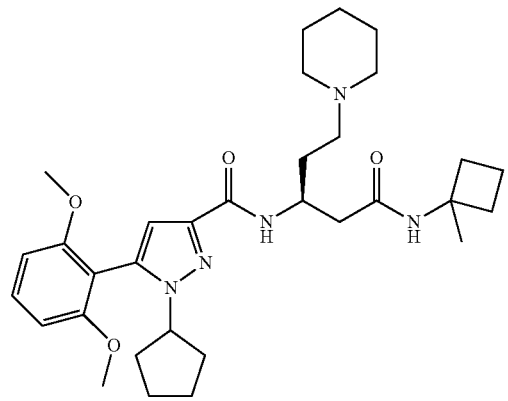 [SMILES: COc1cccc(OC)c1-c1cc(C(=O)N[C@@H](CCN2CCCCC2)CC(=O)NC2(C)CCC2)nn1C1CCCC1] | 565.8 |
| 327 | 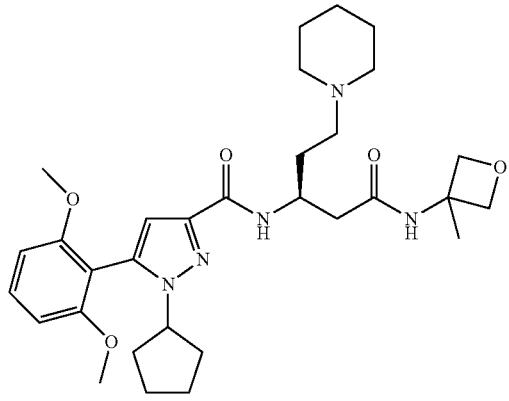 [SMILES: COc1cccc(OC)c1-c1cc(C(=O)N[C@@H](CCN2CCCCC2)CC(=O)NC2(C)COC2)nn1C1CCCC1] | 568.7 |
| 328 | 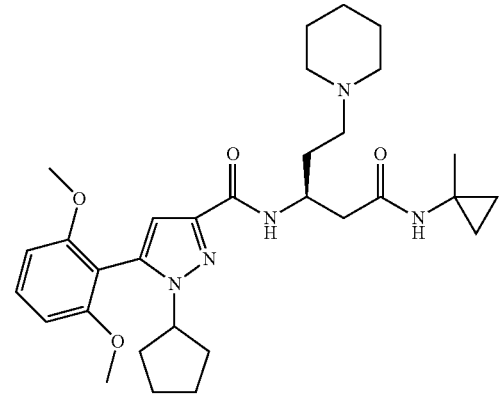 [SMILES: COc1cccc(OC)c1-c1cc(C(=O)N[C@@H](CCN2CCCCC2)CC(=O)NC2(C)CC2)nn1C1CCCC1] | 552.9 |

TABLE 1-continued
| ID # | STRUCTURE | [M + H]+/ [M − H]− |
|---|---|---|
| 329 | 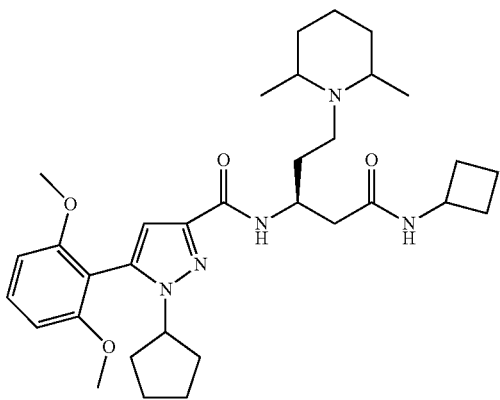 [SMILES: COc1cccc(OC)c1-c1cc(C(=O)N[C@@H](CCN2C(C)CCCC2C)CC(=O)NC2CCC2)nn1C1CCCC1] | 580.8 |
| 330 | 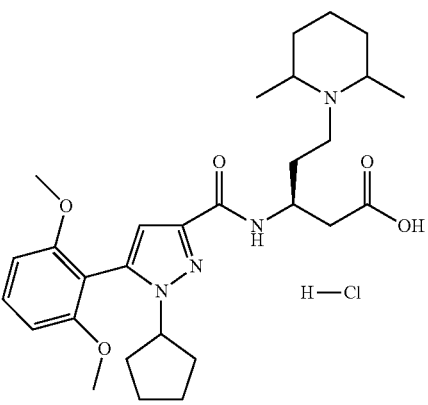 [SMILES: COc1cccc(OC)c1-c1cc(C(=O)N[C@@H](CCN2C(C)CCCC2C)CC(=O)O)nn1C1CCCC1 ; Cl] | 527.7 |
| 331 | 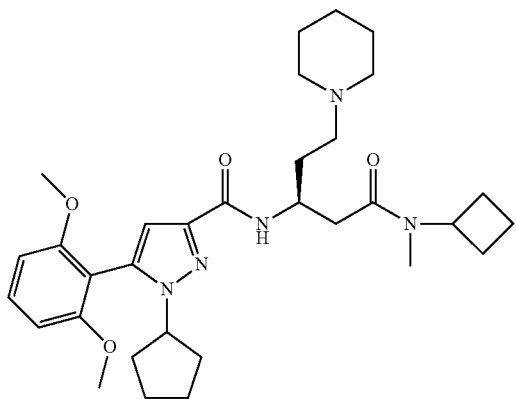 [SMILES: COc1cccc(OC)c1-c1cc(C(=O)N[C@@H](CCN2CCCCC2)CC(=O)N(C)C2CCC2)nn1C1CCCC1] | 566.4 |

TABLE 1-continued

| ID # | STRUCTURE | [M + H]+/ [M − H]− |
|---|---|---|
| 332 | 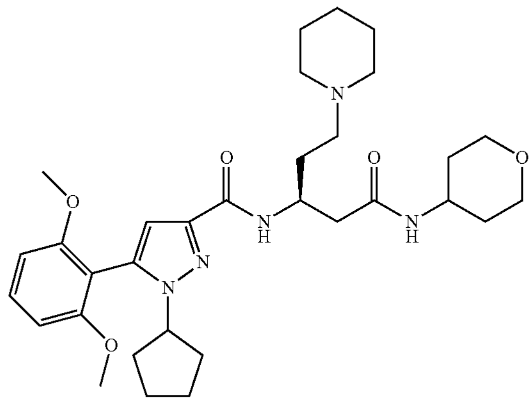 [SMILES: COc1cccc(OC)c1-c1cc(C(=O)N[C@@H](CCN2CCCCC2)CC(=O)NC2CCOCC2)nn1C1CCCC1] | 583.1 |
| 333 | 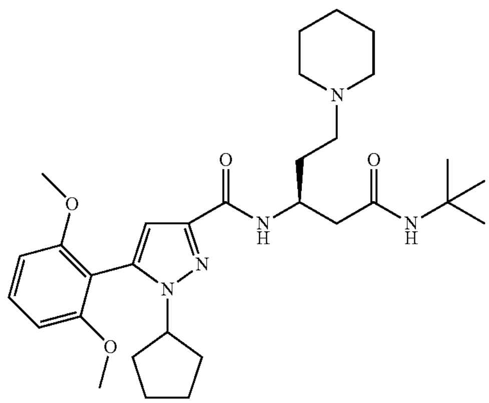 [SMILES: COc1cccc(OC)c1-c1cc(C(=O)N[C@@H](CCN2CCCCC2)CC(=O)NC(C)(C)C)nn1C1CCCC1] | 555.0 |
| 334 | 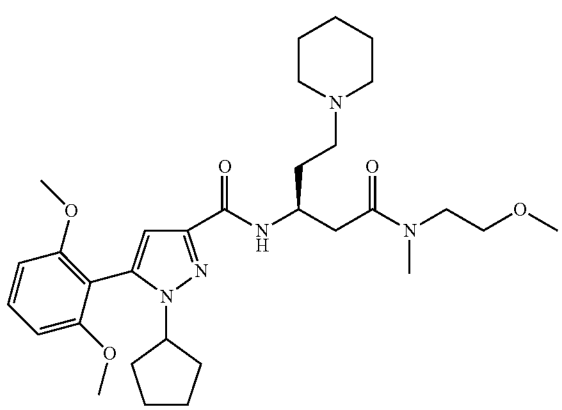 [SMILES: COCCN(C)C(=O)C[C@H](CCN1CCCCC1)NC(=O)c1cc(-c2c(OC)cccc2OC)n(C2CCCC2)n1] | 570.9 |

TABLE 1-continued
| ID # | STRUCTURE | [M + H]+/ [M − H]− |
|---|---|---|
| 335 | 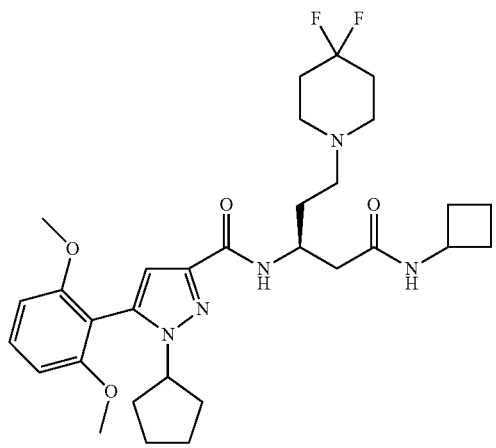 [SMILES: COc1cccc(OC)c1-c1cc(C(=O)N[C@@H](CCN2CCC(F)(F)CC2)CC(=O)NC2CCC2)nn1C1CCCC1] | 588.5 |
| 336 | 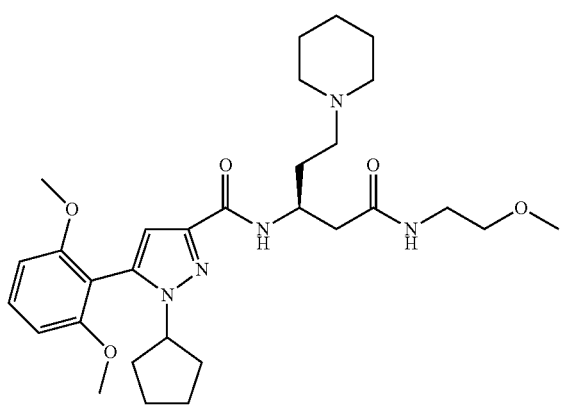 | 557.1 |
| 337 | 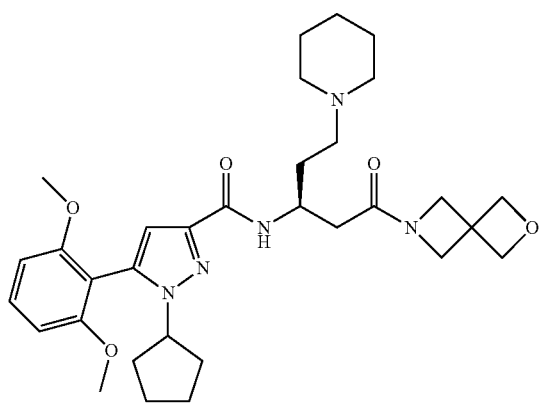 [SMILES: COc1cccc(OC)c1-c1cc(C(=O)N[C@@H](CCN2CCCCC2)CC(=O)N2CC3(COC3)C2)nn1C1CCCC1] | 580.7 |

TABLE 1-continued

| ID # | STRUCTURE | [M + H]+/ [M − H]− |
|---|---|---|
| 338 | 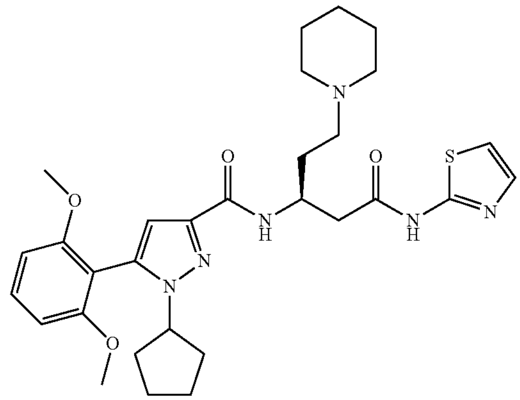 | 582.0 |
| 339 | 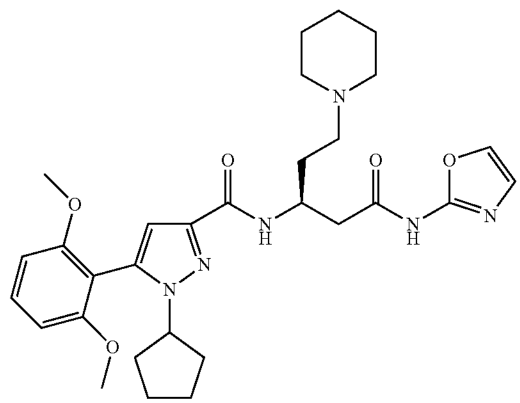 [SMILES: COc1cccc(OC)c1-c1cc(C(=O)N[C@@H](CCN2CCCCC2)CC(=O)Nc2ncco2)nn1C1CCCC1] | 565.4 |
| 340 | 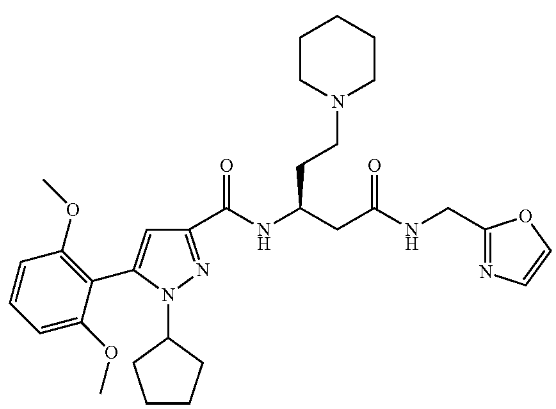 [SMILES: COc1cccc(OC)c1-c1cc(C(=O)N[C@@H](CCN2CCCCC2)CC(=O)NCc2ncco2)nn1C1CCCC1] | 579.9 |

TABLE 1-continued

| ID # | STRUCTURE | [M + H]+/ [M - H]- |
|---|---|---|
| 341 | 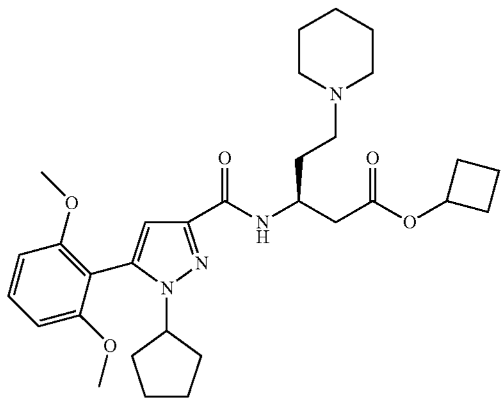 [SMILES: COc1cccc(OC)c1-c1cc(C(=O)N[C@@H](CCN2CCCCC2)CC(=O)OC2CCC2)nn1C1CCCC1] | 553.8 |
| 342 | 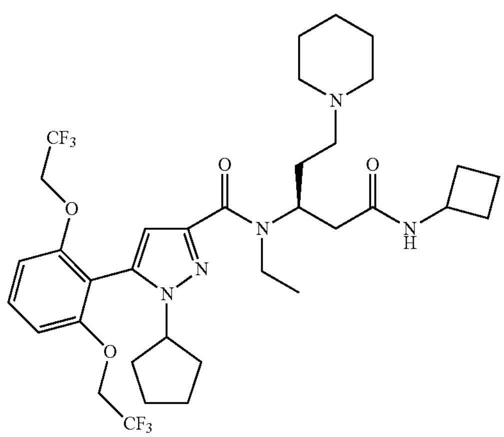 [SMILES: CCN(C(=O)c1cc(-c2c(OCC(F)(F)F)cccc2OCC(F)(F)F)n(C2CCCC2)n1)[C@@H](CCN1CCCCC1)CC(=O)NC1CCC1] | 716.4 |
| 343 | 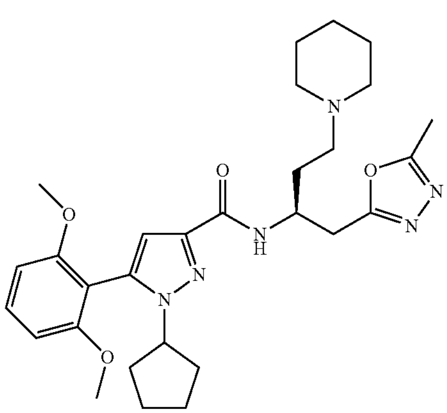 [SMILES: COc1cccc(OC)c1-c1cc(C(=O)N[C@@H](CCN2CCCCC2)Cc2nnc(C)o2)nn1C1CCCC1] | 537.6 |

TABLE 1-continued
| ID # | STRUCTURE | [M + H]+/ [M − H]− |
|---|---|---|
| 344 | 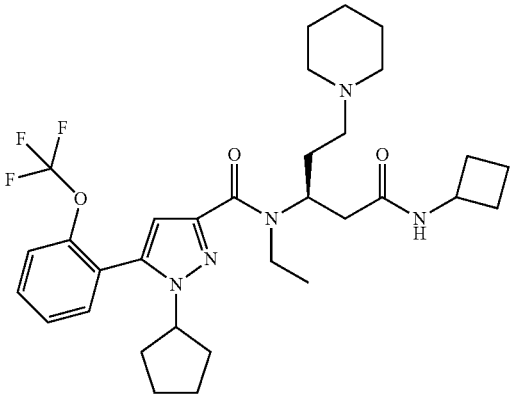 [SMILES: CCN(C(=O)c1cc(-c2ccccc2OC(F)(F)F)n(C2CCCC2)n1)[C@@H](CCN1CCCCC1)CC(=O)NC1CCC1] | 604.4 |
| 345 | 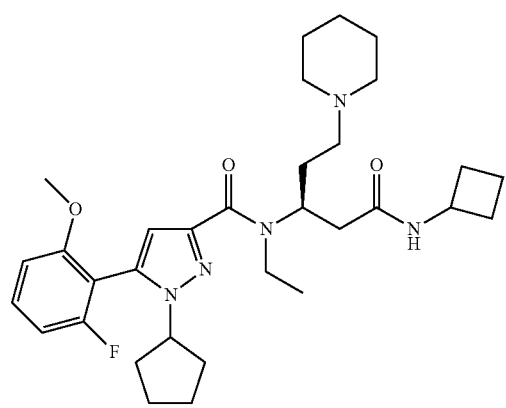 [SMILES: CCN(C(=O)c1cc(-c2c(F)cccc2OC)n(C2CCCC2)n1)[C@@H](CCN1CCCCC1)CC(=O)NC1CCC1] | 568.4 |
| 346 | 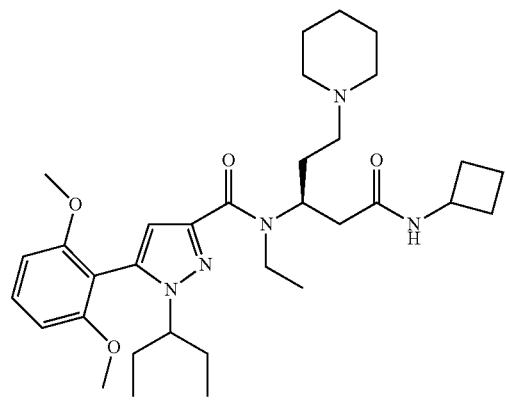 [SMILES: CCC(CC)n1nc(C(=O)N(CC)[C@@H](CCN2CCCCC2)CC(=O)NC2CCC2)cc1-c1c(OC)cccc1OC] | 582.5 |
| 347 | 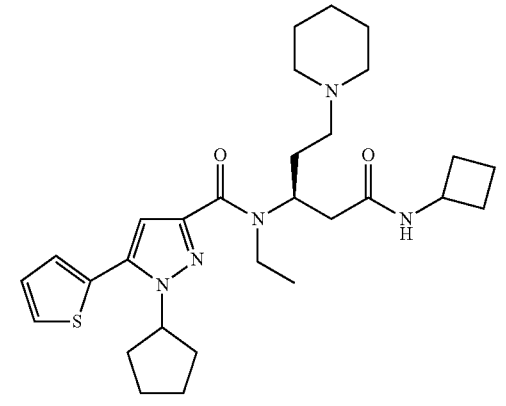 [SMILES: CCN(C(=O)c1cc(-c2cccs2)n(C2CCCC2)n1)[C@@H](CCN1CCCCC1)CC(=O)NC1CCC1] | 526.4 |

TABLE 1-continued
| ID # | STRUCTURE | [M + H]+/[M − H]− |
|---|---|---|
| 348 | 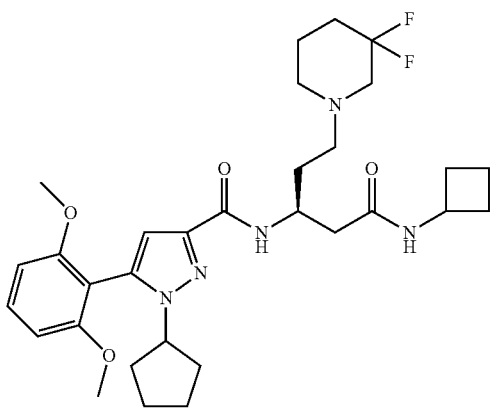 [SMILES: COc1cccc(OC)c1-c1cc(C(=O)N[C@@H](CCN2CCCC(F)(F)C2)CC(=O)NC2CCC2)nn1C1CCCC1] | 588.6 |
| 349 | 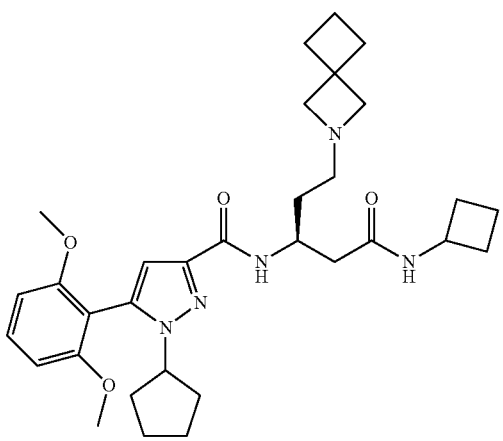 [SMILES: COc1cccc(OC)c1-c1cc(C(=O)N[C@@H](CCN2CC3(CCC3)C2)CC(=O)NC2CCC2)nn1C1CCCC1] | 564.6 |
| 350 | 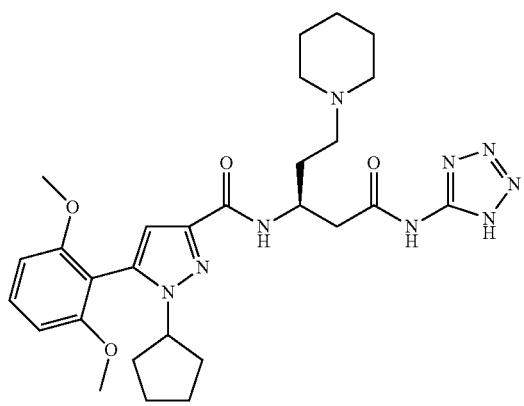 [SMILES: COc1cccc(OC)c1-c1cc(C(=O)N[C@@H](CCN2CCCCC2)CC(=O)Nc2nnn[nH]2)nn1C1CCCC1] | 566.5 |

TABLE 1-continued
| ID # | STRUCTURE | [M + H]+/[M − H]− |
|---|---|---|
| 351 | 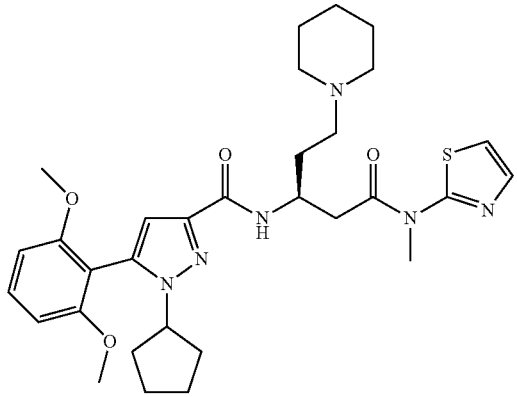 [SMILES: COc1cccc(OC)c1-c1cc(C(=O)N[C@@H](CCN2CCCCC2)CC(=O)N(C)c2nccs2)nn1C1CCCC1] | 595.6 |
| 352 | 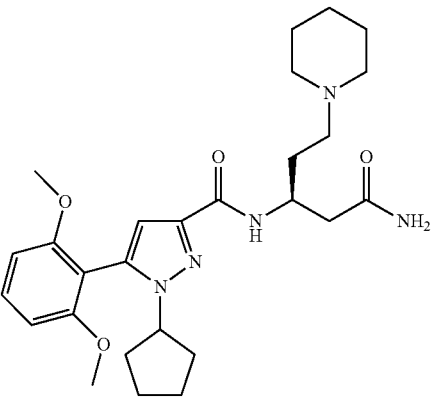 [SMILES: COc1cccc(OC)c1-c1cc(C(=O)N[C@@H](CCN2CCCCC2)CC(N)=O)nn1C1CCCC1] | 497.6 |
| 353 | 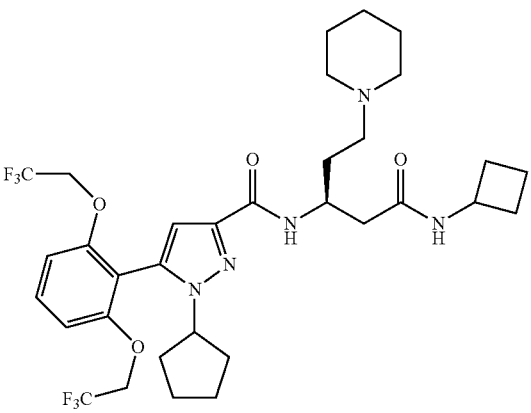 [SMILES: O=C(C[C@H](CCN1CCCCC1)NC(=O)c1cc(-c2c(OCC(F)(F)F)cccc2OCC(F)(F)F)n(C2CCCC2)n1)NC1CCC1] | 688.5 |

TABLE 1-continued

| ID # | STRUCTURE | [M + H]+/ [M − H]− |
|---|---|---|
| 354 | 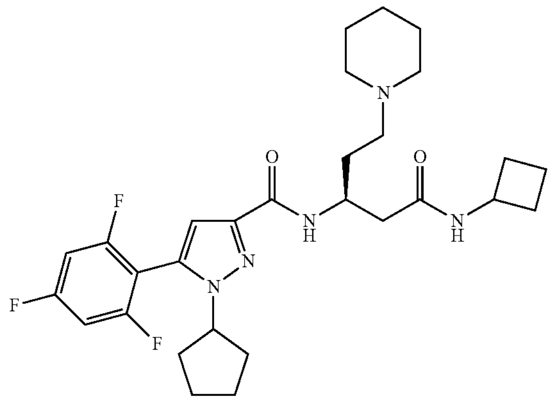 [SMILES: O=C(C[C@H](CCN1CCCCC1)NC(=O)c1cc(-c2c(F)cc(F)cc2F)n(C2CCCC2)n1)NC1CCC1] | 546.4 |
| 355 | 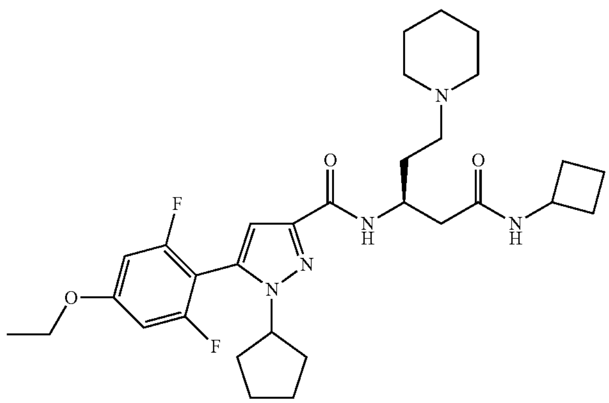 [SMILES: CCOc1cc(F)c(-c2cc(C(=O)N[C@@H](CCN3CCCCC3)CC(=O)NC3CCC3)nn2C2CCCC2)c(F)c1] | 572.4 |
| 356 | 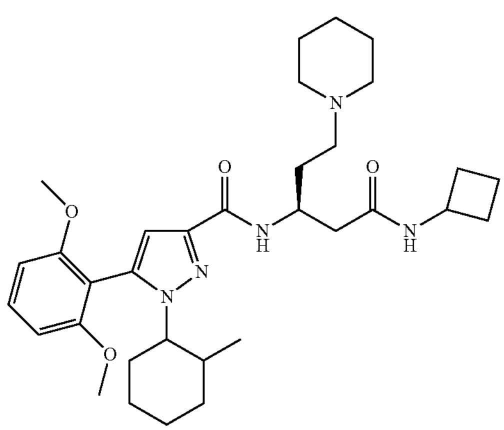 [SMILES: COc1cccc(OC)c1-c1cc(C(=O)N[C@@H](CCN2CCCCC2)CC(=O)NC2CCC2)nn1C1CCCCC1C] | 580.5 |

TABLE 1-continued
| ID # | STRUCTURE | [M + H]+/[M − H]− |
|---|---|---|
| 357 | 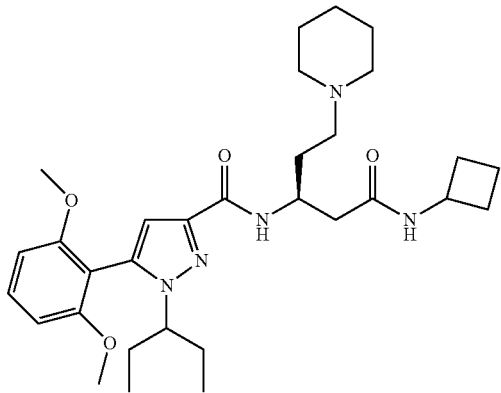 [SMILES: CCC(CC)n1nc(C(=O)N[C@@H](CCN2CCCCC2)CC(=O)NC2CCC2)cc1-c1c(OC)cccc1OC] | 554.5 |
| 358 | 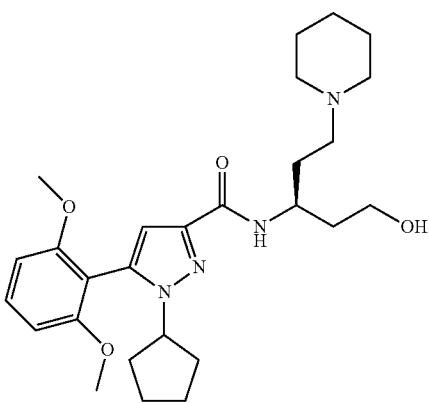 [SMILES: COc1cccc(OC)c1-c1cc(C(=O)N[C@H](CCO)CCN2CCCCC2)nn1C1CCCC1] | 484.6 |
| 359 | 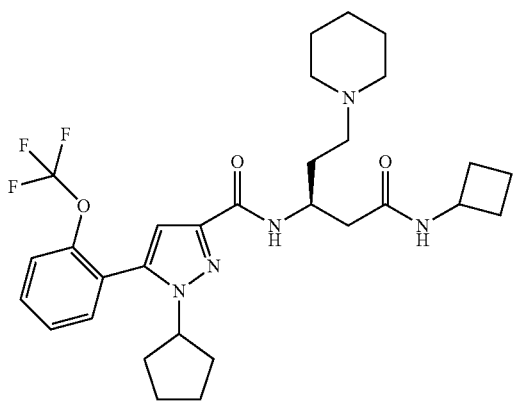 [SMILES: O=C(C[C@H](CCN1CCCCC1)NC(=O)c1cc(-c2ccccc2OC(F)(F)F)n(C2CCCC2)n1)NC1CCC1] | 576.4 |

TABLE 1-continued
| ID # | STRUCTURE | [M + H]+/ [M − H]− |
|---|---|---|
| 360 | 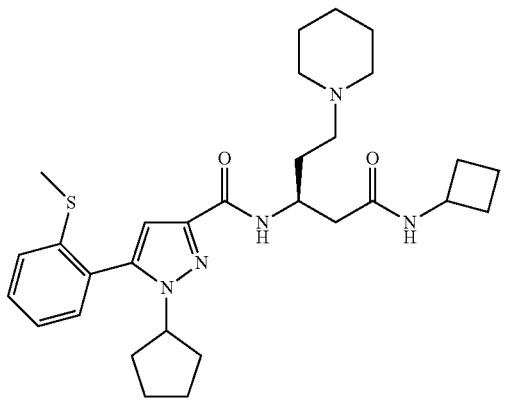 | 538.4 |
| 361 | 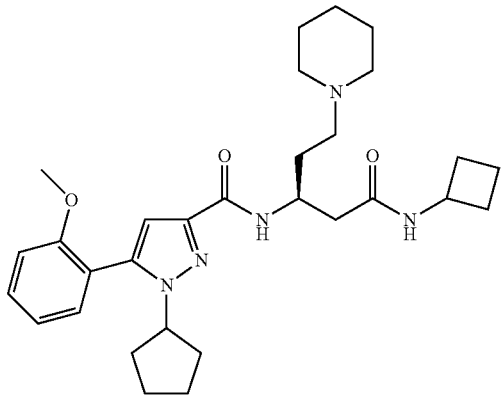 [SMILES: COc1ccccc1-c1cc(C(=O)N[C@@H](CCN2CCCCC2)CC(=O)NC2CCC2)nn1C1CCCC1] | 522.5 |
| 362 | 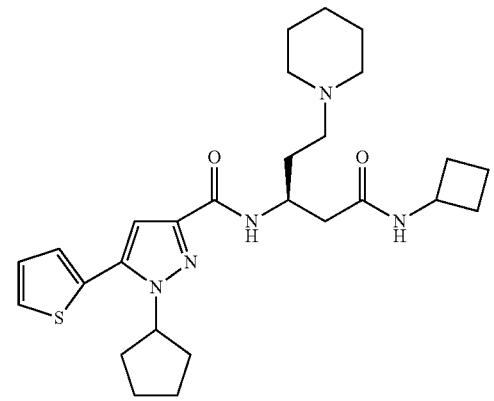 [SMILES: O=C(C[C@H](CCN1CCCCC1)NC(=O)c1cc(-c2cccs2)n(C2CCCC2)n1)NC1CCC1] | 498.4 |

TABLE 1-continued
| ID # | STRUCTURE | [M + H]+/ [M − H]− |
|---|---|---|
| 363 | 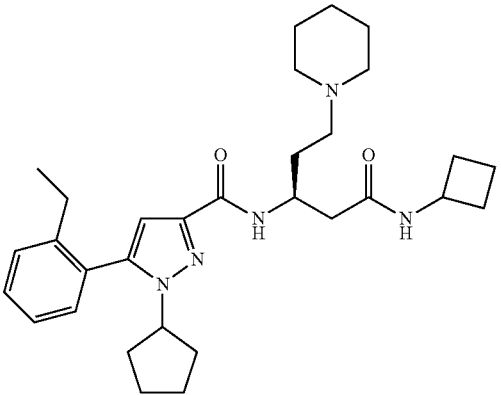 | 520.5 |
| 364 | 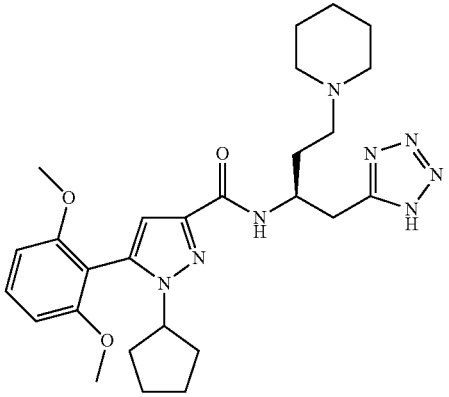 [SMILES: COc1cccc(OC)c1-c1cc(C(=O)N[C@@H](CCN2CCCCC2)Cc2nnn[nH]2)nn1C1CCCC1] | 523.6 |
| 365 | 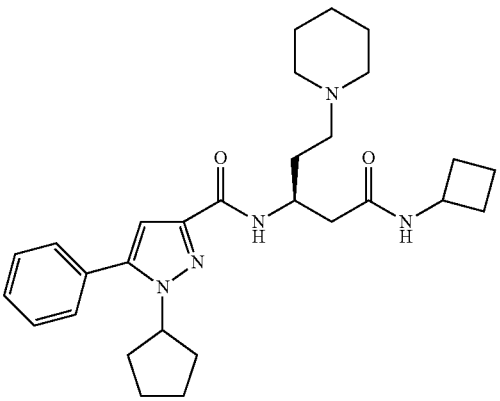 [SMILES: O=C(C[C@H](CCN1CCCCC1)NC(=O)c1cc(-c2ccccc2)n(C2CCCC2)n1)NC1CCC1] | 492.5 |

TABLE 1-continued

| ID # | STRUCTURE | [M + H]+/ [M − H]− |
|---|---|---|
| 366 | 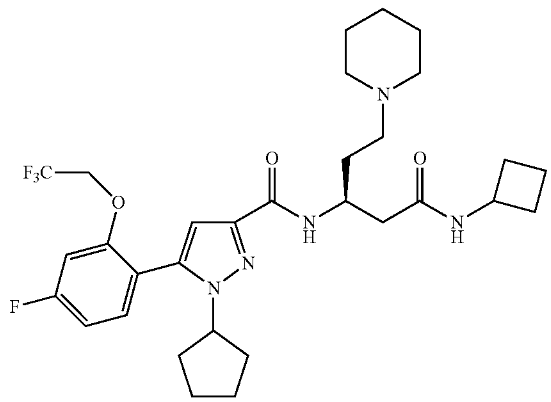 [SMILES: O=C(C[C@H](CCN1CCCCC1)NC(=O)c1cc(-c2ccc(F)cc2OCC(F)(F)F)n(C2CCCC2)n1)NC1CCC1] | 608.4 |
| 367 | 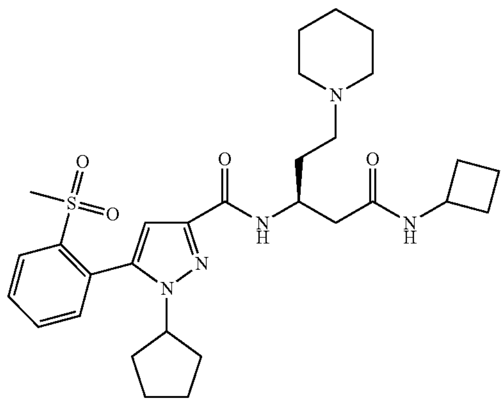 [SMILES: CS(=O)(=O)c1ccccc1-c1cc(C(=O)N[C@@H](CCN2CCCCC2)CC(=O)NC2CCC2)nn1C1CCCC1] | 570.4 |
| 368 | 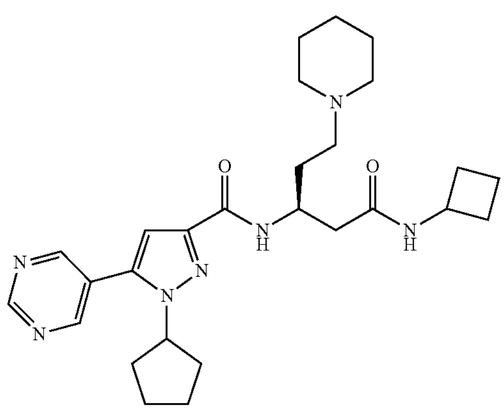 [SMILES: O=C(C[C@H](CCN1CCCCC1)NC(=O)c1cc(-c2cncnc2)n(C2CCCC2)n1)NC1CCC1] | 494.5 |

TABLE 1-continued
| ID # | STRUCTURE | [M + H]+/ [M − H]− |
|---|---|---|
| 369 | 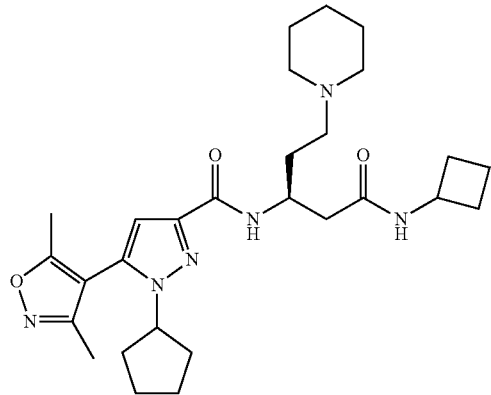 [SMILES: Cc1noc(C)c1-c1cc(C(=O)N[C@@H](CCN2CCCCC2)CC(=O)NC2CCC2)nn1C1CCCC1] | 511.5 |
| 370 | 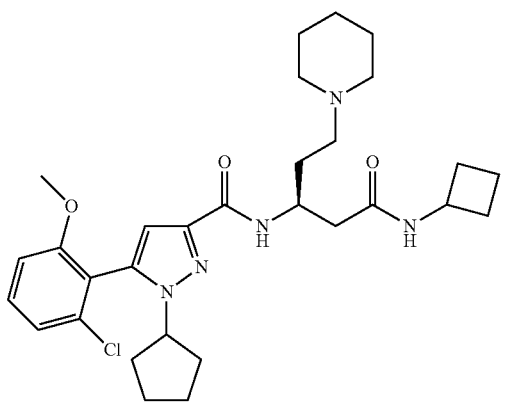 | 556.5 |
| 371 | 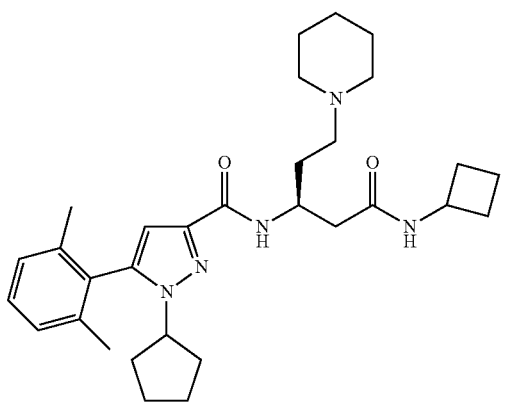 [SMILES: Cc1cccc(C)c1-c1cc(C(=O)N[C@@H](CCN2CCCCC2)CC(=O)NC2CCC2)nn1C1CCCC1] | 520.5 |

TABLE 1-continued

| ID # | STRUCTURE | [M + H]+/ [M − H]− |
|---|---|---|
| 372 | 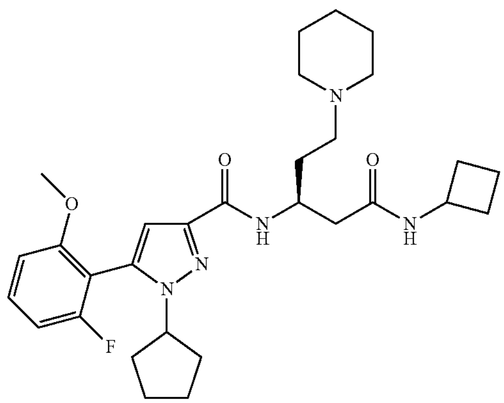 [SMILES: COc1cccc(F)c1-c1cc(C(=O)N[C@@H](CCN2CCCCC2)CC(=O)NC2CCC2)nn1C1CCCC1] | 540.5 |
| 373 | 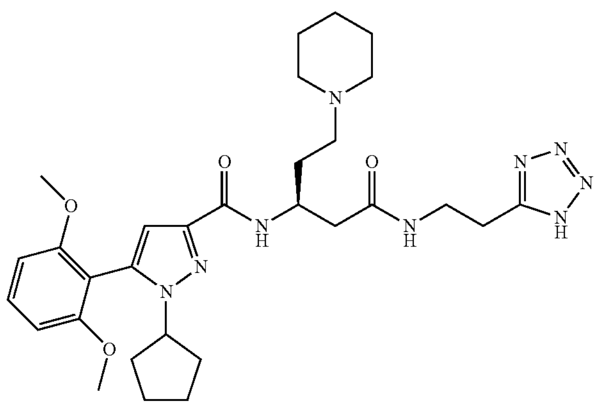 [SMILES: COc1cccc(OC)c1-c1cc(C(=O)N[C@@H](CCN2CCCCC2)CC(=O)NCCc2nnn[nH]2)nn1C1CCCC1] | 594.5 |
| 374 | 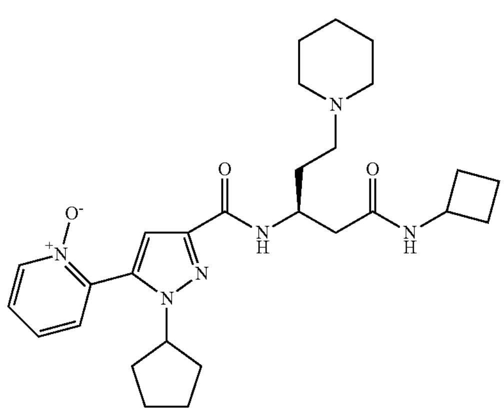 | 509.4 |

TABLE 1-continued

| ID # | STRUCTURE | [M + H]+/ [M − H]− |
|---|---|---|
| 375 | 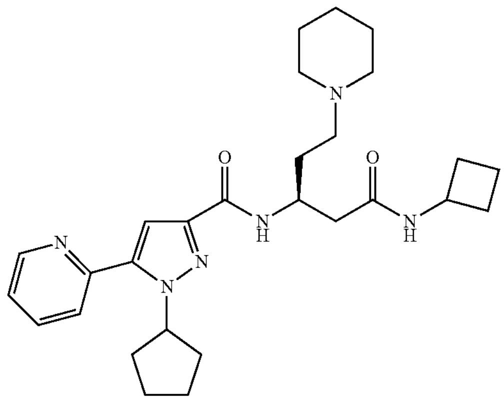 [SMILES: O=C(C[C@H](CCN1CCCCC1)NC(=O)c1cc(-c2ccccn2)n(C2CCCC2)n1)NC1CCC1] | 493.5 |
| 376 | 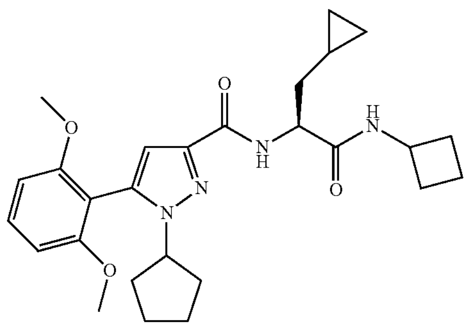 [SMILES: COc1cccc(OC)c1-c1cc(C(=O)N[C@@H](CC2CC2)C(=O)NC2CCC2)nn1C1CCCC1] | 481.2 |
| 377 | 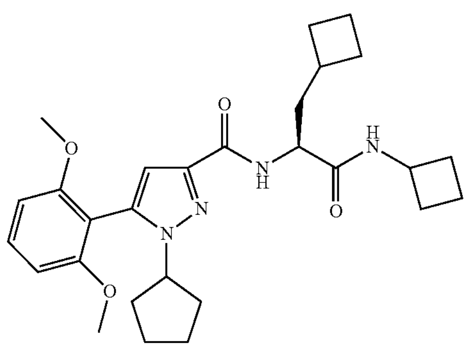 [SMILES: COc1cccc(OC)c1-c1cc(C(=O)N[C@@H](CC2CCC2)C(=O)NC2CCC2)nn1C1CCCC1] | 495.2 |
| 378 | 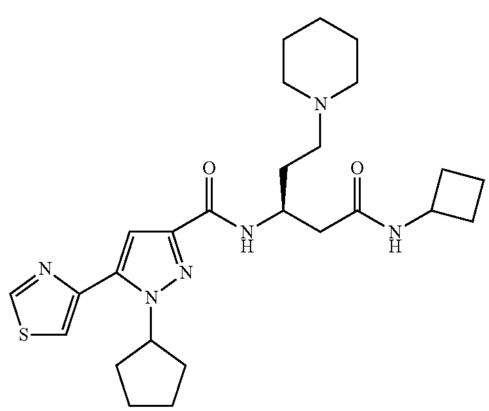 [SMILES: O=C(C[C@H](CCN1CCCCC1)NC(=O)c1cc(-c2cscn2)n(C2CCCC2)n1)NC1CCC1] | 499.4 |

TABLE 1-continued

| ID # | STRUCTURE | [M + H]+/ [M − H]− |
|---|---|---|
| 379 | 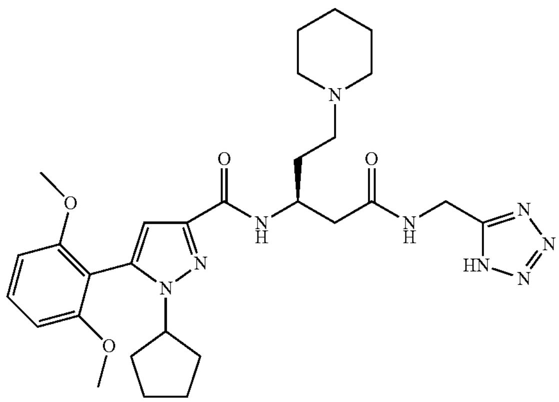 [SMILES: COc1cccc(OC)c1-c1cc(C(=O)N[C@@H](CCN2CCCCC2)CC(=O)NCc2nnn[nH]2)nn1C1CCCC1] | 580.7 |
| 380 | 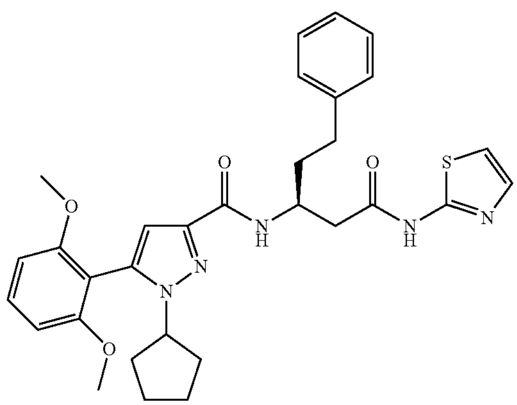 [SMILES: COc1cccc(OC)c1-c1cc(C(=O)N[C@@H](CCc2ccccc2)CC(=O)Nc2nccs2)nn1C1CCCC1] | 574.7 |
| 381 | 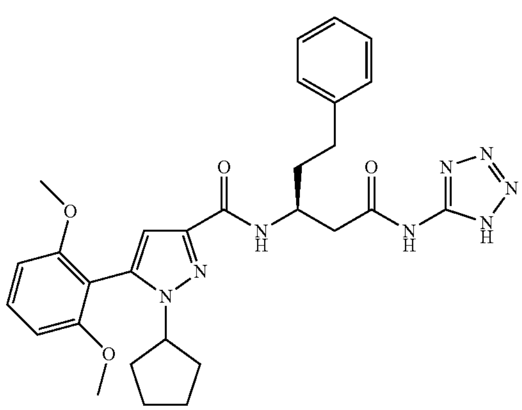 [SMILES: COc1cccc(OC)c1-c1cc(C(=O)N[C@@H](CCc2ccccc2)CC(=O)Nc2nnn[nH]2)nn1C1CCCC1] | 557.9 |

TABLE 1-continued
| ID # | STRUCTURE | [M + H]+/[M − H]− |
|---|---|---|
| 382 | 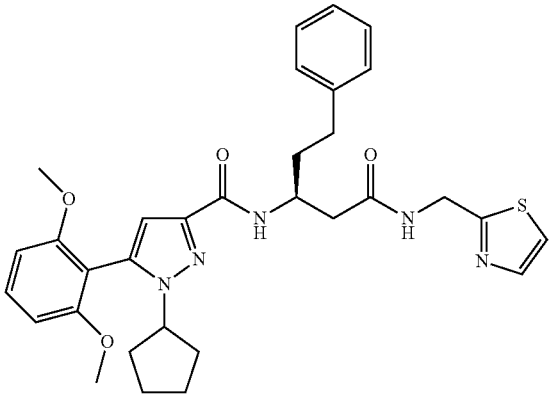 [SMILES: COc1cccc(OC)c1-c1cc(C(=O)N[C@@H](CCc2ccccc2)CC(=O)NCc2nccs2)nn1C1CCCC1] | 588.5 |
| 383 | 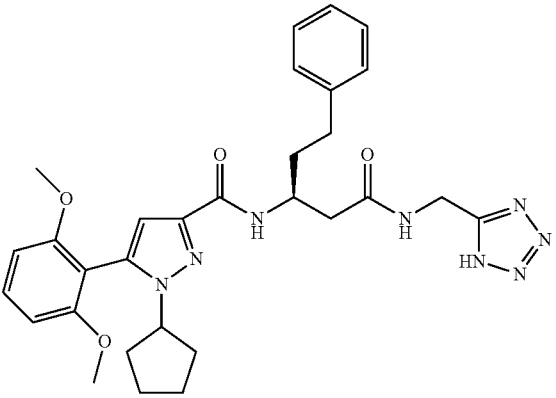 [SMILES: COc1cccc(OC)c1-c1cc(C(=O)N[C@@H](CCc2ccccc2)CC(=O)NCc2nnn[nH]2)nn1C1CCCC1] | 573.6 |
| 384 | 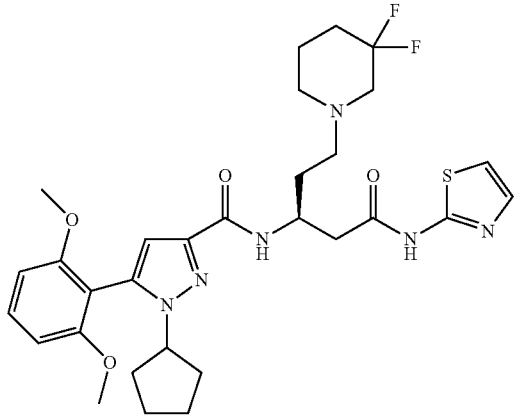 [SMILES: COc1cccc(OC)c1-c1cc(C(=O)N[C@@H](CCN2CCCC(F)(F)C2)CC(=O)Nc2nccs2)nn1C1CCCC1] | 617.4 |
| 385 | 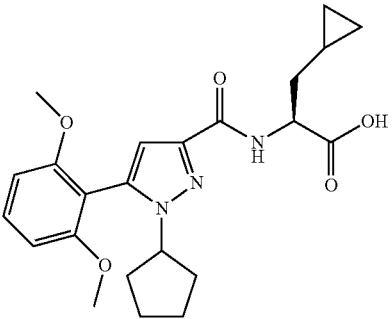 [SMILES: COc1cccc(OC)c1-c1cc(C(=O)N[C@@H](CC2CC2)C(=O)O)nn1C1CCCC1] | 428.3 |

TABLE 1-continued
| ID # | STRUCTURE | [M + H]+/ [M − H]− |
|---|---|---|
| 386 | 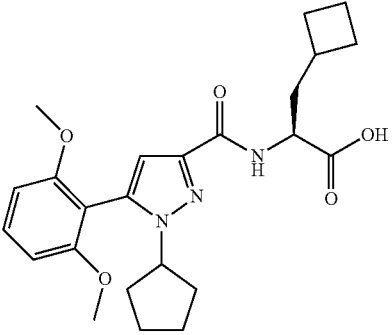 [SMILES: COc1cccc(OC)c1-c1cc(C(=O)N[C@@H](CC2CCC2)C(=O)O)nn1C1CCCC1] | 442.2 |
| 387 | 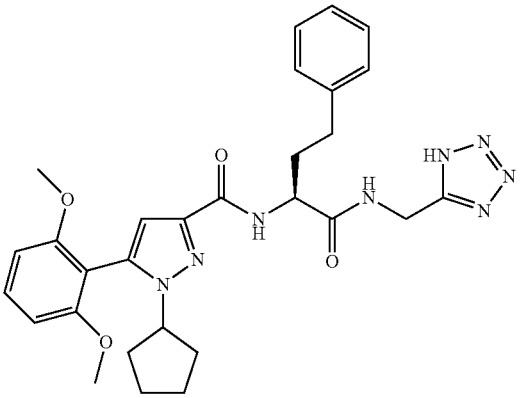 [SMILES: COc1cccc(OC)c1-c1cc(C(=O)N[C@@H](CCc2ccccc2)C(=O)NCc2nnn[nH]2)nn1C1CCCC1] | 559.2 |
| 388 | 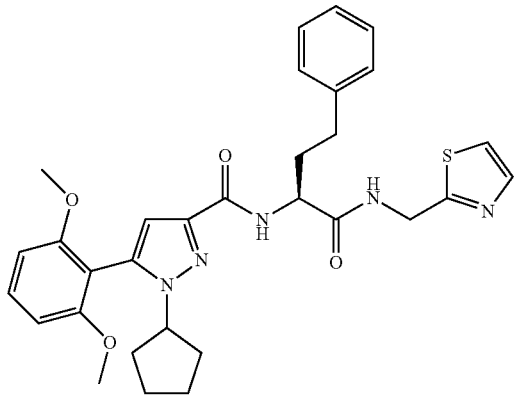 [SMILES: COc1cccc(OC)c1-c1cc(C(=O)N[C@@H](CCc2ccccc2)C(=O)NCc2nccs2)nn1C1CCCC1] | 574.2 |
| 389 | 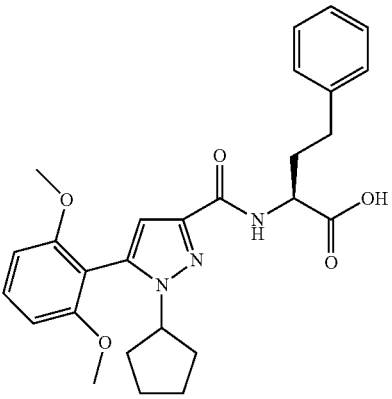 [SMILES: COc1cccc(OC)c1-c1cc(C(=O)N[C@@H](CCc2ccccc2)C(=O)O)nn1C1CCCC1] | 478.3 |

TABLE 1-continued

| ID # | STRUCTURE | [M + H]+/ [M − H]− |
|---|---|---|
| 390 | 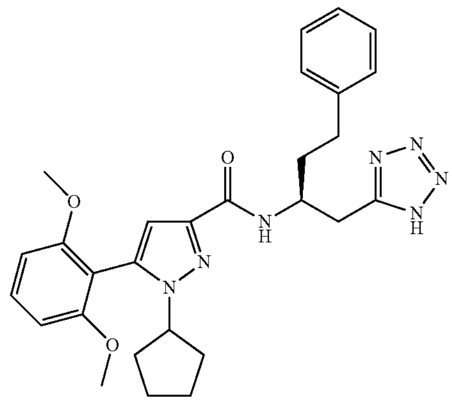 [SMILES: COc1cccc(OC)c1-c1cc(C(=O)N[C@@H](CCc2ccccc2)Cc2nnn[nH]2)nn1C1CCCC1] | 517.0 |
| 391 | 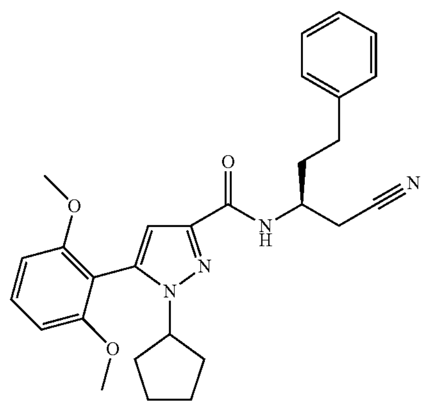 [SMILES: COc1cccc(OC)c1-c1cc(C(=O)N[C@H](CC#N)CCc2ccccc2)nn1C1CCCC1] | 473.6 |
| 392 | 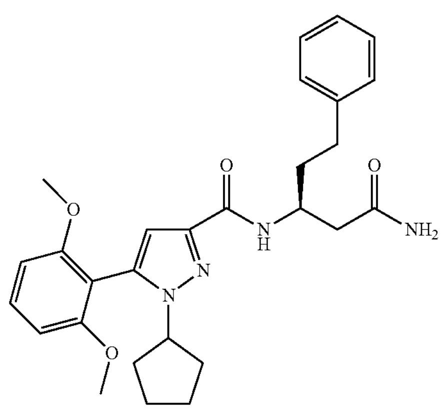 [SMILES: COc1cccc(OC)c1-c1cc(C(=O)N[C@@H](CCc2ccccc2)CC(N)=O)nn1C1CCCC1] | 491.4 |
| 393 | 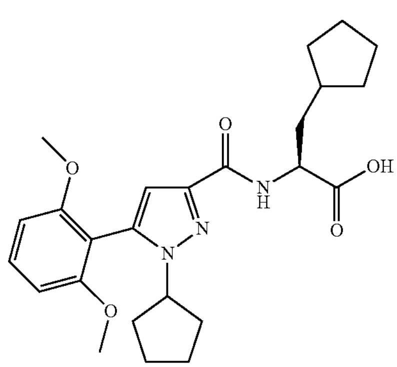 [SMILES: COc1cccc(OC)c1-c1cc(C(=O)N[C@@H](CC2CCCC2)C(=O)O)nn1C1CCCC1] | 456.4 |

TABLE 1-continued
| ID # | STRUCTURE | [M + H]+/ [M − H]− |
|---|---|---|
| 394 | 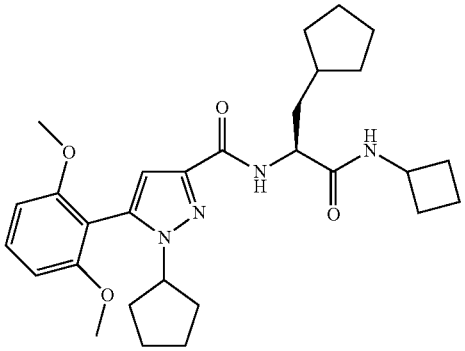 [SMILES: COc1cccc(OC)c1-c1cc(C(=O)N[C@@H](CC2CCCC2)C(=O)NC2CCC2)nn1C1CCCC1] | 509.3 |
| 395 | 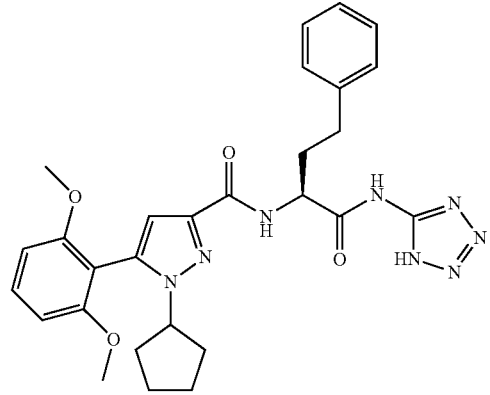 [SMILES: COc1cccc(OC)c1-c1cc(C(=O)N[C@@H](CCc2ccccc2)C(=O)Nc2nnn[nH]2)nn1C1CCCC1] | 545.2 |
| 396 | 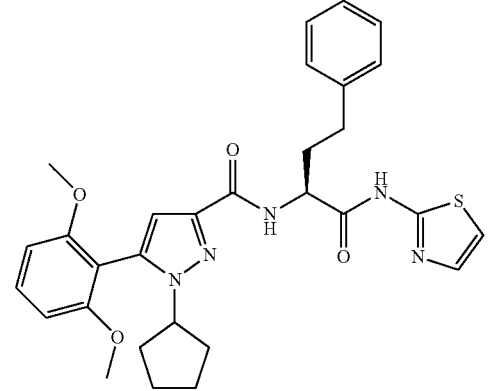 [SMILES: COc1cccc(OC)c1-c1cc(C(=O)N[C@@H](CCc2ccccc2)C(=O)Nc2nccs2)nn1C1CCCC1] | 560.1 |
| 397 | 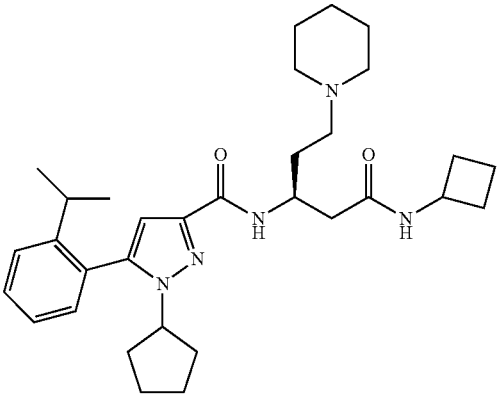 [SMILES: CC(C)c1ccccc1-c1cc(C(=O)N[C@@H](CCN2CCCCC2)CC(=O)NC2CCC2)nn1C1CCCC1] | 534.5 |

TABLE 1-continued

| ID # | STRUCTURE | [M + H]+/ [M − H]− |
|---|---|---|
| 398 | 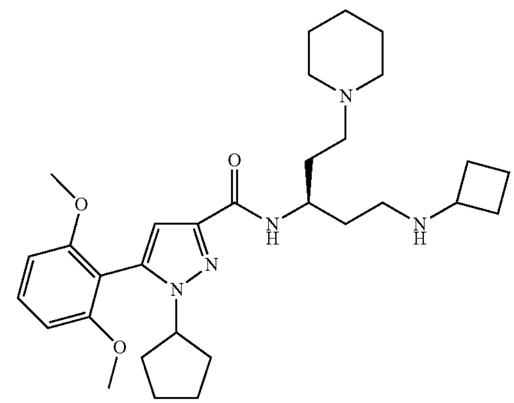 [SMILES: COc1cccc(OC)c1-c1cc(C(=O)N[C@H](CCNC2CCC2)CCN2CCCCC2)nn1C1CCCC1] | 538.4 |
| 399 | 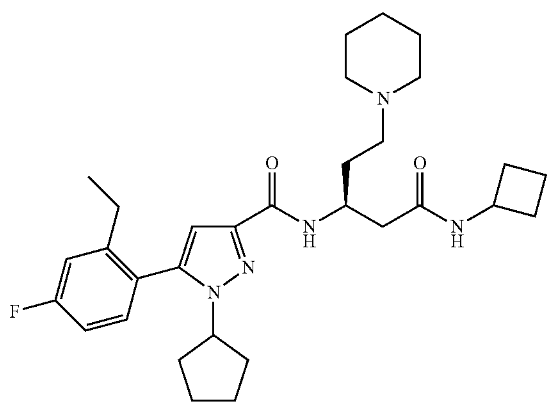 [SMILES: CCc1cc(F)ccc1-c1cc(C(=O)N[C@@H](CCN2CCCCC2)CC(=O)NC2CCC2)nn1C1CCCC1] | 538.5 |
| 400 | 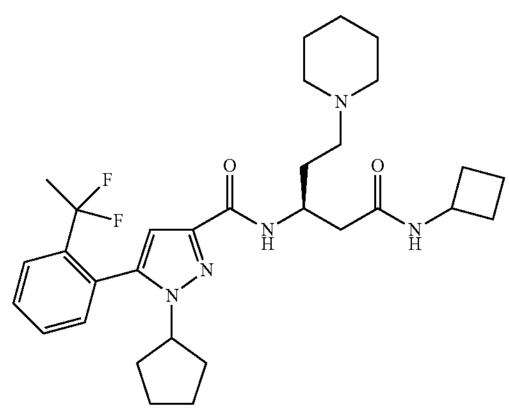 [SMILES: CC(F)(F)c1ccccc1-c1cc(C(=O)N[C@@H](CCN2CCCCC2)CC(=O)NC2CCC2)nn1C1CCCC1] | 556.5 |
| 401 | 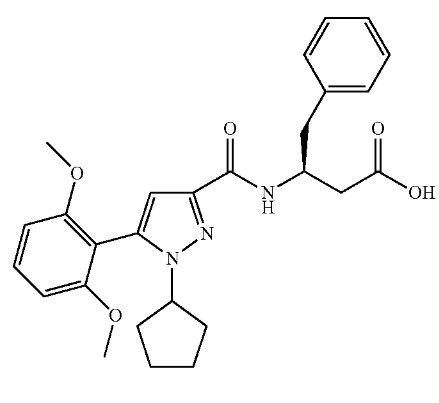 [SMILES: COc1cccc(OC)c1-c1cc(C(=O)N[C@H](CC(=O)O)Cc2ccccc2)nn1C1CCCC1] | 476.8 |

TABLE 1-continued
| ID # | STRUCTURE | [M + H]+/ [M − H]− |
|---|---|---|
| 402 | 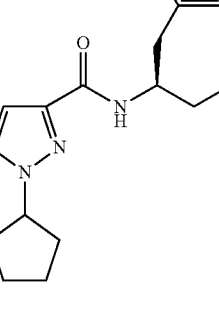 | 560.6 |
| 403 | 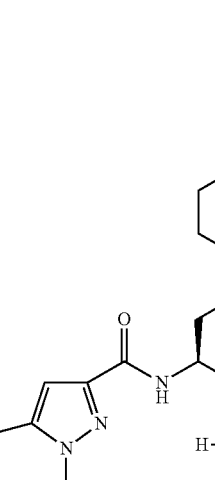 | 502.0 |
| 404 | 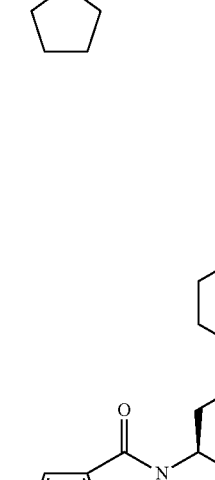 | 539.1 |

TABLE 1-continued
| ID # | STRUCTURE | [M + H]+/ [M − H]− |
|---|---|---|
| 405 | 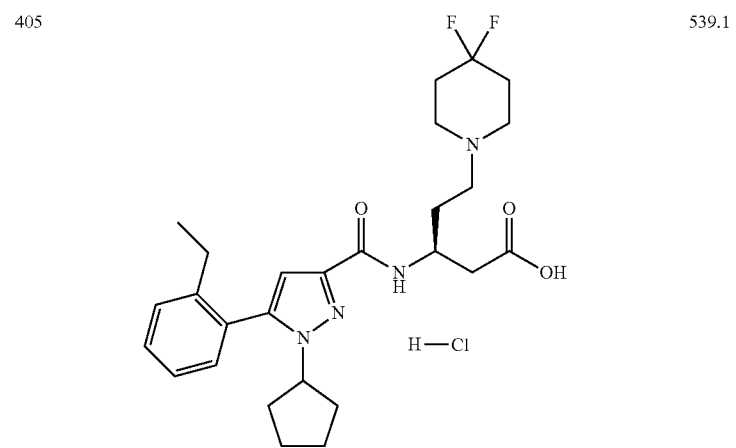 | 539.1 |
| 406 | 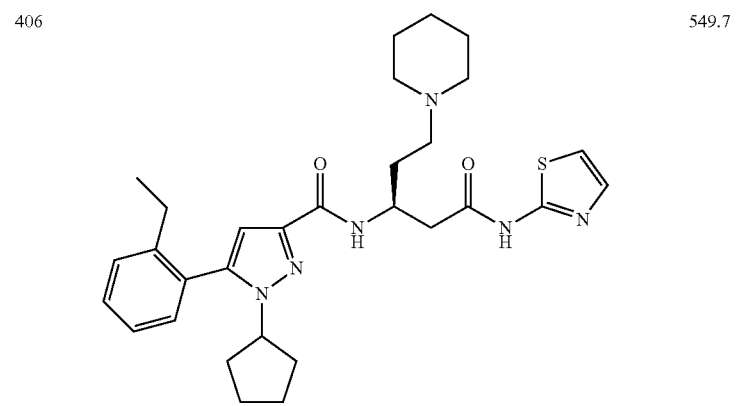 | 549.7 |
| 407 | 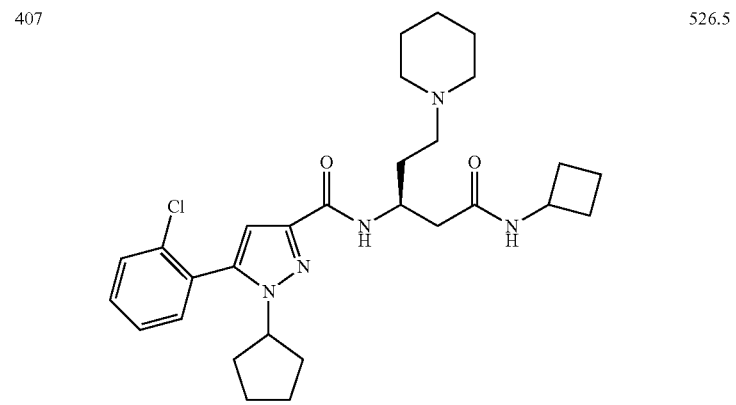 | 526.5 |

TABLE 1-continued
| ID # | STRUCTURE | [M + H]+/ [M − H]− |
|---|---|---|
| 408 | 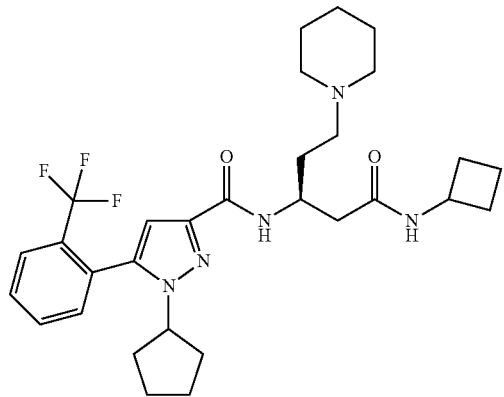 [SMILES: O=C(C[C@H](CCN1CCCCC1)NC(=O)c1cc(-c2ccccc2C(F)(F)F)n(C2CCCC2)n1)NC1CCC1] | 560.5 |
| 409 | 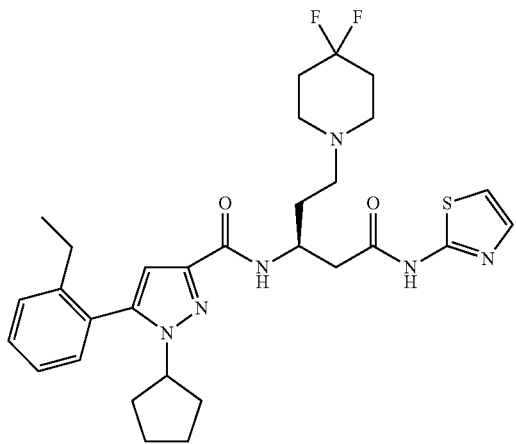 [SMILES: CCc1ccccc1-c1cc(C(=O)N[C@@H](CCN2CCC(F)(F)CC2)CC(=O)Nc2nccs2)nn1C1CCCC1] | 585.7 |
| 410 | 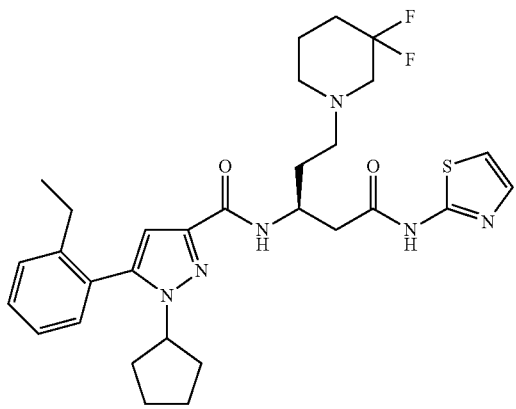 [SMILES: CCc1ccccc1-c1cc(C(=O)N[C@@H](CCN2CCCC(F)(F)C2)CC(=O)Nc2nccs2)nn1C1CCCC1] | 585.6 |

TABLE 1-continued
| ID # | STRUCTURE | [M + H]+/ [M − H]− |
|---|---|---|
| 411 | 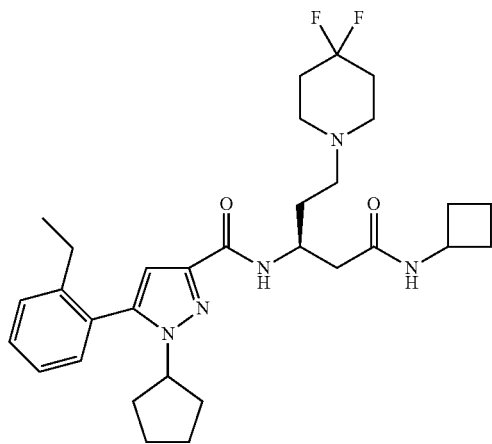 [SMILES: CCc1ccccc1-c1cc(C(=O)N[C@@H](CCN2CCC(F)(F)CC2)CC(=O)NC2CCC2)nn1C1CCCC1] | 556.9 |
| 412 | 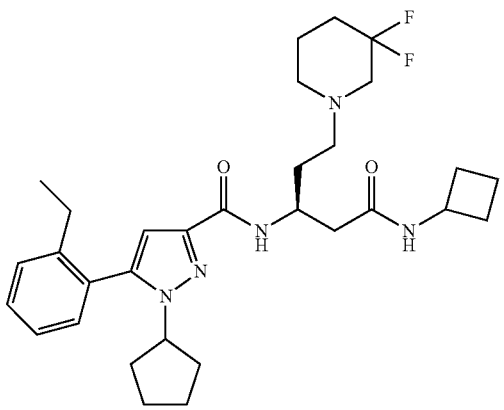 [SMILES: CCc1ccccc1-c1cc(C(=O)N[C@@H](CCN2CCCC(F)(F)C2)CC(=O)NC2CCC2)nn1C1CCCC1] | 557.0 |
| 413 | 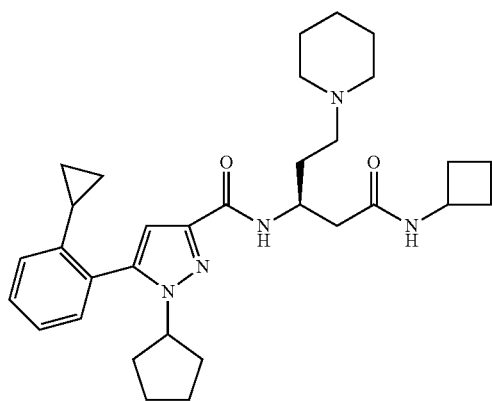 [SMILES: O=C(C[C@H](CCN1CCCCC1)NC(=O)c1cc(-c2ccccc2C2CC2)n(C2CCCC2)n1)NC1CCC1] | 532.4 |

| ID # | STRUCTURE | [M + H]+/ [M − H]− |
|---|---|---|
| 414 | 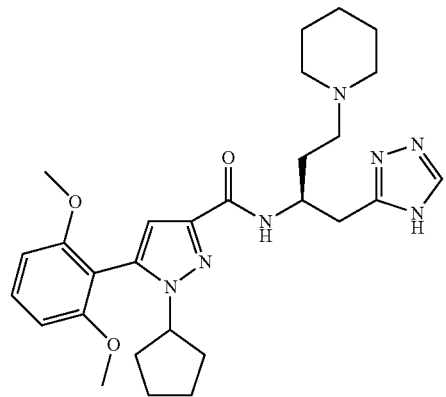 [SMILES: COc1cccc(OC)c1-c1cc(C(=O)N[C@@H](CCN2CCCCC2)Cc2nnc[nH]2)nn1C1CCCC1] | 522.4 |
| 415 | 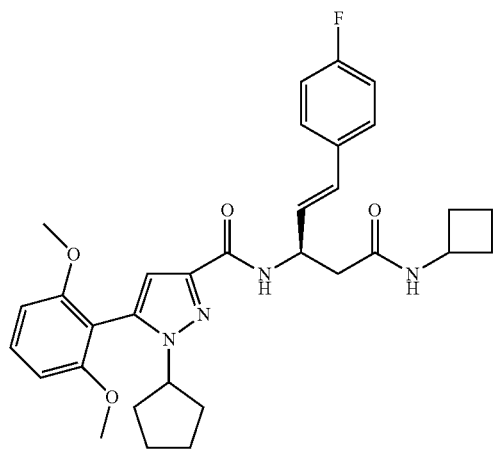 [SMILES: COc1cccc(OC)c1-c1cc(C(=O)N[C@@H](/C=C/c2ccc(F)cc2)CC(=O)NC2CCC2)nn1C1CCCC1] | 561.2 |
| 416 | 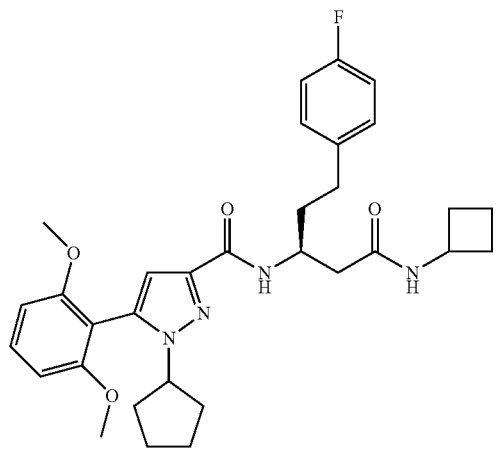 [SMILES: COc1cccc(OC)c1-c1cc(C(=O)N[C@@H](CCc2ccc(F)cc2)CC(=O)NC2CCC2)nn1C1CCCC1] | 563.1 |

TABLE 1-continued
| ID # | STRUCTURE | [M + H]+/ [M − H]− |
|---|---|---|
| 417 | 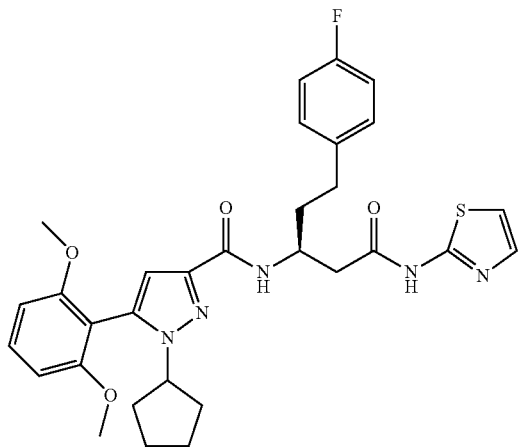 [SMILES: COc1cccc(OC)c1-c1cc(C(=O)N[C@@H](CCc2ccc(F)cc2)CC(=O)Nc2nccs2)nn1C1CCCC1] | 592.3 |
| 418 | 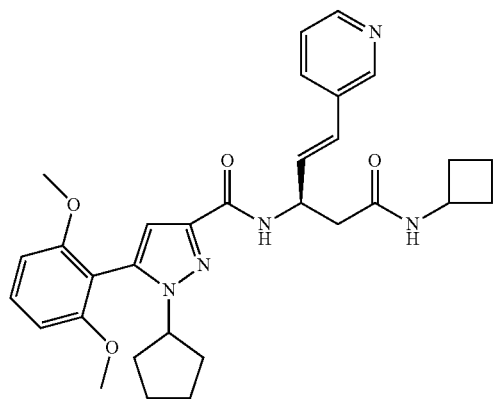 [SMILES: COc1cccc(OC)c1-c1cc(C(=O)N[C@@H](/C=C/c2cccnc2)CC(=O)NC2CCC2)nn1C1CCCC1] | 544.1 |
| 419 | 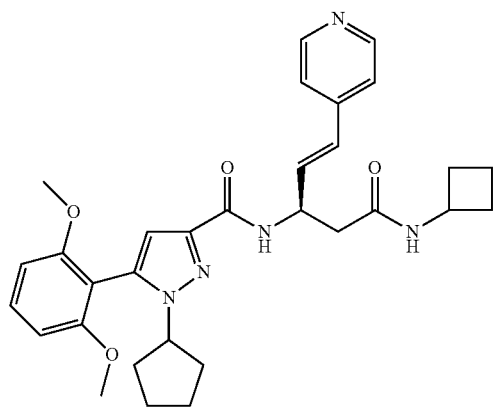 [SMILES: COc1cccc(OC)c1-c1cc(C(=O)N[C@@H](/C=C/c2ccncc2)CC(=O)NC2CCC2)nn1C1CCCC1] | 543.9 |

TABLE 1-continued
| ID # | STRUCTURE | [M + H]+/ [M − H]− |
|---|---|---|
| 420 | 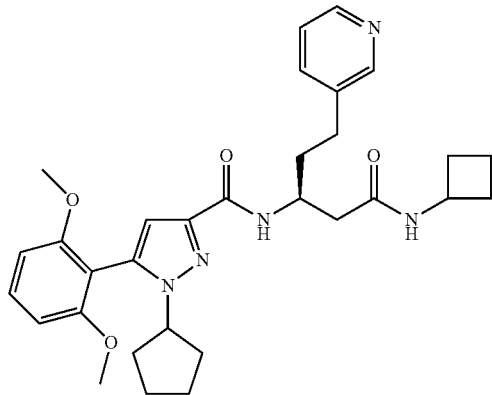 [SMILES: COc1cccc(OC)c1-c1cc(C(=O)N[C@@H](CCc2cccnc2)CC(=O)NC2CCC2)nn1C1CCCC1] | 545.8 |
| 421 | 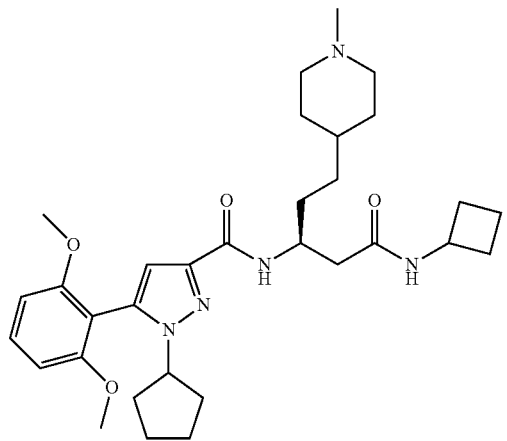 [SMILES: COc1cccc(OC)c1-c1cc(C(=O)N[C@@H](CCC2CCN(C)CC2)CC(=O)NC2CCC2)nn1C1CCCC1] | 566.1 |
| 422 | 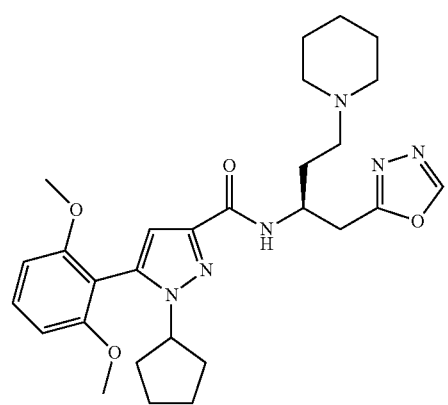 [SMILES: COc1cccc(OC)c1-c1cc(C(=O)N[C@@H](CCN2CCCCC2)Cc2nnco2)nn1C1CCCC1] | 523.1 |

TABLE 1-continued
| ID # | STRUCTURE | [M + H]+/[M − H]− |
|---|---|---|
| 423 | 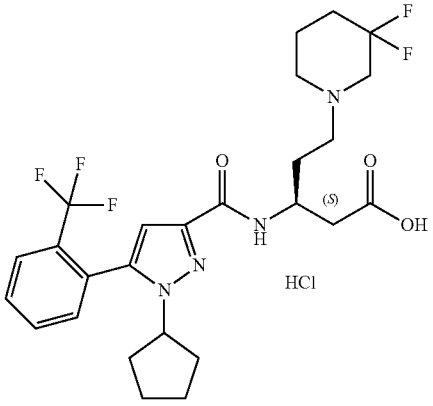 | 543.2 |
| 424 | 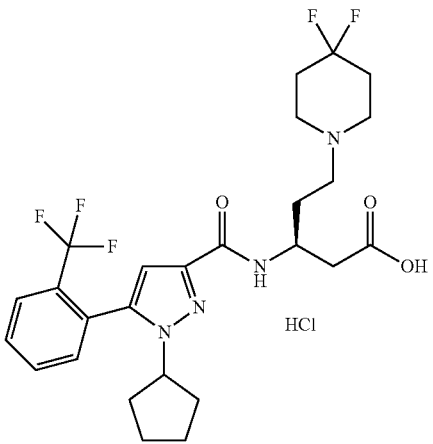 [SMILES: O=C(O)C[C@H](CCN1CCC(F)(F)CC1)NC(=O)c1cc(-c2ccccc2C(F)(F)F)n(C2CCCC2)n1 ; Cl] | 543.9 |
| 425 | 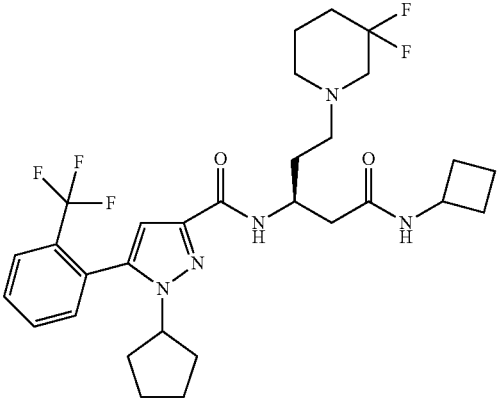 [SMILES: O=C(C[C@H](CCN1CCCC(F)(F)C1)NC(=O)c1cc(-c2ccccc2C(F)(F)F)n(C2CCCC2)n1)NC1CCC1] | 596.9 |

TABLE 1-continued
| ID # | STRUCTURE | [M + H]+/ [M − H]− |
|---|---|---|
| 426 | 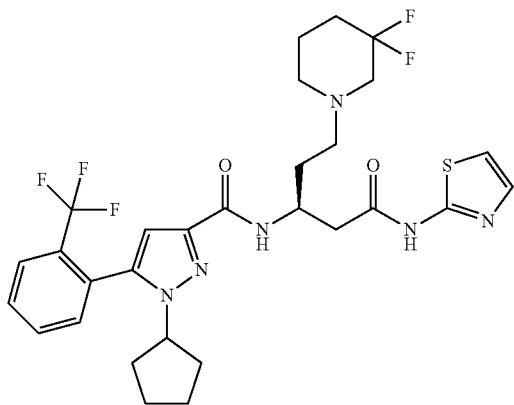 | 625.7 |
| 427 | 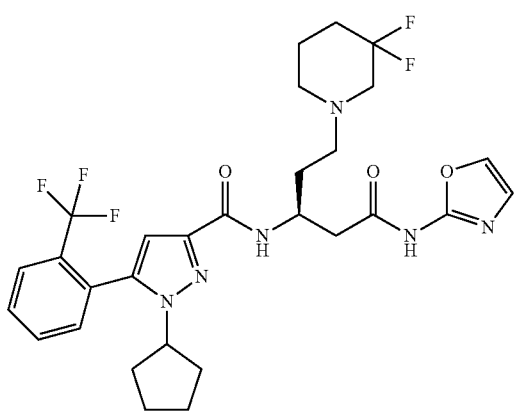 [SMILES: O=C(C[C@H](CCN1CCCC(F)(F)C1)NC(=O)c1cc(-c2ccccc2C(F)(F)F)n(C2CCCC2)n1)Nc1ncco1] | 609.0 |
| 428 | 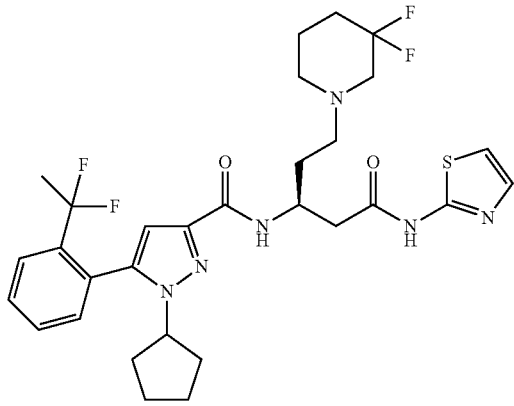 [SMILES: CC(F)(F)c1ccccc1-c1cc(C(=O)N[C@@H](CCN2CCCC(F)(F)C2)CC(=O)Nc2nccs2)nn1C1CCCC1] | 621.0 |

TABLE 1-continued
| ID # | STRUCTURE | [M + H]+/[M − H]− |
|---|---|---|
| 429 | 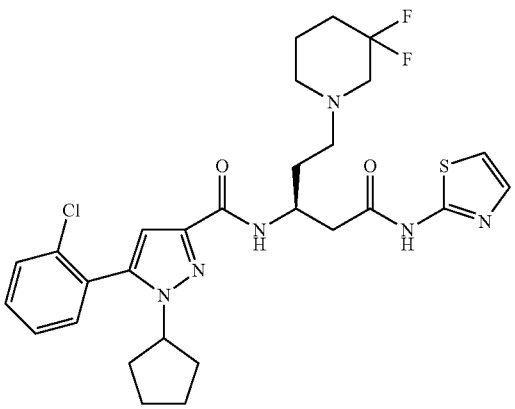 [SMILES: O=C(C[C@H](CCN1CCCC(F)(F)C1)NC(=O)c1cc(-c2ccccc2Cl)n(C2CCCC2)n1)Nc1nccs1] | 591.0 |
| 430 | 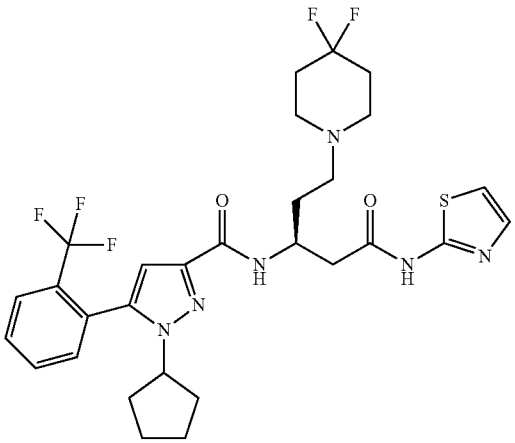 [SMILES: O=C(C[C@H](CCN1CCC(F)(F)CC1)NC(=O)c1cc(-c2ccccc2C(F)(F)F)n(C2CCCC2)n1)Nc1nccs1] | 625.9 |
| 431 | 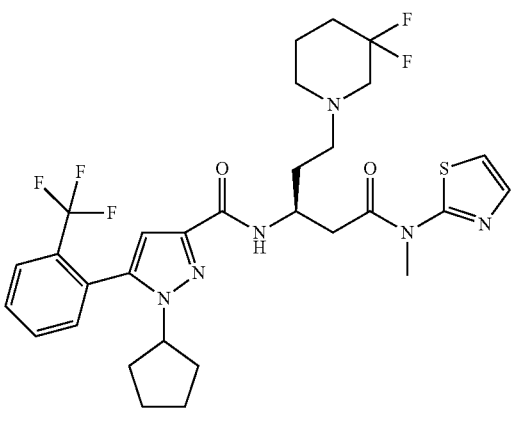 [SMILES: CN(C(=O)C[C@H](CCN1CCCC(F)(F)C1)NC(=O)c1cc(-c2ccccc2C(F)(F)F)n(C2CCCC2)n1)c1nccs1] | 639.0 |

TABLE 1-continued
| ID # | STRUCTURE | [M + H]+/[M − H]− |
|---|---|---|
| 432 | 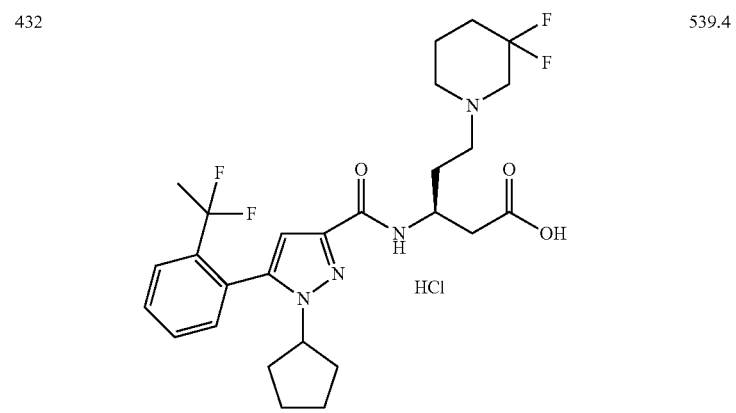 | 539.4 |
| 433 | 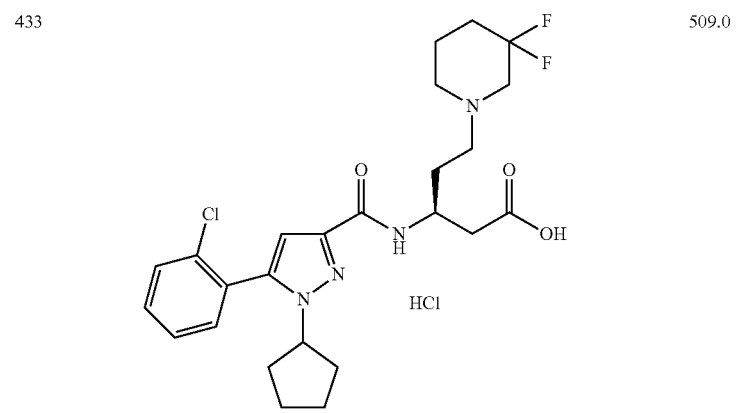 | 509.0 |
| 434 | 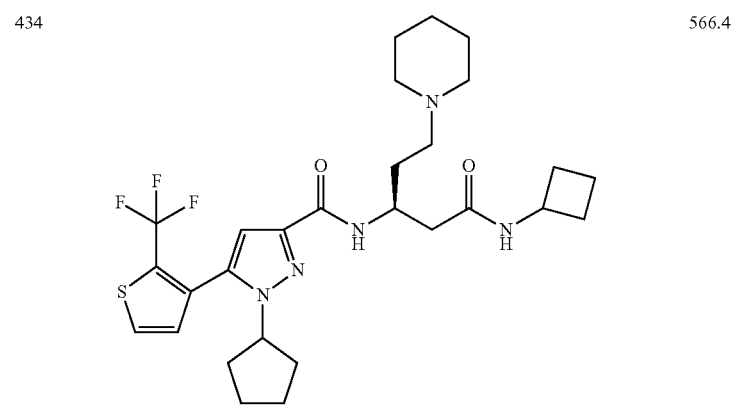 | 566.4 |

TABLE 1-continued
| ID # | STRUCTURE | [M + H]+/ [M − H]− |
|---|---|---|
| 435 | 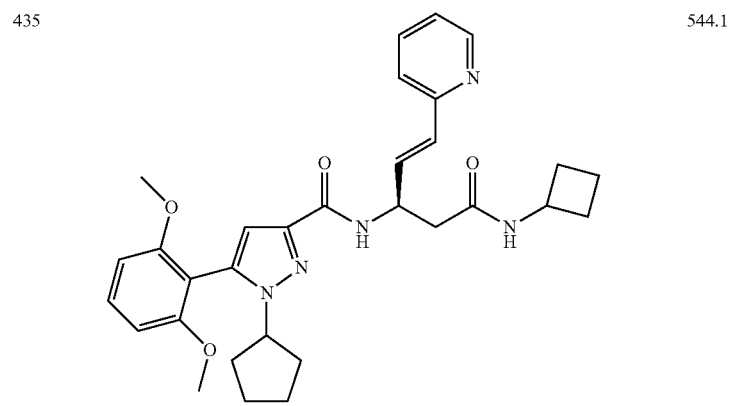 | 544.1 |
| 436 | 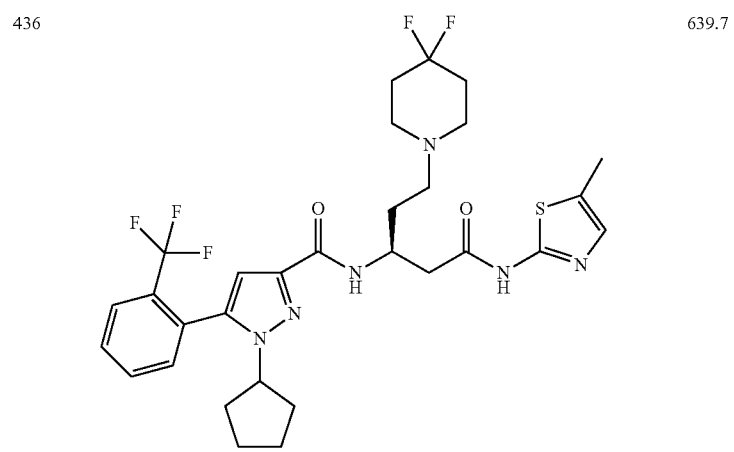 | 639.7 |
| 437 | 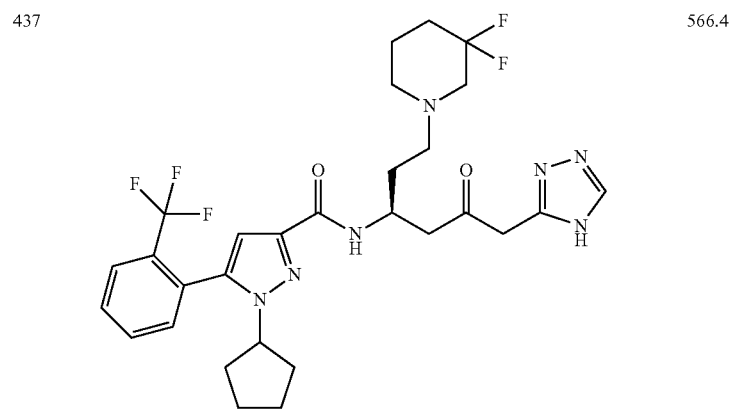 | 566.4 |

TABLE 1-continued
| ID # | STRUCTURE | [M + H]+/ [M − H]− |
|---|---|---|
| 438 | 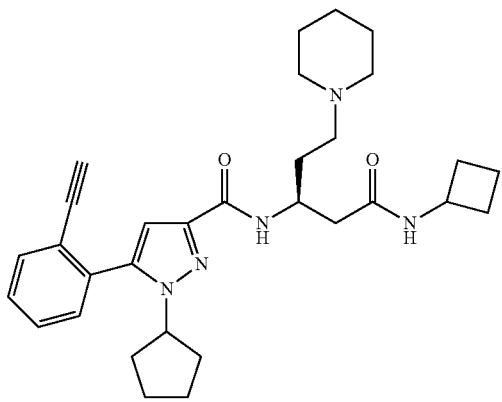 [SMILES: C#Cc1ccccc1-c1cc(C(=O)N[C@@H](CCN2CCCCC2)CC(=O)NC2CCC2)nn1C1CCCC1] | 516.9 |
| 439 | 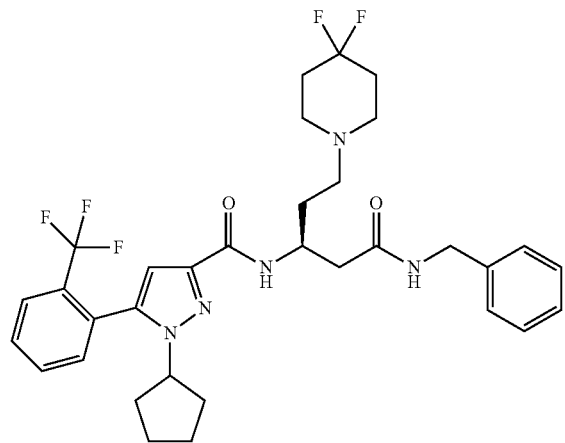 [SMILES: O=C(C[C@H](CCN1CCC(F)(F)CC1)NC(=O)c1cc(-c2ccccc2C(F)(F)F)n(C2CCCC2)n1)NCc1ccccc1] | 632.7 |
| 440 | 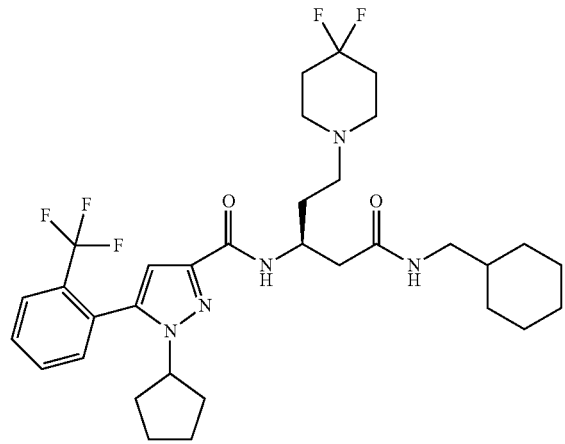 [SMILES: O=C(C[C@H](CCN1CCC(F)(F)CC1)NC(=O)c1cc(-c2ccccc2C(F)(F)F)n(C2CCCC2)n1)NCC1CCCCC1] | 638.9 |

TABLE 1-continued

| ID # | STRUCTURE | [M + H]+/[M − H]− |
|---|---|---|
| 441 | 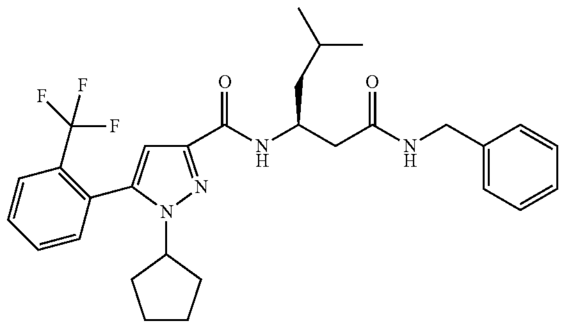 [SMILES: CC(C)C[C@@H](CC(=O)NCc1ccccc1)NC(=O)c1cc(-c2ccccc2C(F)(F)F)n(C2CCCC2)n1] | 541.5 |
| 442 | 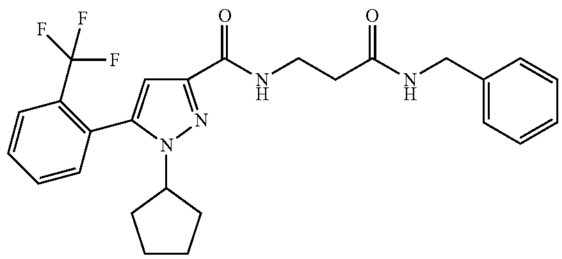 [SMILES: O=C(CCNC(=O)c1cc(-c2ccccc2C(F)(F)F)n(C2CCCC2)n1)NCc1ccccc1] | 485.4 |
| 443 | 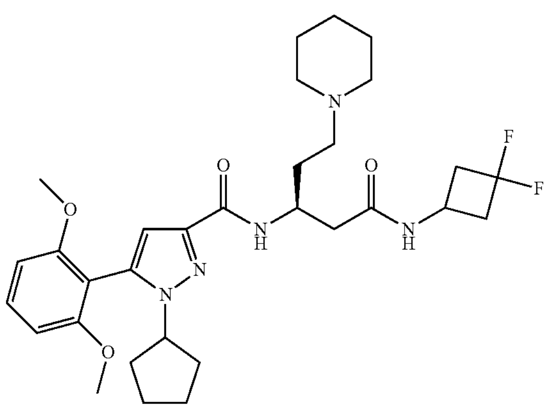 [SMILES: COc1cccc(OC)c1-c1cc(C(=O)N[C@@H](CCN2CCCCC2)CC(=O)NC2CC(F)(F)C2)nn1C1CCCC1] | 588.4 |
| 445 | 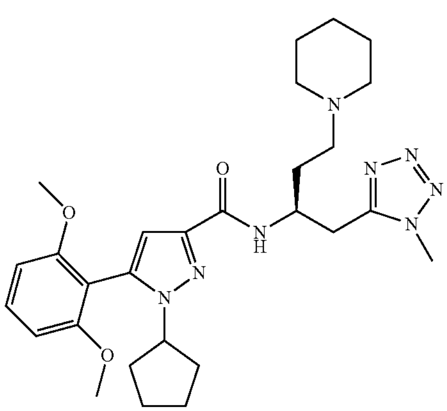 [SMILES: COc1cccc(OC)c1-c1cc(C(=O)N[C@@H](CCN2CCCCC2)Cc2nnnn2C)nn1C1CCCC1] | 536.9 |

TABLE 1-continued
| ID # | STRUCTURE | [M + H]+/ [M − H]− |
|---|---|---|
| 447 | 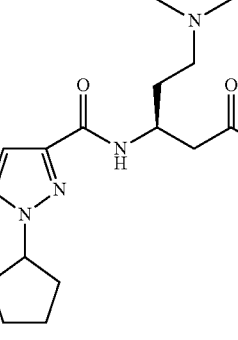 | 605.8 |
| 448 | 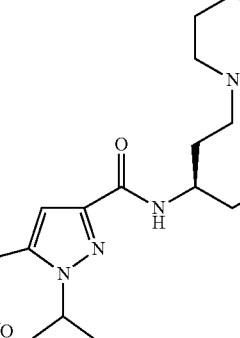 | 539.9 |
| 449 | 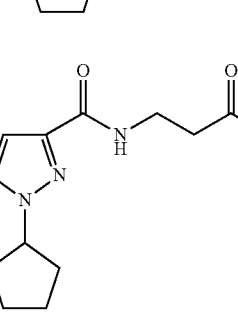 | 478.3 |
| 450 | 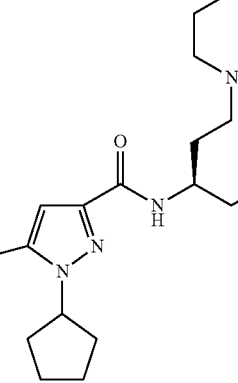 | 532.6 |

TABLE 1-continued
| ID # | STRUCTURE | [M + H]+/[M − H]− |
|---|---|---|
| 451 | 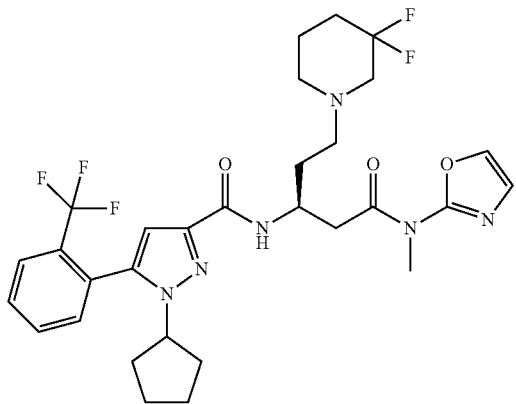 | 623.4 |
| 452 | 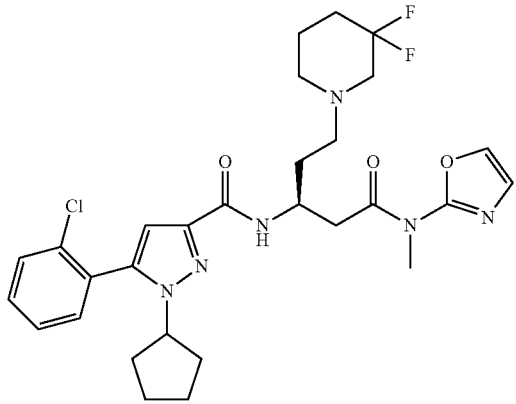 [SMILES: CN(C(=O)C[C@H](CCN1CCCC(F)(F)C1)NC(=O)c1cc(-c2ccccc2Cl)n(C2CCCC2)n1)c1nccs1] | 588.9 |
| 457 | 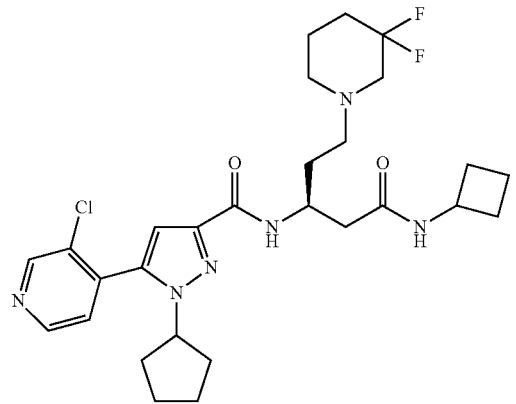 [SMILES: O=C(C[C@H](CCN1CCCC(F)(F)C1)NC(=O)c1cc(-c2ccncc2Cl)n(C2CCCC2)n1)NC1CCC1] | 563.5 |

TABLE 1-continued
| ID # | STRUCTURE | [M + H]+/ [M − H]− |
|---|---|---|
| 458 | 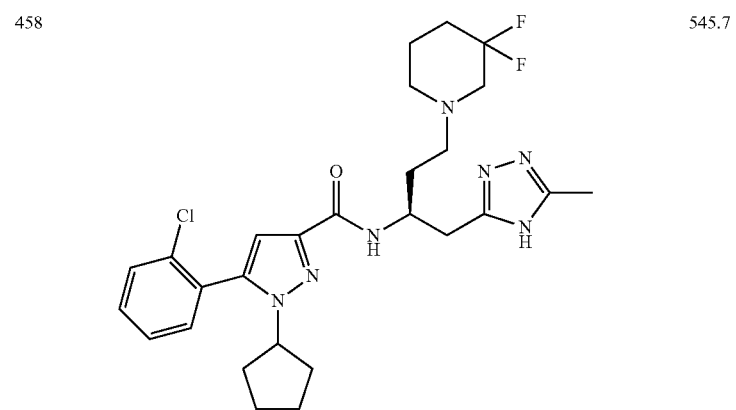 | 545.7 |
| 459 | 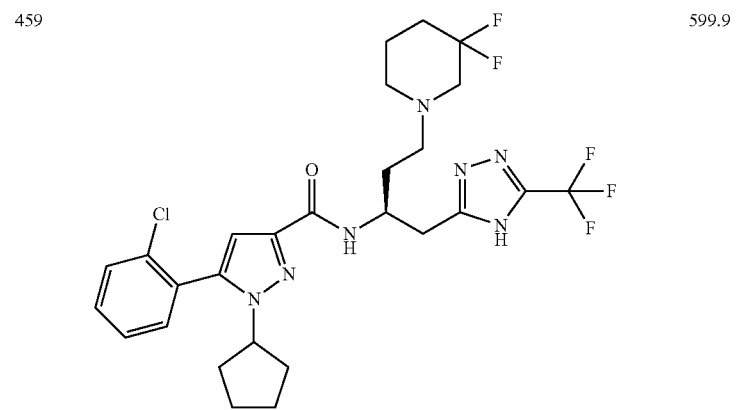 | 599.9 |
| 460 | 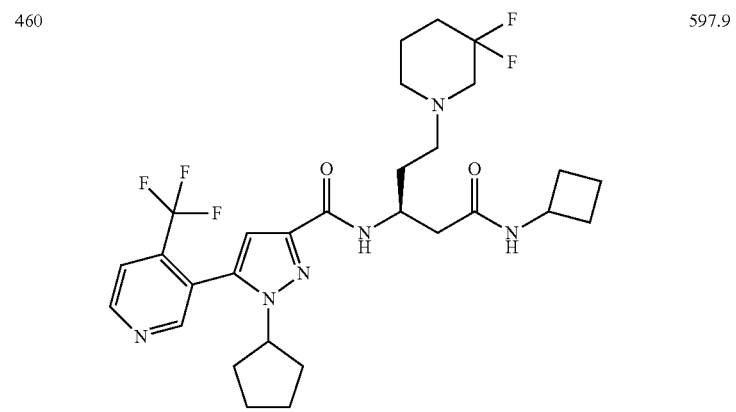 | 597.9 |

TABLE 1-continued
| ID # | STRUCTURE | [M + H]+/ [M − H]− |
|---|---|---|
| 463 | 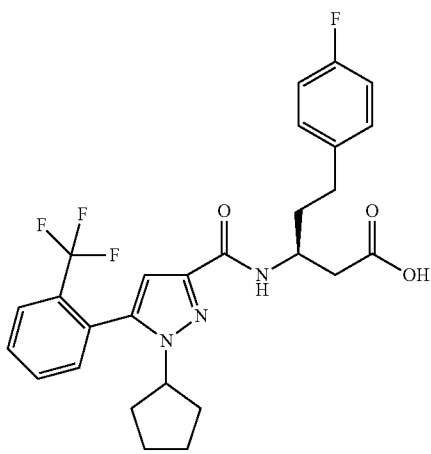 [SMILES: O=C(O)C[C@H](CCc1ccc(F)cc1)NC(=O)c1cc(-c2ccccc2C(F)(F)F)n(C2CCCC2)n1] | 518.0 |
| 464 | 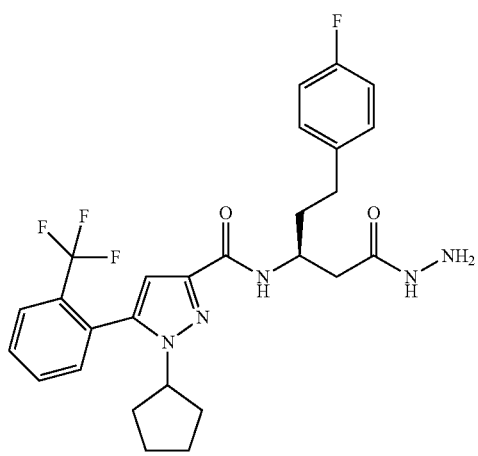 [SMILES: NNC(=O)C[C@H](CCc1ccc(F)cc1)NC(=O)c1cc(-c2ccccc2C(F)(F)F)n(C2CCCC2)n1] | 532.0 |
| 465 | 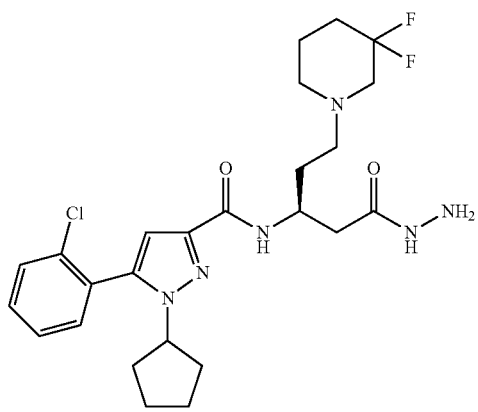 [SMILES: NNC(=O)C[C@H](CCN1CCCC(F)(F)C1)NC(=O)c1cc(-c2ccccc2Cl)n(C2CCCC2)n1] | 522.7 |

TABLE 1-continued
| ID # | STRUCTURE | [M + H]+/[M − H]− |
|---|---|---|
| 466 | 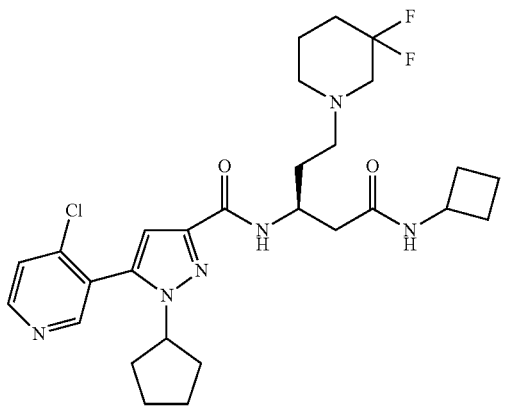 [SMILES: O=C(C[C@H](CCN1CCCC(F)(F)C1)NC(=O)c1cc(-c2cnccc2Cl)n(C2CCCC2)n1)NC1CCC1] | 563.5 |
| 467 | 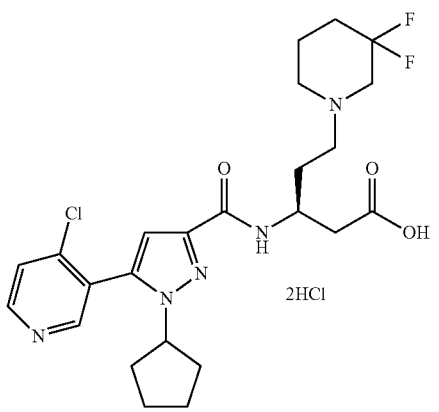 [SMILES: O=C(O)C[C@H](CCN1CCCC(F)(F)C1)NC(=O)c1cc(-c2cnccc2Cl)n(C2CCCC2)n1] | 508.5 |
| 468 | 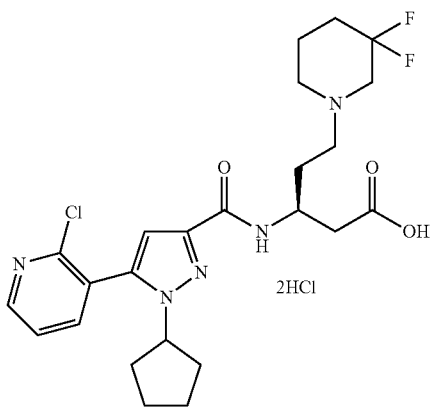 [SMILES: O=C(O)C[C@H](CCN1CCCC(F)(F)C1)NC(=O)c1cc(-c2cccnc2Cl)n(C2CCCC2)n1] | 508.5 |

TABLE 1-continued
| ID # | STRUCTURE | [M + H]+/ [M − H]− |
|---|---|---|
| 469 | 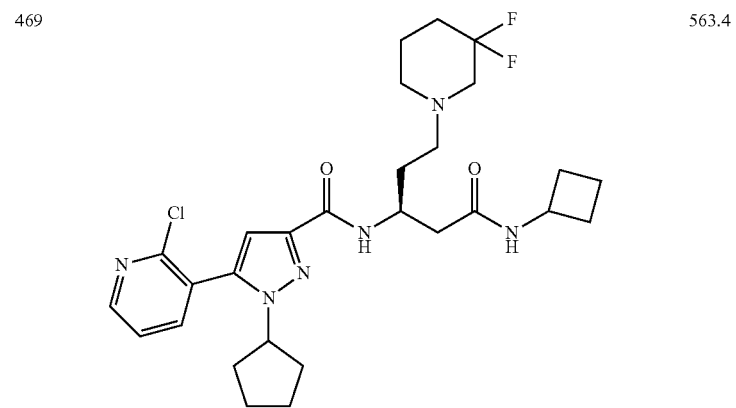 | 563.4 |
| 470 | 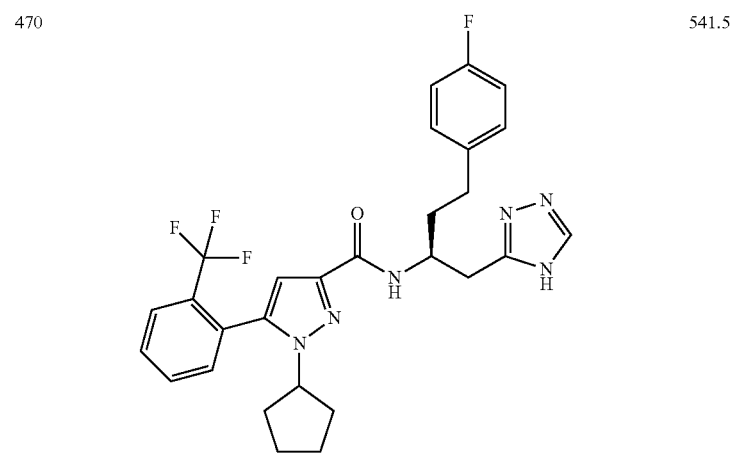 | 541.5 |
| 471 | 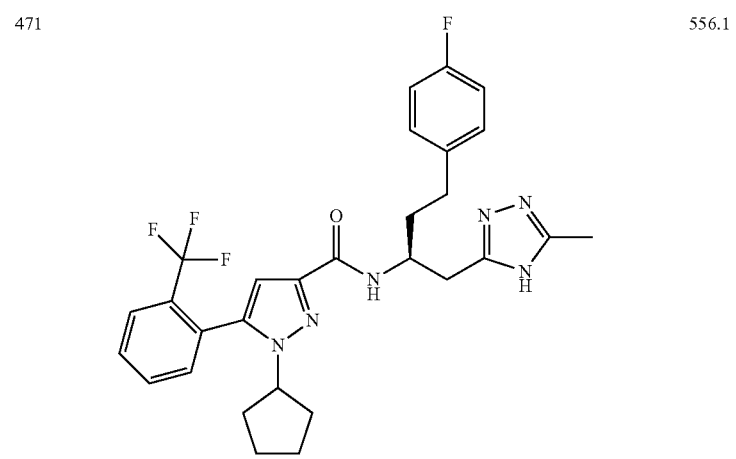 | 556.1 |

TABLE 1-continued
| ID # | STRUCTURE | [M + H]+/ [M − H]− |
|---|---|---|
| 475 | 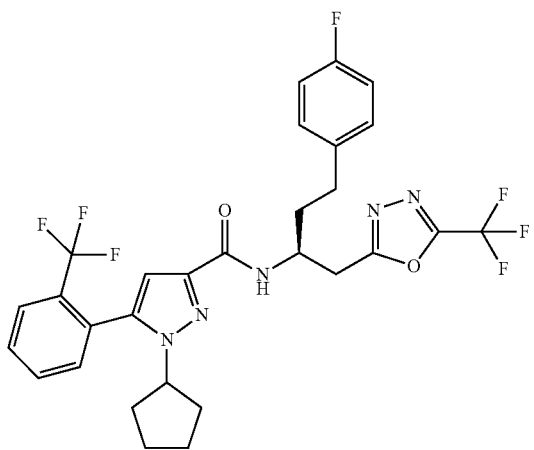 [SMILES: O=C(N[C@@H](CCc1ccc(F)cc1)Cc1nnc(C(F)(F)F)o1)c1cc(-c2ccccc2C(F)(F)F)n(C2CCCC2)n1] | 610.0 |
| 479 | 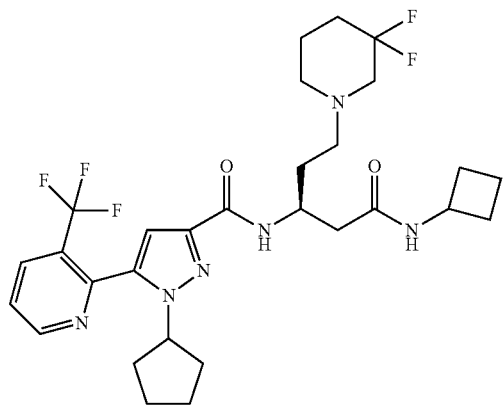 [SMILES: O=C(C[C@H](CCN1CCCC(F)(F)C1)NC(=O)c1cc(-c2ncccc2C(F)(F)F)n(C2CCCC2)n1)NC1CCC1] | 598.2 |
| 480 | 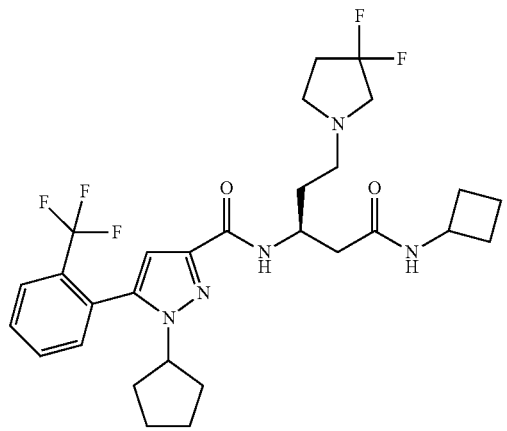 [SMILES: O=C(C[C@H](CCN1CCC(F)(F)C1)NC(=O)c1cc(-c2ccccc2C(F)(F)F)n(C2CCCC2)n1)NC1CCC1] | 582.9 |

TABLE 1-continued
| ID # | STRUCTURE | [M + H]+/ [M − H]− |
|---|---|---|
| 481 | 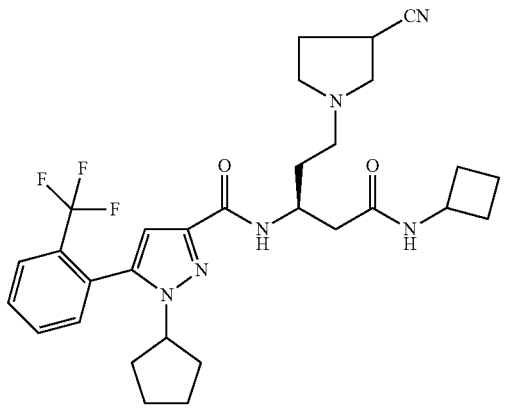 [SMILES: N#CC1CCN(CC[C@@H](CC(=O)NC2CCC2)NC(=O)c2cc(-c3ccccc3C(F)(F)F)n(C3CCCC3)n2)C1] | 571.9 |
| 482 | 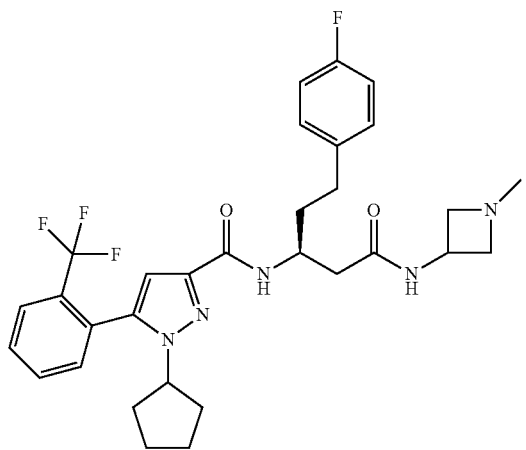 [SMILES: CN1CC(NC(=O)C[C@H](CCc2ccc(F)cc2)NC(=O)c2cc(-c3ccccc3C(F)(F)F)n(C3CCCC3)n2)C1] | 585.8 |
| 483 | 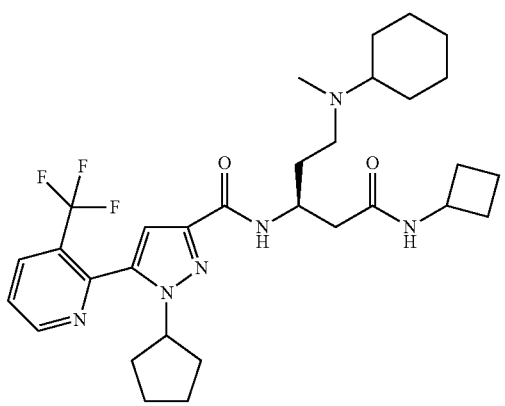 [SMILES: CN(CC[C@@H](CC(=O)NC1CCC1)NC(=O)c1cc(-c2ncccc2C(F)(F)F)n(C2CCCC2)n1)C1CCCCC1] | 588.4 |

TABLE 1-continued
| ID # | STRUCTURE | [M + H]+/[M − H]− |
|---|---|---|
| 484 | 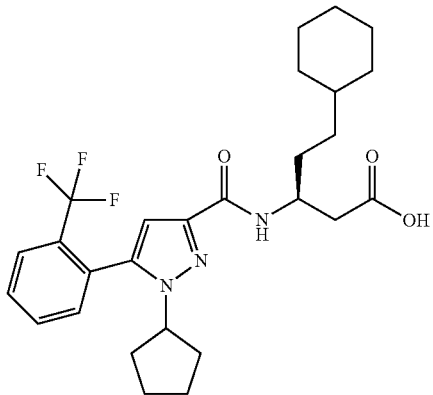 [SMILES: O=C(O)C[C@H](CCC1CCCCC1)NC(=O)c1cc(-c2ccccc2C(F)(F)F)n(C2CCCC2)n1] | 506.5 |
| 485 | 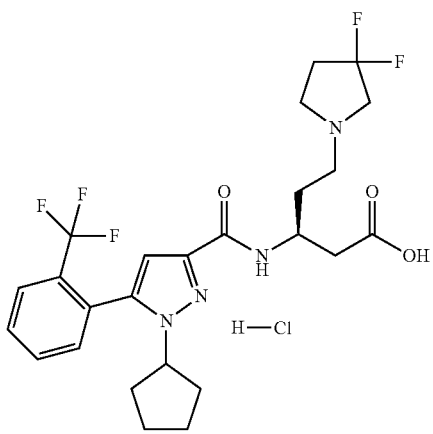 | 527.8 |
| 486 | 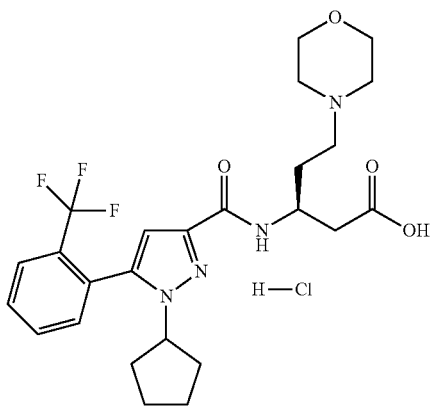 | 508.5 |

TABLE 1-continued

| ID # | STRUCTURE | [M + H]+/ [M − H]− |
|---|---|---|
| 487 | 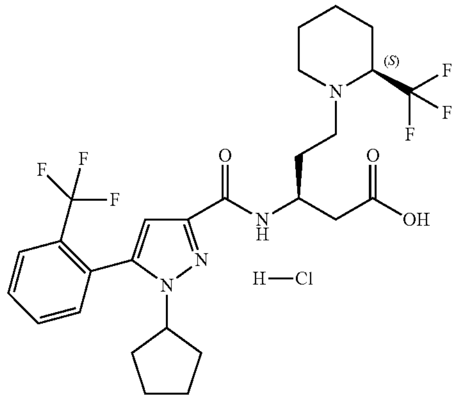 | 573.7 |
| 488 | 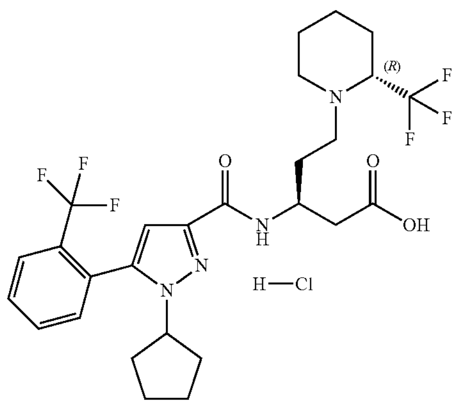 | 573.7 |
| 489 | 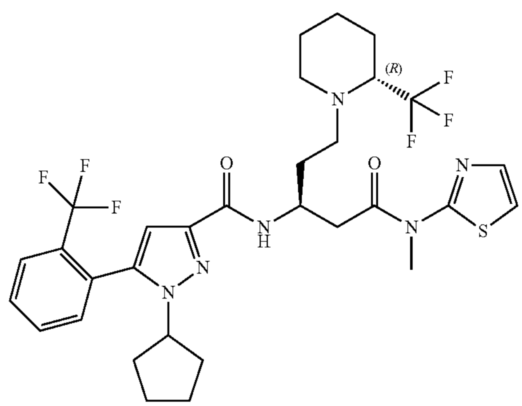 | 671.7 |
| 490 | 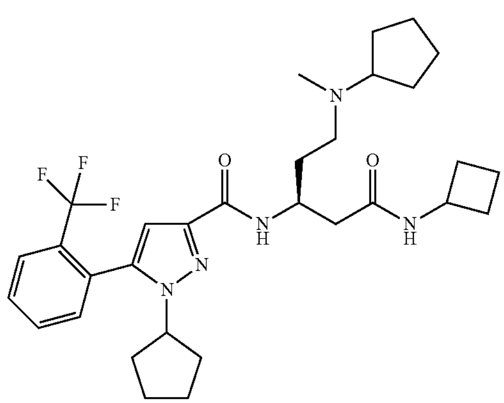 [SMILES: CN(CC[C@@H](CC(=O)NC1CCC1)NC(=O)c1cc(-c2ccccc2C(F)(F)F)n(C2CCCC2)n1)C1CCCC1] | 573.9 |

TABLE 1-continued
| ID # | STRUCTURE | [M + H]+/[M − H]− |
|---|---|---|
| 491 | 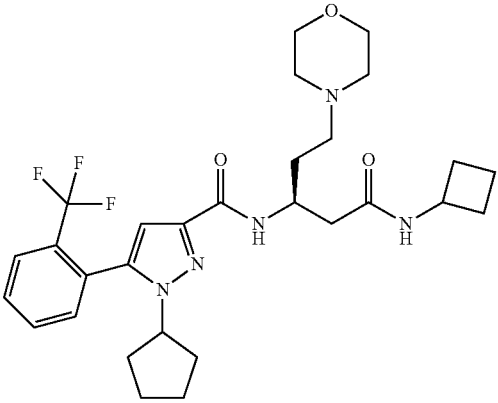 [SMILES: O=C(C[C@H](CCN1CCOCC1)NC(=O)c1cc(-c2ccccc2C(F)(F)F)n(C2CCCC2)n1)NC1CCC1] | 561.9 |
| 492 | 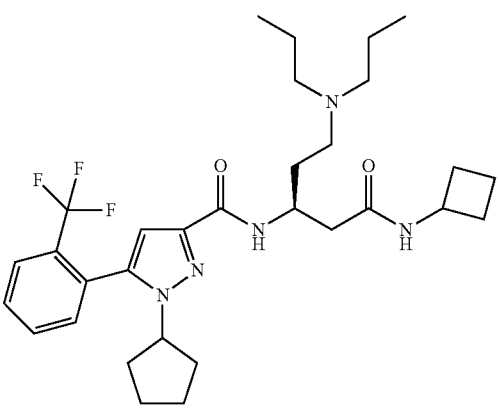 [SMILES: CCCN(CCC)CC[C@@H](CC(=O)NC1CCC1)NC(=O)c1cc(-c2ccccc2C(F)(F)F)n(C2CCCC2)n1] | 575.8 |
| 493 | 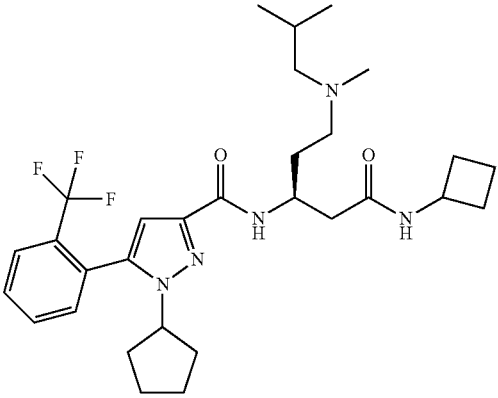 [SMILES: CC(C)CN(C)CC[C@@H](CC(=O)NC1CCC1)NC(=O)c1cc(-c2ccccc2C(F)(F)F)n(C2CCCC2)n1] | 561.9 |

TABLE 1-continued
| ID # | STRUCTURE | [M + H]+/ [M − H]− |
|---|---|---|
| 494 | 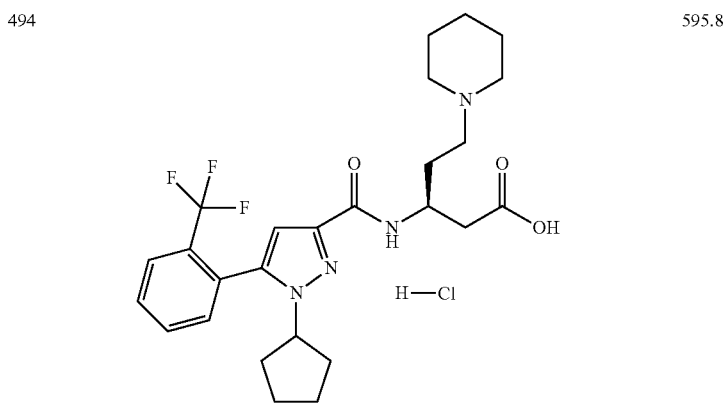 | 595.8 |
| 495 | 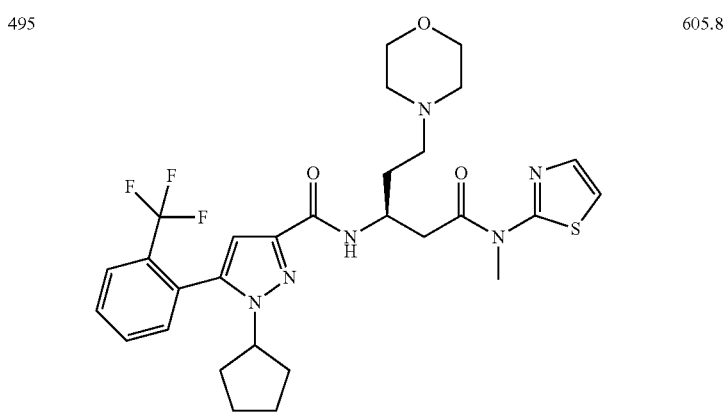 | 605.8 |
| 496 | 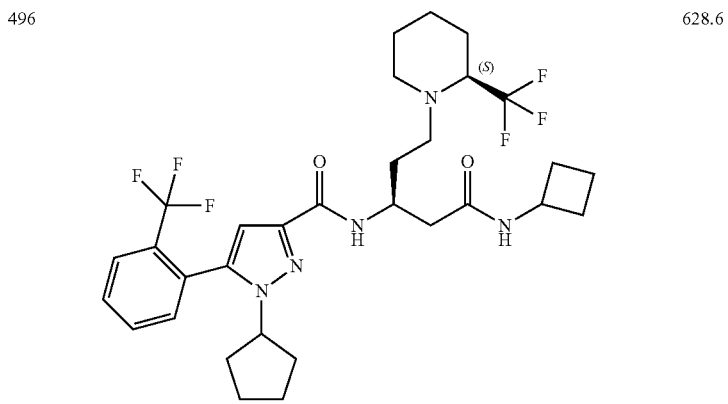 | 628.6 |

TABLE 1-continued
| ID # | STRUCTURE | [M + H]+/ [M − H]− |
|---|---|---|
| 497 | 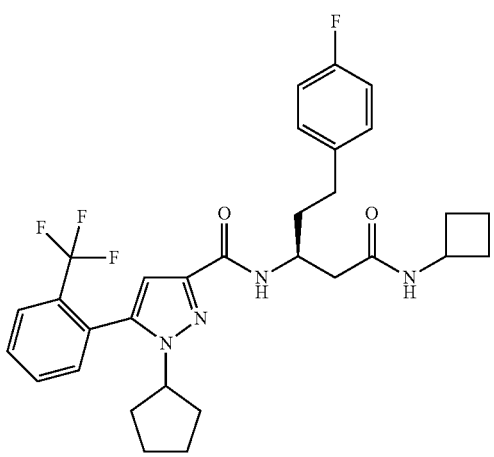 [SMILES: O=C(C[C@H](CCc1ccc(F)cc1)NC(=O)c1cc(-c2ccccc2C(F)(F)F)n(C2CCCC2)n1)NC1CCC1] | 570.7 |
| 498 | 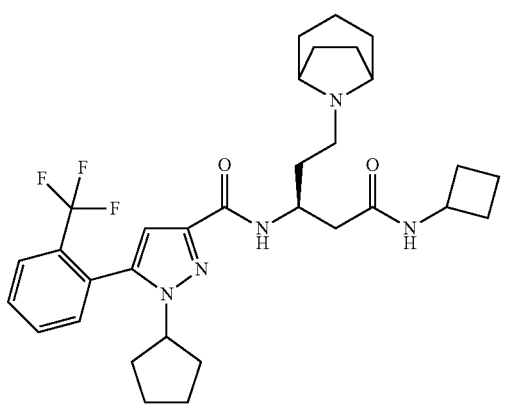 [SMILES: O=C(C[C@H](CCN1C2CCCC1CC2)NC(=O)c1cc(-c2ccccc2C(F)(F)F)n(C2CCCC2)n1)NC1CCC1] | 585.8 |
| 499 | 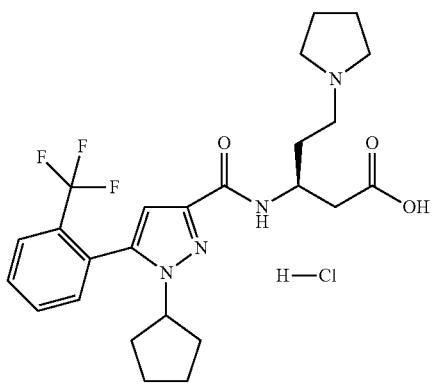 [SMILES: O=C(O)C[C@H](CCN1CCCC1)NC(=O)c1cc(-c2ccccc2C(F)(F)F)n(C2CCCC2)n1 ; Cl] | 491.7 |

TABLE 1-continued
| ID # | STRUCTURE | [M + H]+/[M − H]− |
|---|---|---|
| 500 | 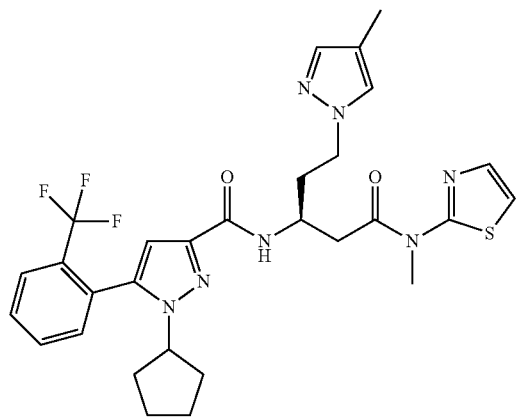 [SMILES: Cc1cnn(CC[C@@H](CC(=O)N(C)c2nccs2)NC(=O)c2cc(-c3ccccc3C(F)(F)F)n(C3CCCC3)n2)c1] | 600.5 |
| 501 | 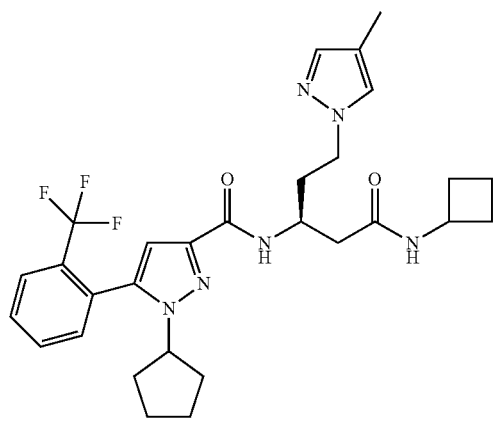 [SMILES: Cc1cnn(CC[C@@H](CC(=O)NC2CCC2)NC(=O)c2cc(-c3ccccc3C(F)(F)F)n(C3CCCC3)n2)c1] | 557.6 |
| 502 | 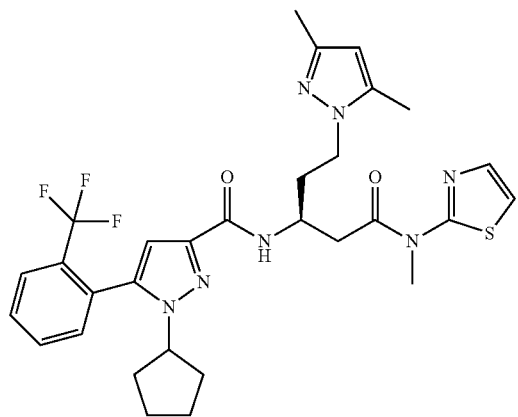 [SMILES: Cc1cc(C)n(CC[C@@H](CC(=O)N(C)c2nccs2)NC(=O)c2cc(-c3ccccc3C(F)(F)F)n(C3CCCC3)n2)n1] | 614.6 |

TABLE 1-continued

| ID # | STRUCTURE | [M + H]+/ [M − H]− |
|---|---|---|
| 503 | 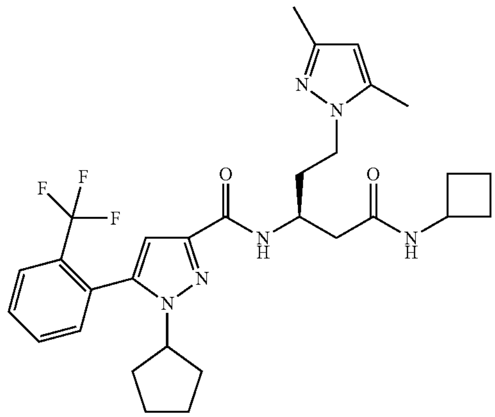 [SMILES: Cc1cc(C)n(CC[C@@H](CC(=O)NC2CCC2)NC(=O)c2cc(-c3ccccc3C(F)(F)F)n(C3CCCC3)n2)n1] | 571.7 |
| 504 | 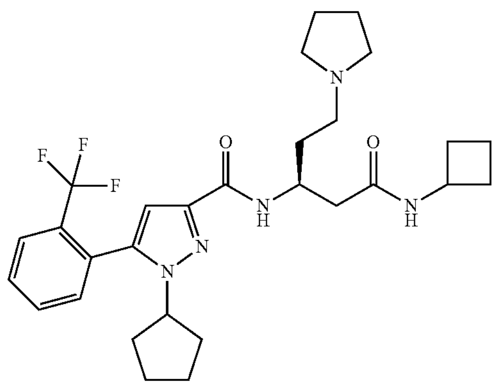 [SMILES: O=C(C[C@H](CCN1CCCC1)NC(=O)c1cc(-c2ccccc2C(F)(F)F)n(C2CCCC2)n1)NC1CCC1] | 546.7 |
| 505 | 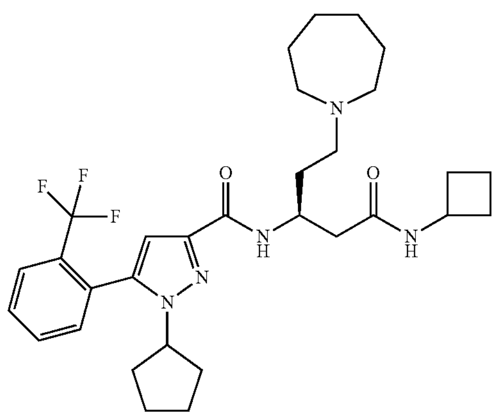 [SMILES: O=C(C[C@H](CCN1CCCCCC1)NC(=O)c1cc(-c2ccccc2C(F)(F)F)n(C2CCCC2)n1)NC1CCC1] | 573.7 |
| 506 | 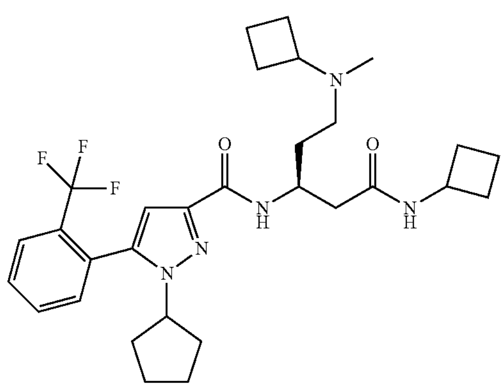 [SMILES: CN(CC[C@@H](CC(=O)NC1CCC1)NC(=O)c1cc(-c2ccccc2C(F)(F)F)n(C2CCCC2)n1)C1CCC1] | 559.6 |

TABLE 1-continued
| ID # | STRUCTURE | [M + H]+/ [M − H]− |
|---|---|---|
| 507 | 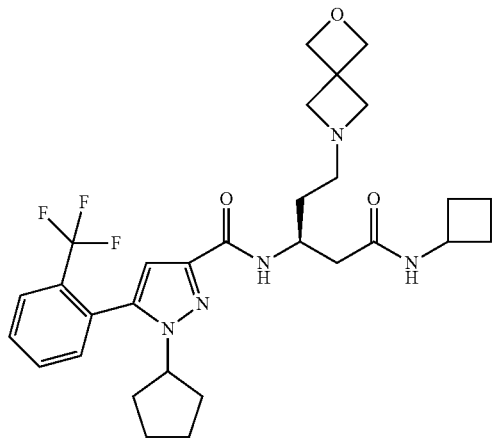 [SMILES: O=C(C[C@H](CCN1CC2(COC2)C1)NC(=O)c1cc(-c2ccccc2C(F)(F)F)n(C2CCCC2)n1)NC1CCC1] | 573.4 |
| 508 | 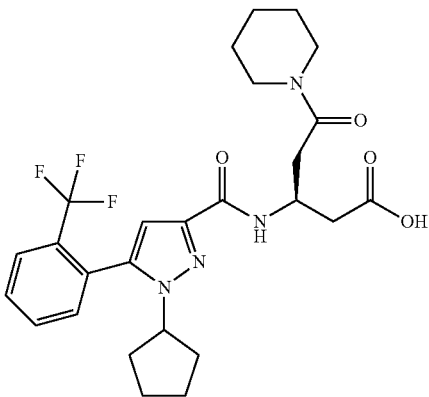 [SMILES: O=C(O)C[C@H](CC(=O)N1CCCCC1)NC(=O)c1cc(-c2ccccc2C(F)(F)F)n(C2CCCC2)n1] | 521.3 |
| 509 | 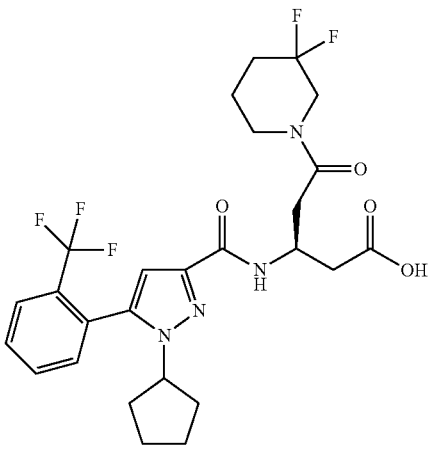 [SMILES: O=C(O)C[C@H](CC(=O)N1CCCC(F)(F)C1)NC(=O)c1cc(-c2ccccc2C(F)(F)F)n(C2CCCC2)n1] | 557.2 |

TABLE 1-continued

| ID # | STRUCTURE | [M + H]+/ [M − H]− |
|---|---|---|
| 510 | 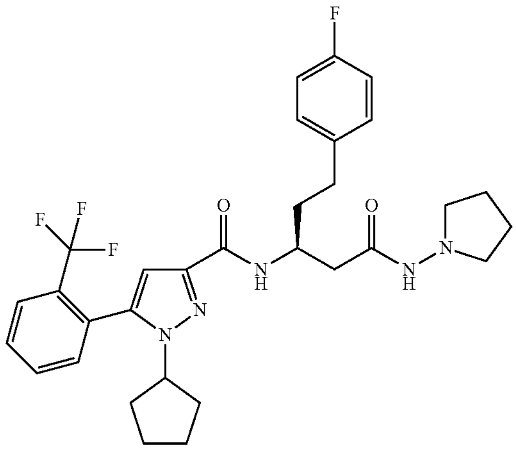 [SMILES: O=C(C[C@H](CCc1ccc(F)cc1)NC(=O)c1cc(-c2ccccc2C(F)(F)F)n(C2CCCC2)n1)NN1CCCC1] | 585.9 |
| 511 | 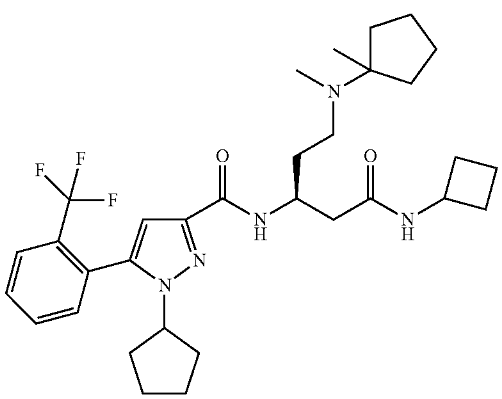 [SMILES: CN(CC[C@@H](CC(=O)NC1CCC1)NC(=O)c1cc(-c2ccccc2C(F)(F)F)n(C2CCCC2)n1)C1(C)CCCC1] | 588.0 |
| 514 | 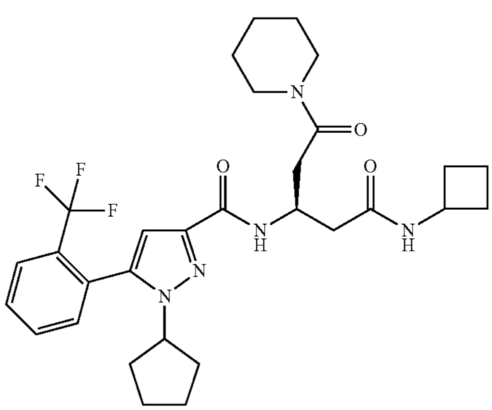 [SMILES: O=C(C[C@H](CC(=O)N1CCCCC1)NC(=O)c1cc(-c2ccccc2C(F)(F)F)n(C2CCCC2)n1)NC1CCC1] | 574.3 |

TABLE 1-continued

| ID # | STRUCTURE | [M + H]+/ [M − H]− |
|---|---|---|
| 515 | 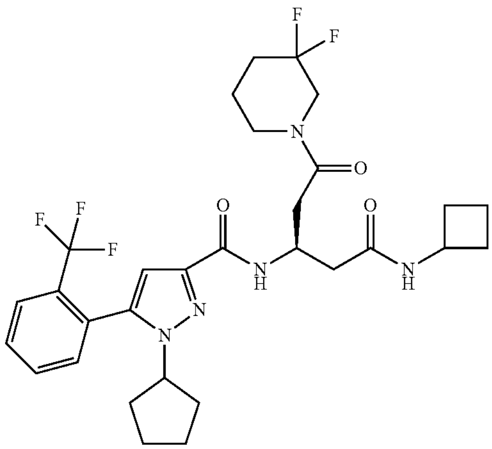 [SMILES: O=C(C[C@H](CC(=O)N1CCCC(F)(F)C1)NC(=O)c1cc(-c2ccccc2C(F)(F)F)n(C2CCCC2)n1)NC1CCC1] | 610.4 |
| 516 | 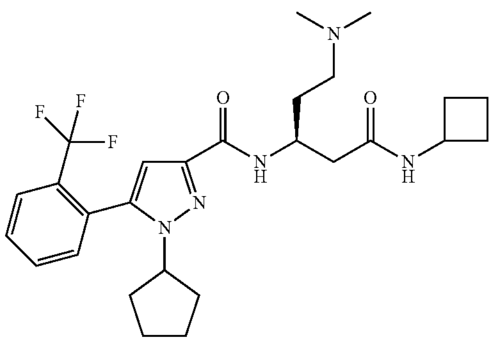 [SMILES: CN(C)CC[C@@H](CC(=O)NC1CCC1)NC(=O)c1cc(-c2ccccc2C(F)(F)F)n(C2CCCC2)n1] | 519.2 |
| 517 | 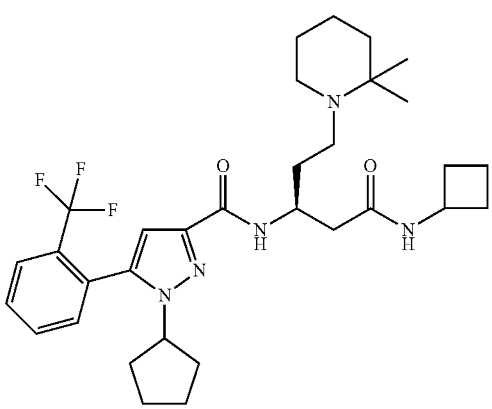 [SMILES: CC1(C)CCCCN1CC[C@@H](CC(=O)NC1CCC1)NC(=O)c1cc(-c2ccccc2C(F)(F)F)n(C2CCCC2)n1] | 588.3 |
| 518 | 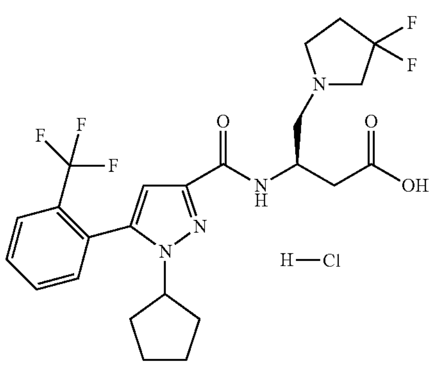 [SMILES: O=C(O)C[C@H](CN1CCC(F)(F)C1)NC(=O)c1cc(-c2ccccc2C(F)(F)F)n(C2CCCC2)n1 ; Cl] | 513.6 |

TABLE 1-continued
| ID # | STRUCTURE | [M + H]+/[M − H]− |
|---|---|---|
| 519 | 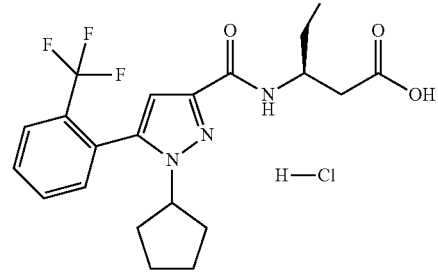 | 528.0 |
| 520 | 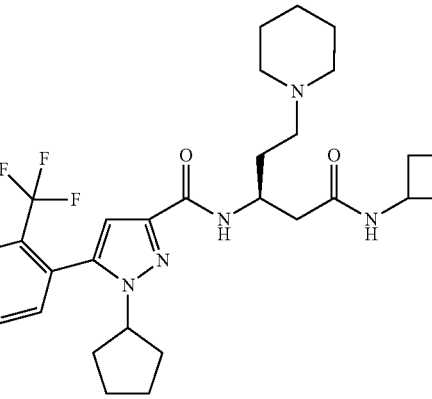 | 595.8 |
| 521 | 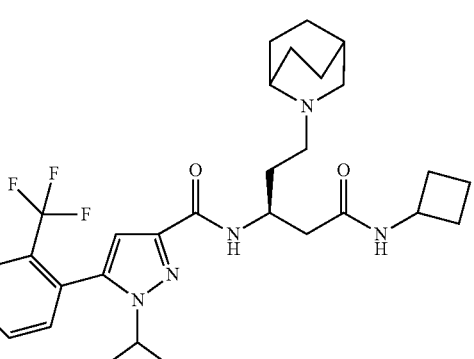 | 586.2 |
| 522 | 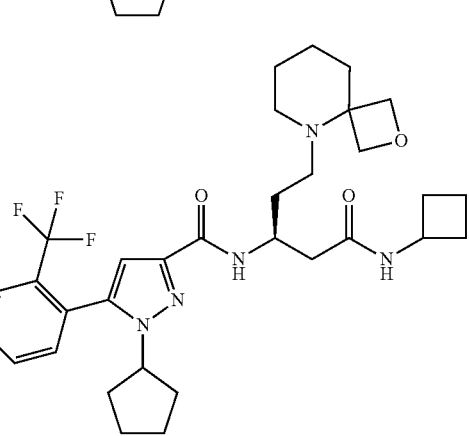 | 603.1 |

TABLE 1-continued

| ID # | STRUCTURE | [M + H]+/[M − H]− |
|---|---|---|
| 523 | 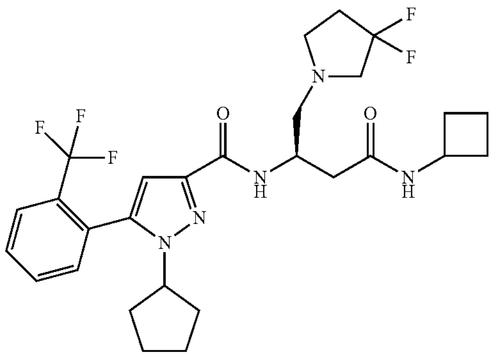 [SMILES: O=C(C[C@H](CN1CCC(F)(F)C1)NC(=O)c1cc(-c2ccccc2C(F)(F)F)n(C2CCCC2)n1)NC1CCC1] | 568.6 |
| 524 | 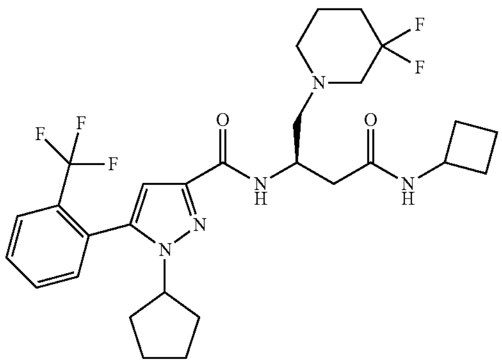 [SMILES: O=C(C[C@H](CN1CCCC(F)(F)C1)NC(=O)c1cc(-c2ccccc2C(F)(F)F)n(C2CCCC2)n1)NC1CCC1] | 582.9 |
| 526 | 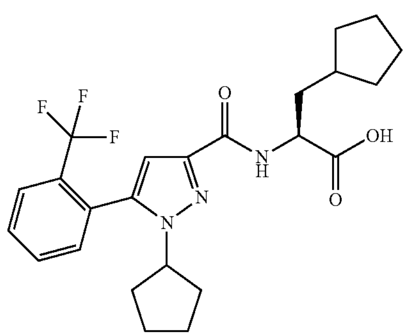 [SMILES: O=C(N[C@@H](CC1CCCC1)C(=O)O)c1cc(-c2ccccc2C(F)(F)F)n(C2CCCC2)n1] | 464.2 |
| 527 | 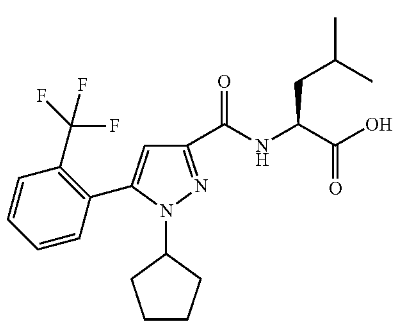 [SMILES: CC(C)C[C@H](NC(=O)c1cc(-c2ccccc2C(F)(F)F)n(C2CCCC2)n1)C(=O)O] | 438.1 |

TABLE 1-continued
| ID # | STRUCTURE | [M + H]+/[M − H]− |
|---|---|---|
| 528 | 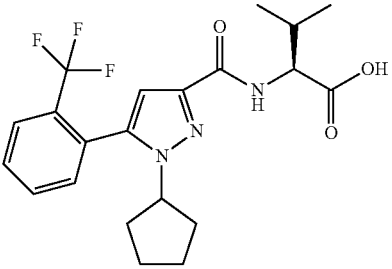 [SMILES: CC(C)[C@H](NC(=O)c1cc(-c2ccccc2C(F)(F)F)n(C2CCCC2)n1)C(=O)O] | 424.1 |
| 529 | 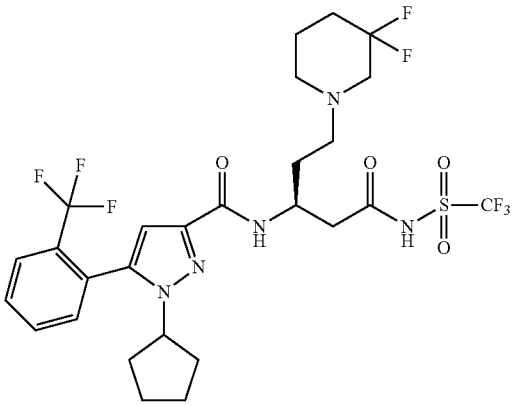 [SMILES: O=C(C[C@H](CCN1CCCC(F)(F)C1)NC(=O)c1cc(-c2ccccc2C(F)(F)F)n(C2CCCC2)n1)NS(=O)(=O)C(F)(F)F] | 672.5 |
| 533 | 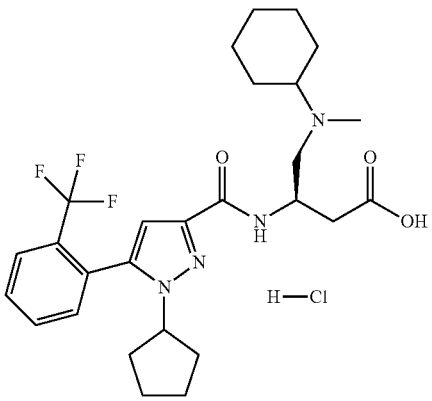 [SMILES: CN(C[C@@H](CC(=O)O)NC(=O)c1cc(-c2ccccc2C(F)(F)F)n(C2CCCC2)n1)C1CCCCC1 ; Cl] | 519.8 |
| 534 | 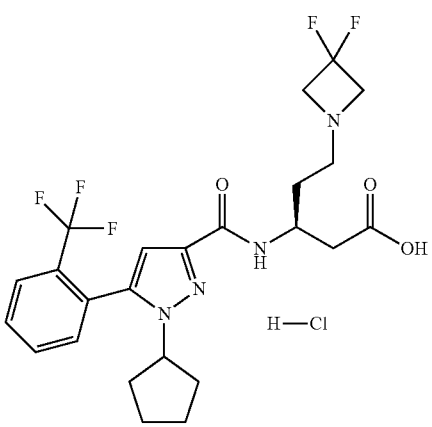 [SMILES: O=C(O)C[C@H](CCN1CC(F)(F)C1)NC(=O)c1cc(-c2ccccc2C(F)(F)F)n(C2CCCC2)n1 ; Cl] | 515.2 |

TABLE 1-continued
| ID # | STRUCTURE | [M + H]+/[M − H]− |
|---|---|---|
| 535 | 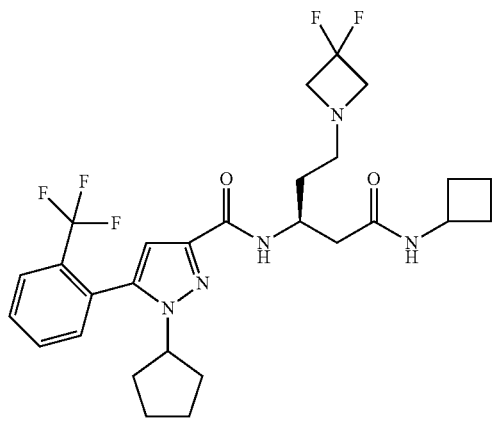 [SMILES: O=C(C[C@H](CCN1CC(F)(F)C1)NC(=O)c1cc(-c2ccccc2C(F)(F)F)n(C2CCCC2)n1)NC1CCC1] | 568.2 |
| 536 | 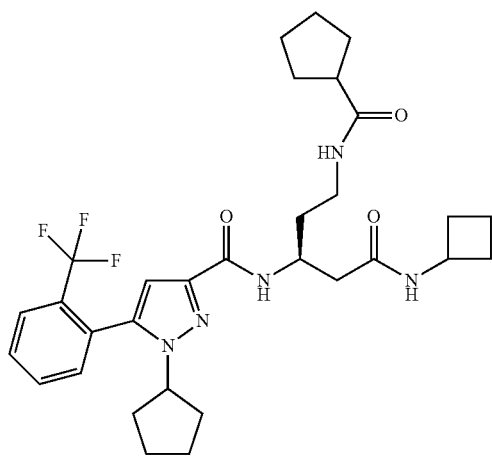 [SMILES: O=C(C[C@H](CCNC(=O)C1CCCC1)NC(=O)c1cc(-c2ccccc2C(F)(F)F)n(C2CCCC2)n1)NC1CCC1] | 588.2 |
| 537 | 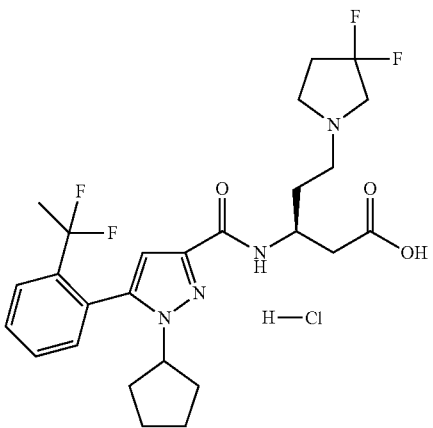 [SMILES: CC(F)(F)c1ccccc1-c1cc(C(=O)N[C@@H](CCN2CCC(F)(F)C2)CC(=O)O)nn1C1CCCC1 ; Cl] | 525.2 |

TABLE 1-continued
| ID # | STRUCTURE | [M + H]+/[M − H]− |
|---|---|---|
| 538 | 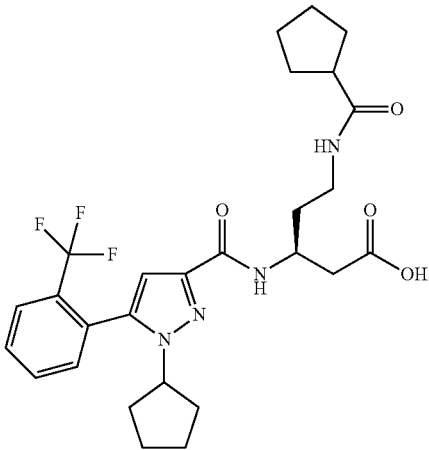 [SMILES: O=C(O)C[C@H](CCNC(=O)C1CCCC1)NC(=O)c1cc(-c2ccccc2C(F)(F)F)n(C2CCCC2)n1] | 535.2 |
| 539 | 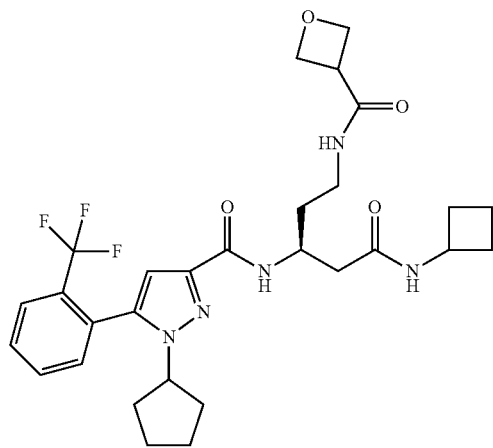 [SMILES: O=C(C[C@H](CCNC(=O)C1COC1)NC(=O)c1cc(-c2ccccc2C(F)(F)F)n(C2CCCC2)n1)NC1CCC1] | 576.2 |
| 540 | 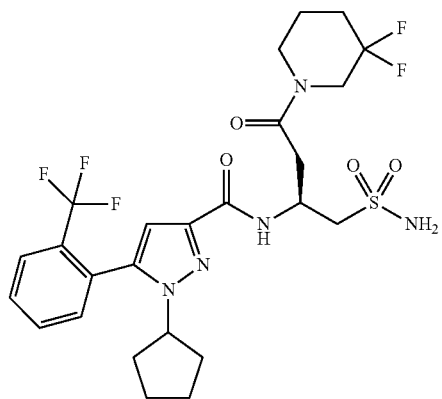 [SMILES: NS(=O)(=O)C[C@H](CC(=O)N1CCCC(F)(F)C1)NC(=O)c1cc(-c2ccccc2C(F)(F)F)n(C2CCCC2)n1] | 592.3 |

TABLE 1-continued
| ID # | STRUCTURE | [M + H]+/ [M − H]− |
|---|---|---|
| 541 | 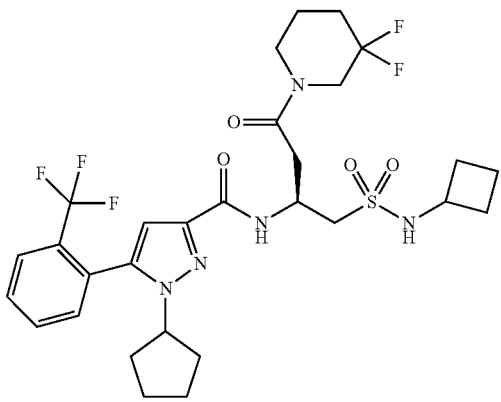 [SMILES: O=C(N[C@@H](CC(=O)N1CCCC(F)(F)C1)CS(=O)(=O)NC1CCC1)c1cc(-c2ccccc2C(F)(F)F)n(C2CCCC2)n1] | 646.3 |
| 542 | 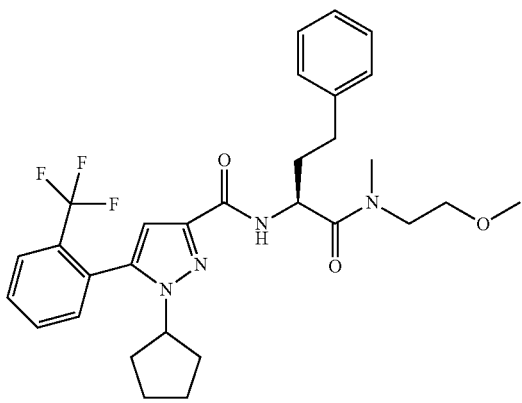 [SMILES: COCCN(C)C(=O)[C@H](CCc1ccccc1)NC(=O)c1cc(-c2ccccc2C(F)(F)F)n(C2CCCC2)n1] | 557.3 |
| 544 | 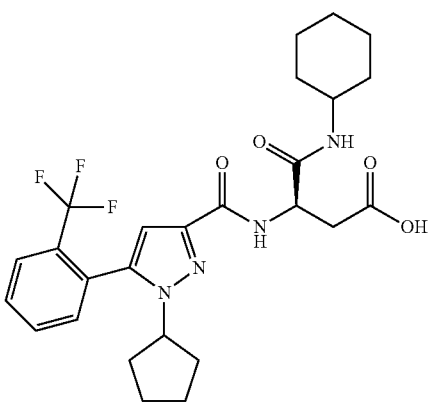 [SMILES: O=C(O)C[C@@H](NC(=O)c1cc(-c2ccccc2C(F)(F)F)n(C2CCCC2)n1)C(=O)NC1CCCCC1] | 521.1 |

TABLE 1-continued
| ID # | STRUCTURE | [M + H]+/ [M − H]− |
|---|---|---|
| 545 | 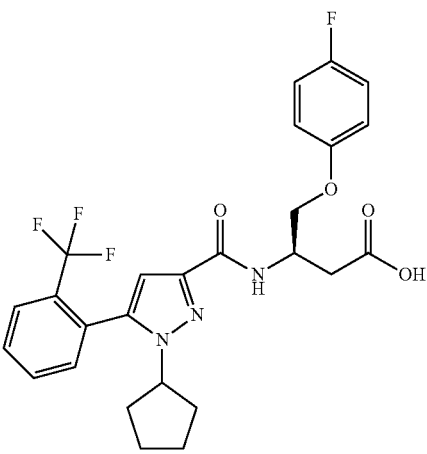 [SMILES: O=C(O)C[C@H](COc1ccc(F)cc1)NC(=O)c1cc(-c2ccccc2C(F)(F)F)n(C2CCCC2)n1] | 520.3 |
| 546 | 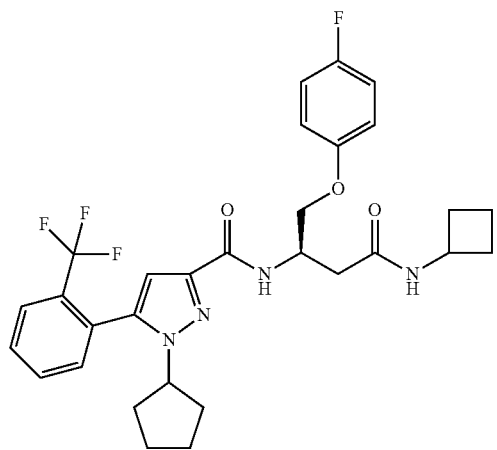 [SMILES: O=C(C[C@H](COc1ccc(F)cc1)NC(=O)c1cc(-c2ccccc2C(F)(F)F)n(C2CCCC2)n1)NC1CCC1] | 573.4 |
| 547 | 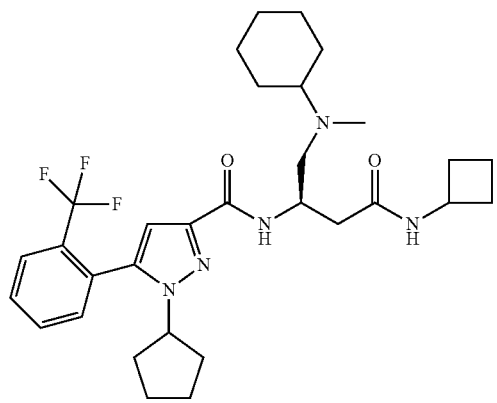 [SMILES: CN(C[C@@H](CC(=O)NC1CCC1)NC(=O)c1cc(-c2ccccc2C(F)(F)F)n(C2CCCC2)n1)C1CCCCC1] | 574.9 |

TABLE 1-continued
| ID # | STRUCTURE | [M + H]+/ [M − H]− |
|---|---|---|
| 548 | 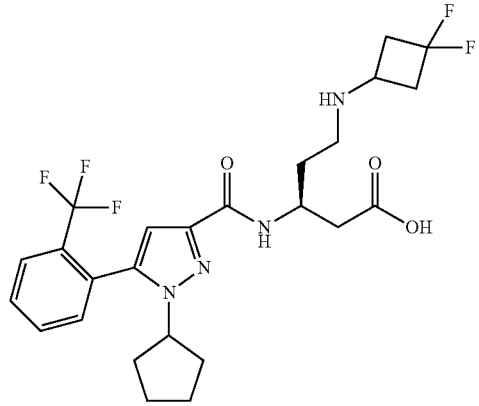 [SMILES: O=C(O)C[C@H](CCNC1CC(F)(F)C1)NC(=O)c1cc(-c2ccccc2C(F)(F)F)n(C2CCCC2)n1] | 529.2 |
| 549 | 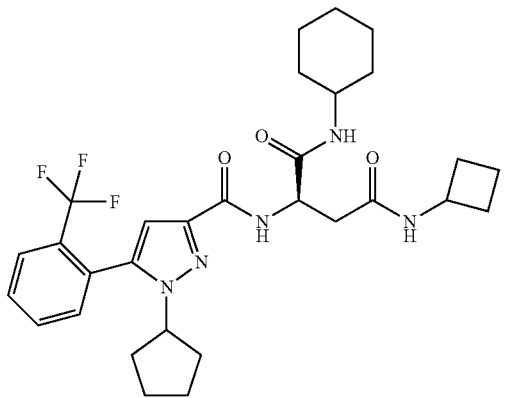 [SMILES: O=C(C[C@@H](NC(=O)c1cc(-c2ccccc2C(F)(F)F)n(C2CCCC2)n1)C(=O)NC1CCCCC1)NC1CCC1] | 574.3 |
| 550 | 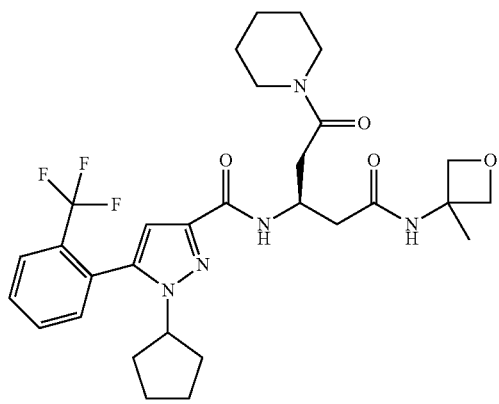 [SMILES: CC1(NC(=O)C[C@H](CC(=O)N2CCCCC2)NC(=O)c2cc(-c3ccccc3C(F)(F)F)n(C3CCCC3)n2)COC1] | 590.6 |

TABLE 1-continued

| ID # | STRUCTURE | [M + H]+/[M − H]− |
|---|---|---|
| 551 | 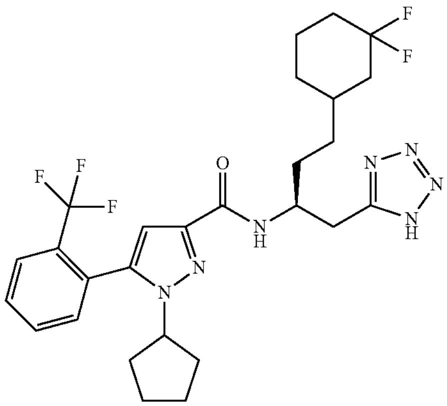 [SMILES: O=C(N[C@@H](CCC1CCCC(F)(F)C1)Cc1nnn[nH]1)c1cc(-c2ccccc2C(F)(F)F)n(C2CCCC2)n1] | 567.3 |
| 552 | 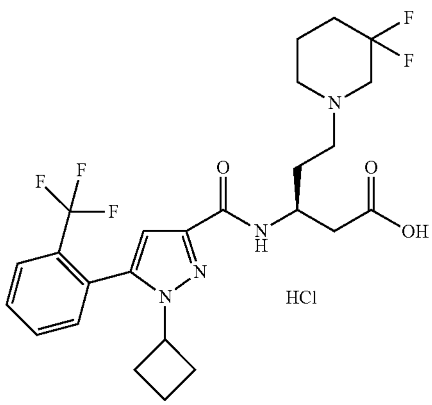 [SMILES: O=C(O)C[C@H](CCN1CCCC(F)(F)C1)NC(=O)c1cc(-c2ccccc2C(F)(F)F)n(C2CCC2)n1 ; Cl] | 529.2 |
| 553 | 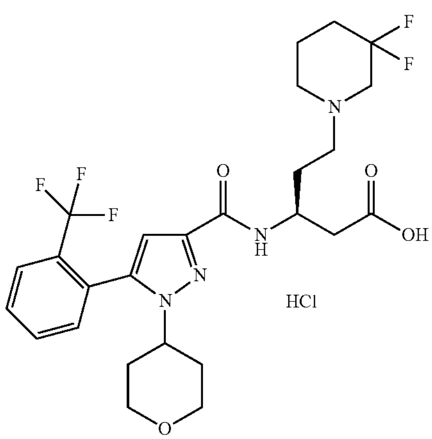 [SMILES: O=C(O)C[C@H](CCN1CCCC(F)(F)C1)NC(=O)c1cc(-c2ccccc2C(F)(F)F)n(C2CCOCC2)n1 ; Cl] | 559.2 |

TABLE 1-continued
| ID # | STRUCTURE | [M + H]+/[M − H]− |
|---|---|---|
| 554 | 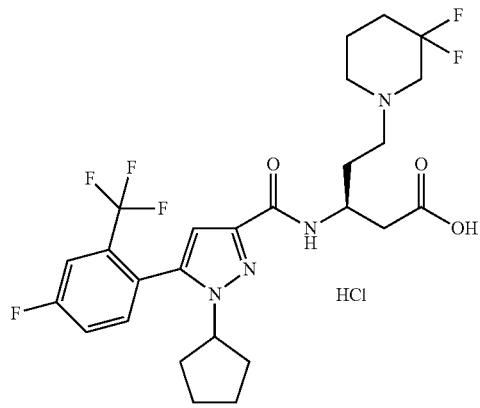 [SMILES: O=C(O)C[C@H](CCN1CCCC(F)(F)C1)NC(=O)c1cc(-c2ccc(F)cc2C(F)(F)F)n(C2CCCC2)n1 ; Cl] | 559.8 |
| 555 | 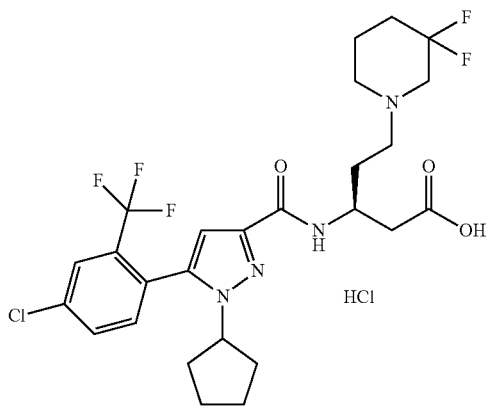 [SMILES: O=C(O)C[C@H](CCN1CCCC(F)(F)C1)NC(=O)c1cc(-c2ccc(Cl)cc2C(F)(F)F)n(C2CCCC2)n1 ; Cl] | 575.8 |
| 556 | 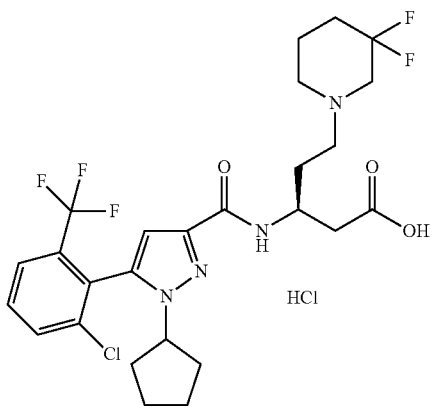 [SMILES: O=C(O)C[C@H](CCN1CCCC(F)(F)C1)NC(=O)c1cc(-c2c(Cl)cccc2C(F)(F)F)n(C2CCCC2)n1 ; Cl] | 577.6 |

TABLE 1-continued
| ID # | STRUCTURE | [M + H]+/ [M − H]− |
|---|---|---|
| 557 | 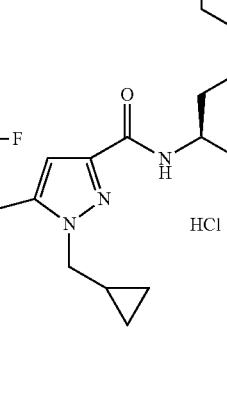 HCl | 529.2 |
| 558 | 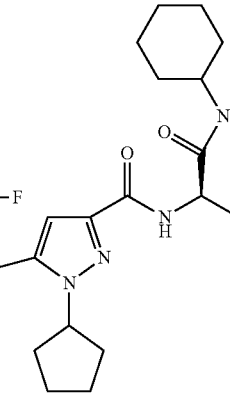 | 535.2 |
| 559 | 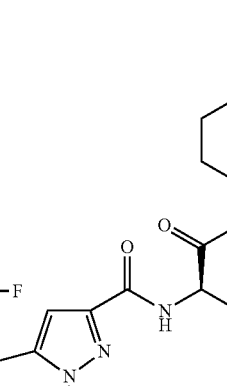 | 523.2 |

US 11,535,630 B2
TABLE 1-continued
| ID # | STRUCTURE | [M + H]+/ [M − H]− |
|---|---|---|
| 560 | 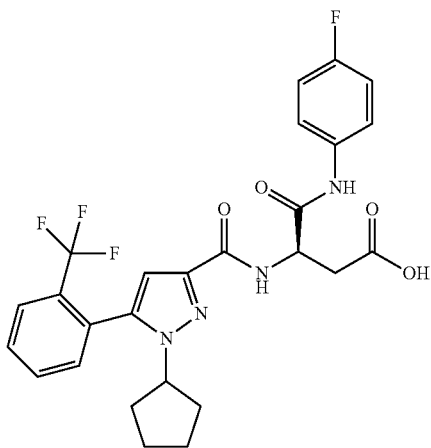 [SMILES: O=C(O)C[C@@H](NC(=O)c1cc(-c2ccccc2C(F)(F)F)n(C2CCCC2)n1)C(=O)Nc1ccc(F)cc1] | 533.1 |
| 561 | 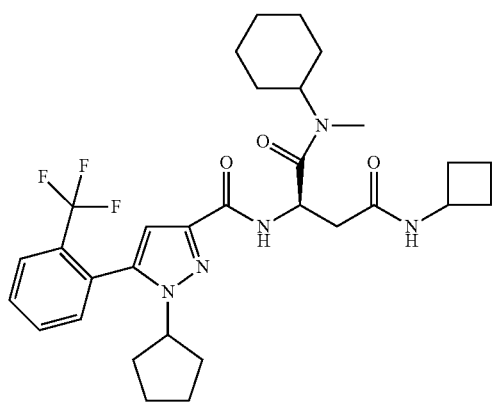 [SMILES: CN(C(=O)[C@@H](CC(=O)NC1CCC1)NC(=O)c1cc(-c2ccccc2C(F)(F)F)n(C2CCCC2)n1)C1CCCCC1] | 588.4 |
| 562 | 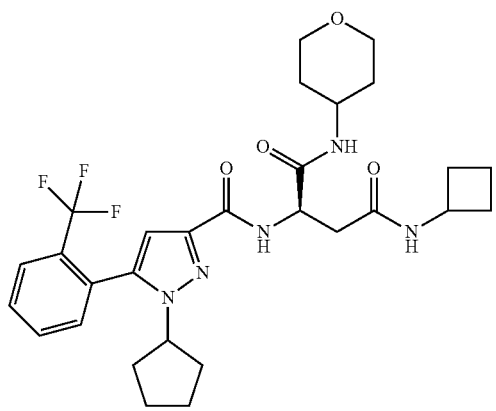 [SMILES: O=C(C[C@@H](NC(=O)c1cc(-c2ccccc2C(F)(F)F)n(C2CCCC2)n1)C(=O)NC1CCOCC1)NC1CCC1] | 576.3 |

| ID # | STRUCTURE | [M + H]+/ [M − H]− |
|---|---|---|
| 563 | 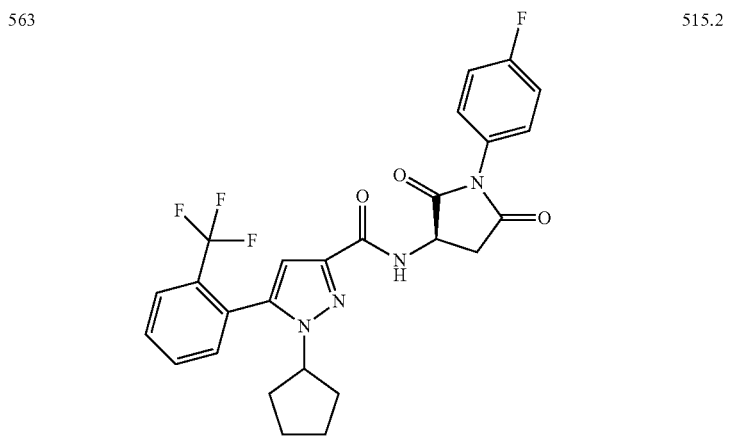 | 515.2 |
| 565 | 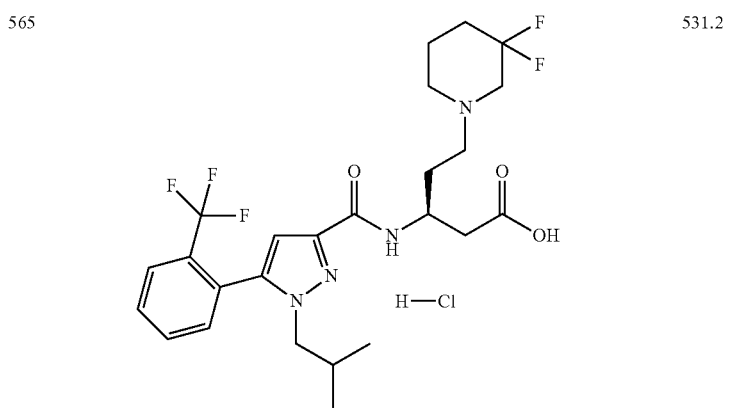 | 531.2 |
| 566 | 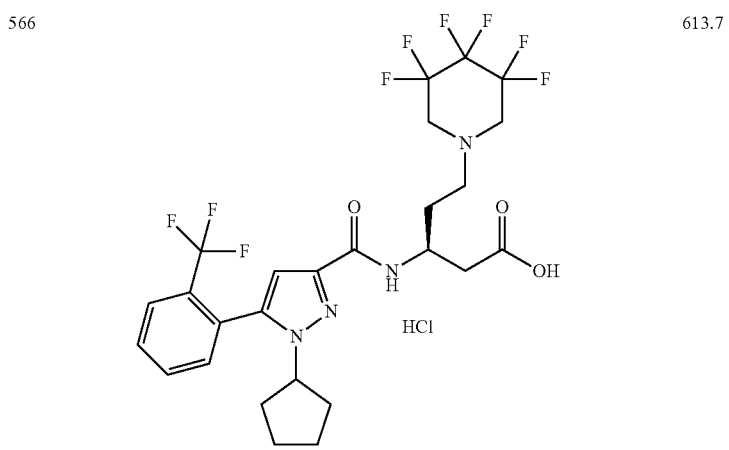 | 613.7 |

TABLE 1-continued
| ID # | STRUCTURE | [M + H]+/ [M − H]− |
|---|---|---|
| 567 | 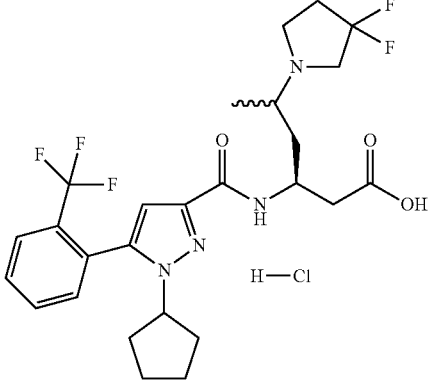 | 541.7 |
| 568 | 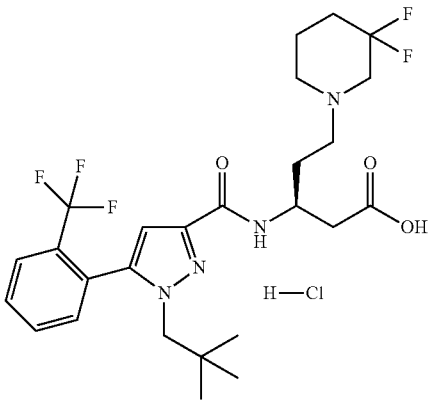 | 545.3 |
| 570 | 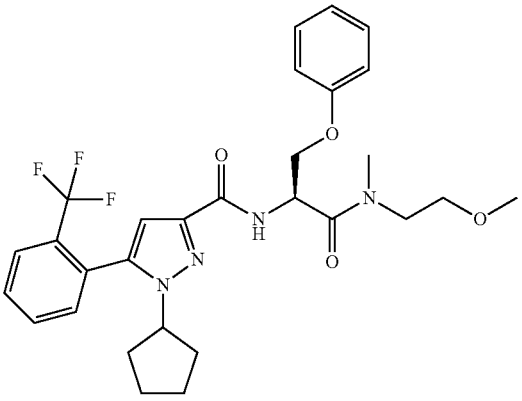 [SMILES: COCCN(C)C(=O)[C@H](COc1ccccc1)NC(=O)c1cc(-c2ccccc2C(F)(F)F)n(C2CCCC2)n1] | 559.3 |
| 571 | 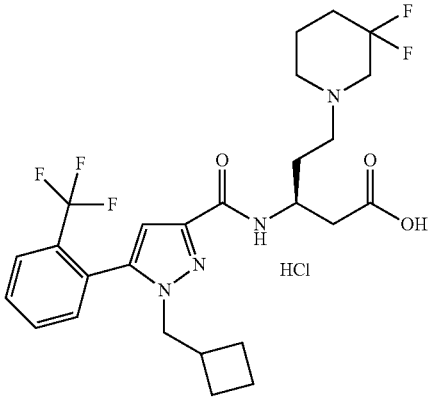 [SMILES: O=C(O)C[C@H](CCN1CCCC(F)(F)C1)NC(=O)c1cc(-c2ccccc2C(F)(F)F)n(CC2CCC2)n1 ; Cl] | 543.2 |

TABLE 1-continued
| ID # | STRUCTURE | [M + H]+/ [M − H]− |
|---|---|---|
| 572 | 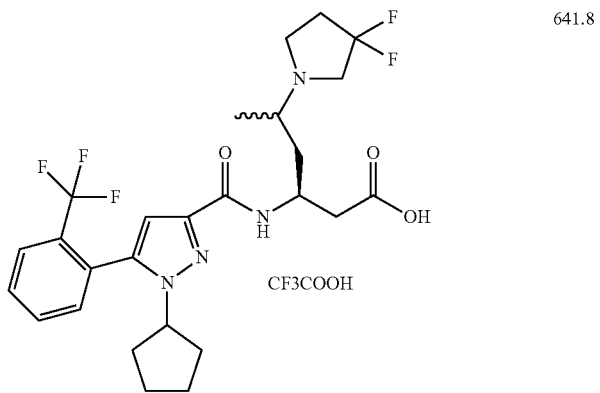 | 641.8 |
| 573 | 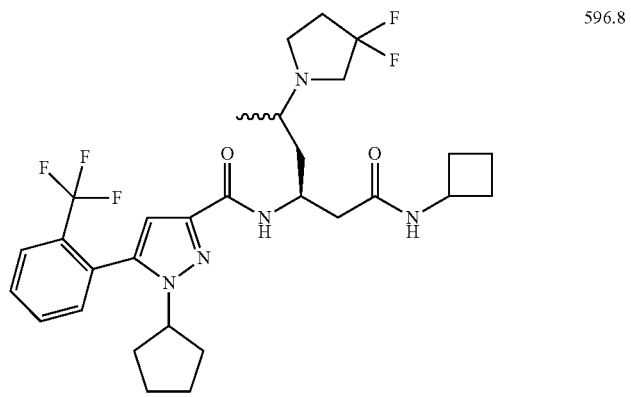 | 596.8 |
| 574 | 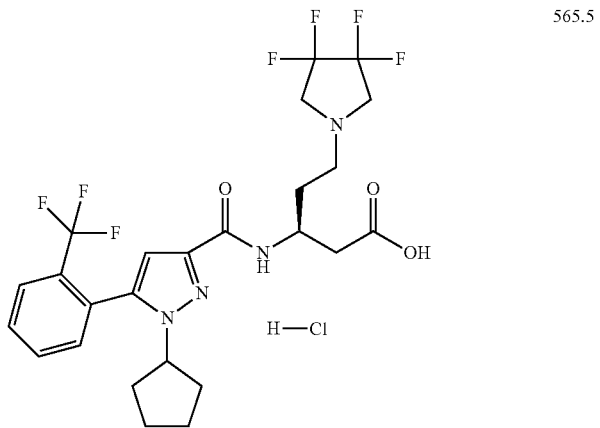 | 565.5 |

TABLE 1-continued

| ID # | STRUCTURE | [M + H]+/ [M − H]− |
|---|---|---|
| 575 | 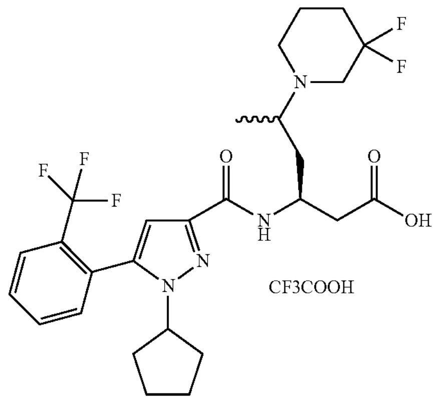 [SMILES: CC(C[C@@H](CC(=O)O)NC(=O)c1cc(-c2ccccc2C(F)(F)F)n(C2CCCC2)n1)N1CCCC(F)(F)C1 ; "CF3COOH"] | 556.0 |
| 576 | 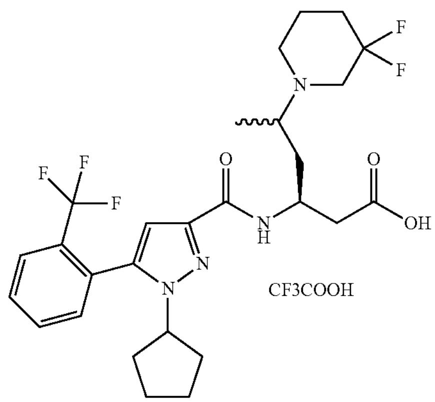 [SMILES: CC(C[C@@H](CC(=O)O)NC(=O)c1cc(-c2ccccc2C(F)(F)F)n(C2CCCC2)n1)N1CCCC(F)(F)C1 ; "CF3COOH"] | 556.1 |
| 577 | 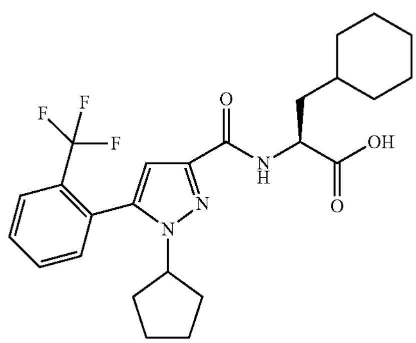 [SMILES: O=C(N[C@@H](CC1CCCCC1)C(=O)O)c1cc(-c2ccccc2C(F)(F)F)n(C2CCCC2)n1] | 478.3 |
| 578 | 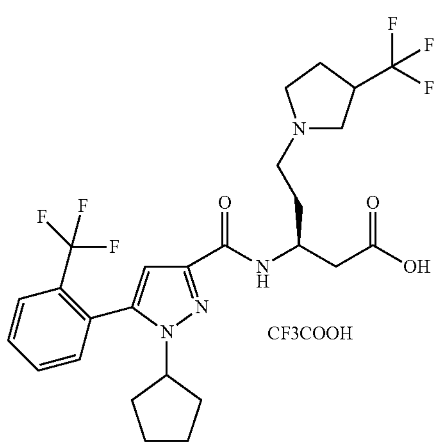 [SMILES: O=C(O)C[C@H](CCN1CCC(C(F)(F)F)C1)NC(=O)c1cc(-c2ccccc2C(F)(F)F)n(C2CCCC2)n1 ; "CF3COOH"] | 561.4 |

TABLE 1-continued

| ID # | STRUCTURE | [M + H]+/ [M − H]− |
|---|---|---|
| 579 | 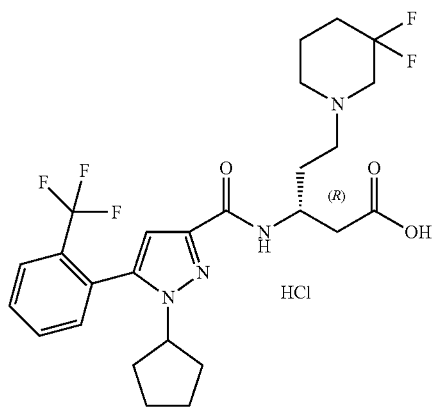 | 543.2 |
| 580 | 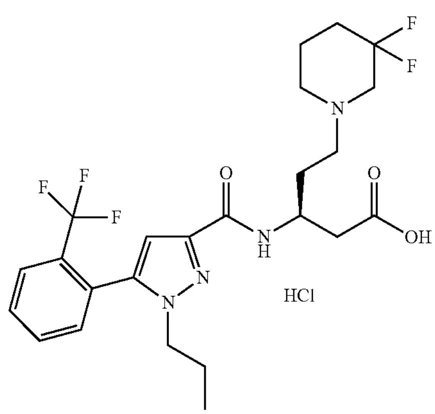 [SMILES: CCCn1nc(C(=O)N[C@@H](CCN2CCCC(F)(F)C2)CC(=O)O)cc1-c1ccccc1C(F)(F)F ; Cl] | 517.2 |
| 581 | 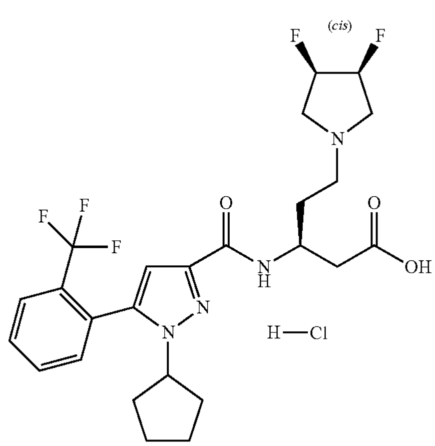 [SMILES: O=C(O)C[C@H](CCN1C[C@@H](F)[C@@H](F)C1)NC(=O)c1cc(-c2ccccc2C(F)(F)F)n(C2CCCC2)n1 ; Cl] | 530.1 |

TABLE 1-continued
| ID # | STRUCTURE | [M + H]+/ [M − H]− |
|---|---|---|
| 582 | 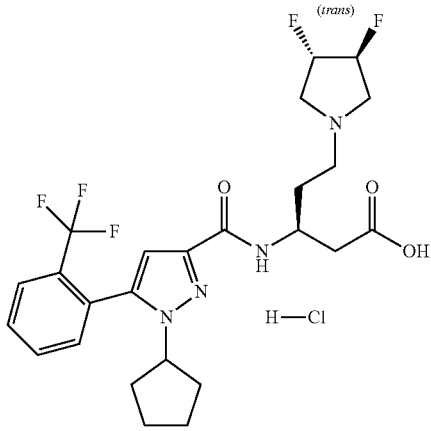 [SMILES: O=C(O)C[C@H](CCN1C[C@H](F)[C@@H](F)C1)NC(=O)c1cc(-c2ccccc2C(F)(F)F)n(C2CCCC2)n1 ; Cl] | 527.8 |
| 583 | 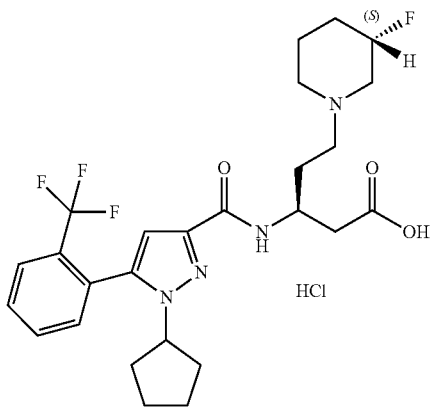 | 525.7 |
| 584 | 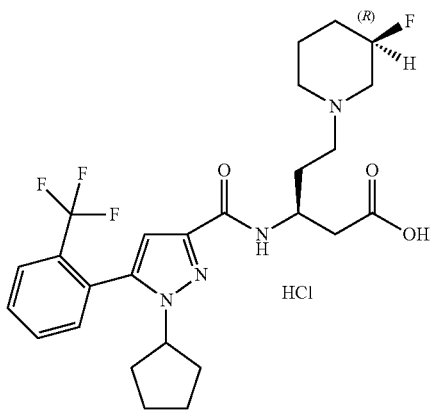 | 523.7 |

TABLE 1-continued
| ID # | STRUCTURE | [M + H]+/ [M − H]− |
|---|---|---|
| 585 | 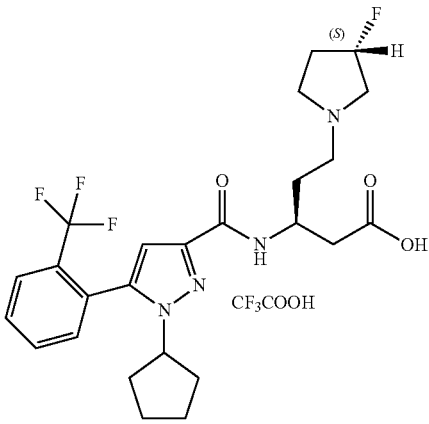 | 509.7 |
| 587 | 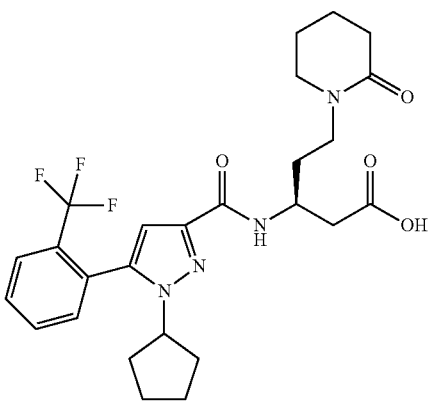 [SMILES: O=C(O)C[C@H](CCN1CCCCC1=O)NC(=O)c1cc(-c2ccccc2C(F)(F)F)n(C2CCCC2)n1] | 521.3 |
| 588 | 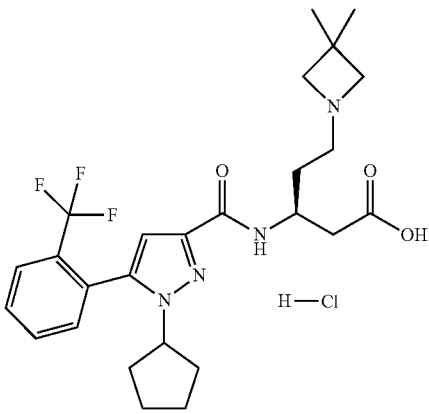 [SMILES: CC1(C)CN(CC[C@@H](CC(=O)O)NC(=O)c2cc(-c3ccccc3C(F)(F)F)n(C3CCCC3)n2)C1 ; Cl] | 507.4 |

TABLE 1-continued

| ID # | STRUCTURE | [M + H]+/ [M − H]− |
|---|---|---|
| 589 | 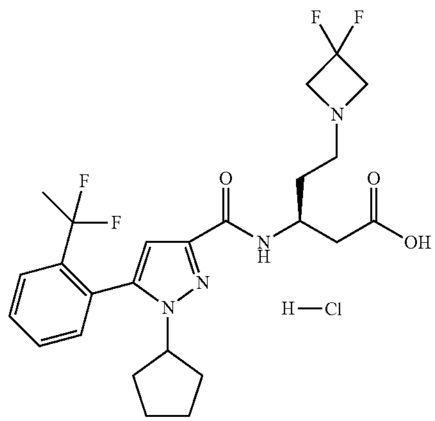 [SMILES: CC(F)(F)c1ccccc1-c1cc(C(=O)N[C@@H](CCN2CC(F)(F)C2)CC(=O)O)nn1C1CCCC1 ; Cl] | 511.3 |
| 590 | 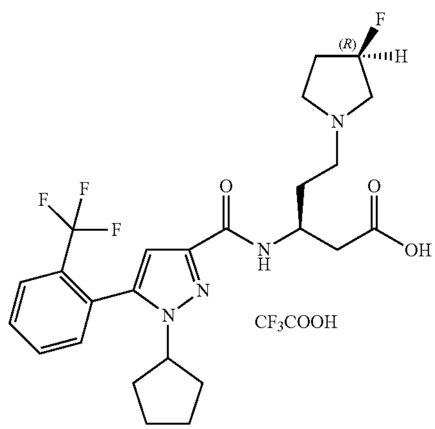 | 509.7 |
| 591 | 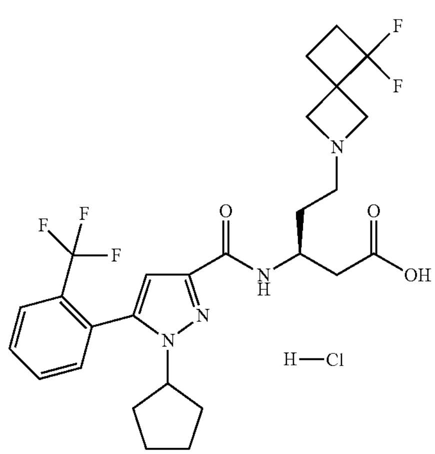 [SMILES: O=C(O)C[C@H](CCN1CC2(CCC2(F)F)C1)NC(=O)c1cc(-c2ccccc2C(F)(F)F)n(C2CCCC2)n1 ; Cl] | 553.7 |

TABLE 1-continued
| ID # | STRUCTURE | [M + H]+/ [M − H]− |
|---|---|---|
| 592 | 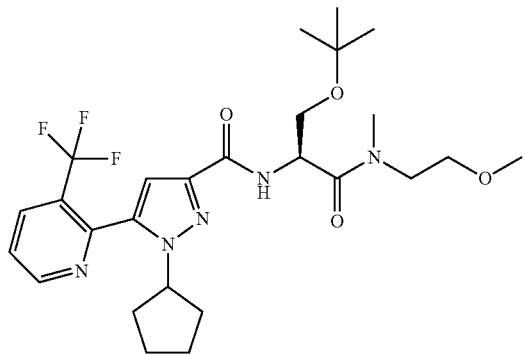 [SMILES: COCCN(C)C(=O)[C@H](COC(C)(C)C)NC(=O)c1cc(-c2ncccc2C(F)(F)F)n(C2CCCC2)n1] | 539.3 |
| 593 | 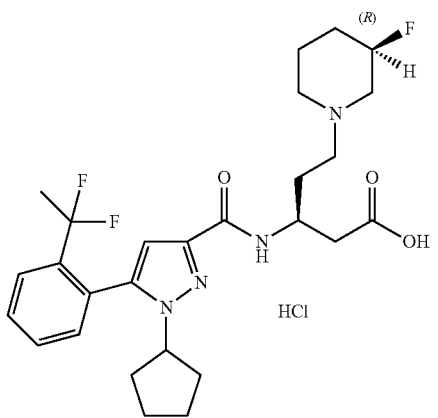 | 519.8 |
| 594 | 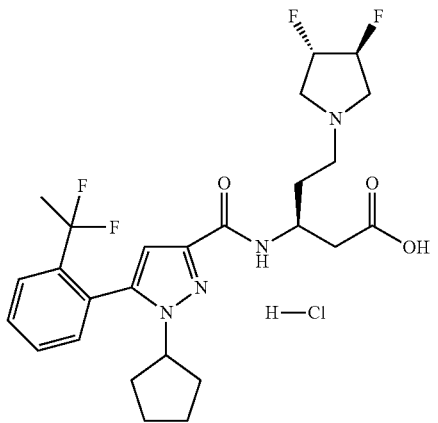 [SMILES: CC(F)(F)c1ccccc1-c1cc(C(=O)N[C@@H](CCN2C[C@H](F)[C@@H](F)C2)CC(=O)O)nn1C1CCCC1 ; Cl] | 525.7 |

TABLE 1-continued
| ID # | STRUCTURE | [M + H]+/ [M − H]− |
|---|---|---|
| 595 | 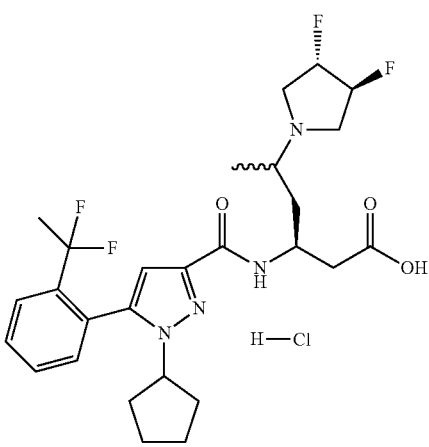 [SMILES: CC(C[C@@H](CC(=O)O)NC(=O)c1cc(-c2ccccc2C(C)(F)F)n(C2CCCC2)n1)N1C[C@H](F)[C@@H](F)C1 ; Cl] | 537.6 |
| 596 | 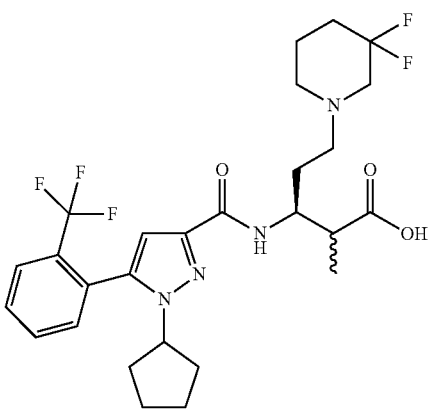 [SMILES: CC(C(=O)O)[C@H](CCN1CCCC(F)(F)C1)NC(=O)c1cc(-c2ccccc2C(F)(F)F)n(C2CCCC2)n1] | 557.3 |
| 597 | 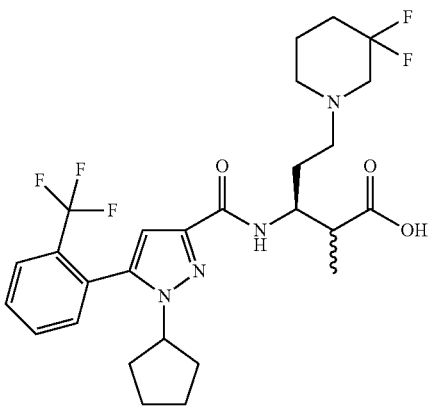 [SMILES: CC(C(=O)O)[C@H](CCN1CCCC(F)(F)C1)NC(=O)c1cc(-c2ccccc2C(F)(F)F)n(C2CCCC2)n1] | 557.2 |

TABLE 1-continued

| ID # | STRUCTURE | [M + H]+/ [M − H]− |
|---|---|---|
| 598 | 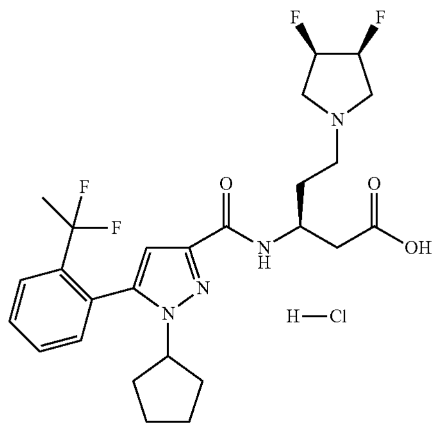 [SMILES: CC(F)(F)c1ccccc1-c1cc(C(=O)N[C@@H](CCN2C[C@@H](F)[C@@H](F)C2)CC(=O)O)nn1C1CCCC1 ; Cl] | 525.5 |
| 599 | 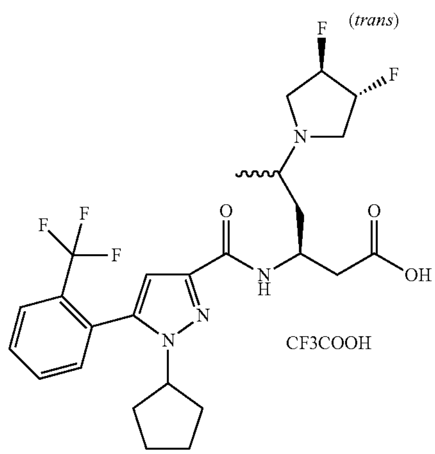 [SMILES: CC(C[C@@H](CC(=O)O)NC(=O)c1cc(-c2ccccc2C(F)(F)F)n(C2CCCC2)n1)N1C[C@@H](F)[C@H](F)C1 ; "CF3COOH"] | 537.4 |
| 600 | 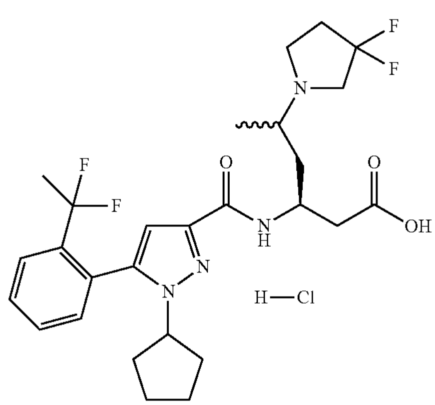 [SMILES: CC(C[C@@H](CC(=O)O)NC(=O)c1cc(-c2ccccc2C(C)(F)F)n(C2CCCC2)n1)N1CCC(F)(F)C1 ; Cl] | 537.5 |

TABLE 1-continued
| ID # | STRUCTURE | [M + H]+/[M − H]− |
|---|---|---|
| 601 | 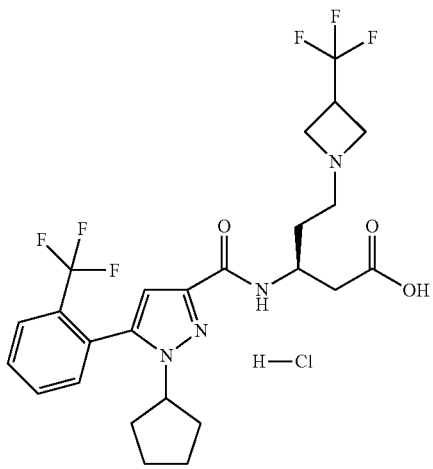 [SMILES: O=C(O)C[C@H](CCN1CC(C(F)(F)F)C1)NC(=O)c1cc(-c2ccccc2C(F)(F)F)n(C2CCCC2)n1 ; Cl] | 537.4 |
| 602 | 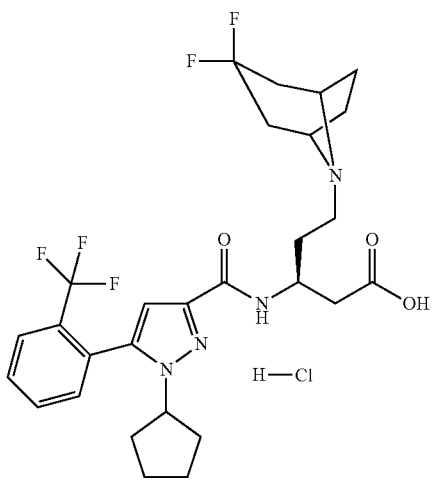 [SMILES: O=C(O)C[C@H](CCN1C2CCC1CC(F)(F)C2)NC(=O)c1cc(-c2ccccc2C(F)(F)F)n(C2CCCC2)n1 ; Cl] | 567.7 |
| 603 | 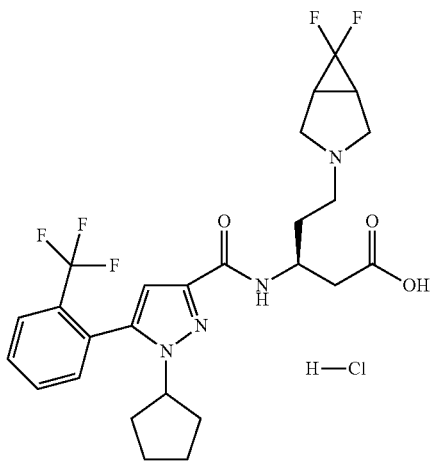 [SMILES: O=C(O)C[C@H](CCN1CC2C(C1)C2(F)F)NC(=O)c1cc(-c2ccccc2C(F)(F)F)n(C2CCCC2)n1 ; Cl] | 539.5 |

TABLE 1-continued

| ID # | STRUCTURE | [M + H]+/ [M − H]− |
|---|---|---|
| 604 | 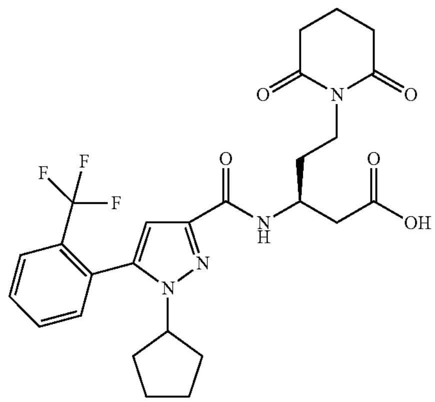 [SMILES: O=C(O)C[C@H](CCN1C(=O)CCCC1=O)NC(=O)c1cc(-c2ccccc2C(F)(F)F)n(C2CCCC2)n1] | 535.3 |
| 605 | 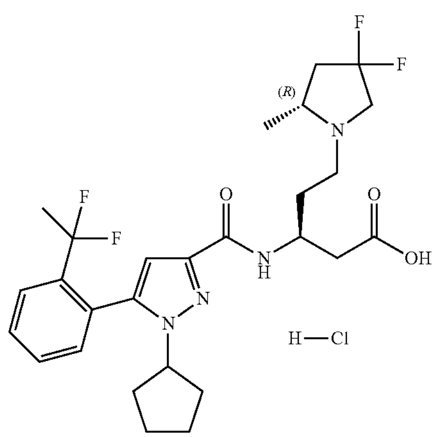 | 539.3 |
| 606 | 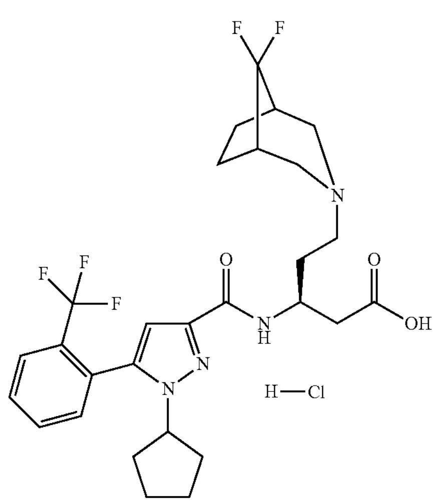 [SMILES: O=C(O)C[C@H](CCN1CC2CCC(C1)C2(F)F)NC(=O)c1cc(-c2ccccc2C(F)(F)F)n(C2CCCC2)n1 ; Cl] | 569.8 |

TABLE 1-continued

| ID # | STRUCTURE | [M + H]+/ [M − H]− |
|---|---|---|
| 607 | 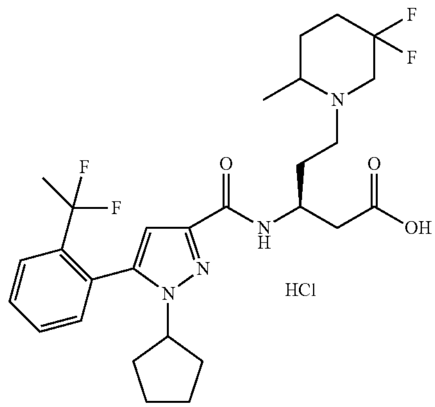 [SMILES: CC1CCC(F)(F)CN1CC[C@@H](CC(=O)O)NC(=O)c1cc(-c2ccccc2C(C)(F)F)n(C2CCCC2)n1 ; Cl] | 553.3 |
| 608 | 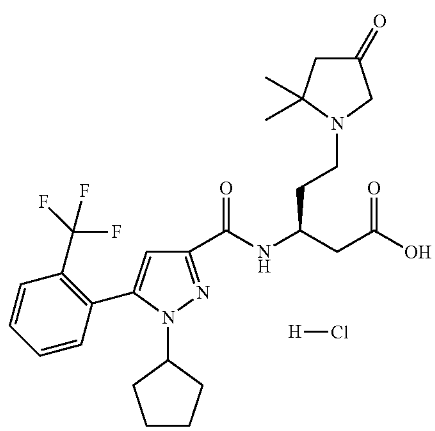 [SMILES: CC1(C)CC(=O)CN1CC[C@@H](CC(=O)O)NC(=O)c1cc(-c2ccccc2C(F)(F)F)n(C2CCCC2)n1 ; Cl] | 535.3 |
| 609 | 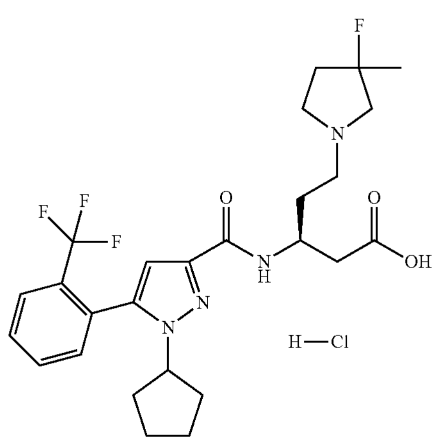 [SMILES: CC1(F)CCN(CC[C@@H](CC(=O)O)NC(=O)c2cc(-c3ccccc3C(F)(F)F)n(C3CCCC3)n2)C1 ; Cl] | 523.7 |

US 11,535,630 B2
TABLE 1-continued
| ID # | STRUCTURE | [M + H]+/ [M − H]− |
|---|---|---|
| 610 | 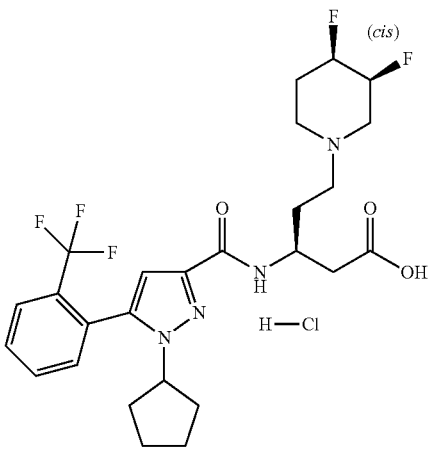 | 541.3 |
| 611 | 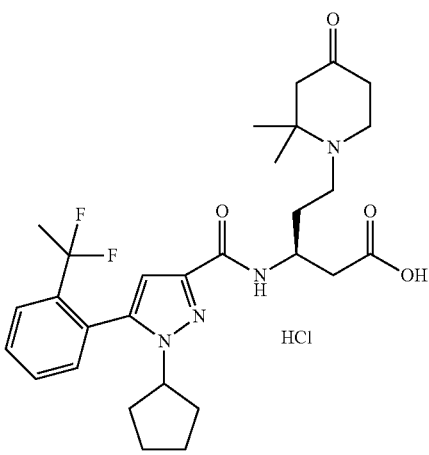 [SMILES: CC(F)(F)c1ccccc1-c1cc(C(=O)N[C@@H](CCN2CCC(=O)CC2(C)C)CC(=O)O)nn1C1CCCC1 ; Cl] | 545.4 |
| 612 | 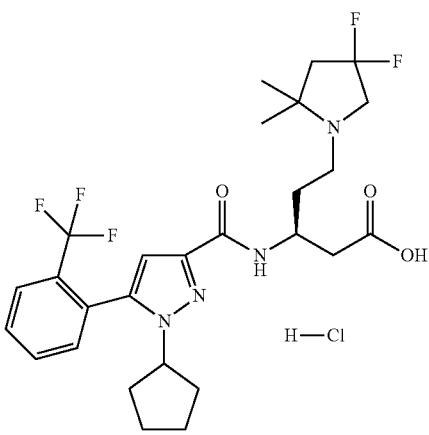 [SMILES: CC1(C)CC(F)(F)CN1CC[C@@H](CC(=O)O)NC(=O)c1cc(-c2ccccc2C(F)(F)F)n(C2CCCC2)n1 ; Cl] | 557.3 |

TABLE 1-continued
| ID # | STRUCTURE | [M + H]+/ [M − H]− |
|---|---|---|
| 613 | 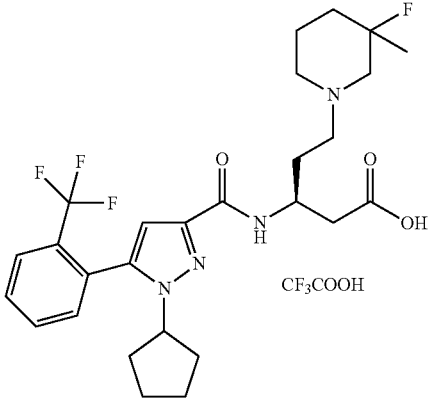 [SMILES: CC1(F)CCCN(CC[C@@H](CC(=O)O)NC(=O)c2cc(-c3ccccc3C(F)(F)F)n(C3CCCC3)n2)C1 ; "CF3COOH"] | 537.3 |
| 614 | 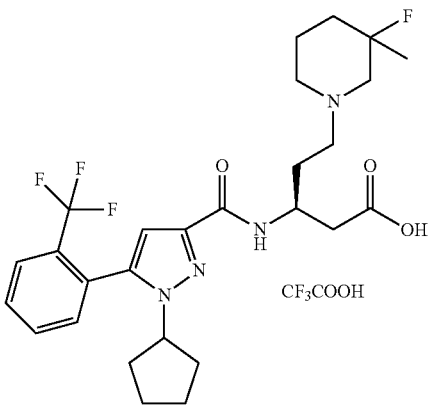 [SMILES: CC1(F)CCCN(CC[C@@H](CC(=O)O)NC(=O)c2cc(-c3ccccc3C(F)(F)F)n(C3CCCC3)n2)C1 ; "CF3COOH"] | 537.5 |
| 615 | 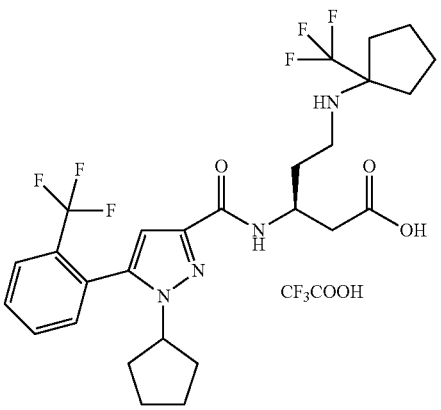 [SMILES: O=C(O)C[C@H](CCNC1(C(F)(F)F)CCCC1)NC(=O)c1cc(-c2ccccc2C(F)(F)F)n(C2CCCC2)n1 ; "CF3COOH"] | 573.7 |

TABLE 1-continued
| ID # | STRUCTURE | [M + H]+/ [M − H]− |
|---|---|---|
| 618 | 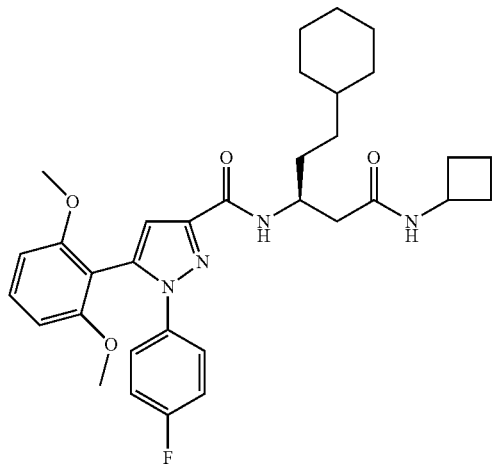 [SMILES: COc1cccc(OC)c1-c1cc(C(=O)N[C@@H](CCC2CCCCC2)CC(=O)NC2CCC2)nn1-c1ccc(F)cc1] | 577.5 |
| 621 | 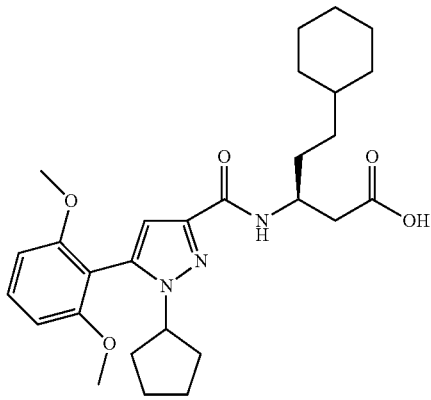 [SMILES: COc1cccc(OC)c1-c1cc(C(=O)N[C@@H](CCC2CCCCC2)CC(=O)O)nn1C1CCCC1] | 496.7 |
| 622 | 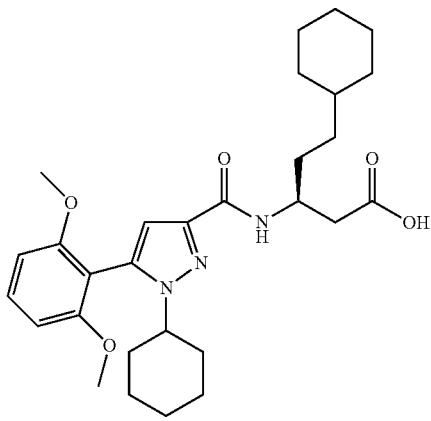 [SMILES: COc1cccc(OC)c1-c1cc(C(=O)N[C@@H](CCC2CCCCC2)CC(=O)O)nn1C1CCCCC1] | 510.6 |

TABLE 1-continued
| ID # | STRUCTURE | [M + H]+/ [M − H]− |
|---|---|---|
| 623 | 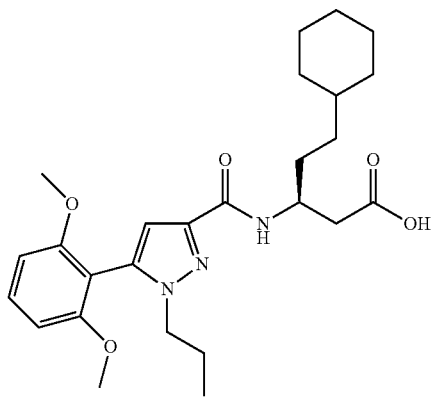 [SMILES: CCCn1nc(C(=O)N[C@@H](CCC2CCCCC2)CC(=O)O)cc1-c1c(OC)cccc1OC] | 470.6 |
| 624 | 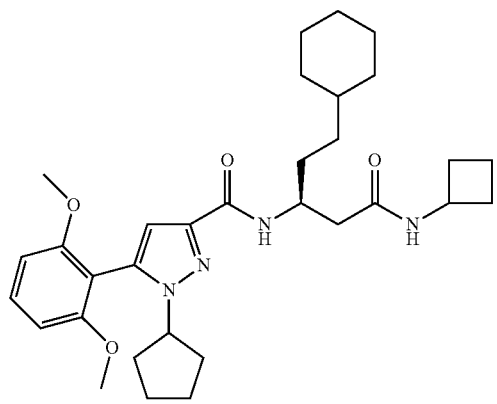 [SMILES: COc1cccc(OC)c1-c1cc(C(=O)N[C@@H](CCC2CCCCC2)CC(=O)NC2CCC2)nn1C1CCCC1] | 551.6 |
| 625 | 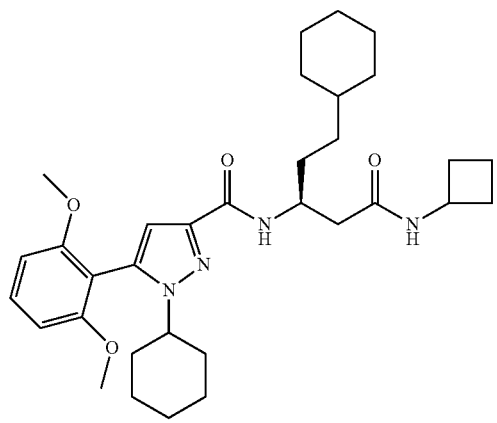 [SMILES: COc1cccc(OC)c1-c1cc(C(=O)N[C@@H](CCC2CCCCC2)CC(=O)NC2CCC2)nn1C1CCCCC1] | 565.7 |

TABLE 1-continued
| ID # | STRUCTURE | [M + H]+/ [M − H]− |
|---|---|---|
| 626 | 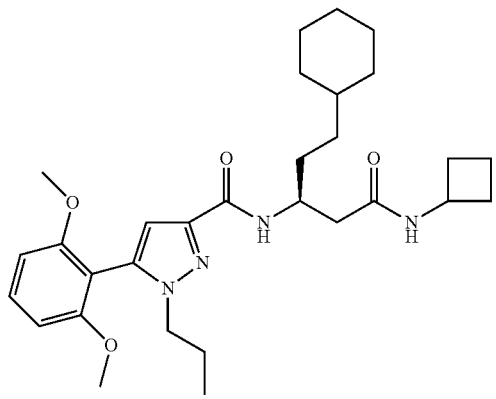 [SMILES: CCCn1nc(C(=O)N[C@@H](CCC2CCCCC2)CC(=O)NC2CCC2)cc1-c1c(OC)cccc1OC] | 526.0 |
| 627 | 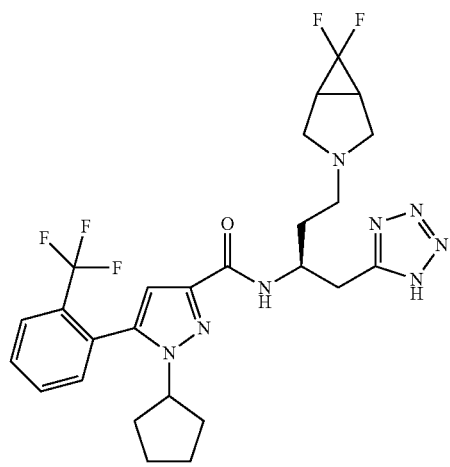 [SMILES: O=C(N[C@@H](CCN1CC2C(C1)C2(F)F)Cc1nnn[nH]1)c1cc(-c2ccccc2C(F)(F)F)n(C2CCCC2)n1] | 571.7 |
| 628 | 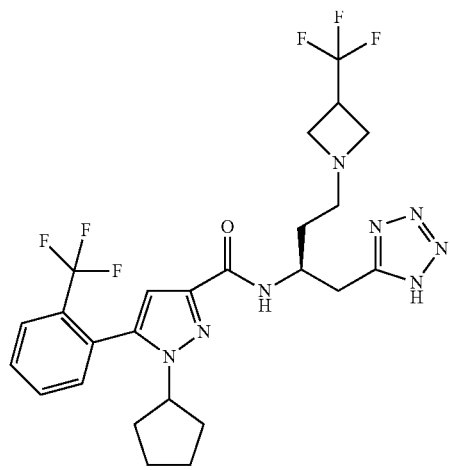 [SMILES: O=C(N[C@@H](CCN1CC(C(F)(F)F)C1)Cc1nnn[nH]1)c1cc(-c2ccccc2C(F)(F)F)n(C2CCCC2)n1] | 565.4 |

TABLE 1-continued
| ID # | STRUCTURE | [M + H]+/[M − H]− |
|---|---|---|
| 629 | 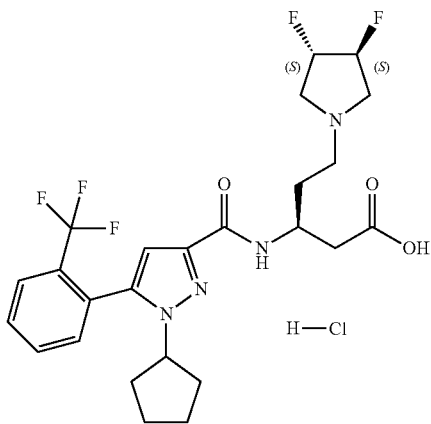 | 527.8 |
| 630 | 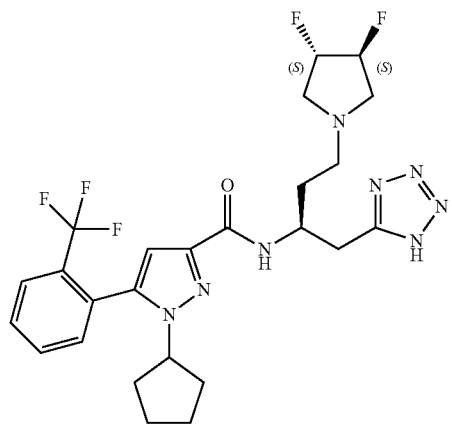 | 553.7 |
| 631 | 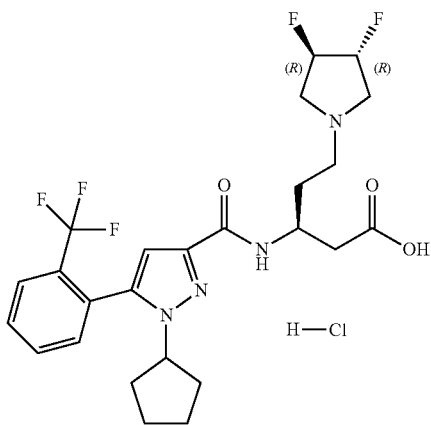 | 528.0 |

TABLE 1-continued
| ID # | STRUCTURE | [M + H]+/ [M − H]− |
|---|---|---|
| 634 | 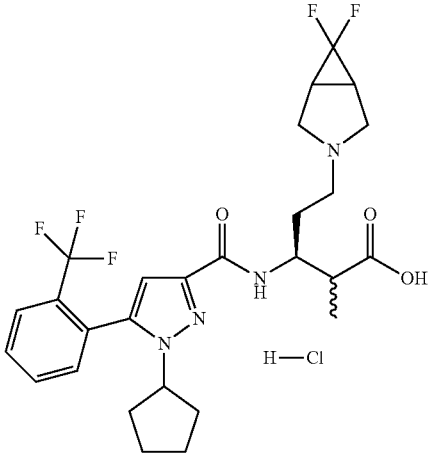 | 555.9 |
| 635 | 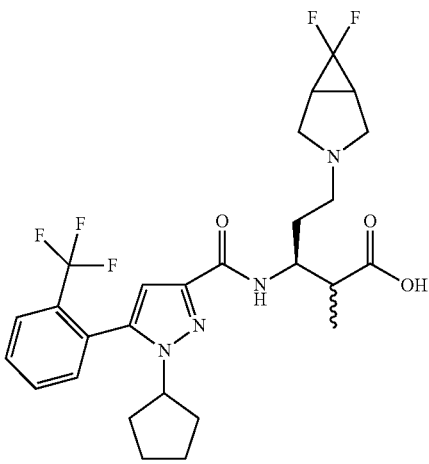 [SMILES: CC(C(=O)O)[C@H](CCN1CC2C(C1)C2(F)F)NC(=O)c1cc(-c2ccccc2C(F)(F)F)n(C2CCCC2)n1] | 555.9 |
| 636 | 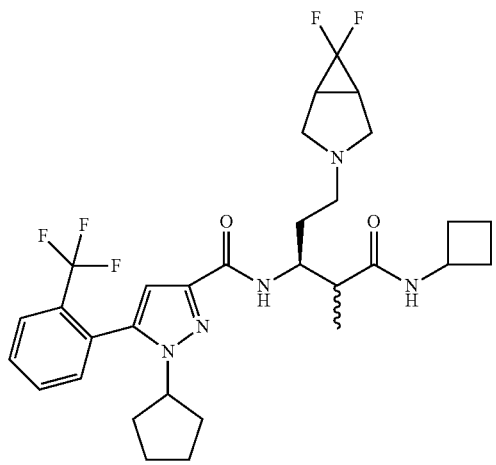 [SMILES: CC(C(=O)NC1CCC1)[C@H](CCN1CC2C(C1)C2(F)F)NC(=O)c1cc(-c2ccccc2C(F)(F)F)n(C2CCCC2)n1] | 608.9 |

TABLE 1-continued
| ID # | STRUCTURE | [M + H]+/ [M − H]− |
|---|---|---|
| 637 | 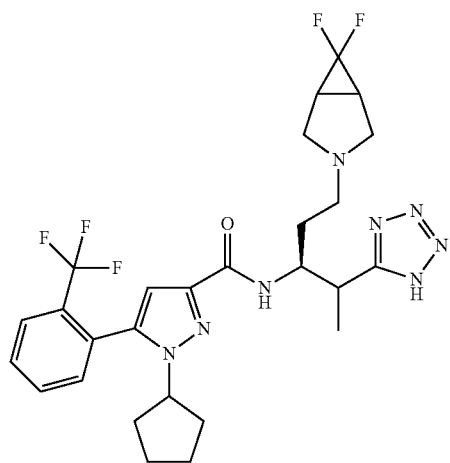 [SMILES: CC(c1nnn[nH]1)[C@H](CCN1CC2C(C1)C2(F)F)NC(=O)c1cc(-c2ccccc2C(F)(F)F)n(C2CCCC2)n1] | 579.8 |
| 638 | 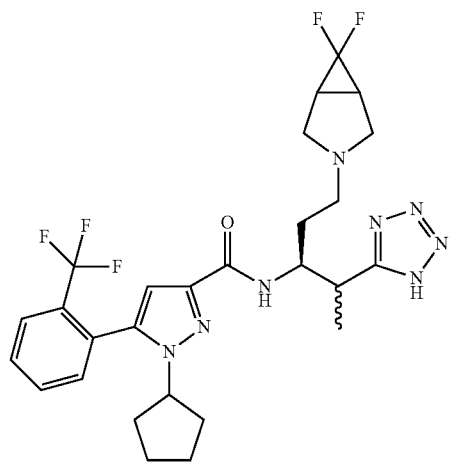 [SMILES: CC(c1nnn[nH]1)[C@H](CCN1CC2C(C1)C2(F)F)NC(=O)c1cc(-c2ccccc2C(F)(F)F)n(C2CCCC2)n1] | 579.8 |
| 639 | 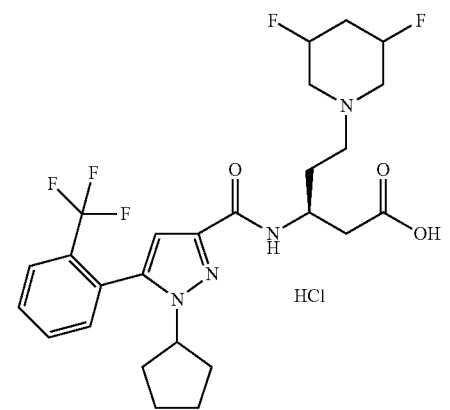 [SMILES: O=C(O)C[C@H](CCN1CC(F)CC(F)C1)NC(=O)c1cc(-c2ccccc2C(F)(F)F)n(C2CCCC2)n1 ; Cl] | 541.5 |

TABLE 1-continued
| ID # | STRUCTURE | [M + H]+/ [M − H]− |
|---|---|---|
| 640 | 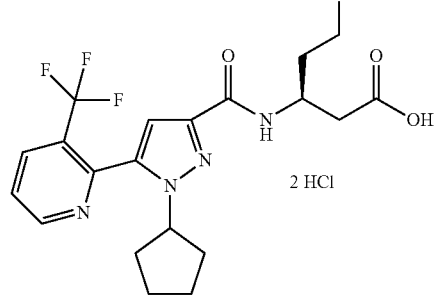 2 HCl | 542.7 |
| 641 | 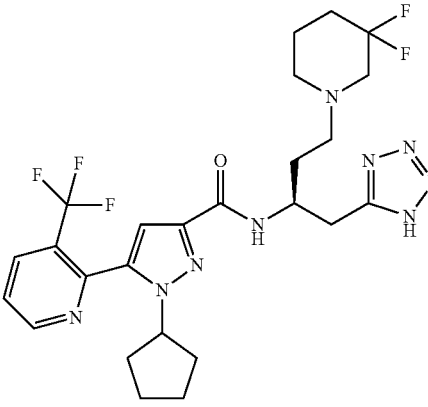 | 568.5 |
| 643 | 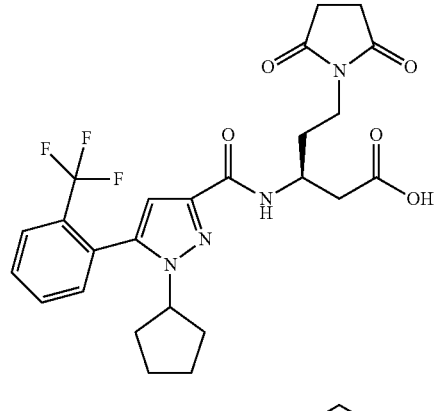 | 519.6 |
| 646 | 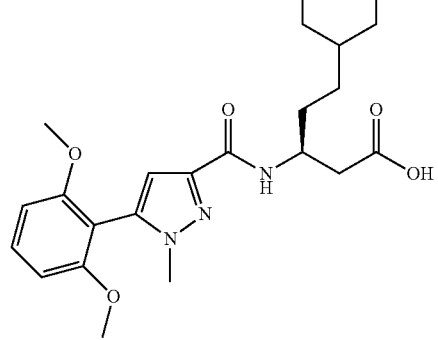 | 442.6 |

TABLE 1-continued
| ID # | STRUCTURE | [M + H]+/ [M − H]− |
|---|---|---|
| 647 | 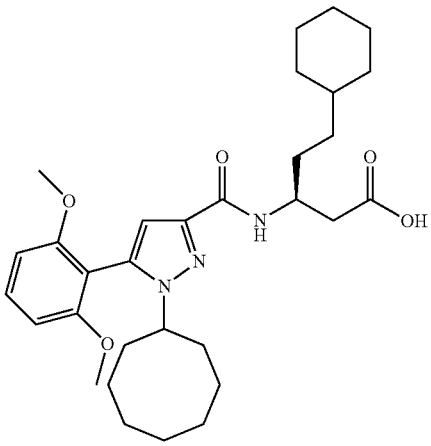 [SMILES: COc1cccc(OC)c1-c1cc(C(=O)N[C@@H](CCC2CCCCC2)CC(=O)O)nn1C1CCCCCCC1] | 538.7 |
| 648 | 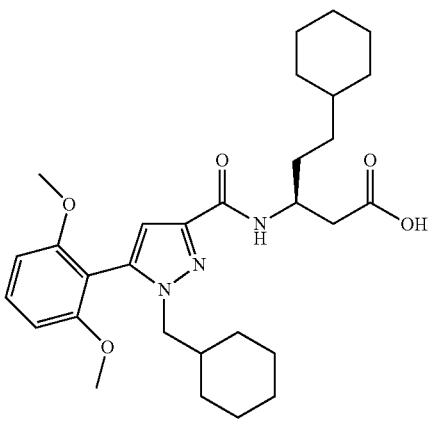 [SMILES: COc1cccc(OC)c1-c1cc(C(=O)N[C@@H](CCC2CCCCC2)CC(=O)O)nn1CC1CCCCC1] | 524.8 |
| 649 | 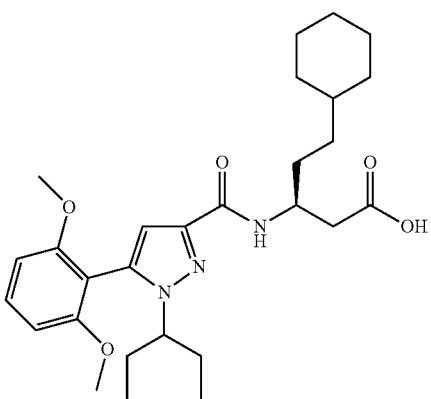 [SMILES: CCC(CC)n1nc(C(=O)N[C@@H](CCC2CCCCC2)CC(=O)O)cc1-c1c(OC)cccc1OC] | 498.9 |

TABLE 1-continued

| ID # | STRUCTURE | [M + H]+/ [M − H]− |
|---|---|---|
| 655 | 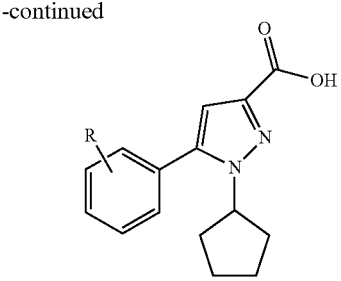 | 559.3 |

5.2. Method and Preparation of Representative Compounds

Scheme 2. Preparation of 5-substituted pyrazoles

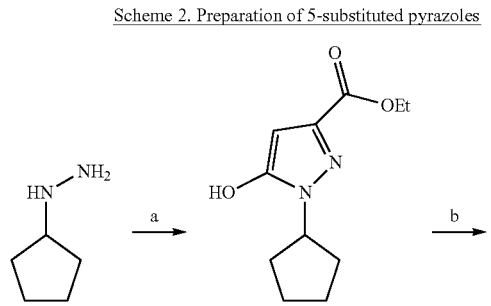

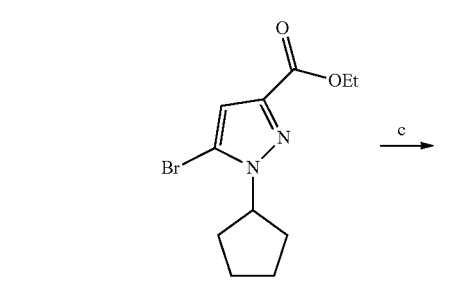

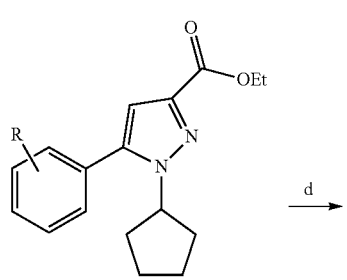

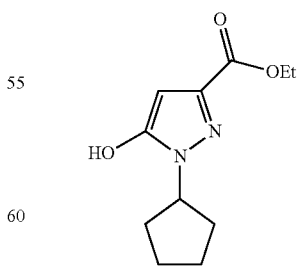

Reagents and conditions: (a) sodium diethyl oxaloacetate, AcOH, EtOH, reflux; 24 h; (b) POBr₃, ACN, reflux; 18 h; (c) Ar—B(OH)₂, Pd(PPh₃)₄, 2M Na₂CO₃, THF, reflux, 18 h (d) LiOH, THF, MeOH, H₂O, rt, 18 h Intermediates 1-cyclopentyl-5-phenyl-1H-pyrazole-3-carboxylic acids were synthesized as described in Scheme 2. Ethyl 1-cyclopentyl-5-hydroxy-1H-pyrazole-3-carboxylate was obtained by reacting cyclopentylhydrazine-TFA salt and sodium diethyl oxaloacetate in the presence of acetic acid. Treatment of ethyl 1-cyclopentyl-5-hydroxy-1H-pyrazole-3-carboxylate with phosphorus oxybromide provided ethyl 5-bromo-1-cyclopentyl-1H-pyrazole-3-carboxylatein 51% yield. Suzuki coupling of ethyl 5-bromo-1-cyclopentyl-1H-pyrazole-3-carboxylatewith appropriate aryl boronic acids provided intermediates with diverse 5-substituted pyrazole ester that were then subjected to basic hydrolysis to afford carboxylic acid intermediates.

Ethyl 5-hydroxy-1-cylopentyl-1H-pyrazole-3-carboxylate: To a solution of cyclopentyl hydrazine ditrifluoroacetic acid salt (85 g, 251 mmol) in 500 mL EtOH was added AcOH (14.4 mL, 251 mmol). Sodium diethyl oxaloacetate (48 g, 228 mmol) was added portionwise under stirring and the resulting mixture was heated to reflux for 24 h. The reaction mixture was cooled to rt and the solvent was evaporated in vacuo. The residue was partitioned between EtOAc (500 mL) and 0.5 N HCl (750 mL) and the organic phase was separated. The aqueous phase was extracted with EtOAc (200 mL×2) and the organic phases were combined, washed with brine (300 mL), dried using $Na_2SO_4$ and concentrated to afford crude oil. Crude oil was diluted with 30 mL EtOAc and then MTBE (200 mL) was added to afford a white crystalline precipitate which was filtered and dried to give 32.6 g of ethyl 5-hydroxy-1-cylopentyl-1H-pyrazole-3-carboxylateas white solid. TLC $R_f$=0.50 (hexane/EtOAc, 3:1); $^1$H NMR (200 MHz, $CDCl_3$): δ=1.22-1.30 (t, 3H, $CH_3$), 1.58-1.68 (m, 2H, $CH_2$), 1.82-2.10 (m, 6H, $CH_2$×3), 4.22-4.32 (q, 2H, $CH_2$), 4.80-4.90 (m, 1H, CH), 6.90 (s, 1H, Ar). LCMS (ESI): m/z calculated for $C_{11}H_{16}N_2O_3$ [M+H$^+$]: 225, Found: 225.2.

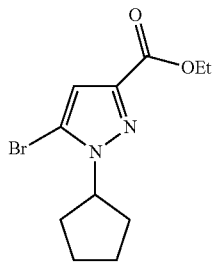 [SMILES: CCOC(=O)c1cc(Br)n(C2CCCC2)n1]

Ethyl 5-bromo-1-cylopentyl-1H-pyrazole-3-carboxylate: To a suspension of ethyl 5-hydroxy-1-cyclopentyl-1H-pyrazole-3-carboxylate (32.6 g, 145 mmol) in $CH_3CN$ (360 mL) was added $POBr_3$ (209 g, 725 mmol) in portions and the mixture was heated to reflux for 18 h. Reaction mixture was cooled to 0° C. and added slowly to sat. $Na_2CO_3$ (1000 mL) at 0° C. The product was extracted using EtOAc (500 mL×3) and the organic phase was dried using $Na_2SO_4$, silica gel (60 g) was added, and the solvent were evaporated in vacuo to afford a silica plug. Purification was performed by flash chromatography using Combiflash® $R_f$ (0-10% EtOAc in Hexanes) and the fractions containing the product (TLC) were pooled and evaporated to provide 21 g of ethyl 5-bromo-1-cylopentyl-1H-pyrazole-3-carboxylateas a brown oil. TLC $R_f$=0.80 (hexane/EtOAc, 3:1); $^1$H NMR (200 MHz, $CDCl_3$): δ=1.22-1.30 (t, 3H, $CH_3$), 1.58-1.68 (m, 2H, $CH_2$), 1.82-2.10 (m, 6H, $CH_2$×3), 4.22-4.32 (q, 2H, $CH_2$), 4.80-4.90 (m, 1H, CH), 6.90 (s, 1H, Ar). LCMS (ESI): m/z calculated for $C_{11}H_{15}BrN_2O_2$ [M$^+$, Br$^{79}$]: 287, Found: 287.3; m/z calculated for $C_{11}H_{15}BrN_2O_2$ [M$^+$, Br$^{81}$]: 289, Found: 289.2.

General procedure for the synthesis of ethyl 1-cylopentyl-5-aryl-1H-pyrazole-3-carboxylates: To a solution of ethyl 5-bromo-1-cyclopentyl-1H-pyrazole-3-carboxylate (1 equiv.) in THF under nitrogen atmosphere was added Pd(PPh$_3$)$_4$ (2 or 5 mol %) and appropriate aryl boronic acid (1.2 or 2.0 equiv.) followed by 2 M $Na_2CO_3$ (3 equiv.). The mixture was heated to reflux until TLC/LCMS showed no further utilization of reactant 5-bromo-1-cyclopentyl-1H-pyrazole-3-carboxylate. Reaction mixture was cooled to rt and then quenched with water (2 mL) and extracted with EtOAc (2 mL×2). Organic phases were combined, dried using $Na_2SO_4$, silica gel (200 mg) was added, and the solvent were evaporated in vacuo to afford a silica plug. Purification was performed by flash chromatography using Combiflash® $R_f$ (0-10% EtOAc in Hexanes) and the fractions containing the product (TLC) were pooled and evaporated to provide ethyl 1-cylopentyl-5-aryl-1H-pyrazole-3-carboxylates.

EXAMPLES

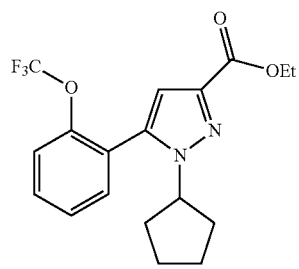 [SMILES: CCOC(=O)c1cc(-c2ccccc2OC(F)(F)F)n(C2CCCC2)n1]

Ethyl 1-cyclopentyl-5-(2-(trifluoromethoxy)phenyl)-1H-pyrazole-3-carboxylate: Using the general procedure described above, reaction between 5-bromo-1-cyclopentyl-1H-pyrazole-3-carboxylate (200 mg, 0.70 mmol) and 2-trifluoromethoxyphenyl boronic acid (172.2 mg, 0.84 mmol) in the presence of Pd(PPh$_3$)$_4$ (16 mg, 0.014 mmol) and 2 M $Na_2CO_3$ (1.04 mL, 2.1 mmol) in THF (5 mL) for 18 h provided 204 mg (80%) of ethyl 1-cyclopentyl-5-(2-(trifluoromethoxy)phenyl)-1H-pyrazole-3-carboxylate as a colorless oil. TLC $R_f$=0.85 (hexane/EtOAc, 3:1); $^1$H NMR (200 MHz, $CDCl_3$): δ=1.30-1.40 (t, 3H, $CH_3$), 1.42-1.60 (m, 2H, $CH_2$), 1.80-2.25 (m, 6H, $CH_2$×3), 4.20-4.45 (m, 3H, CH and $CH_2$), 6.85 (s, 1H, Ar), 7.20-7.50 (m, 4H, Ar). LCMS (ESI): m/z calculated for $C_{18}H_{19}F_3N_2O_3$+H [M+H$^+$]: 369, Found: 369.1.

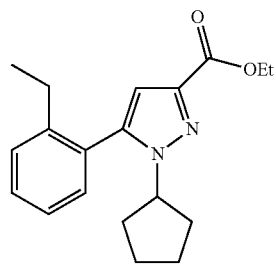 [SMILES: CCOC(=O)c1cc(-c2ccccc2CC)n(C2CCCC2)n1]

Ethyl 1-cyclopentyl-5-(2-ethylphenyl)-1H-pyrazole-3-carboxylate: Using the general procedure described above, reaction between 5-bromo-1-cyclopentyl-1H-pyrazole-3-carboxylate (200 mg, 0.7 mmol) and 2-ethylphenyl boronic acid (125.4 mg, 0.84 mmol) in the presence of Pd(PPh$_3$)$_4$ (16 mg, 0.014 mmol) and 2 M $Na_2CO_3$ (1.04 mL, 2.1 mmol) in THF (5 mL) for 18 h provided 180 mg (83%) of ethyl 1-cyclopentyl-5-(2-ethylphenyl)-1H-pyrazole-3-carboxylate as a colorless oil. TLC $R_f$=0.76 (hexane/EtOAc, 3:1); $^1$H NMR (200 MHz, $CDCl_3$): δ=1.00-1.15 (t, 3H, $CH_3$), 1.25-1.40 (t, 3H, $CH_3$), 1.40-1.60 (m, 2H, $CH_2$), 1.80-2.30 (m, 6H, $CH_2$×3), 2.40-2.55 (q, 2H, $CH_2$), 4.15-4.25 (m, 1H, CH), 4.25-4.35 (q, 2H, $CH_2$), 6.60 (s, 1H, Ar), 7.05-7.40 (m, 4H, Ar).LCMS (ESI): m/z calculated for $C_{19}H_{24}N_2O_2$ [M+H$^+$]: 313, Found: 313.2.

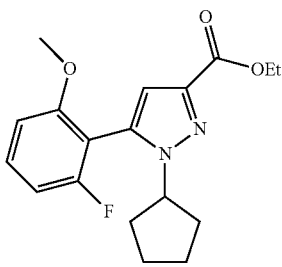 [SMILES: CCOC(=O)c1cc(-c2c(F)cccc2OC)n(C2CCCC2)n1]

Ethyl 1-cyclopentyl-5-(2-fluoro-6-methoxyphenyl)-1H-pyrazole-3-carboxylate: Using the general procedure described above, reaction between 5-bromo-1-cyclopentyl-1H-pyrazole-3-carboxylate (150 mg, 0.52 mmol) and 2-methoxy, 6-fluorophenyl boronic acid (178 mg, 1.04 mmol) in the presence of Pd(PPh$_3$)$_4$ (21 mg, 0.026 mmol) and 2 M Na$_2$CO$_3$ (0.78 mL, 1.56 mmol) in THF (5 mL) for 18 h provided 80 mg (46%) of ethyl 1-cyclopentyl-5-(2-fluoro-6-methoxyphenyl)-1H-pyrazole-3-carboxylateas a colorless oil. TLC R$_f$=0.75 (hexane/EtOAc, 3:1); $^1$H NMR (200 MHz, CDCl$_3$): δ=1.30-1.40 (t, 3H, CH$_3$), 1.40-1.60 (m, 2H, CH$_2$), 1.80-2.25 (m, 6H, CH$_2$×3), 3.80 (s, 3H, CH$_3$), 4.20-4.40 (m, 3H, CH and CH$_2$), 6.70-6.85 (m, 3H, Ar), 7.30-7.40 (m, 1H, Ar). LCMS (ESI): m/z calculated for C$_{18}$H$_{21}$FN$_2$O$_3$ [M+H$^+$]: 333, Found: 333.4.

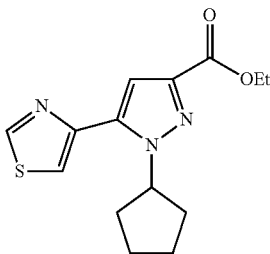 [SMILES: CCOC(=O)c1cc(-c2cscn2)n(C2CCCC2)n1]

Ethyl 1-cyclopentyl-5-(thiazol-4-yl)-1H-pyrazole-3-carboxylate: Using the general procedure described above, reaction between 5-bromo-1-cyclopentyl-1H-pyrazole-3-carboxylate (150 mg, 0.52 mmol) and thiazol-4-yl boronic acid (135 mg, 1.04 mmol) in the presence of Pd(PPh$_3$)$_4$ (21 mg, 0.026 mmol) and 2 M Na$_2$CO$_3$ (0.78 mL, 1.56 mmol) in THF (5 mL) for 24 h provided 15 mg (10%) of ethyl 1-cyclopentyl-5-(thiazol-4-yl)-1H-pyrazole-3-carboxylateas a colorless oil. TLC R$_f$=0.72 (hexane/EtOAc, 3:1); $^1$H NMR (200 MHz, CDCl$_3$): δ=1.20-1.30 (t, 3H, CH$_3$), 1.80-2.25 (m, 8H, CH$_2$×4), 4.65-4.80 (m, 2H, CH$_2$), 5.20-5.40 (m, 1H, CH), 6.75 (s, 1H, Ar), 7.40 (s, 1H, Ar), 8.90 (s, 1H, Ar). $^1$H NMR purity: 85-90%. LCMS (ESI): m/z calculated for C$_{14}$H$_{17}$N$_3$O$_2$ S [M+H$^+$]: 292, Found: 292.2.

General Procedure for the Synthesis of 1-cylopentyl-5-aryl-1H-pyrazole-3-carboxylic Acids:

To a solution of appropriate ester ethyl 1-cylopentyl-5-aryl-1H-pyrazole-3-carboxylate (1 equiv.) in THF (1 mL), MeOH (2 mL) and H$_2$O (1 mL) was added LiOH.H$_2$O (5 equiv.) and stirred at rt for 18 h. Solvent was evaporated in vacuo and the reaction mixture was acidified to pH=4.0 using 1 N HCl and extracted with EtOAc (3 mL×2). Organic phases were combined, washed with brine (3 mL), dried using Na$_2$SO$_4$, and the solvent were evaporated in vacuo to provide intermediates 1-cylopentyl-5-aryl-1H-pyrazole-3-carboxylic acids.

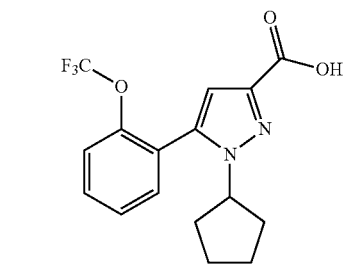 [SMILES: O=C(O)c1cc(-c2ccccc2OC(F)(F)F)n(C2CCCC2)n1]

1-Cyclopentyl-5-(2-(trifluoromethoxy)phenyl)-1H-pyrazole-3-carboxylic acid: Using the general procedure described above, reaction between ethyl 1-cyclopentyl-5-(2-(trifluoromethoxy)phenyl)-1H-pyrazole-3-carboxylate (120 mg, 0.33 mmol) and LiOH.H$_2$O (68.4 mg, 1.65 mmol) provided103 mg (93%) of 1-cyclopentyl-5-(2-(trifluoromethoxy)phenyl)-1H-pyrazole-3-carboxylic acid as a white solid. TLC R$_f$=0.45 (CHCl$_3$/MeOH, 10:1); $^1$H NMR (200 MHz, DMSO-d$_6$): δ=1.40-1.60 (m, 2H, CH$_2$), 1.70-2.00 (m, 6H, CH$_2$×3), 4.25-4.40 (m, 1H, CH), 6.70 (s, 1H, Ar), 7.50-7.70 (m, 4H, Ar). LCMS (ESI): m/z calculated for C$_{16}$H$_{15}$F$_3$N$_2$O$_3$ [M+H$^+$]: 341, Found: 341.1.

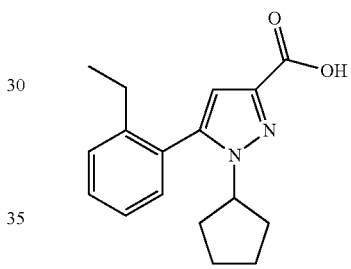

1-Cyclopentyl-5-(2-ethylphenyl)-1H-pyrazole-3-carboxylic acid: Using the general procedure described above, reaction between ethyl 1-cyclopentyl-5-(2-ethylphenyl)-1H-pyrazole-3-carboxylate(120 mg, 0.38 mmol) and LiOH.H$_2$O (80.7 mg, 1.90 mmol) provided 109 mg (99%) of 1-cyclopentyl-5-(2-ethylphenyl)-1H-pyrazole-3-carboxylic acid as a white solid. TLC R$_f$=0.50 (CHCl$_3$/MeOH,10:1); $^1$H NMR (200 MHz,DMSO-d$_6$): δ=0.95-1.05 (t, 3H, CH$_3$), 1.40-1.60 (m, 2H, CH$_2$), 1.65-1.95 (m, 6H, CH$_2$×3), 2.30-2.40 (q, 2H, CH$_2$), 4.15-4.30 (m, 1H, CH), 6.60 (s, 1H, Ar), 7.15-7.45 (m, 4H, Ar). LCMS (ESI): m/z calculated for C$_{17}$H$_{20}$N$_2$O$_2$ [M+H$^+$]: 285, Found: 285.2.

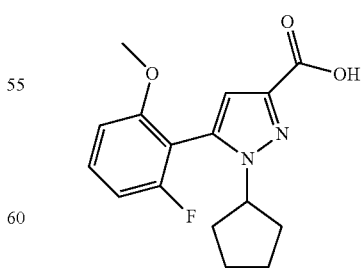

1-Cyclopentyl-5-(2-fluoro-6-methoxyphenyl)-1H-pyrazole-3-carboxylic acid: Using the general procedure described above, reaction between ethyl 1-cyclopentyl-5-(2-fluoro-6-methoxyphenyl)-1H-pyrazole-3-carboxylate (80 mg, 0.24 mmol) and LiOH.H$_2$O (50.5 mg, 1.20 mmol) provided 80 mg (93% pure, 99%) of 1-cyclopentyl-5-(2-fluoro-6-methoxyphenyl)-1H-pyrazole-3-carboxylic acid as a white solid. TLC R$_f$=0.35 (CHCl$_3$/MeOH, 10:1); $^1$H NMR (200 MHz, CDCl$_3$): δ=1.40-1.60 (m, 2H, CH$_2$), 1.80-2.25 (m, 6H, CH$_2$×3), 3.80 (s, 3H, CH$_3$), 4.25-4.40 (m, 1H, CH), 6.70-6.85 (m, 3H, Ar), 7.30-7.50 (m, 1H, Ar). LCMS (ESI): m/z calculated for C$_{16}$H$_{17}$FN$_2$O$_3$ [M+H$^{30}$]: 305, Found: 305.2.

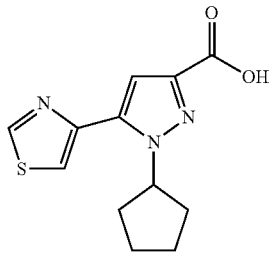 [SMILES: O=C(O)c1cc(-c2cscn2)n(C2CCCC2)n1]

1-Cyclopentyl-5-(thiazol-4-yl)-1H-pyrazole-3-carboxylic acid: Using the general procedure described above, reaction between ethyl 1-cyclopentyl-5-(thiazol-4-yl)-1H-pyrazole-3-carboxylate (15 mg, 0.05 mmol) and LiOH.H$_2$O (10.8 mg, 0.25 mmol) provided 13 mg (96%) of 1-cyclopentyl-5-(thiazol-4-yl)-1H-pyrazole-3-carboxylic acid as a white solid. TLC R$_f$=0.35 (CHCl$_3$/MeOH, 10:1); NMR, LCMS (ESI): m/z calculated for C$_{12}$H$_{13}$N$_3$O$_2$ S [M+H$^+$]: 264, Found: 264.0.

Scheme 3. Synthesis of (R,E)-N-(5-(cyclobutylamino)-1-(4-fluorophenyl)-5-oxopent-1-en-3-yl)-1-cyclopentyl-5-(2,6-dimethoxyphenyl)-1H-pyrazole-3-carboxamide

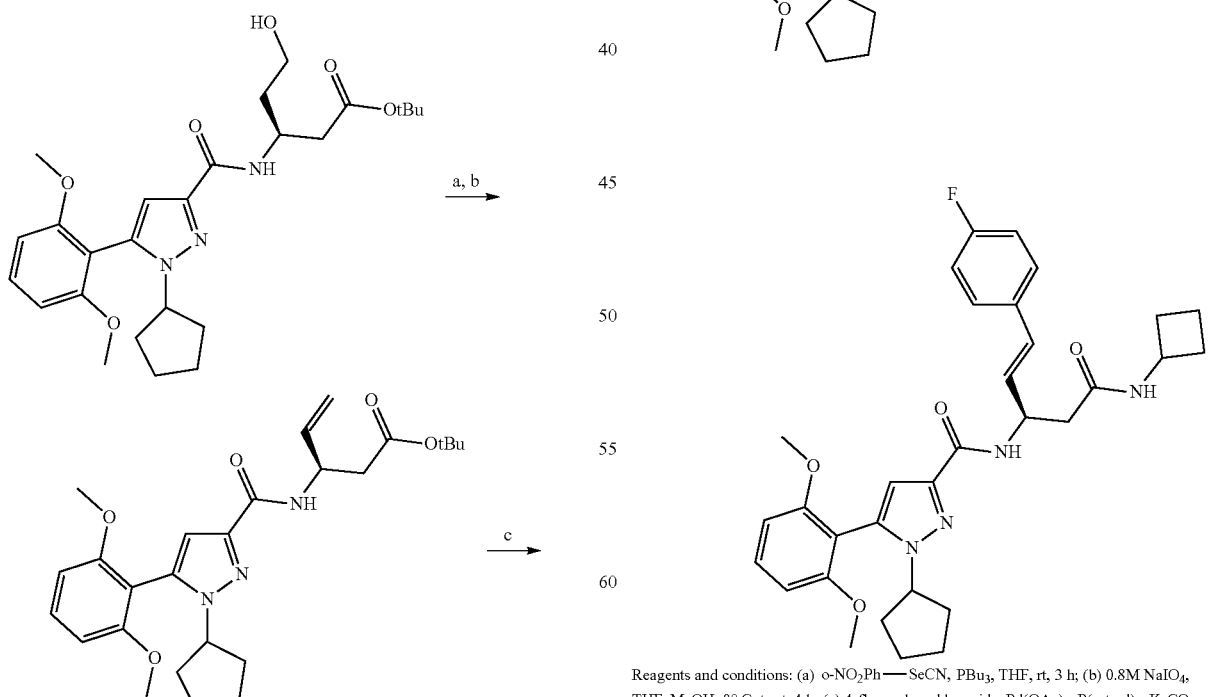

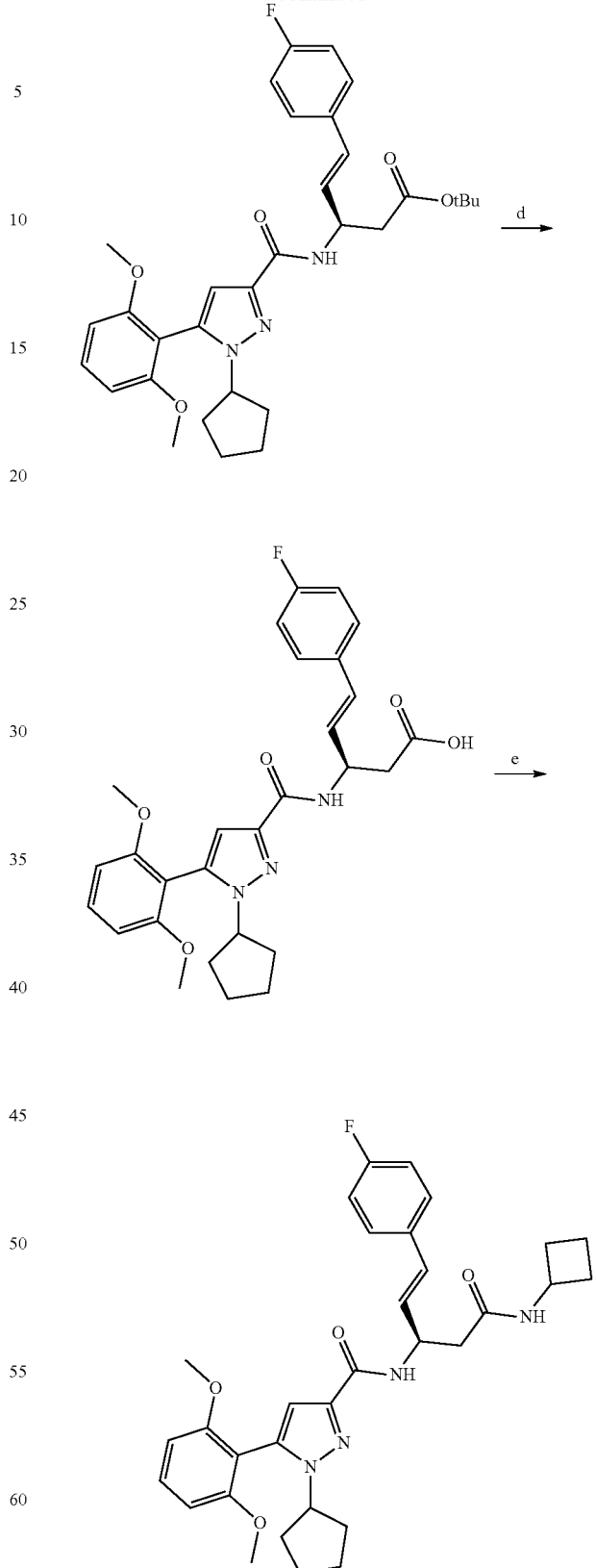

Reagents and conditions: (a) o-NO$_2$Ph—SeCN, PBu$_3$, THF, rt, 3 h; (b) 0.8M NaIO$_4$, THF, MeOH, 0° C. to rt, 4 h; (c) 4-fluorophenyl bromide, Pd(OAc)$_2$, P(o-toyl)$_3$, K$_2$CO$_3$, DMF, 110° C., 20 h; (d) TFA, DCM, rt, 2 h; (e) cyclobutylamine, TBTU, NEt$_3$, CH$_3$CN, rt, 18 h.

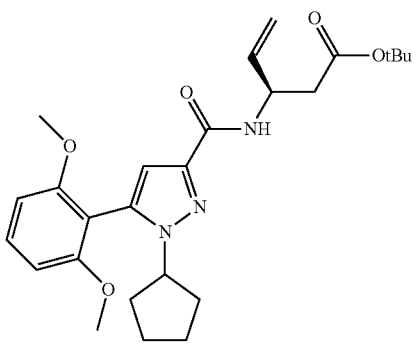 [SMILES: C=C[C@@H](CC(=O)OC(C)(C)C)NC(=O)c1cc(-c2c(OC)cccc2OC)n(C2CCCC2)n1]

(R)-tert-butyl 3-(1-cyclopentyl-5-(2,6-dimethoxyphenyl)-1H-pyrazole-3-carboxamido)pent-4-enoate: To a stirred solution of (S)-tert-butyl 3-(1-cyclopentyl-5-(2,6-dimethoxyphenyl)-1H-pyrazole-3-carboxamido)-5-hydroxypentanoate (1.07 g, 22 mmol) and o-nitrophenylselenocyanate (1 g, 44 mmol) in THF (30 mL) at 0° C. was added tributylphosphine (1.1 mL, 44 mmol) under nitrogen atmosphere. The reaction mixture was stirred at rt for 3 h. Silica gel (4 g) was added and the solvent was removed under reduced pressure. Reaction mixture was purified using Combiflash® $R_f$ (0-40% of EtOAc in hexanes) and the fractions containing the product (TLC) were pooled and evaporated to afford 1.38 g (93%) of o-nitrophenylselenide derivative as a reddish brown solid. TLC $R_f$=0.40 (hexanes/EtOAc, 2:1); LCMS (ESI): m/z calculated for $C_{32}H_{40}N_4O_7Se+[M+H^+]$: 673; Found: 673.2.

To a stirred solution of o-nitrophenylselenide derivative (1.38 g, 20 mmol) in THF (6 mL) and MeOH (40 mL) was added 0.8 M aq. $NaIO_4$ solution (8 mL, 60 mmol) dropwise at 0° C. Reaction mixture was brought to rt and stirred for 4 h. Ether was added and the mixture was washed with saturated NaHCO3 solution, brine and dried over $Na_2SO_4$. Silica gel (3 g) was added and the solvent was removed under reduced pressure to afford a silica gel plug which was purified using Combiflash® $R_f$ (0-5% of EtOAc in hexanes). Fractions containing the product (TLC) were pooled and evaporated to provide 940 mg (97%) of (R)-tert-butyl 3-(1-cyclopentyl-5-(2,6-dimethoxyphenyl)-1H-pyrazole-3-carboxamido)pent-4-enoateas red semisolid. TLC $R_f$=0.50 (hexanes/EtOAc, 2:1); $^1$H NMR (200 MHz, CDCl$_3$): δ=1.45 (s, 9H, CH$_3$×3), 1.50-1.60 (m, 2H, CH$_2$), 1.80-2.10 (m, 6H, CH$_2$×3), 2.60-2.70 (d, 2H, CH$_2$), 3.70 (s, 6H, CH$_3$×2), 4.20-4.35 (m, 1H, CH), 4.95-5.10 (m, 1H, CH), 5.15-5.20 (m, 1H, CH), 5.25-5.35 (m, 1H, CH), 5.85-6.05 (m, 1H, CH), 6.55-6.70 (m, 3H, Ar), 7.30-7.40 (t, 1H, Ar), 7.45-7.55 (d, 1H, NH). LCMS (ESI): m/z calculated for $C_{26}H_{37}N_3O_5$ [M+H$^{30}$]: 470; Found: 470.2.

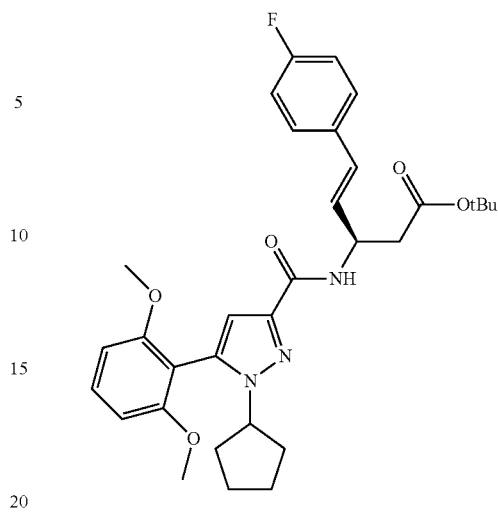

(R,E)-tert-butyl 3-(1-cyclopentyl-5-(2,6-dimethoxyphenyl)-1H-pyrazole-3-carboxamido)-5-(4-fluorophenyl)pent-4-enoate: To a solution of (R)-tert-butyl 3-(1-cyclopentyl-5-(2,6-dimethoxyphenyl)-1H-pyrazole-3-carboxamido)pent-4-enoate (185 mg, 0.40 mmol) in anhydrous DMF (4 mL) was added 4-flourophenyl bromide (0.08 mL, 0.80 mmol) and degassed for 5 min. Under argon atmosphere, Pd(OAc)$_2$ (8.5 mg, 0.04 mmol), P(o-tolyl)$_3$ (23.5 mg, 0.08 mmol) and K$_2$CO$_3$ (204 mg, 1.60 mmol) were added and the reaction mixture was stirred at 110° C. for 20 h. Reaction mixture was cooled to rt, diluted with H$_2$O (10 mL) and extracted with EtOAc (10 mL×2). Combined organic phases were washed with brine and dried over Na$_2$SO$_4$. Silica gel (300 mg) was added and the solvent was removed in vacuo to afford a silica gel plug which was purified using Combiflash® $R_f$ (0-30% of EtOAc in hexanes). Fractions containing the product (TLC) were pooled and evaporated to provide 160 mg (72%) of (R,E)-tert-butyl 3-(1-cyclopentyl-5-(2, 6-dimethoxyphenyl)-1H-pyrazole-3-carboxamido)-5-(4-fluorophenyl)pent-4-enoateas red oil. TLC $R_f$=0.55 (hexanes/EtOAc, 2:1); $^1$H NMR (200 MHz, CDCl$_3$): δ=1.40 (s, 9H, CH$_3$×3), 1.50-1.60 (m, 2H, CH$_2$), 1.75-2.10 (m, 6H, CH$_2$×3),2.70-2.80 (d, 2H, CH$_2$), 2.80 (s, 1.2H, DMF "CH$_3$"), 2.90 (s, 1.2H, DMF "CH$_3$"), 3.70 (s, 6H, CH$_3$×2), 4.20-4.35 (m, 1H, CH), 5.10-5.20 (m, 1H, CH), 6.20-6.30 (m, 1H, CH), 6.55-6.70 (m, 4H, Ar and CH), 6.90-7.05 (m, 2H, Ar), 7.30-7.40 (m, 3H, Ar), 7.45-7.55 (d, 1H, NH), 8.00 (s, 0.4H, DMF "CHO"). LCMS (ESI): m/z calculated for $C_{32}H_{38}FN_3O_5+H^+$ [M+H$^+$]: 564; Found: 564.0.

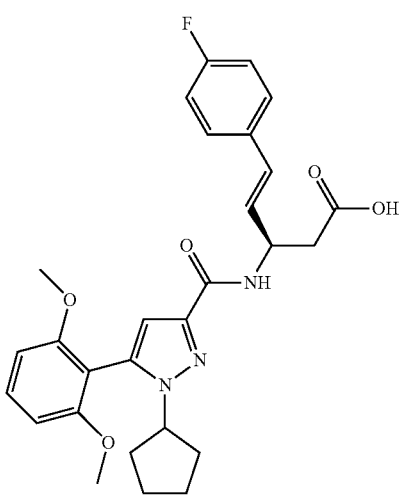 [SMILES: COc1cccc(OC)c1-c1cc(C(=O)N[C@@H](/C=C/c2ccc(F)cc2)CC(=O)O)nn1C1CCCC1]

(R,E)-3-(1-cyclopentyl-5-(2,6-dimethoxyphenyl)-1H-pyrazole-3-carboxamido)-5-(4-fluorophenyl)pent-4-enoic acid: To a solution of(R,E)-tert-butyl 3-(1-cyclopentyl-5-(2,6-dimethoxyphenyl)-1H-pyrazole-3-carboxamido)-5-(4-fluorophenyl)pent-4-enoate (40 mg, 0.07 mmol) in DCM (1 mL) was added TFA (0.25 mL, 3.5 mmol) and stirred at rt for 2 h. Solvent was removed in vacuo and diluted with CHCl$_3$. Solvent was removed to provide 45 mg (99%) of (R,E)-3-(1-cyclopentyl-5-(2,6-dimethoxyphenyl)-1H-pyrazole-3-carboxamido)-5-(4-fluorophenyl)pent-4-enoic acid as colorless oil. TLC R$_f$=0.25 (CHCl$_3$/MeOH, 10:1); LCMS (ESI): m/z calculated for C$_{28}$H$_{30}$FN$_3$O$_5$ [M+H$^+$]: 508, Found: 508.0.

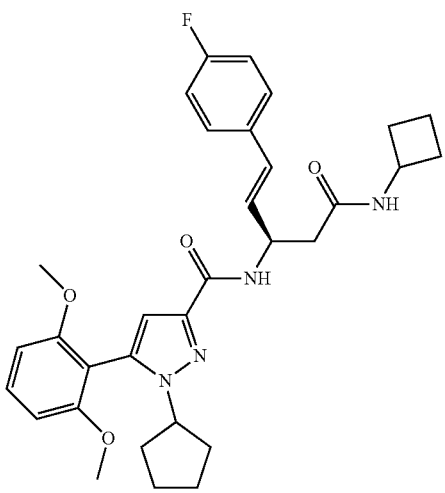 [SMILES: COc1cccc(OC)c1-c1cc(C(=O)N[C@@H](/C=C/c2ccc(F)cc2)CC(=O)NC2CCC2)nn1C1CCCC1]

(R,E)-N-(5-(cyclobutylamino)-1-(4-fluorophenyl)-5-oxo-pent-1-en-3-yl)-1-cyclopentyl-5-(2,6-dimethoxyphenyl)-1H-pyrazole-3-carboxamide: To a solution of (R,E)-3-(1-cyclopentyl-5-(2,6-dimethoxyphenyl)-1H-pyrazole-3-carboxamido)-5-(4-fluorophenyl)pent-4-enoic acid (45 mg, 0.08 mmol) and cyclobutylamine (16 mg, 0.2 mmol) in ACN (1 mL) was added anhydrous NEt$_3$ (0.12 mL, 0.8 mmol) followed by TBTU (64 mg, 0.2 mmol). The reaction mixture was stirred at rt for 18 h. Reaction mixture was diluted with EtOAc (3 mL), and washed with sat. NaHCO$_3$ (2 mL). Organic phase was extracted, added silica gel (100 mg) and purified using Combiflash® R$_f$ (0-60% of EtOAc in hexanes) and the fractions containing the product (TLC) were pooled and evaporated to afford 35 mg (86%) of (R,E)-N-(5-(cyclobutylamino)-1-(4-fluorophenyl)-5-oxo-pent-1-en-3-yl)-1-cyclopentyl-5-(2,6-dimethoxyphenyl)-1H-pyrazole-3-carboxamideas a white sticky solid. TLC R$_f$=0.45 (hexanes/EtOAc, 2:1); $^1$H NMR (200 MHz, CDCl$_3$): δ=1.45-2.05 (m, 12H, CH$_2$×6), 2.20-2.40 (m, 2H, CH$_2$), 2.70-2.85 (m, 2H, CH$_2$), 3.70 (s, 6H, CH$_3$×2), 4.20-4.45 (m, 3H, CH×3), 5.00-5.10 (m, 1H, CH),6.25-6.50 (m, 2H, CH and NH), 6.50-6.60 (m, 1H, Ar), 6.60-6.70 (m, 2H, Ar), 6.90-7.00 (m, 2H, Ar), 7.25-7.40 (m, 3H, Ar), 7.45-7.60 (d, 1H, NH). LCMS (ESI): m/z calculated for C$_{32}$H$_{37}$FN$_4$O$_4$ [M+H$^+$]: 561; Found: 561.2.

Scheme 4. Synthesis of (S)-N-(1-(cyclobutylamino)-5-(4-fluorophenyl)-1-oxopentan-3-yl)-1-cyclopentyl-5-(2,6-dimethoxyphenyl)-1H-pyrazole-3-carboxamide

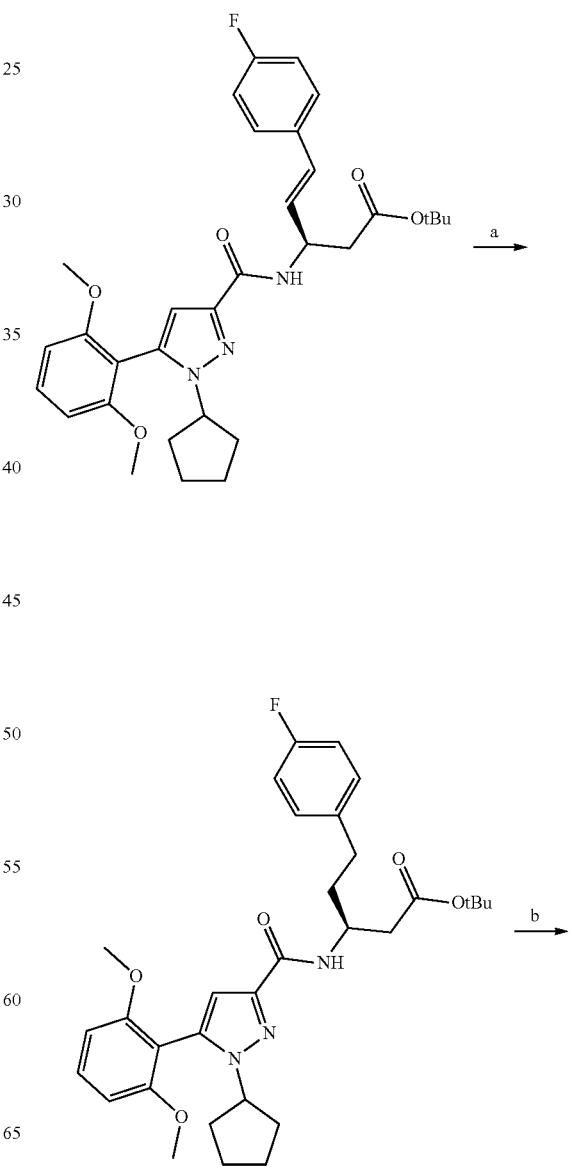

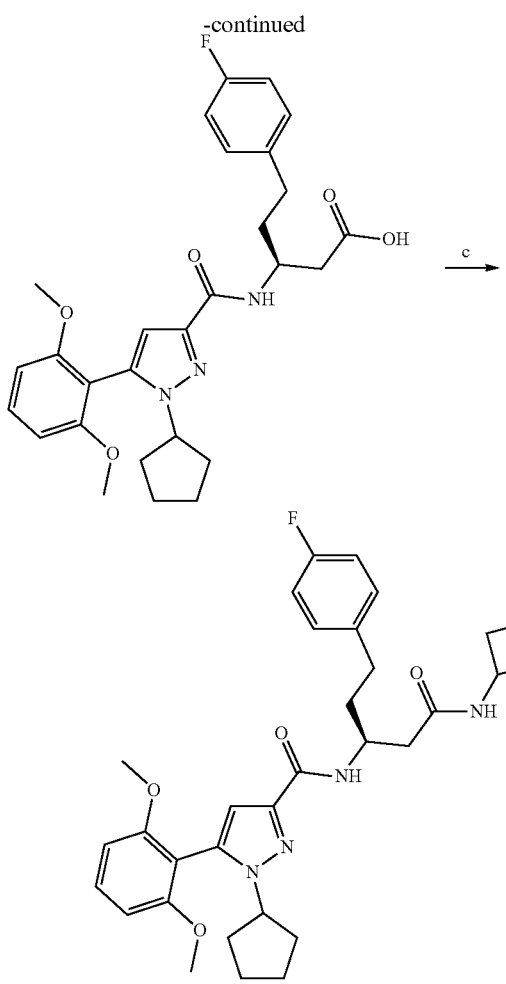

Reagents and conditions: (a) 10% Pd/C, H₂ (balloon), EtOAc, rt, 18 h; (b) TFA, DCM, rt, 2 h; (c) cyclobutylamine, TBTU, NEt₃, ACN, rt, 18 h (S)-tert-butyl 3-(1-cyclopentyl-5-(2,6-dimethoxyphenyl)-1H-pyrazole-3-carboxamido)-5-(4-fluorophenyl)pentanoate: To a solution of(R,E)-tert-butyl 3-(1-cyclopentyl-5-(2,6-dimethoxyphenyl)-1H-pyrazole-3-carboxamido)-5-(4-fluorophenyl)pent-4-enoate (120 mg, 0.2 mmol) in EtOAc (5 mL) was added 10% Pd/C (23 mg, 0.02 mmol) and stirred at rt under hydrogen atmosphere (balloon) for 18 h. Reaction mixture was filtered over Celite®, washed with EtOAc (15 mL), concentrated, and dried to obtain 120 mg (99%) of (S)-tert-butyl 3-(1-cyclopentyl-5-(2,6-dimethoxyphenyl)-1H-pyrazole-3-carboxamido)-5-(4-fluorophenyl)pentanoateas colorless oil. TLC R$_f$=0.50 (hexanes/EtOAc, 2:1); LCMS (ESI): m/z calculated for C₃₂H₄₀FN₃O₅ [M+H⁺]: 566, Found: 566.1.

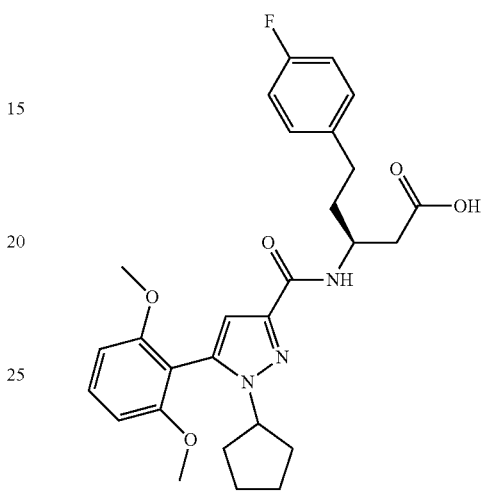

(S)-3-(1-cyclopentyl-5-(2,6-dimethoxyphenyl)-1H-pyrazole-3-carboxamido)-5-(4-fluorophenyl)pentanoic acid: To a solution of (S)-tert-butyl 3-(1-cyclopentyl-5-(2,6-dimethoxyphenyl)-1H-pyrazole-3-carboxamido)-5-(4-fluorophenyl)pentanoate (115 mg, 0.2 mmol) in DCM (3 mL) was added TFA (0.50 mL, 7 mmol) and stirred at rt for 2 h. Solvent was removed in vacuo and diluted with CHCl₃. Solvent was removed to provide 98 mg (95%) of (S)-3-(1-cyclopentyl-5-(2,6-dimethoxyphenyl)-1H-pyrazole-3-carboxamido)-5-(4-fluorophenyl)pentanoic acid as colorless oil. TLC R$_f$=0.25 (CHCl₁₃/MeOH, 10:1); LCMS (ESI): m/z calculated for C₂₈H₃₂FN₃O₅ [M+H⁺]: 510, Found: 510.2.

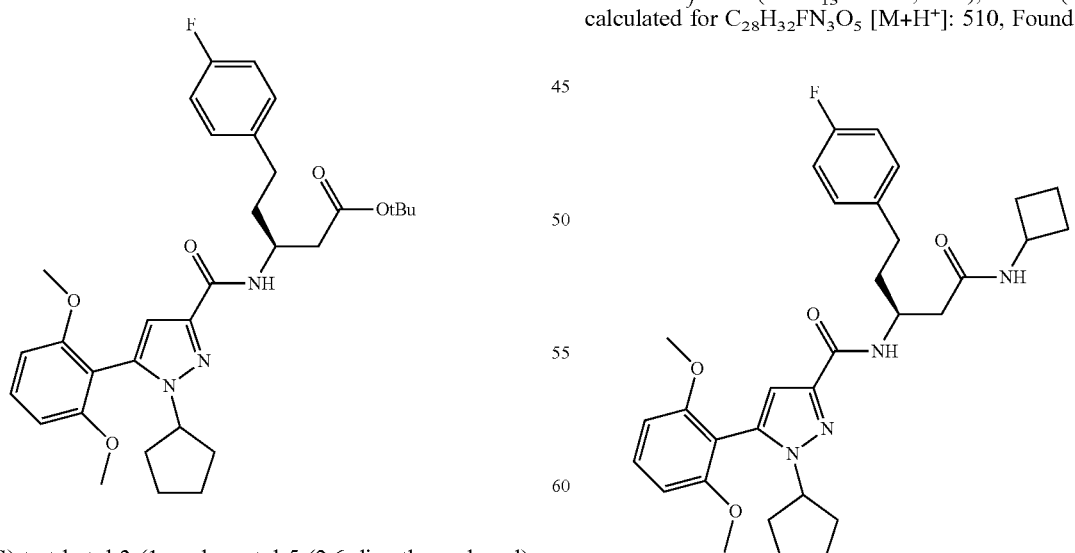

(S)—N—(1-(cyclobutylamino)-5-(4-fluorophenyl)-1-oxopentan-3-yl)-1-cyclopentyl-5-(2,6-dimethoxyphenyl)-1H-pyrazole-3-carboxamide: To a solution of (S)-3-(1-cyclopentyl-5-(2,6-dimethoxyphenyl)-1H-pyrazole-3-carboxamido)-5-(4-fluorophenyl)pentanoic acid (50 mg, 0.1 mmol) and cyclobutylamine (16 mg, 0.2 mmol) in ACN (1 mL) was added anhydrous Et$_3$N (0.12 mL, 0.8 mmol) followed by TBTU (64 mg, 0.2 mmol). The reaction mixture was stirred at rt for 18 h. Reaction mixture was diluted with EtOAc (3 mL), and washed with sat. NaHCO$_3$ (2 mL). Organic phase was extracted, added silica gel (100 mg) and purified using Combiflash® R$_f$ (0-60% of EtOAc in hexanes) and the fractions containing the product (TLC) were pooled and evaporated to afford 30 mg (54%) of (S)—N—(1-(cyclobutylamino)-5-(4-fluorophenyl)-1-oxo-pentan-3-yl)-1-cyclopentyl-5-(2,6-dimethoxyphenyl)-1H-pyrazole-3-carboxamide as a white sticky solid. TLC R$_f$=0.25 (hexanes/EtOAc, 2:1); $^1$H NMR (200 MHz, CDCl$_3$): δ=1.45-2.10 (m, 14H, CH$_2$×7), 2.10-2.25 (m, 2H, CH$_2$), 2.45-2.60 (m, 2H, CH$_2$), 2.60-2.80 (m, 2H, CH$_2$), 3.70 (s, 6H, CH$_3$×2), 4.20-4.45 (m, 3H, CH×3), 6.50-6.70 (m, 4H, Ar and NH), 6.85-7.00 (m, 2H, Ar), 7.05-7.40 (m, 4H, Ar and NH). LCMS (ESI): m/z calculated for C$_{32}$H$_{39}$FN$_4$O$_4$ [M+H$^+$]: 563; Found: 563.1.

(S)-tert-butyl 3-(1-cyclopentyl-5-(2,6-dimethoxyphenyl)-1H-pyrazole-3-carboxamido)-5-(piperidin-1-yl)pentanoate:

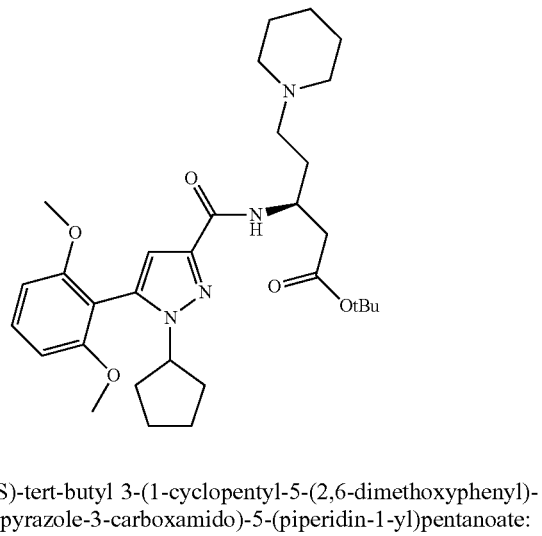

Scheme 5: Preparation of heterocycles

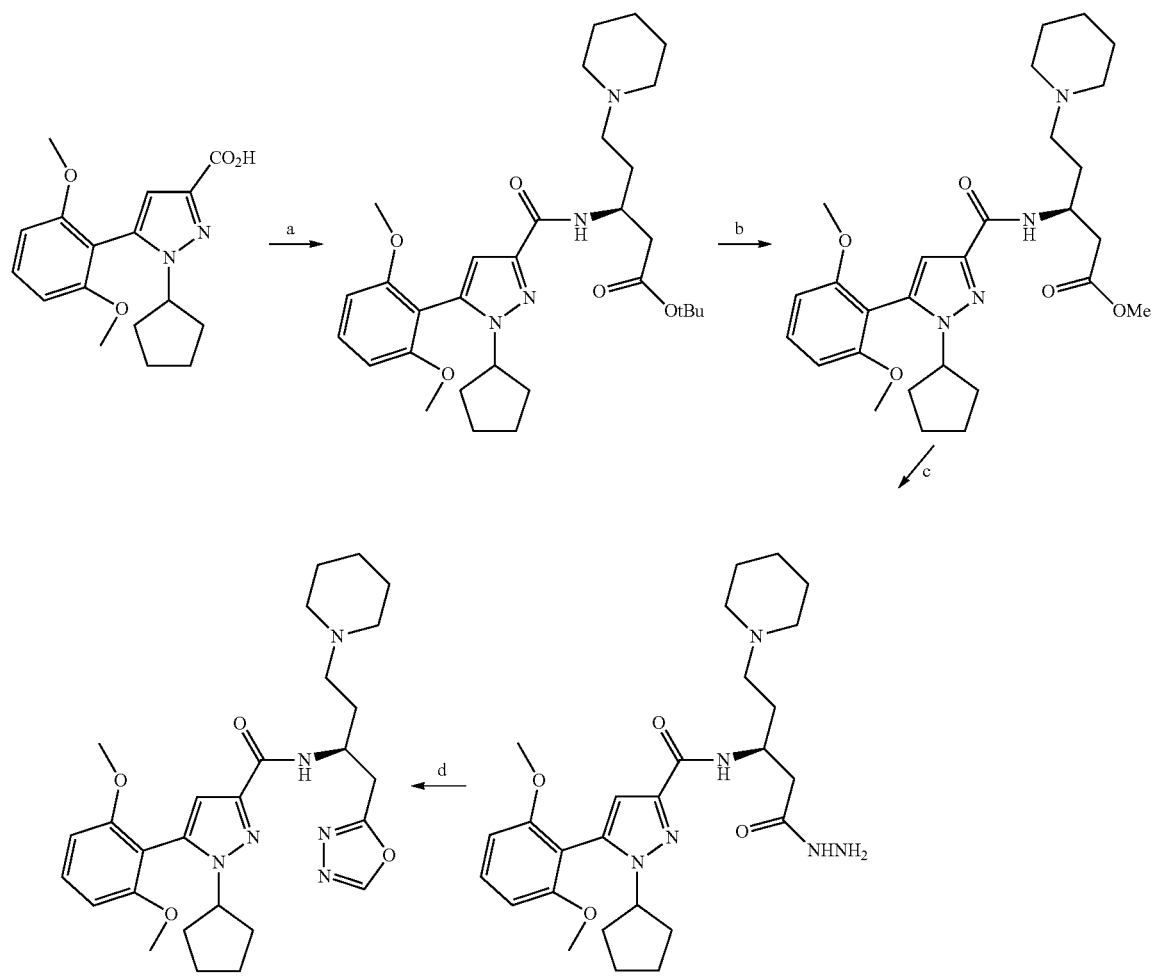

Reagents and conditions:
(a) oxalyl chloride, DMF (1 drop), DCM, (S)-tert-butyl 3-amino-5-(piperidin-1-yl)pentanoate, Et$_3$N, rt, 2 h;
(b) TFA, DCM, rt, MeOH, H$_2$SO$_4$, rt, 15 h;
(c) NH$_2$NH$_2$•H$_2$O, EtOH, 80° C., 3 h;
(d) CH(OMe)$_3$, PTSA•H$_2$O, 85° C., 2 h To a solution of 1-cyclopentyl-5-(2,6-dimethoxyphenyl)-1H-pyrazole-3-carboxylic acid (0.31 g, 0.98 mmol) in DCM (6 ml) were added DMF (1 drop) and oxalyl chloride (0.11 ml, 1.28 mmol). The solution was stirred at rt for 1 h, concentrated to dryness and dissolved in DCM (3 ml). The DCM solution was added dropwise to a solution of (S)-tert-butyl 3-amino-5-(piperidin-1-yl)pentanoate(0.23 g, 0.90 mmol) and Et$_3$N (0.42 ml, 2.7 mmol) in DCM (5 ml) at rt, and the mixture was stirred at rt for 2 h. It was washed with NaHCO$_3$ (sat., 10 mL), dried (Na$_2$SO$_4$), concentrated, and purified using 0-3% MeOH in DCM (with 1% NH$_3$) to give the title product (S)-tert-butyl 3-(1-cyclopentyl-5-(2,6-dimethoxyphenyl)-1H-pyrazole-3-carboxamido)-5-(piperidin-1-yl)pentanoate(0.30 g) as a white foam. TLC R$_f$=0.35 (DCM: MeOH 10:1); $^1$H NMR (200 MHz, CDCl$_3$): δ=1.45 (s,3H), 1.50-1.70 (m, 6H), 1.70-2.20 (m, 10H), 2.30-2.80 (m, 8H), 3.71 and 3.73 (s and s, total 6H), 4.15-4.40 (m, 1H), 4.30-4.60 (m, 1H), 6.62 (d, 2H, J=8.4 Hz); 6.66 (s, 1H), 7.36 (t, 1H J=8.5 Hz), 7.66 (d, 1H, J=8.4 Hz); LC-MS (ESI): m/z calculated for C$_{31}$H$_{47}$N$_4$O$_5$ [M+H$^+$]: 555, Found: 555.3.

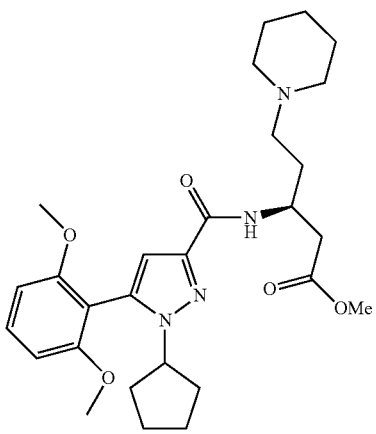 [SMILES: COC(=O)C[C@H](CCN1CCCCC1)NC(=O)c1cc(-c2c(OC)cccc2OC)n(C2CCCC2)n1]

(S)-methyl 3-(1-cyclopentyl-5-(2,6-dimethoxyphenyl)-1H-pyrazole-3-carboxamido)-5-(piperidin-1-yl)pentanoate: To a solution of (S)-tert-butyl 3-(1-cyclopentyl-5-(2,6-dimethoxyphenyl)-1H-pyrazole-3-carboxamido)-5-(piperidin-1-yl)pentanoate (1.73 g, 5.5 mmol) in DCM (10 mL) was added TFA (2 mL, 28 mmol) and stirred at rt for 2 h. Solvent was removed to provide crude (S)-3-(1-cyclopentyl-5-(2,6-dimethoxyphenyl)-1H-pyrazole-3-carboxamido)-5-(piperidin-1-yl)pentanoic acid as yellow solid (2.1 g), which was used as is for the next reaction without further purification; LC-MS (ESI): m/z calculated for C$_{27}$H$_{39}$N$_4$O$_5$ [M+H$^+$]: 499, Found: 499.5. To a solution of acid (120 mg, 0.24 mmol) in MeOH (2 ml) was added sulfuric acid (conc., 0.20 mL), and stirred at rt for 15 h. The solution was quenched with NaHCO$_3$ (sat., 20 mL), extracted with EtOAc (10 mL), dried (Na$_2$SO$_4$) and concentrated to give crude (9-methyl 3-(1-cyclopentyl-5-(2,6-dimethoxyphenyl)-1H-pyrazole-3-carboxamido)-5-(piperidin-1-yl)pentanoate (0.11 g) as a colorless oil, which was used as is for the next without further purification; LC-MS (ESI): m/z calculated for C$_{27}$H$_{41}$N$_6$O$_4$ [M+H$^+$]: 513, Found: 513.1.

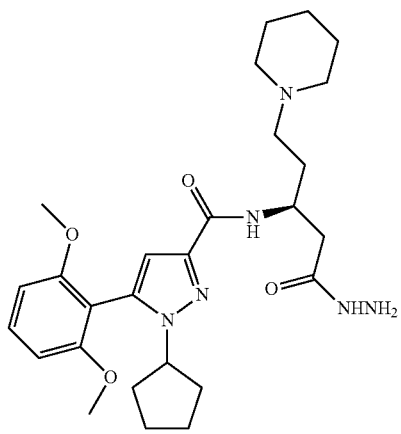 [SMILES: COc1cccc(OC)c1-c1cc(C(=O)N[C@@H](CCN2CCCCC2)CC(=O)NN)nn1C1CCCC1]

(S)-1-cyclopentyl-5-(2,6-dimethoxyphenyl)-N-(1-hydrazinyl-1-oxo-5-(piperidin-1-yl)pentan-3-yl)-1H-pyrazole-3-carboxamide: A mixture of (9-methyl 3-(1-cyclopentyl-5-(2,6-dimethoxyphenyl)-1H-pyrazole-3-carboxamido)-5-(piperidin-1-yl)pentanoate (0.11 g), NH$_2$NH$_2$.H$_2$O (1.0 ml) and EtOH (3.0 ml) was heated at 80° C. for 3 h. The solution was cooled to rt, concentrated and purified using 0-15% MeOH in DCM (with 1% NH$_3$) to give (S)-1-cyclopentyl-5-(2,6-dimethoxyphenyl)-N-(1-hydrazinyl-1-oxo-5-(piperidin-1-yl)pentan-3-yl)-1H-pyrazole-3-carboxamide(50 mg) as a colorless material; $^1$H NMR (200 MHz, CDCl$_3$): δ=1.40-2.20 (m, 18H), 2.20-2.80 (m, 6H), 3.73 (s, 6H), 3.89 (br s, 2H), 4.15-4.30 (m, 1H), 4.30-4.50 (m, 1H), 6.62 (d, 2H, J=8.4 Hz), 6.66 (s, 1H), 7.37 (t, 1H J=8.4 Hz), 8.06 (d, 1H, J=7.4 Hz), 8.37 (br s, 1H); LC-MS (ESI): m/z calculated for C$_{28}$H$_{41}$N$_4$O$_5$ [M+H$^+$]: 513, Found: 513.1

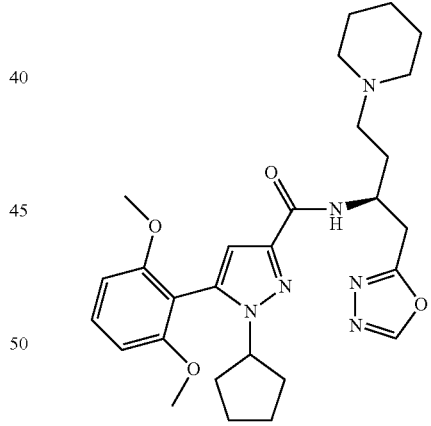

(S)—N—(1-(1,3,4-oxadiazol-2-yl)-4-(piperidin-1-yl)butan-2-yl)-1-cyclopentyl-5-(2,6-dimethoxyphenyl)-1H-pyrazole-3-carboxamide: To a solution of (S)-1-cyclopentyl-5-(2,6-dimethoxyphenyl)-N-(1-hydrazinyl-1-oxo-5-(piperidin-1-yl)pentan-3-yl)-1H-pyrazole-3-carboxamide (50 mg, 0.10 mmol) in CH(OMe)$_3$ was added PTSA.H$_2$O (25 mg, 0.13 mmol). The mixture was heated at 85° C. for 2 h, cooled to rt, diluted with EtOAc (10 mL) and washed with NaHCO$_3$ (sat., 10 mL). The EtOAc solution was dried (Na$_2$SO$_4$), concentrated, and purified using 0-15% MeOH in DCM (with 1% NH3) to give the title product (S)—N—(1-(1,3,4-oxadiazol-2-yl)-4-(piperidin-1-yl)butan-2-yl)-1-cyclopentyl-5-(2,6-dimethoxyphenyl)-1H-pyrazole-3-carboxamide(30 mg) as a white foam; ¹H NMR (200 MHz, CDCl₃): δ=1.40-2.20 (m, 18H), 2.20-2.80 (m, 4H), 3.15-3.50 (m, 2H), 3.73 (s, 6H), 4.15-4.30 (m, 1H), 4.30-4.50 (m, 1H), 6.62 (d, 2H, J=8.0 Hz), 6.65 (s, 1H), 7.37 (t, 1H J=8.4 Hz), 7.90 (d, 1H, J=8.4 Hz), 8.36 (s, 1H); LC-MS (ESI): m/z calculated for $C_{28}H_{40}N_7O_3$ [M+H⁺]: 523, Found: 523.2

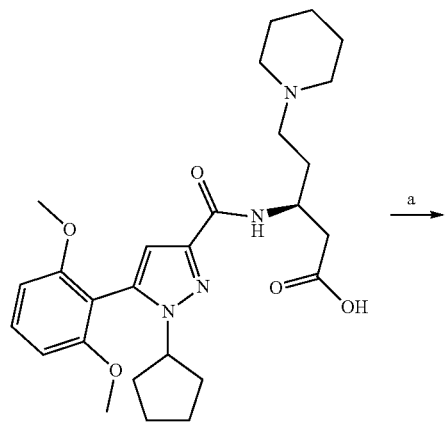

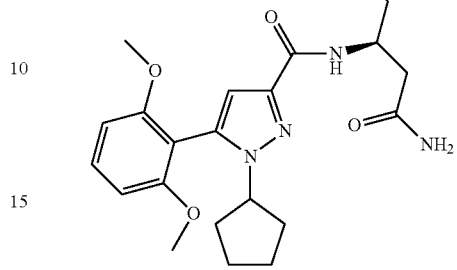

(S)—N—(1-amino-1-oxo-5-(piperidin-1-yl)pentan-3-yl)-1-cyclopentyl-5-(2,6-dimethoxyphenyl)-1H-pyrazole-3-carboxamide: To a solution of (S)-3-(1-cyclopentyl-5-(2,6-dimethoxyphenyl)-1H-pyrazole-3-carboxamido)-5-(piperidin-1-yl)pentanoic acid(1.0 g, 1.8 mmol) in pyridine (20 ml) and dioxane (20 ml) were added ammonium carbonate (0.21 g, 2.7 mmol), followed by Boc₂O (0.47 g, 2.16 mmol). The progress of the reaction was monitored by LC-MS. Additional ammonium carbonate and Boc₂O (2 eq each) were added after 1 h. Stirring was continued for 12 h, and additional ammonium carbonate and Boc₂O (2 eq each) were added. After further stirring for 1 h, LC-MS indicated the completion of the reaction. The mixture was concentrated to dryness, quenched with NaHCO₃ (sat., 20 ml) and extracted with EtOAc (20 ml). The EtOAc solution was dried (Na₂SO₄), concentrated, and purified using 0-15% MeOH in DCM (with 1% NH₃) to give the title product (S)—N—(1-amino-1-oxo-5-(piperidin-1-yl)pentan-3-yl)-1-cyclopentyl-5-(2,6-dimethoxyphenyl)-1H-pyrazole-3-carboxamide(0.64 g) as a white solid; ¹H NMR (200 MHz, CDCl₃): δ=1.50-2.20 (m, 16H), 2.20-2.80 (m, 8H), 3.15-3.50 (m, 2H), 3.72 (s, 6H), 4.15-4.30 (m, 1H), 4.30-4.50 (m, 1H), 5.37 (br s, 1H), 6.62 (d, 2H, J=8.4 Hz), 6.65 (s, 1H), 7.18 (br s, 1H), 7.20-7.40 (m, 2H), 7.64 (t, 1H, J=7.0 Hz), 8.13 (d, 1H, J=8.4 Hz), 8.61 (d, 1H, J=4.0 Hz); LC-MS (ESI): m/z calculated for $C_{27}H_{40}N_5O_4$ [M+H⁺]: 498, Found: 498.3

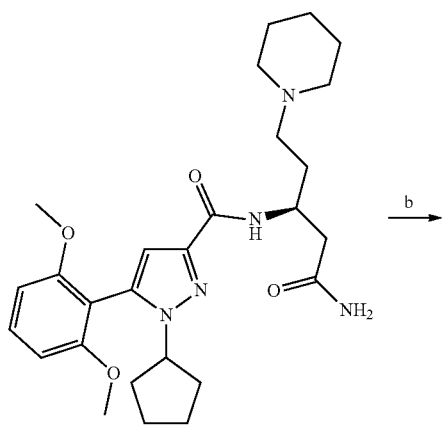

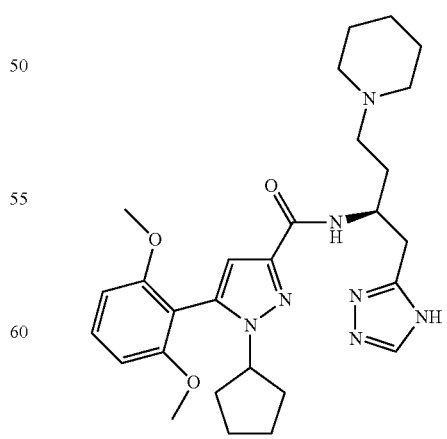

Reagents and conditions: (a) ammonium carbonate, Boc₂O, pyridine, dioxane, 12 h; (b) DMF-DMA, 120° C., 2 h; NH₂NH₂•H₂O, HOAc, 90° C., 2 h (S)-1-cyclopentyl-5-(2,6-dimethoxyphenyl)-N-(4-(piperidin-1-yl)-1-(4H-1,2,4-triazol-3-yl)butan-2-yl)-1H-pyrazole-3-carboxamide: A solution of (S)—N—(1-amino-1-oxo-5-(piperidin-1-yl)pentan-3-yl)-1-cyclopentyl-5-(2,6-dimethoxyphenyl)-1H-pyrazole-3-carboxamide (40 mg, 0.80 mmol) in DMF-DMA (1 ml) was heated at 120° C. for 2 h. The solution was concentrated to dryness and the residue was dissolved in HOAc (1.0 ml), followed by addition of $NH_2NH_2 \cdot H_2O$ (0.10 ml). The resulting solution was heated at 90° C. for 2 h, cooled to rt, quenched with $NaHCO_3$ (sat., 20 ml), and extracted with EtOAc (10 ml). The EtOAc solution was dried ($Na_2SO_4$), concentrated, and purified using 0-15% MeOH in DCM (with 1% $NH_3$) to give the title product (S)-1-cyclopentyl-5-(2,6-dimethoxyphenyl)-N-(4-(piperidin-1-yl)-1-(4H-1,2,4-triazol-3-yl)butan-2-yl)-1H-pyrazole-3-carboxamide(24 mg) as a white solid; $^1$H NMR (200 MHz, $CDCl_3$): δ 1.40-2.20 (m, 16H), 2.30-2.80 (m, 6H), 3.20-3.40 (m, 2H), 3.72 (s, 6H), 4.15-4.30 (m, 1H), 4.50-4.70 (m, 1H), 6.62 (d, 2H, J=8.6 Hz), 6.68 (s, 1H), 7.35 (t, 1H, J=7.5 Hz), 7.91 (s, 1H), 8.20 (d, 1H, J=8.6 Hz); LC-MS (ESI): m/z calculated for $C_{28}H_{39}N_7O_3$ [M+HU+]: 522, Found: 522.3.

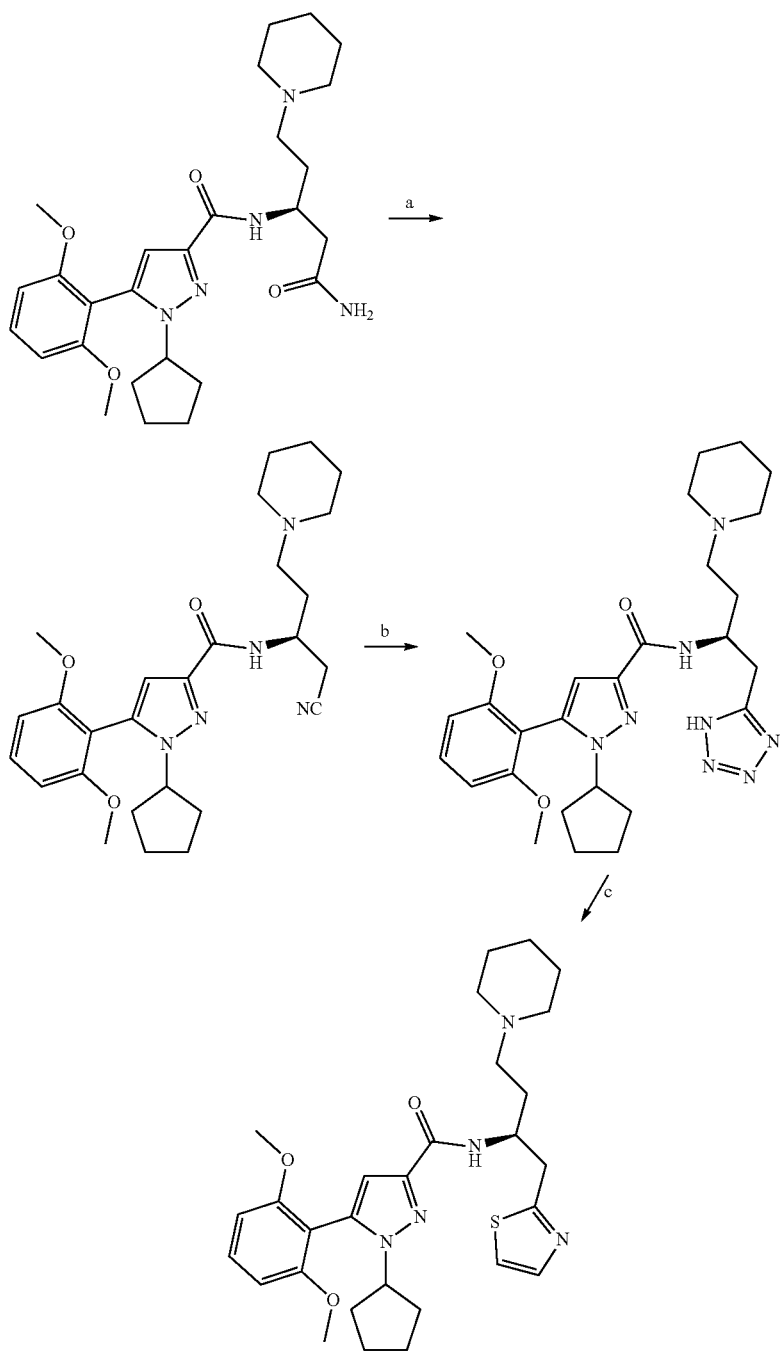

Reagents and conditions: (a) trifluoroacetic anhydride, $Et_3N$, DCM, rt, 15 h; (b) $Me_3SnN_3$, toluene, 100° C., 20 h: (c) $P_2S_5$, EtOH, 80° C., 17 h; ethyl 2-bromo acetate, acetic acid, 60-80° C., 3 h

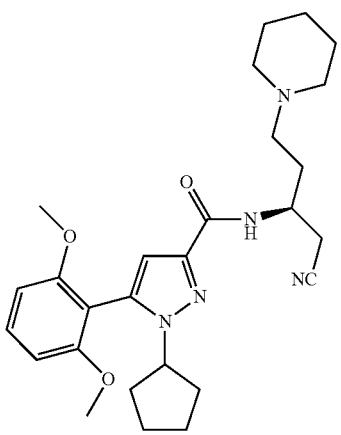 [SMILES: COc1cccc(OC)c1-c1cc(C(=O)N[C@H](CC#N)CCN2CCCCC2)nn1C1CCCC1]

(S)—N—(1-cyano-4-(piperidin-1-yl)butan-2-yl)-1-cyclopentyl-5-(2,6-dimethoxyphenyl)-1H-pyrazole-3-carboxamide: To a solution of (S)-1-cyclopentyl-5-(2,6-dimethoxyphenyl)-N-(4-(piperidin-1-yl)-1-(4H-1,2,4-triazol-3-yl)butan-2-yl)-1H-pyrazole-3-carboxamide (50 mg, 0.10 mmol) in DCM (1 ml) at rt were added Et$_3$N (56 μL, 0.40 mmol) and trifluoroacetic anhydride (56 μL, 0.40 mmol). The solution was stirred at rt for 15 h. LC-MS analysis showed the completion of the reaction. The mixture was quenched with NaHCO$_3$ (sat., 10 ml) and extracted with DCM (10 ml). The extract was dried (Na$_2$SO$_4$), concentrated, and purified using 0-10% MeOH in DCM to give the title product (S)—N—(1-cyano-4-(piperidin-1-yl)butan-2-yl)-1-cyclopentyl-5-(2,6-dimethoxyphenyl)-1H-pyrazole-3-carboxamide(13 mg) as a yellow solid; $^1$H NMR (200 MHz, CDCl$_3$): δ=1.40-2.20 (m, 24H), 2.79 (d, 2H, J=6.1 Hz) 3.74 and 3.75 (s and s, total 6H), 4.20-4.30 (m, 1H), 4.30-4.50 (m, 1H), 6.63 (d, 2H, J=8.2 Hz); 6.67 (s, 1H), 7.38 (t, 1H, J=8.4 Hz), 7.98 (br s, 1H); LC-MS (ESI): m/z calculated for C$_{27}$H$_{38}$N$_5$O$_3$ [M+H$^+$]: 411: 480, Found: 479.9.

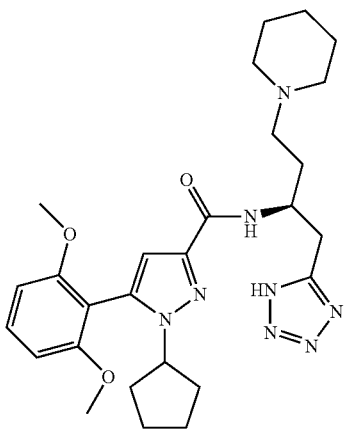 [SMILES: COc1cccc(OC)c1-c1cc(C(=O)N[C@@H](CCN2CCCCC2)Cc2nnn[nH]2)nn1C1CCCC1]

(S)-1-cyclopentyl-5-(2,6-dimethoxyphenyl)-N-(4-(piperidin-1-yl)-1-(1H-tetrazol-5-yl)butan-2-yl)-1H-pyrazole-3-carboxamide: A mixture of (S)—N—(1-cyano-4-(piperidin-1-yl)butan-2-yl)-1-cyclopentyl-5-(2,6-dimethoxyphenyl)-1H-pyrazole-3-carboxamide (50 mg) and Me$_3$SnN$_3$ (71 mg) in toluene (1 ml) was heated at 100° C. for 20 h. The mixture was concentrated and purified using 0-15% MeOH in DCM (with 1% NH$_3$) to give the title product (S)-1-cyclopentyl-5-(2,6-dimethoxyphenyl)-N-(4-(piperidin-1-yl)-1-(1H-tetrazol-5-yl)butan-2-yl)-1H-pyrazole-3-carboxamide(42 mg) as an orange foam; $^1$H NMR (200 MHz, CDCl$_3$): δ=1.40-2.20 (m, 24H), 3.29 (d, 2H, J=4.6 Hz) 3.73 and 3.74 (s and s, total 6H), 4.20-4.40 (m, 1H), 4.50-4.70 (m, 1H), 6.62 (d, 2H, J=8.4 Hz); 6.67 (s, 1H), 7.37 (t, 2H, J=8.4 Hz), 9.68 (s, 1H); LC-MS (ESI): m/z calculated for C$_{27}$H$_{39}$N$_8$O$_3$ [M+H$^+$]: 523, Found: 522.9.

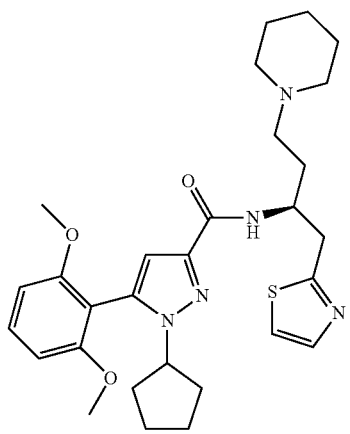 [SMILES: COc1cccc(OC)c1-c1cc(C(=O)N[C@@H](CCN2CCCCC2)Cc2nccs2)nn1C1CCCC1]

(S)-1-cyclopentyl-5-(2,6-dimethoxyphenyl)-N-(4-(piperidin-1-yl)-1-(thiazol-2-yl)butan-2-yl)-1H-pyrazole-3-carboxamide: A mixture of (S)—N—(1-cyano-4-(piperidin-1-yl)butan-2-yl)-1-cyclopentyl-5-(2,6-dimethoxyphenyl)-1H-pyrazole-3-carboxamide (96 mg, 0.20 mmol), P$_2$S$_5$ (90 mg, 0.40 mmol) and EtOH (2 ml) was heated at 80° C. for 17 h. The mixture was concentrated to dryness to give a yellow solid. The solid was triturated with DCM and filtered through a short pad of Celite®. The filtrate was concentrated and treated with ethyl 2-bromo acetate (90 μL, 0.60 mmol) in acetic acid (2 ml) at 60° C. for 1 h, 70° C. for 1 h and 80° C. for 1 h. The mixture was cooled to rt, and diluted with EtOAc (20 ml), washed with NaHCO$_3$ (20 ml×2), dried (Na$_2$SO$_4$), concentrated, and purified using 0-15% MeOH in DCM (with 1% NH$_3$) to give (S)-1-cyclopentyl-5-(2,6-dimethoxyphenyl)-N-(4-(piperidin-1-yl)-1-(thiazol-2-yl)butan-2-yl)-1H-pyrazole-3-carboxamide (20 mg) as a yellow oil; $^1$H NMR (200 MHz, CDCl$_3$): δ 1.40-2.00 (m, 14H), 2.30-2.60 (m, 6H), 3.30-3.50 (m, 2H), 3.40-3.70 (m, 2H), 3.73 (s, 6H), 4.20-4.35 (m, 1H), 4.50-4.70 (m, 1H), 6.62 (d, 2H, J=8.4 Hz); 6.67 (s, 1H), 7.22 (d, 1H, J=3.2 Hz), 7.36 (t, 1H, J=8.4 Hz), 7.70 (d, 1H, J=3.4 Hz), 7.99 (d, 1H, J=5.8 Hz); LC-MS (ESI): m/z calculated for C$_{29}$H$_{40}$N$_5$O$_3$S [M+H$^+$]: 538, Found: 537.8.

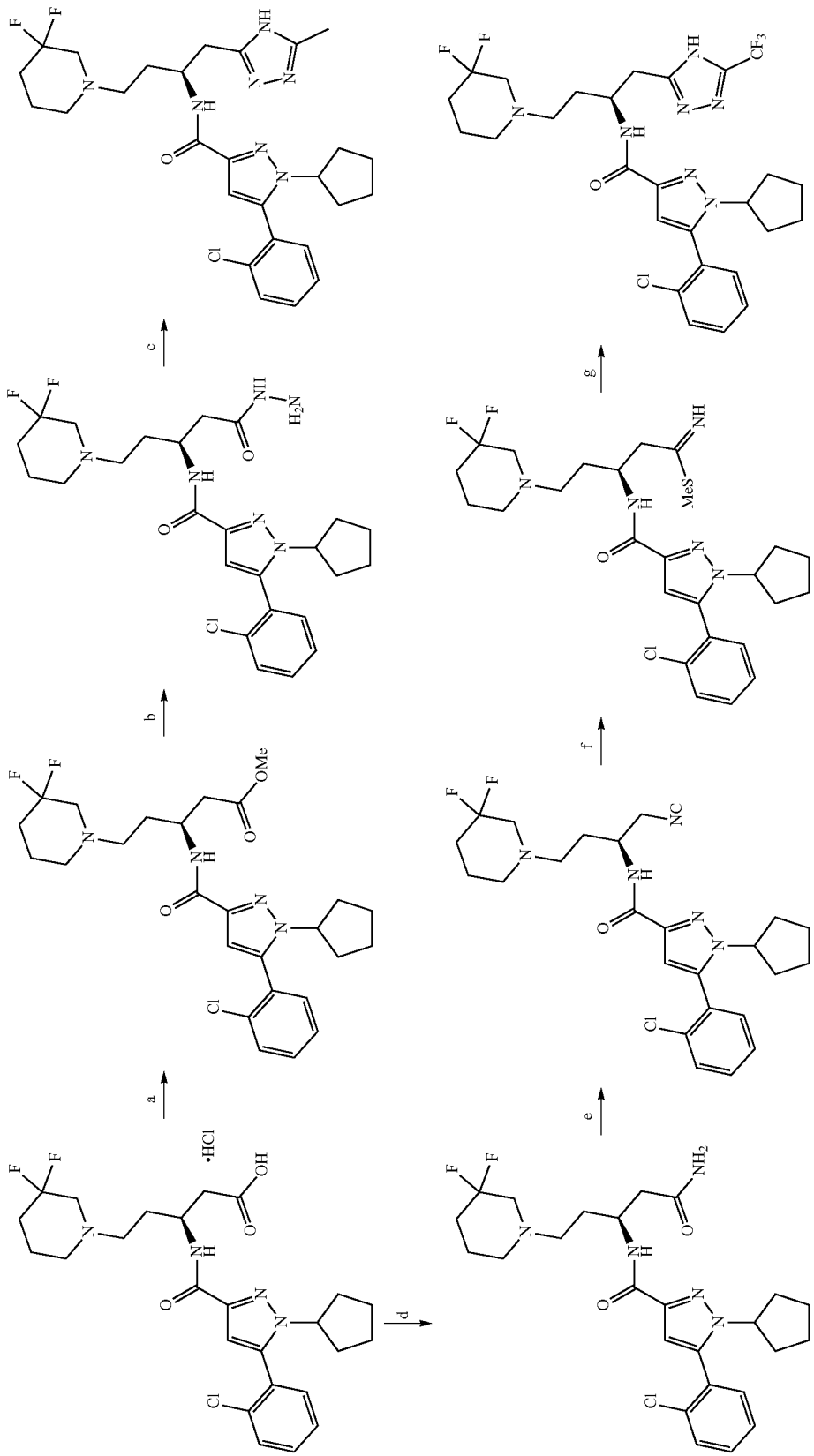
Reagents and conditions: (a) MeOH, H₂SO₄, 75° C., 18 h; (b) hydrazine monohydrate, EtOH, 85° C., 8 h; (c) amidine·HCl, KOtBu (1.0M in THF), BuOH, 120° C., 4 h; (d) ammonium carbonate, Boc₂O, pyridine, dioxane, 12 h; (e) POCl₃, imidazole, pyridine, 5° C., 1 h; (f) P₂S₅, EtOH, 85° C., rt, 17 h; (g) trifluoroacetyl hydrazide, toluene, 110° C., 4 h; 1,2-dichloro benzene, 160° C., 17 h.

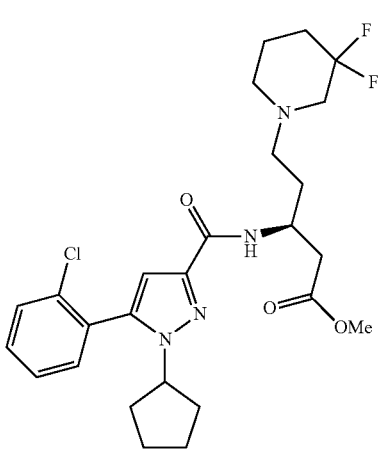 [SMILES: COC(=O)C[C@H](CCN1CCCC(F)(F)C1)NC(=O)c1cc(-c2ccccc2Cl)n(C2CCCC2)n1]

(S)-methyl 3-(5-(2-chlorophenyl)-1-cyclopentyl-1H-pyrazole-3-carboxamido)-5-(3,3-difluoropiperidin-1-yl)pentanoate: To a solution of (S)-3-(5-(2-chlorophenyl)-1-cyclopentyl-1H-pyrazole-3-carboxamido)-5-(3,3-difluoropiperidin-1-yl)pentanoic acid hydrochloride (0.50 g) in MeOH (10 ml) was added sulfuric acid (con., 0.30 mL). The solution was heated at 50° C. for 1 h and 75° C. for 18 h. The mixture was diluted with EtOAc and washed with NaHCO₃. The EtOAc layer was dried (Na₂SO₄), and concentrated to give crude (S)-methyl 3-(5-(2-chlorophenyl)-1-cyclopentyl-1H-pyrazole-3-carboxamido)-5-(3,3-difluoropiperidin-1-yl)pentanoate(0.41 g) as a white foam; $^1$H NMR (200 MHz, CDCl₃): δ 1.40-2.20 (m, 14H), 2.30-2.80 (m, 8H), 3.67 (s, 3H), 4.20-4.40 (m, 1H), 4.40-4.60 (m, 1H), 6.68 (s, 1H), 7.20-7.60 (m, 5H); LC-MS (ESI): m/z calculated for $C_{26}H_{34}F_2ClN_4O_3$ [M+H⁺]: 523 and 525, Found: 523.1 and 525.2.

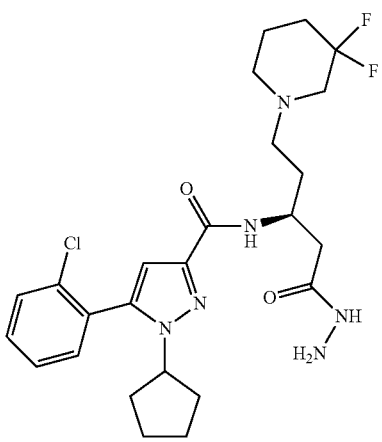 [SMILES: NNC(=O)C[C@H](CCN1CCCC(F)(F)C1)NC(=O)c1cc(-c2ccccc2Cl)n(C2CCCC2)n1]

(S)-5-(2-chlorophenyl)-1-cyclopentyl-N-(5-(3,3-difluoropiperidin-1-yl)-1-hydrazinyl-1-oxopentan-3-yl)-1H-pyrazole-3-carboxamide: A mixture of (9-methyl 3-(5-(2-chlorophenyl)-1-cyclopentyl-1H-pyrazole-3-carboxamido)-5-(3,3-difluoropiperidin-1-yl)pentanoate (0.40 g), hydrazine monohydrate (1.0 ml) and EtOH (5 ml) was refluxed at 85° C. for 4 h. Additional hydrazine monohydrate (2.0 ml) was added, and refluxed at 90° C. for 4 h. LC-MS indicated the completion of the reaction. The mixture was concentrated to dryness, and purified using 0-15% MeOH in DCM (with 1% NH₃) to give (S)-5-(2-chlorophenyl)-1-cyclopentyl-N-(5-(3, 3-difluoropiperidin-1-yl)-1-hydrazinyl-1-oxopentan-3-yl)-1H-pyrazole-3-carboxamide (0.35 g) as a white foam; $^1$H NMR (200 MHz, CDCl₃): δ 1.40-2.20 (m, 14H), 2.30-2.80 (m, 8H), 4.20-4.50 (m, 2H), 6.72 (s, 1H), 7.20-7.60 (m, 4H), 7.65 (s, 1H), 7.72 (d, 1H, J=8.4 Hz); LC-MS (ESI): m/z calculated for $C_{25}H_{34}ClN_6O_2$ [M+H⁺]: 523 and 525, Found: 522.7 and 524.9.

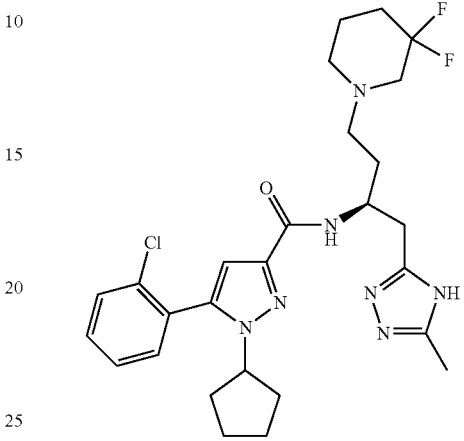

(S)-5-(2-chlorophenyl)-1-cyclopentyl-N-(4-(3,3-difluoropiperidin-1-yl)-1-(5-methyl-4H-1,2,4-triazol-3-yl)butan-2-yl)-1H-pyrazole-3-carboxamide: To a suspension of (S)-5-(2-chlorophenyl)-1-cyclopentyl-N-(5-(3,3-difluoropiperidin-1-yl)-1-hydrazinyl-1-oxopentan-3-yl)-1H-pyrazole-3-carboxamide (104 mg, 0.20 mmol), amidine.HCl (58 mg, 0.60 mmol) in BuOH (20 ml) was added KOtBu (0.60 ml, 1.0M in THF, 0.60 mmol). The mixture was heated at 120° C. for 4 h, cooled to rt, diluted with water (10 ml) and extracted with EA (10 ml). The extract was dried (Na₂SO₄), concentrated, and purified using 0-10% MeOH in DCM (with 1% NH₃) to give (S)-5-(2-chlorophenyl)-1-cyclopentyl-N-(4-(3,3-difluoropiperidin-1-yl)-1-(5-methyl-4H-1,2,4-triazol-3-yl)butan-2-yl)-1H-pyrazole-3-carboxamide (90 mg) as a white foam; $^1$H NMR (200 MHz, CDCl₃): δ 1.40-2.20 (m, 14H), 2.41 (s, 3H), 2.42-2.80 (m, 6H), 3.05-3.20 (m, 2H), 4.20-4.40 (m, 1H), 4.50-4.70 (m, 1H), 6.73 (s, 1H), 7.26-7.60 (m, 4H), 7.80-7.95 (m, 1H); LC-MS (ESI): m/z calculated for $C_{27}H_{35}ClF_2N_7O$ [M+H⁺]: 546 and 548, Found: 545.7 and 547.9.

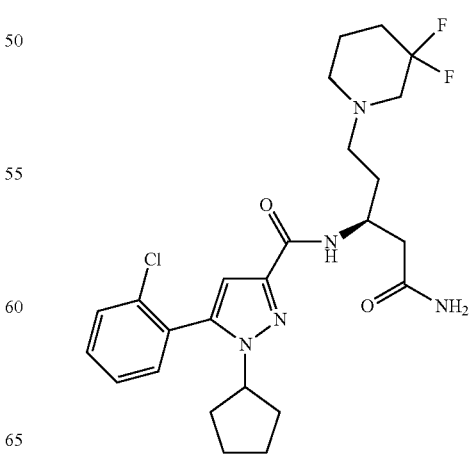

(S)—N—(1-amino-5-(3,3-difluoropiperidin-1-yl)-1-oxopentan-3-yl)-5-(2-chlorophenyl)-1-cyclopentyl-1H-pyrazole-3-carboxamide: To a solution of (S)-3-(5-(2-chlorophenyl)-1-cyclopentyl-1H-pyrazole-3-carboxamido)-5-(3,3-difluoropiperidin-1-yl)pentanoic acid hydrochloride (1.6 g, 2.76 mmol) in pyridine (40 ml) and dioxane (40 ml) was added Boc$_2$O (0.60 g, 2.76 mmol), followed by ammonium carbonate (0.22 g, 2.76 mmol). The progress of the reaction was monitored by LC-MS. Additional ammonium carbonate and Boc$_2$O (2 eq each) were added after 1 h. Stirring was continued for 12 h, and additional ammonium carbonate and Boc$_2$O (2 eq each) were added. After further stirring for 1 h, LC-MS indicated the completion of the reaction. The mixture was concentrated to dryness, quenched with NaHCO$_3$ (sat., 40 ml) and extracted with EtOAc (40 mL). The EtOAc solution was dried (Na$_2$SO$_4$), concentrated, and purified using 0-15% MeOH in DCM (with 1% NH$_3$) to give the title product (S)—N—(1-amino-5-(3,3-difluoropiperidin-1-yl)-1-oxopentan-3-yl)-5-(2-chlorophenyl)-1-cyclopentyl-1H-pyrazole-3-carboxamide(1.30 g) as a white foam; $^1$H NMR (200 MHz, CDCl$_3$): δ 1.40-2.20 (m, 14H), 2.30-2.80 (m, 8H), 4.20-4.60 (m, 2H), 5.33 (br s, 1H), 6.50 (br s, 1H), 6.72 (s, 1H), 7.20-7.60 (m, 4H), 7.71 (d, 1H, J=9.0 Hz); LC-MS (ESI): m/z calculated for C$_{25}$H$_{33}$ClN$_5$O$_2$ [M+H$^+$]: 508 and 510, Found: 508.0 and 510.1.

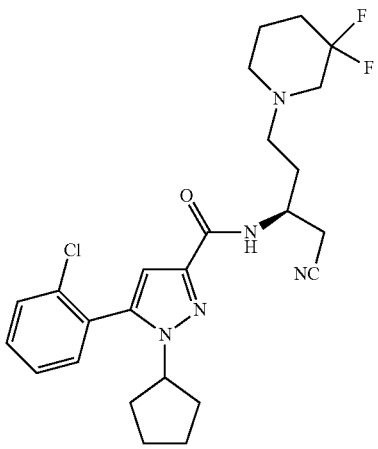 [SMILES: N#CC[C@H](CCN1CCCC(F)(F)C1)NC(=O)c1cc(-c2ccccc2Cl)n(C2CCCC2)n1]

(S)-5-(2-chlorophenyl)-N-(1-cyano-4-(3,3-difluoropiperidin-1-yl)butan-2-yl)-1-cyclopentyl-1H-pyrazole-3-carboxamide: To a mixture of (S)—N—(1-amino-5-(3,3-difluoropiperidin-1-yl)-1-oxopentan-3-yl)-5-(2-chlorophenyl)-1-cyclopentyl-1H-pyrazole-3-carboxamide (0.80 g, 1.6 mmol) and imidazole (109 mg, 1.6 mmol) in pyridine (15 ml) at 5° C. was added dropwise of POCl$_3$ (0.30 ml, 3.2 mmol). After addition, the mixture was continued to stir at 5° C. for 1 h before it was quenched with NaHCO$_3$, and extracted with EtOAc. The EtOAc solution was dried (Na$_2$SO$_4$), concentrated, and purified using 0-10% MeOH in DCM (with 1% NH3) to give the title product (S)-5-(2-chlorophenyl)-N-(1-cyano-4-(3,3-difluoropiperidin-1-yl)butan-2-yl)-1-cyclopentyl-1H-pyrazole-3-carboxamide (0.80 g) as a brown oil (contaminated with pyridine); $^1$H NMR (200 MHz, CDCl$_3$): δ 1.70-2.20 (m, 14H), 2.40-2.80 (m, 6H), 2.86 (d, 2H, J=5.0 Hz), 4.20-4.50 (m, 2H), 6.74 (s, 1H), 7.20-7.60 (m, 5H); LC-MS (ESI): m/z calculated for C$_{25}$H$_{31}$ClF$_2$N$_5$O [M30 H$^+$]: 490 and 492, Found: 489.9 and 492.2.

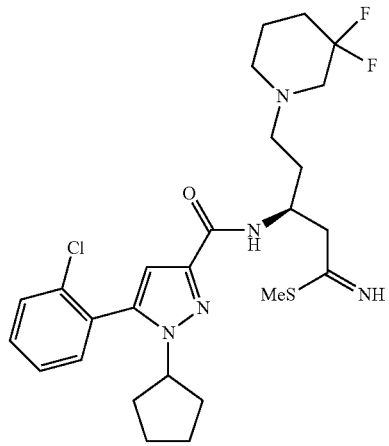 [SMILES: CSC(=N)C[C@H](CCN1CCCC(F)(F)C1)NC(=O)c1cc(-c2ccccc2Cl)n(C2CCCC2)n1]

(S)-methyl 3-(5-(2-chlorophenyl)-1-cyclopentyl-1H-pyrazole-3-carboxamido)-5-(3,3-difluoropiperidin-1-yl)pentanimidothioate: A mixture of (S)-5-(2-chlorophenyl)-N-(1-cyano-4-(3,3-difluoropiperidin-1-yl)butan-2-yl)-1-cyclopentyl-1H-pyrazole-3-carboxamide (0.80 g, 1.5 mmol), P$_2$S$_5$ (1.0 g, 4.5 mmol) and EtOH (15 ml) was heated at 85° C. for 17 h. It was cooled to rt, diluted with EtOAc and washed with NaHCO$_3$. The EtOAc layer was dried (Na$_2$SO$_4$) and concentrated to give a yellow foam.

To a mixture of the above yellow foam (0.53 g, about 1.0 mmol), K$_2$CO$_3$ (0.55 g, 4.0 mmol) and acetone (10 ml) was added MeI (0.25 ml, 4.0 mmol). The mixture was stirred at rt for 1.5 h before quenched with water and EA. The EtOAc layer was separated, dried (Na$_2$SO$_4$) and concentrated to give crude (9-methyl 3-(5-(2-chlorophenyl)-1-cyclopentyl-1H-pyrazole-3-carboxamido)-5-(3,3-difluoropiperidin-1-yl)pentanimidothioate(0.53 g) as a brown oil.

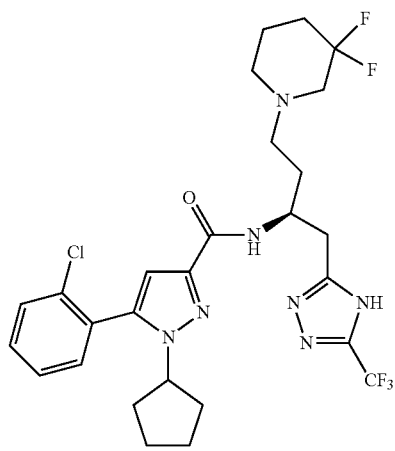 [SMILES: O=C(N[C@@H](CCN1CCCC(F)(F)C1)Cc1nnc(C(F)(F)F)[nH]1)c1cc(-c2ccccc2Cl)n(C2CCCC2)n1]

(S)-5-(2-chlorophenyl)-1-cyclopentyl-N-(4-(3,3-difluoropiperidin-1-yl)-1-(5-(trifluoromethyl)-4H-1,2,4-triazol-3-yl)butan-2-yl)-1H-pyrazole-3-carboxamide: A mixture of (5)-methyl 3-(5-(2-chlorophenyl)-1-cyclopentyl-1H-pyrazole-3-carboxamido)-5-(3,3-difluoropiperidin-1-yl)pentanimidothioate (0.12 g, 0.24 mmol), trifluoroacetyl hydrazide (30 mg, 0.24 mmol) and toluene (3 ml) was heated at 110° C. for 4 h. LC-MS showed little progress. Then 1,2-dichloro benzene was added, and the mixture was heated at 160° C. for 17 h. It was cooled to rt, concentrated to dryness and purified to give (S)-5-(2-chlorophenyl)-1-cyclopentyl-N-(4-

(3,3-difluoropiperidin-1-yl)-1-(5-(trifluoromethyl)-4H-1,2,4-triazol-3-yl)butan-2-yl)-1H-pyrazole-3-carboxamide (20 mg) as an off-white foam; $^1$H NMR (200 MHz, CDCl$_3$): δ 1.40-2.20 (m, 14H), 2.30-2.80 (m, 6H), 3.10-3.40 (m, 2H), 4.20-4.40 (m, 2H), 4.60-4.80 (m, 1H), 6.75 (s, 1H), 7.20-7.60 (m, 4H), 7.72 (d, 1H, J=8.4 Hz); LC-MS (ESI): m/z calculated for $C_{27}H_{32}ClF_5N_7O$ [M+H$^+$]: 600 and 602, Found: 599.9 and 602.0.

Scheme 6: Preparation of (S)-tert-butyl 3-amino-5-(3,3-difluoropiperidin-1-yl)pentanoate and (S)-tert-butyl 3-amino-5-(4,4-difluoropiperidine-1-yl)pentanoate

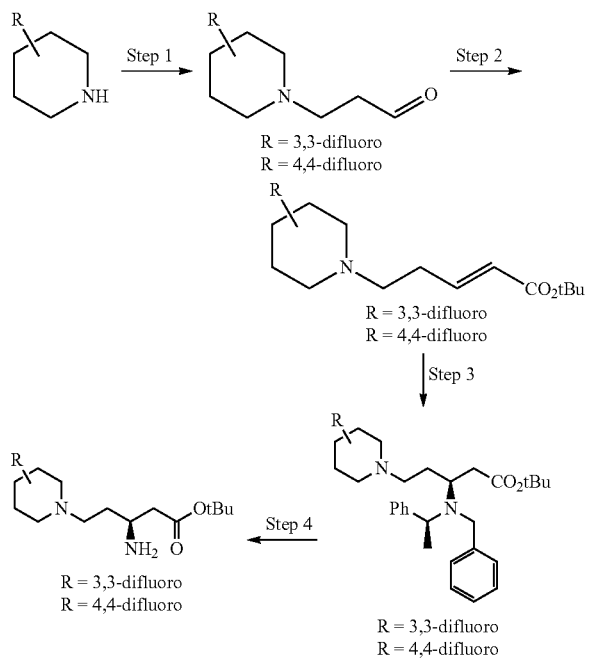

General Procedure for the Synthesis of (S)-tert-butyl 3-amino-5-(difluoropiperidin-1-yl)pentanoates Step 1: To a solution of difluoropiperidine.HCl (1 eq) in water (1 mL/mmol of piperidine) was added Na$_2$CO$_3$ (1 eq), and stirred at rt for 10 min. THF (2 mL/mmol of piperidine) was added, and the mixture was cooled to −15° C. DBU (1%) was added, followed by acrolein (90%, 1 eq). After addition, the mixture was stirred at −15° C. for 30 min, and the compound 3-(difluoropiperidin-1-yl)propanal in THF and water was used as is for the next step.

Step 2: To a solution of t-butyl diethylphosphonoacetate (1.2 eq to dilfluoropiperidine) in THF (1 mL/mmol of phosphonoacetate) at rt was added KOtBu (1.2 eq to 1 eq of dilfluoropiperidine). The mixture was stirred at rt for 10 min and then cooled to 5° C. Then, the solution 3-(difluoropiperidin-1-yl)propanal was added, and the resulting mixture was slowly warmed to rt. Stirring was continued at rt for 2 h before the mixture was quenched with water extracted with hexanes/EtOAc. The extract was dried (Na$_2$SO$_4$), concentrated and purified using 0-10% EtOAc in Hexanes to give compound (E)-tert-butyl 5-(difluoropiperidin-1-yl)pent-2-enoate Step 3: To a solution of (S)-(N)-benzyl-1-phenylethylamine (1.5 eq) in THF (2 mL/mmol of amine) at −75° C. was added slowly n-BuLi (1.5 eq). Stirring was continued at −75° C. for 30 min before dropwise addition of a solution of (E)-tert-butyl 5-(difluoropiperidin-1-yl)pent-2-enoate (1 eq) in THF (1 ml/mmol of amine). After addition, the mixture was continued to stir at −75° C. for 3 h, quenched with citric acid, and extracted with hexanes. The extract was dried (Na$_2$SO$_4$), concentrated and purified using 0-10% EtOAc in Hexanes to give (S)-tert-butyl 3-(benzyl((S)-1-phenylethyl)amino)-5-(difluoropiperidin-1-yl)pentanoate.

Step 4: A mixture of (S)-tert-butyl 3-(benzyl((S)-1-phenylethyl)amino)-5-(difluoropiperidin-1-yl)pentanoate(1 eq), Pd/C (10% on carbon, 0.3 eq by mass) and MeOH (50 ml/g of amine) was hydrogenated under H$_2$ (50 Psi) using a Parr-Shaker at rt for 3 days until the completion of reaction monitored by LC-MS analysis. The mixture was then quenched with celited, and filtered through a short-pad of Celite®, concentrated to give crude (S)-tert-butyl 3-amino-5-(difluoropiperidin-1-yl)pentanoate.

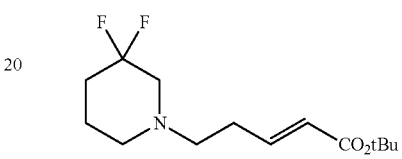

(E)-tert-butyl 5-(3,3-difluoropiperidin-1-yl)pent-2-enoate: Using the general procedure (Step1 and 2) described above,3,3-difluoropipiridine.HCl (4.36 g, 27.7 mmol) was used to give (E)-tert-butyl 5-(3,3-difluoropiperidin-1-yl) pent-2-enoate (1.96 g) as a colorless oil after column purification using 0-10% EtOAc in Hexanes; $^1$H NMR (200 MHz, CDCl$_3$): δ 1.57 (s,9H),1.60-2.00 (m, 4H), 2.30-2.80 (m, 8H), 5.78 (m, 1H), 6.82 (m, 1H); LC-MS (ESI): m/z calculated for $C_{14}H_{26}NO_2$ [M+H$^+$]: 240, Found: 240.1.

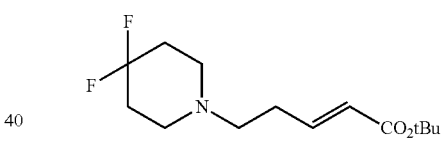

(E)-tert-butyl 5-(4,4-difluoropiperidin-1-yl)pent-2-enoate: Using the general procedure (Step 1 and 2) described above,4,4-difluoropipiridine.HCl (5.0 g, 31.7 mmol) was used to give (E)-tert-butyl 5-(4,4-difluoropiperidin-1-yl) pent-2-enoate (3.59 g) as white solid after column purification using 0-10% EtOAc in Hexanes;'H NMR (200 MHz, CDCl$_3$): δ 1.50 (s,9H),1.80-2.20 (m, 4H), 2.30-2.60 (m, 8H), 5.78 (m, 1H), 6.82 (m, 1H); LC-MS (ESI): m/z calculated for $C_{14}H_{24}F_2NO_2$ [M+H$^+$]: 276, Found: 275.8.

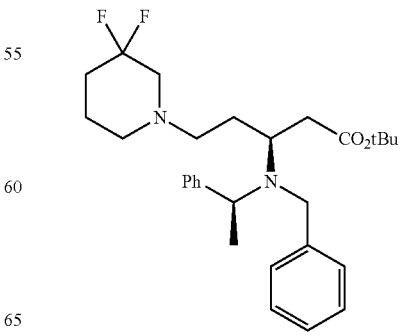

(S)-tert-butyl 3-(benzyl((S)-1-phenylethyl)amino)-5-(3,3-difluoropiperidin-1-yl)pentanoate: Using the general procedure (Step 3) described above, (E)-tert-butyl 5-(3,3-difluoropiperidin-1-yl)pent-2-enoate(1.96 g, 7.1 mmol) was used to give (S)-tert-butyl 3-(benzyl((S)-1-phenylethyl)amino)-5-(3,3-difluoropiperidin-1-yl)pentanoate (1.87 g) as a white solid after column purification using 0-10% EtOAc in Hexanes. $^1$H NMR (200 MHz, CDCl$_3$): δ 1.35 (d, 3H, J=7.4 Hz), 1.45 (s, 9H), 1.50-2.00 (m,8H),2.30-2.80 (m, 6H), 3.30-3.40 (m, 1H), 3.48 (d, 1H, J=15.0 Hz), 3.70-3.90 (m, 2H), 7.15-7.45 (m, 10H); LC-MS (ESI): m/z calculated for C$_{29}$H$_{41}$F$_2$N$_2$O$_2$ [M+H$^+$]: 487, Found: 486.7.

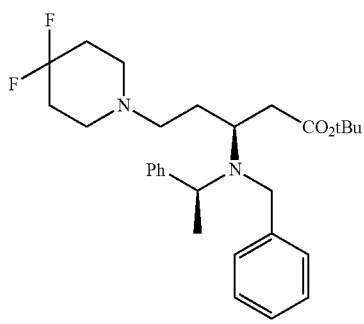 [SMILES: C[C@@H](c1ccccc1)N(Cc1ccccc1)[C@@H](CCN1CCC(F)(F)CC1)CC(=O)OC(C)(C)C]

(S)-tert-butyl 3-(benzyl((S)-1-phenylethyl)amino)-5-(4,4-difluoropiperidin-1-yl)pentanoate: Using the general procedure (Step 3) described above, (E)-tert-butyl 5-(4,4-difluoropiperidin-1-yl)pent-2-enoate (4.0 g, 19.1 mmol) was used to give (S)-tert-butyl 3-(benzyl((S)-1-phenylethyl)amino)-5-(4,4-difluoropiperidin-1-yl)pentanoate (3.78 g) as a colorless oil after column purification using 0-10% EtOAc in Hexanes.$^1$H NMR (200 MHz, CDCl$_3$): δ 1.34 (d, 3H, J=7.0 Hz), 1.42 (s, 9H), 1.40-1.60 (m, 2H), 1.80-2.10 (m,6H), 2.30-2.70 (m, 6H), 3.30-3.40 (m, 1H), 3.48 (d, 1H, J=15.0 Hz), 3.70-3.90 (m, 2H), 7.15-7.45 (m, 10H); LC-MS (ESI): m/z calculated for C$_{29}$H$_{41}$F$_2$N$_2$O$_2$ [M+H$^+$]: 487, Found: 486.6

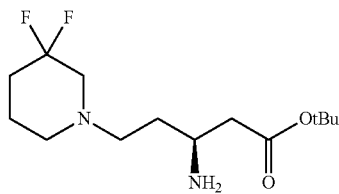 [SMILES: CC(C)(C)OC(=O)C[C@@H](N)CCN1CCCC(F)(F)C1]

(S)-tert-butyl 3-amino-5-(3,3-difluoropiperidin-1-yl)pentanoate: Using the general procedure (Step 4) described above,(S)-tert-butyl 3-(benzyl((S)-1-phenylethyl)amino)-5-(3,3-difluoropiperidin-1-yl)pentanoate (1.9 g, 3.9 mmol) was used to give crude (S)-tert-butyl 3-amino-5-(3,3-difluoropiperidin-1-yl)pentanoate (1.29 g) as a white foam, $^1$H NMR (200 MHz, CDCl$_3$): δ 1.43 (s, 9H), 1.70-2.40 (m,8H), 2.60-3.20 (m, 7H), 3.60-3.80 (m, 1H); LC-MS (ESI): m/z calculated for C$_{14}$H$_{28}$F$_2$N$_2$O$_2$ [M+H$^+$]: 293, Found: 292.8.

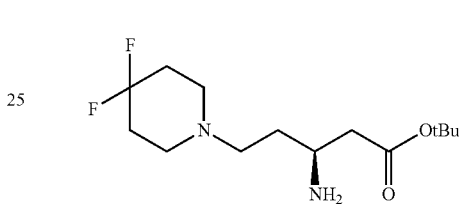

(S)-tert-butyl 3-amino-5-(4,4-difluoropiperidin-1-yl)pentanoate: Using the general procedure (Step 4) described above, (S)-tert-butyl 3-(benzyl((S)-1-phenylethyl)amino)-5-(4,4-difluoropiperidin-1-yl)pentanoate (9.3 g, 19.1 mmol) was used to give crude (S)-tert-butyl 3-amino-5-(4,4-difluoropiperidin-1-yl)pentanoate (5.5 g) as a white solid; δ 1.45 (s, 9H), 1.70-2.40 (m,8H), 2.50-3.20 (m, 7H), 3.60-3.80 (m, 1H); LC-MS (ESI): m/z calculated for C$_{14}$H$_{28}$F$_2$N$_2$O$_2$ [M+H$^+$]: 293, Found: 292.8.

Scheme7: (S)-1-cyclopentyl-5-(2-(1,1-difluoroethyl)-N-(5-(3,3-difluoropiperidin-1-yl)-1-oxo-1-(thiazol-2-ylamino)pentan-3-yl)-1H-pyrazole-3-carboxamide

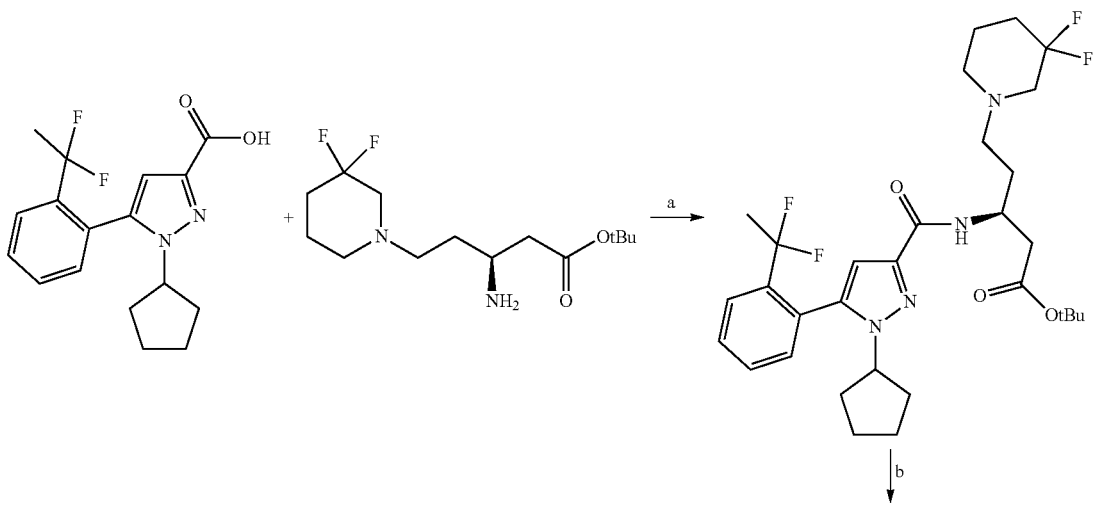

-continued

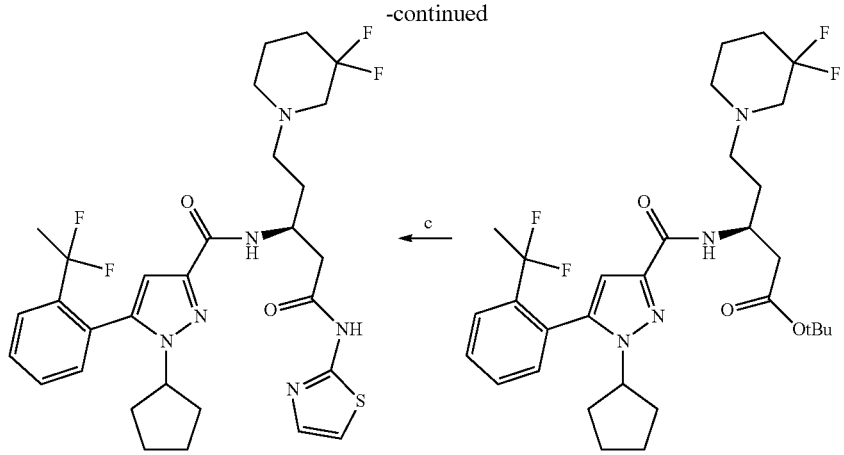

Reagents and conditions:
(a) TBTU, Et₃N, MeCN, rt, 15 h;
(b) TFA, DCM, rt, 2 h;
(c) 2-aminothiozole, TBTU, Et₃N, DMF, rt, 15 h (S)-tert-butyl 3-(1-cyclopentyl-5-(2-(1,1-difluoroethyl)phenyl)-1H-pyrazole-3-carboxamido)-5-(3,3-difluoropiperidin-1-yl)pentanoate: A mixture of 1-cyclopentyl-5-(2-(1,1-difluoroethyl)phenyl)-1H-pyrazole-3-carboxylic acid (70 mg, 0.24 mmol), (S)-tert-butyl 3-amino-5-(3,3-difluoropiperidin-1-yl)pentanoate (58 mg, 0.20 mmol), Et₃N (81 0.80 mmol) and TBTU (96 mg, 0.30 mmol) in MeCN (4 ml) was stirred at rt for 15 h. The mixture was diluted with EtOAc and washed with NaHCO₃. The organic layer was dried (Na₂SO₄), concentrated, and purified using EtOAc/Hex to give (S)-tert-butyl 3-(1-cyclopentyl-5-(2-(1,1-difluoroethyl)phenyl)-1H-pyrazole-3-carboxamido)-5-(3,3-difluoropiperidin-1-yl)pentanoate(50 mg) as a colorless oil; $^1$H NMR (200 MHz, CDCl₃): δ 1.44 (s, 9H), 1.60-2.20 (m, 15H), 2.10-2.80 (m, 10H), 4.00-4.20 (m, 1H), 4.30-4.50 (m, 1H), 6.67 (s, 1H), 7.19 (d, 1H, J=6.2 Hz), 7.30-7.60 (m, 3H), 7.60-7.80 (m, 1H); LC-MS (ESI): m/z calculated for $C_{31}H_{43}F_4N_4O_3$ [M+H⁺]: 595, Found: 594.9

(S)-3-(1-cyclopentyl-5-(2-(1,1-difluoroethyl)phenyl)-1H-pyrazole-3-carboxamido)-5-(3,3-difluoropiperidin-1-yl)pentanoic acid: To a solution of(S)-tert-butyl 3-(1-cyclopentyl-5-(2-(1,1-difluoroethyl)phenyl)-1H-pyrazole-3-carboxamido)-5-(3,3-difluoropiperidin-1-yl)pentanoate (50 mg, 0.096 mmol) in DCM (2 mL) was added TFA (0.5 mL) and stirred at rt for 2 h. Solvent was removed in vacuo and diluted with CHCl₃. Solvent was removed to provide (S)-3-(1-cyclopentyl-5-(2-(1,1-difluoroethyl)phenyl)-1H-pyrazole-3-carboxamido)-5-(3,3-difluoropiperidin-1-yl)pentanoic acid (38 mg) as a white solid;$^1$H NMR (200 MHz, CDCl₃): δ 1.40-2.20 (m, 18H), 2.40-2.80 (m, 7H), 4.00-4.20 (m, 1H), 4.30-4.50 (m, 1H), 6.67 (s, 1H), 7.19 (d, 1H, J=7.6 Hz), 7.40-7.80 (m, 3H); LC-MS (ESI): m/z calculated for $C_{27}H_{35}F_4N_4O_3$ [M+H⁺]: 539, Found: 538.7.

(S)-1-cyclopentyl-5-(2-(1,1-difluoroethyl)phenyl)-N-(5-(3,3-difluoropiperidin-1-yl)-1-oxo-1-(thiazol-2-ylamino)pentan-3-yl)-1H-pyrazole-3-carboxamide: A mixture of (S)-3-(1-cyclopentyl-5-(2-(1,1-difluoroethyl)phenyl)-1H-pyrazole-3-carboxamido)-5-(3,3-difluoropiperidin-1-yl)pentanoic acid (35 mg, 0.065 mmol), 2-aminothiazole (13 mg, 0.13 mmol), Et₃N (36 μL, 0.26 mmol) and TBTU (42 mg, 0.13 mmol) in DMF (1 ml) was stirred at rt for 15 h. The mixture was diluted with EtOAc and washed with water. The organic layer was dried (Na₂SO₄), concentrated, and purified using 0-100% EtOAc in hexanes to give the desired product (S)-1-cyclopentyl-5-(2-(1,1-difluoroethyl)phenyl)-N-(5-(3,3-difluoropiperidin-1-yl)-1-oxo-1-(thiazol-2-ylamino)pentan-3-yl)-1H-pyrazole-3-carboxamide (18 mg) as a white solid; $^1$H NMR (200 MHz, CDCl₃): δ 1.40-2.20 (m, 18H), 2.40-2.80 (m, 7H), 4.00-4.20(m, 1H), 4.40-4.60 (m, 1H), 6.70 (s, 1H), 6.97 (d, 1H, J=3.8 Hz), 7.19 (d, 1H, J=6.6 Hz), 7.40-7.60 (m, 3H), 7.67 (d, 1H, J=6.6 Hz), 7.81 (d, 1H, J=8.0 Hz), 11.5 (br s, 1H); LC-MS (ESI): m/z calculated for $C_{30}H_{37}F_4N_6O_2S$ [M+H⁺]: 621, Found: 620.9.

Scheme 8: Preparation of (S)-N-(1-(cyclobutylamino)-5-(cyclopentyl(mentyl)amino)-1-oxopentan-3-yl)-1-cyclopenyl-5-(2-(trifluoromethyl)phenyl)-1H-pyrazole-3-carboxamide

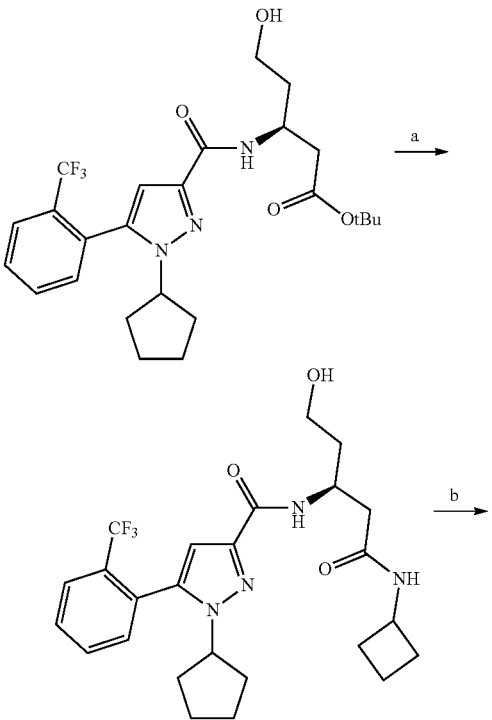

-continued

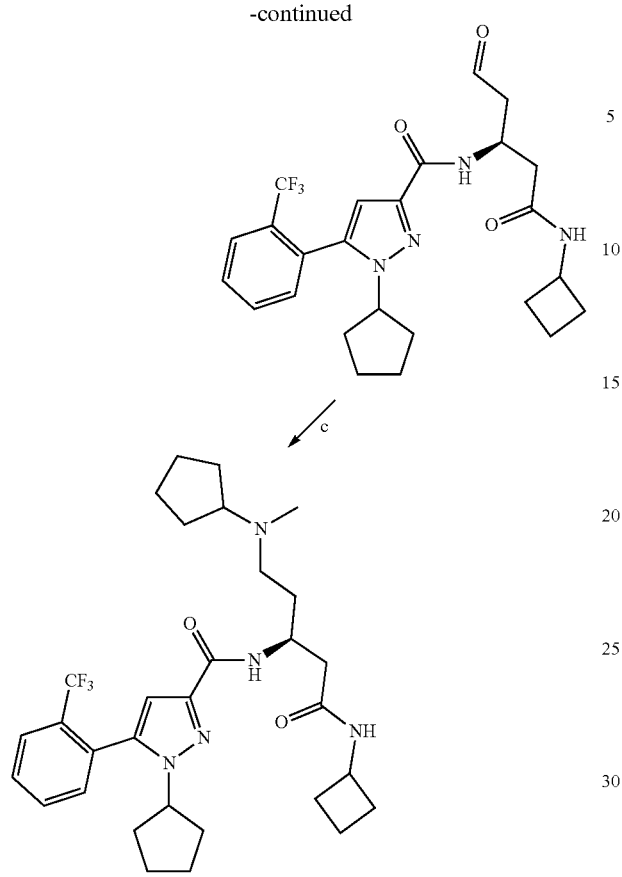

Reagents and conditions:
(a) cyclobutylamine, EtOH, 90° C., 24 h;
(b) Dess-Martin Reagent, DCM, rt, 0.5 h;
(c) N-methylcyclopentanamine, sodium cyanoborohydride, MeOH, rt, 3 h

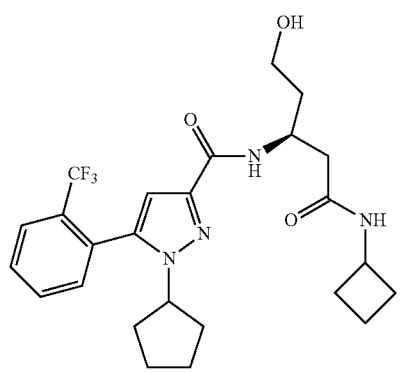 [SMILES: O=C(C[C@H](CCO)NC(=O)c1cc(-c2ccccc2C(F)(F)F)n(C2CCCC2)n1)NC1CCC1]

(S)—N—(1-(cyclobutylamino)-5-hydroxy-1-oxopentan-3-yl)-1-cyclopentyl-5-(2-(trifluoromethyl)phenyl)-1H-pyrazole-3-carboxamide: A mixture of (S)-tert-butyl 3-(1-cyclopentyl-5-(2-(trifluoromethyl)phenyl)-1H-pyrazole-3-carboxamido)-5-hydroxypentanoate (0.15 g), cyclobutylamine (0.50 ml) and EtOH (1 mL) was heated in a sealed tube at 90° C. for 24 h. The mixture was concentrated and purified using EtOAc in hexanes (0-25%) to give (S)—N—(1-(cyclobutylamino)-5-hydroxy-1-oxopentan-3-yl)-1-cyclopentyl-5-(2-(trifluoromethyl)phenyl)-1H-pyrazole-3-carboxamide (97 mg) as a white solid; $^1$H NMR (200 MHz, CDCl$_3$): δ 0.80-0.95 (m, 2H), 1.40-2.70 (m, 16H), 3.60-3.80 (m, 2H), 4.04-4.20 (m, 1H), 4.20-4.45 (m, 1H), 4.50-4.70 (m, 1H), 6.18 (br s, 1H), 6.73 (s, 1H), 7.25-7.40 (m, 1H), 7.50-7.70 (m, 2H), 7.70-7.90 (m,1H), 7.98 (br s, 1H); LC-MS (ESI): m/z calculated for C$_{25}$H$_{32}$F$_3$N$_4$O$_3$ [M+H$^+$]: 493, Found: 493.1.

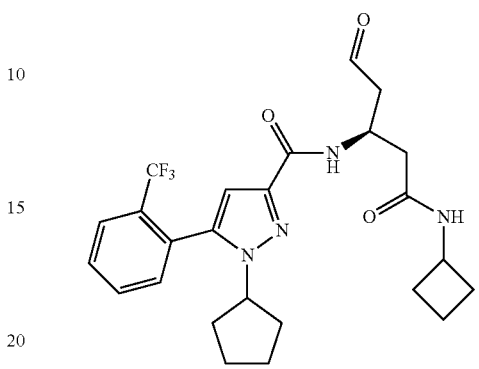

(S)—N—(1-(cyclobutylamino)-1,5-dioxopentan-3-yl)-1-cyclopentyl-5-(2-p(trifluoromethyl)phenyl)-1H-pyrazole-3-carboxamide: To a solution of (S)—N—(1-(cyclobutylamino)-5-hydroxy-1-oxopentan-3-yl)-1-cyclopentyl-5-(2-(trifluoromethyl)phenyl)-1H-pyrazole-3-carboxamide (90 mg, 0.18 mmol) in DCM (2 mL) was added Dess-Martin Reagent (153 mg, 0.36 mmol). The mixture was stirred at rt for 0.5 h before it was quenched with sodium thiosulfate (10%) and NaHCO$_3$. The mixture was extracted with DCM, and the extract was dried (Na$_2$SO$_4$), concentrated and purified using EtOAc in hexanes (0-20%) to give (S)—N—(1-(cyclobutylamino)-1,5-dioxopentan-3-yl)-1-cyclopentyl-5-(2-(trifluoromethyl)phenyl)-1H-pyrazole-3-carboxamide (32 mg) as a white solid; $^1$H NMR (200 MHz, CDCl$_3$): δ 1.29 (t, 2H, J=7.0 Hz), 1.40-2.70 (m, 15H), 2.90-3.10 (m, 1H), 4.04-4.20 (m, 1H), 4.50-4.6 (m, 1H), 4.65-4.90 (m, 1H), 5.28 (br s, 1H), 6.73 (s, 1H), 6.84 (d, 1H, J=7.8 Hz), 7.25-7.40 (m, 1H), 7.50-7.70 (m, 2H), 7.70-7.85 (m,1H), 9.81 (s, 1H); LC-MS (ESI): m/z calculated for C$_{25}$H$_{30}$F$_3$N$_4$O$_3$ [M+H$^+$]: 491, Found: 490.6.

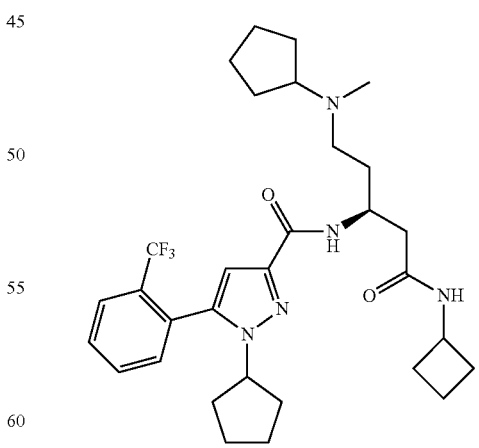

(S)—N—(1-(cyclobutylamino)-5-(cyclopentyl(methyl)amino)-1-oxopentan-3-yl)-1-cyclopentyl-5-(2-(trifluoromethyl)phenyl)-1H-pyrazole-3-carboxamide
To a mixture of crude aldehyde, (S)—N—(1-(cyclobutylamino)-1,5-dioxopentan-3-yl)-1-cyclopentyl-5-(2-(trifluoromethyl)phenyl)-1H-pyrazole-3-carboxamide (74 mg, 0.150 mmol) and N-methylcyclopentanamine (30 mg, 0.300 mmol) in MeOH (4 mL) was added sodium cyanoborohydride (19 mg, 0.300 mmol). The resulting mixture was stirred at rt for 1-3 h until the completion of the reaction by LC-MS analysis. Then mixture was concentrated and purified using MeOH in DCM (with 1% $NH_3$) to give (S)—N—(1-(cyclobutylamino)-5-(cyclopentyl(methyl)amino)-1-oxopentan-3-yl)-1-cyclopentyl-5-(2-(trifluoromethyl)phenyl)-1H-pyrazole-3-carboxamide (23 mg) as a colorless oil; $^1$H NMR (200 MHz, $CDCl_3$): δ 1.40-2.90 (m, 31H), 4.04-4.20 (m, 1H), 4.20-4.50 (m, 2H), 6.74 (s, 1H), 7.03 (br s, 1H), 7.14 (br s, 1H), 7.25-7.40 (m, 1H), 7.50-7.70 (m, 2H), 7.70-7.90 (m,1H), 8.56 (br s, 1H); LC-MS (ESI): m/z calculated for $C_{31}H_{43}F_3N_5O_2$ [M+H$^+$]: 574, Found: 573.9.

Scheme 9: Preparation of (S)-N-(1-(cyclobutylamino)-5-(oxetane-3-carboxamido)-1-oxopentan-3-yl)-1-cyclopentyl-5-(2-(trifluoromethyl)phenyl)-1H-pyrazole-3-carboxamide

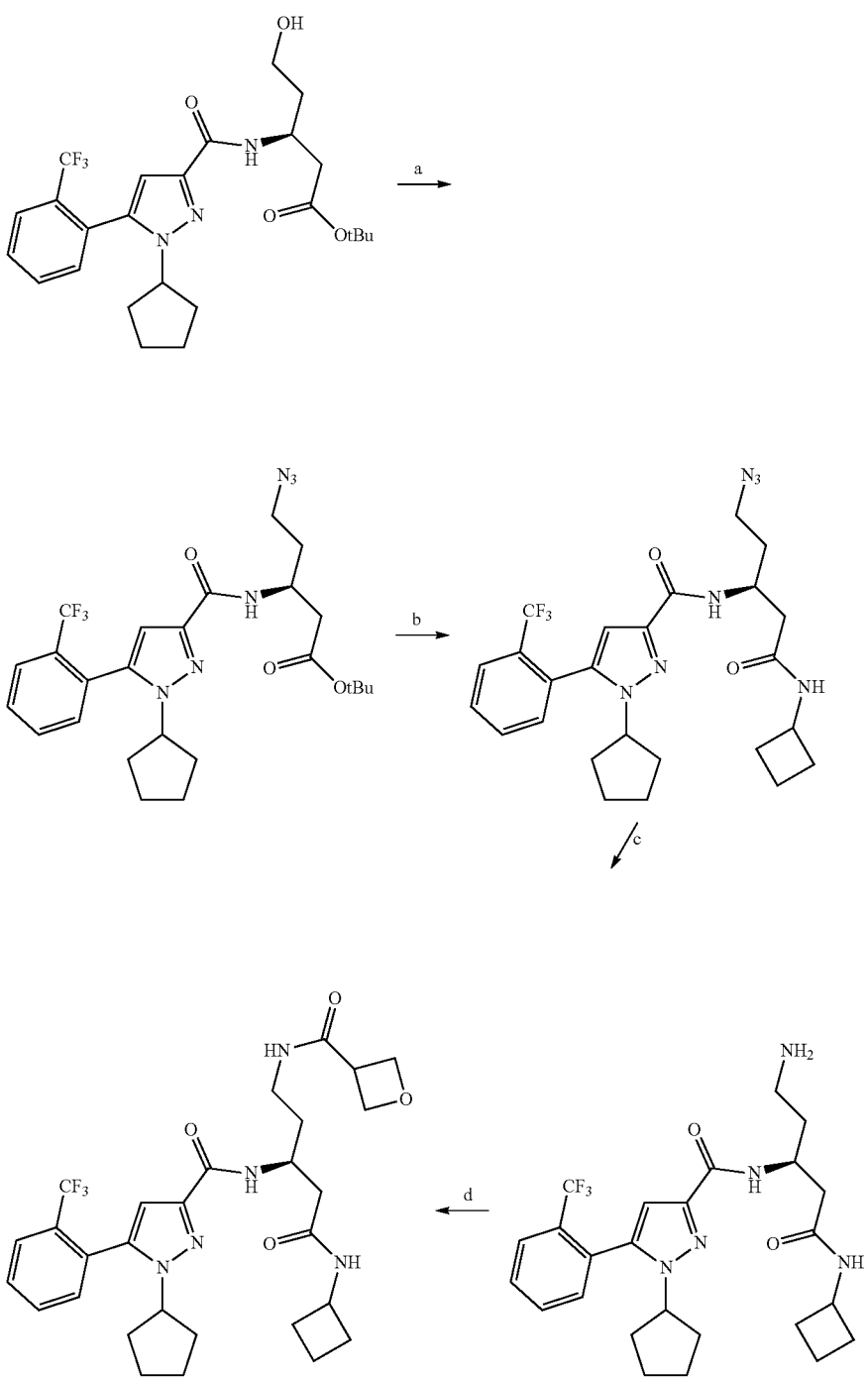

Reagants and conditions: (a) Zn(N$_3$)$_2$•Py$_2$, PPh$_3$, toluene, DIAD, rt, 20 h; (b) TFA, DCM, rt, 2 h; (b) TFA, DCM, rt, 2 h; cyclobutylamine, CH$_3$CN, Et$_3$N, TBTU, rt, 18 h; (c) H$_2$, 10% Pd/C, EtOH, rt, 17 h; (d) 3-oxetanecarboxylic acid, CH$_3$CNm Et$_3$N, TBTU, rt, 18 h Preparation of Zn(N$_3$)$_2$.Py$_2$: To a solution of Zn(NO$_3$)$_2$ (3.57 g, 12 mmol) in water (6 mL) was added a solution of sodium azide (0.78 g, 12.0 mmol) in water (6 mL). The mixture was stirred at rt for 5 min and heated to 50° C., followed by dropwise addition of pyridine (2.0 mL, 24.7 mmol). After addition, the oil bath was removed, and stirring was continued for 1 h to give a cloudy mixture. The suspension was filtered, washed with cold water (5 mL) and air dried to give the title compound (1.3 g) as a white solid.

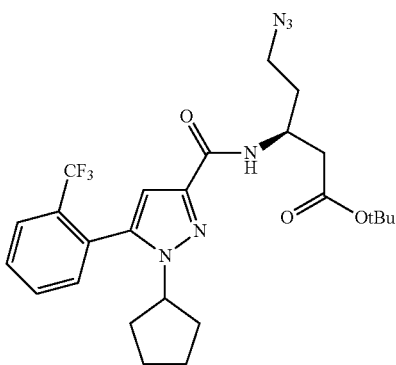 [SMILES: CC(C)(C)OC(=O)C[C@H](CCN=[N+]=[N-])NC(=O)c1cc(-c2ccccc2C(F)(F)F)n(C2CCCC2)n1]

(S)-tert-butyl 5-azido-3-(1-cyclopentyl-5-(2-(trifluoromethyl)phenyl)-1H-pyrazole-3-carboxamido)pentanoate: To a mixture of (S)-tert-butyl 3-(1-cyclopentyl-5-(2-(trifluoromethyl)phenyl)-1H-pyrazole-3-carboxamido)-5-hydroxypentanoate (2.5 g, 5.0 mmol), Zn(N$_3$)$_2$.Py$_2$ (1.15 g, 3.75 mmol), PPh$_3$ (2.62 g, 10.0 mmol) and toluene (50 mL) was added dropwise of DIAD (2.0 mL, 10 mmol) and stirred at rt for 20 h. The mixture was filtered, rinsed with EtOAc, and the filtrate was concentrated and purified using EtOAc in hexanes (0-40%) to give (S)-tert-butyl 5-azido-3-(1-cyclopentyl-5-(2-(trifluoromethyl)phenyl)-1H-pyrazole-3-carboxamido)pentanoate (2.04 g) as a white semi-solid; $^1$H NMR (200 MHz, CDCl$_3$): δ 1.46 (s, 9H), 1.50-1.60 (m, 2H), 1.80-2.10 (m, 8H), 2.55-2.65(m, 2H), 3.45 (t, 2H, J=7.1 Hz), 4.40-4.60 (m, 1H), 4.85-5.05 (m, 1H), 6.31 (br s, 1H), 6.76 (s, 1H), 7.28-7.40 (m, 2H), 7.50-7.70 (m, 2H), 7.70-7.90 (m,1H); LC-MS (ESI): m/z calculated for C$_{25}$H$_{32}$F$_3$N$_6$O$_3$ [M+H$^+$]: 521, Found: 520.9.

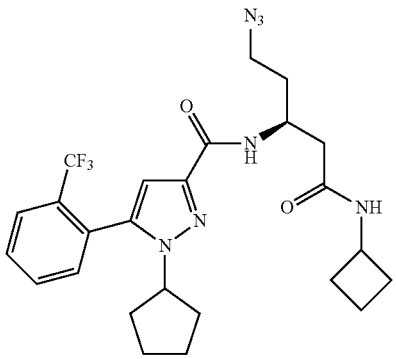 [SMILES: [N-]=[N+]=NCC[C@@H](CC(=O)NC1CCC1)NC(=O)c1cc(-c2ccccc2C(F)(F)F)n(C2CCCC2)n1]

(S)—N—(5-azido-1-(cyclobutylamino)-1-oxopentan-3-yl)-1-cyclopentyl-5-(2-(trifluoromethyl)phenyl)-1H-pyrazole-3-carboxamide: To a solution of (S)-tert-butyl 5-azido-3-(1-cyclopentyl-5-(2-(trifluoromethyl)phenyl)-1H-pyrazole-3-carboxamido)pentanoate (99 mg, 0.190 mmol) in DCM (2 mL) was added TFA (0.15 mL, 1.90 mmol) and stirred at rt for 2 h. Solvent was removed to provide crude (S)-5-azido-3-(1-cyclopentyl-5-(2-(trifluoromethyl)phenyl)-1H-pyrazole-3-carboxamido)pentanoic acid (100 mg) as yellow oil which was used as is for the next reaction without further purification.

To a solution of (S)-5-azido-3-(1-cyclopentyl-5-(2-(trifluoromethyl)phenyl)-1H-pyrazole-3-carboxamido)pentanoic acid(100 mg, 0.215 mmol) and cyclobutylamine (30 mg, 0.430 mmol) in ACN (1 mL) was added anhydrous NEt$_3$ (0.090 mL, 0.645 mmol) followed by TBTU (138 mg, 0.430 mmol). The reaction mixture was stirred at rt for 18 h. Reaction mixture was diluted with EtOAc (10 mL) and washed with sat. NaHCO$_3$ (5 mL). Organic phase was extracted, added silica gel (100 mg) and purified using Combiflash® R$_f$(EtOAc/hexanes) and the fractions containing the product (TLC) were pooled and evaporated to afford 35 mg of (S)—N—(5-azido-1-(cyclobutylamino)-1-oxopentan-3-yl)-1-cyclopentyl-5-(2-(trifluoromethyl)phenyl)-1H-pyrazole-3-carboxamideas a white foam; $^1$H NMR (200 MHz, CDCl$_3$): δ 1.40-2.40 (m, 16H), 2.55-2.65 (m, 2H), 3.44 (t, 2H, J=7.6 Hz), 4.10-4.50 (m, 3H), 6.64 (br s, 1H), 6.75 (s, 1H), 7.28-7.40 (m, 2H), 7.50-7.70 (m, 2H), 7.70-7.90 (m,1H); LC-MS (ESI): m/z calculated for C$_{25}$H$_{30}$F$_3$N$_7$O$_2$ [M+H$^+$]: 518, Found: 518.2.

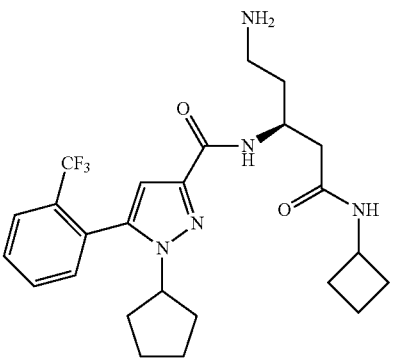 [SMILES: NCC[C@@H](CC(=O)NC1CCC1)NC(=O)c1cc(-c2ccccc2C(F)(F)F)n(C2CCCC2)n1]

(S)—N—(5-amino-1-(cyclobutylamino)-1-oxopentan-3-yl)-1-cyclopentyl-5-(2-(trifluoromethyl)phenyl)-1H-pyrazole-3-carboxamide: A mixture of (S)—N—(5-azido-1-(cyclobutylamino)-1-oxopentan-3-yl)-1-cyclopentyl-5-(2-(trifluoromethyl)phenyl)-1H-pyrazole-3-carboxamide (35 mg) Pd/C (10%, 7 mg) and EtOH (3 mL) was stirred under a balloon of hydrogen for 17 h. LC-MS showed the completion of the reduction. Then the mixture was filtered through a short pad of Celite®, and the filtrate was concentrated to give crude (S)—N—(5-amino-1-(cyclobutylamino)-1-oxopentan-3-yl)-1-cyclopentyl-5-(2-(trifluoromethyl)phenyl)-1H-pyrazole-3-carboxamideas a colorless oil (30 mg); LC-MS (ESI): m/z calculated for C$_{25}$H$_{33}$F$_3$N$_5$O$_2$ [M+H$^+$]: 492, Found: 492.2.

271

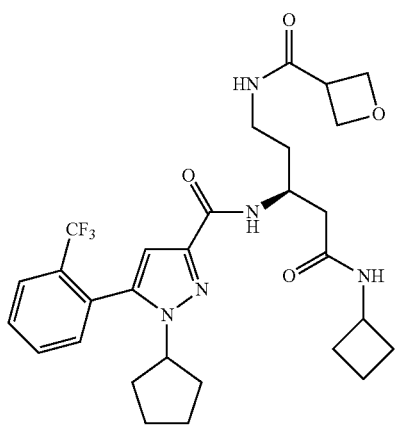 [SMILES: O=C(C[C@H](CCNC(=O)C1COC1)NC(=O)c1cc(-c2ccccc2C(F)(F)F)n(C2CCCC2)n1)NC1CCC1]

(S)—N—(1-(cyclobutylamino)-5-(oxetane-3-carbox-amido)-1-oxopentan-3-yl)-1-cyclopentyl-5-(2-(trifluoromethyl)phenyl)-1H-pyrazole-3-carboxamide: To a solution of (S)—N—(5-amino-1-(cyclobutylamino)-1-oxopentan-3-yl)-1-cyclopentyl-5-(2-(trifluoromethyl)phenyl)-1H-pyrazole-3-carboxamide (30 mg, 0.061 mmol) and 3-oxetanecarboxylic acid (13 mg, 0.122 mmol) in ACN (2 mL) was added anhydrous NEt$_3$ (0.018 mL, 0.183 mmol) followed by TBTU (39 mg, 0.122 mmol). The reaction mixture was stirred at rt for 18 h. The reaction mixture was diluted with EtOAc (10 mL) and washed with sat. NaHCO$_3$ (5 mL). The organic phase was extracted, added silica gel (100 mg) and purified using Combiflash® R$_f$ (EtOAc/hexanes) and the fractions containing the product (TLC) were pooled and evaporated to afford(S)—N—(1-(cyclobutylamino)-5-(oxetane-3-carbox-amido)-1-oxopentan-3-yl)-1-cyclopentyl-5-(2-(trifluoromethyl)phenyl)-1H-pyrazole-3-carboxamide(6 mg) as a white solid; $^1$H NMR (200 MHz, CDCl$_3$): δ 1.40-2.80 (m, 19H), 3.60-3.90 (m, 2H), 4.10-4.50 (m, 3H), 4.70-5.00 (m, 4H). 6.32 (br s, 1H), 6.71 (s, 1H), 7.18 (br s, 1H), 7.28-7.40 (m, 1H), 7.50-7.70 (m, 2H), 7.70-7.90 (m, 1H), 8.15 (d, 1H, J=8.8 Hz); LC-MS (ESI): m/z calculated for C$_{29}$H$_{37}$F$_3$N$_5$O$_4$ [M+H$^+$]: 576, Found: 576.2.

Scheme 10: Preparation of (S)-1-cyclopentyl-N-(4-(3,3-difluoropiperidin-1-yl)-4-oxo-1-sulfamoylbutan-2-yl)-5-(2-(trifluoromethyl)phenyl)-1H-pyrazole-3-carboxamide

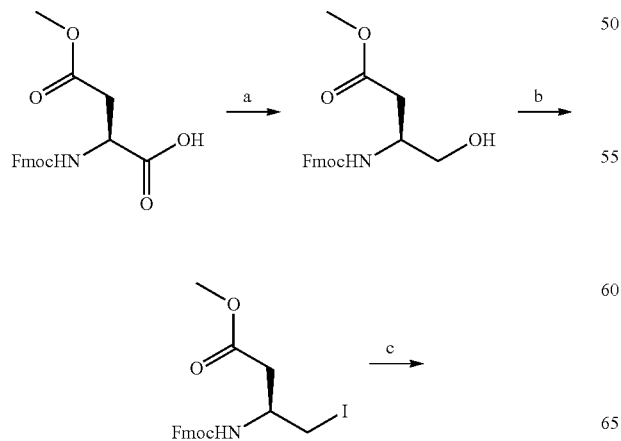

272
-continued

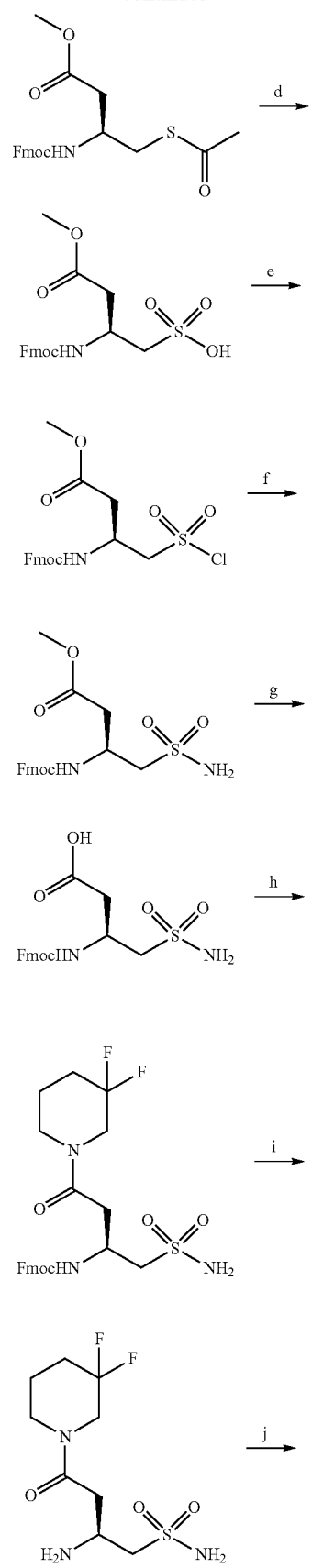

-continued

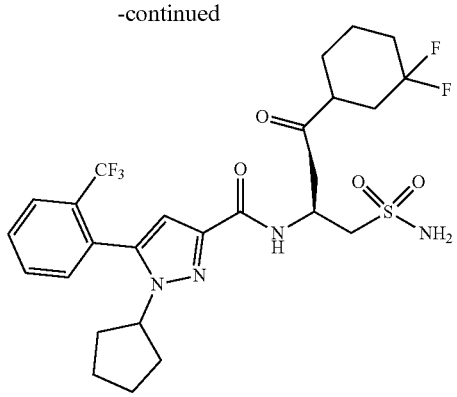

Reagents and conditions: (a) Isobutylchloroformate, N-methylmorpholine, DME, -15° C., 1 h; NaBH$_4$, H$_2$O; (b) Iodine, PPh$_3$, imidazole, DCM, 0° C. to RT, 18 h; (c) Potassium thioacetate, DMF, rt, 15 h; (d) 30% w/w H$_2$O$_2$ soln, formic acid, rt, 18 h; (e) SOCl$_2$, DMF (3 drops), rt, 3 days, 40° C., 1.5 h; (f) ammonium hydroxide solution, THF, 2 min; (g) AcOH, 100° C., 15 h; (h) HATU, HOAt, 3,3-difluoropiperidine hydrochloride, i-PrNEt2, DMF, 0° C., rt, 3 days; (i) Et$_2$NH, CH$_3$CN, rt, 1.5 h; HATU, HOAt, i-PrNEt2, DMF, rt, 2 h

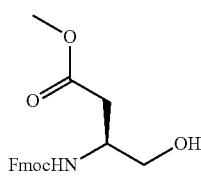

(S)-methyl 3-((((9H-fluoren-9-yl)methoxy)carbonyl) amino)-4-hydroxybutanoate:

N-methylmorpholine (4.46 mL, 40.6 mmol, 1.00 equiv.) was added to a solution of (S)-2-((((9H-fluoren-9-yl)methoxy)carbonyl)amino)-4-methoxy-4-oxobutanoic acid in DME (81 mL) at −15° C. Isobutylchloroformate (5.27 mL, 40.6 mmol, 1.00 equiv.) was then added dropwise. The reaction mixture was stirred at the same temperature for 1 h. The solution was filtered on a frit and the filtrate cooled back to −15° C. A solution of sodium borohydride (2.30 g, 60.9 mmol, 1.50 equiv.) in water (20 mL) was added. Right after this addition, 800 mL of water was added (a white precipitate formed). The solution was filtered, the solid was ground to a fine powder and dried under reduced pressure to provide 9.13 g (63%) of the title compound as a white solid mixed with some of the corresponding lactonized product. m/z (M+H)$^+$=356.1; R$_T$=1.51 min; purity=65%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

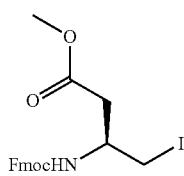

(S)-methyl 3-((((9H-fluoren-9-yl)methoxy)carbonyl) amino)-4-iodobutanoate: Iodine (5.46 g, 21.5 mmol, 1.00 equiv.) was added to a solution of triphenylphosphine (5.65 g, 21.5 mmol, 1.00 equiv.) and imidazole (1.76 g, 25.8 mmol, 1.20 equiv.) in DCM (86 mL) at 0° C. The reaction mixture was stirred for 20 min at the same temperature and the alcohol was added. The reaction mixture was stirred at rt for 18 h. An aqueous saturated solution of Na$_2$S$_2$O$_3$ was added and the mixture was stirred for 10 min and extracted with ethyl acetate (2×). The combined organic layers were dried with sodium sulfate, filtered and evaporated. The crude product was purified by flash chromatography on silica gel (dry packing) using a solution of ethyl acetate in hexane (5 to 30%) to provide 1.27 g (13%) of the title compound as a white solid and 4.0 g of a mixture of the title compound and an impurity (LCMS ratio=58:42). Pure compound: m/z (M+H)$^+$=466.0; R$_T$=1.86 min; purity=94%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile, $^1$H NMR (500 MHz, DMSO) δ 2.57-2.53 (m, 1H), 2.64 (dd, J=15.8, 5.3 Hz, 1H), 3.27 (dd, J=10.0, 6.9 Hz, 1H), 3.37 (dd, J=10.1, 5.2 Hz, 1H), 3.58 (s, 3H), 3.90-3.81 (m, 1H), 4.23 (t, J=6.9 Hz, 1H), 4.37-4.27 (m, 2H), 7.33 (td, J=7.5, 1.1 Hz, 2H), 7.42 (t, J=7.4 Hz, 2H), 7.58 (d, J=7.8 Hz, 1H), 7.70 (d, J=7.5 Hz, 2H), 7.89 (d, J=7.5 Hz, 2H).

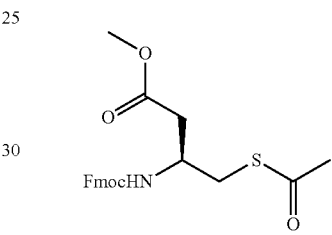

(S)-methyl 3-((((9H-fluoren-9-yl)methoxy)carbonyl) amino)-4-(acetylthio)butanoate: Potassium thioacetate (393 mg, 3.44 mmol, 2.00 equiv.) was added to a solution of (S)-methyl 3-((((9H-fluoren-9-yl)methoxy)carbonyl) amino)-4-iodobutanoate in DMF (6.9 mL). The reaction mixture was stirred for 15 h. An aqueous saturated solution of sodium bicarbonate was added, followed by ethyl acetate. The phases were separated and the organic layer was washed 2× with sat'd aq. NaHCO$_3$, dried with sodium sulfate, filtered and evaporated. The crude product was purified by flash chromatography on silica gel using a solution of ethyl acetate in hexane (5 to 40%) to provide 555 mg (78%) of the title compound as a white solid. m/z (M+H)$^+$=414.1; R$_T$=1.76 min; purity=99.3%. HPLC conditions: Column:) XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile, $^1$H NMR (500 MHz, DMSO) δ 2.32 (s, 3H), 2.54-2.52 (m, 2H), 2.90 (dd, J=13.5, 7.7 Hz, 1H), 3.10 (dd, J=13.5, 5.5 Hz, 1H), 3.57 (s, 3H), 3.96-3.89 (m, 1H), 4.21 (t, J=7.0 Hz, 1H), 4.32-4.27 (m, 2H), 7.33 (td, J=7.4, 1.1 Hz, 2H), 7.45-7.39 (m, 3H), 7.67 (d, J=7.4 Hz, 2H), 7.89 (d, J=7.5 Hz, 2H).

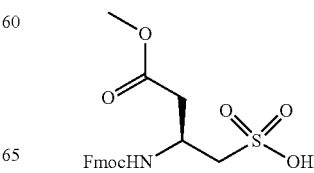

(S)-2-((((9H-fluoren-9-yl)methoxy)carbonyl)amino)-4-methoxy-4-oxobutane-1-sulfonic acid:

A 30% w/w solution of hydrogen peroxide in water (1.3 mL) was added to formic acid (5.0 mL) at 0° C. The reaction mixture was stirred at that temperature for 1 h. A suspension of (S)-methyl 3-((((9H-fluoren-9-yl)methoxy)carbonyl)amino)-4-(acetylthio)butanoate in formic acid (4.0 mL) was added. The reaction mixture was stirred at rt 18. The solvent was evaporated and then the crude product was co-evaporated with toluene and a mixture of DCM/toluene to provide 554 mg (98%) of the title compound as a pale orange solid. m/z (M+H)$^+$=420.1; R$_T$=1.31 min; purity=87.7%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile, $^1$H NMR (500 MHz, DMSO) δ 2.54-2.51 (m, 1H), 2.65-2.59 (m, 1H),2.71-2.65 (m, 1H), 3.06 (dd, J=15.8, 5.0 Hz, 1H), 3.55 (s, 3H), 4.13-4.08 (m, 1H), 4.28-4.18 (m, 3H), 7.19-7.12 (m, 1H), 7.27-7.22 (m, 1H), 7.32 (t, J=7.4 Hz, 2H), 7.41 (dd, J=7.4, 6.5 Hz, 2H), 7.66 (d, J=7.5 Hz, 2H), 7.88 (d, J=7.5 Hz, 2H).

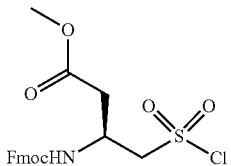

(S)-methyl 3-((((9H-fluoren-9-yl)methoxy)carbonyl)amino)-4-(chlorosulfonyl)butanoate:

Thionyl chloride (1.4 mL, 20 mmol, 15 equiv.), containing three drops of DMF, was added to (S)-2-((((9H-fluoren-9-yl)methoxy)carbonyl)amino)-4-methoxy-4-oxobutane-1-sulfonic acid (554 mg, 1.32 mmol, 1.00 equiv.). The reaction mixture was stirred at rt for 3 days and was heated at 40° C. for 1.5 h. Volatiles were evaporated and the mixture was co-evaporated 2× with DCM to provide 550 mg (95%) of the title compound as a dark orange solid. m/z (M+H)$^+$=438.1; R$_T$=1.77 min; purity=94.8%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.$^1$H NMR (500 MHz, DMSO) δ 2.68 (dd, J=13.4, 4.5 Hz, 1H), 2.54-2.48 (m, J=7.7 Hz, 1H), 2.62 (dd, J=13.8, 7.8 Hz, 1H), 3.06 (dd, J=15.7, 5.0 Hz, 1H), 3.55 (s, 3H), 4.15-4.07 (m, 1H), 4.27-4.18 (m, 3H), 7.26 (d, J=7.9 Hz, 1H), 7.32 (t, J=7.5 Hz, 2H), 7.41 (t, J=7.4 Hz, 2H), 7.66 (d, J=7.0 Hz, 2H), 7.88 (d, J=7.5 Hz, 2H).

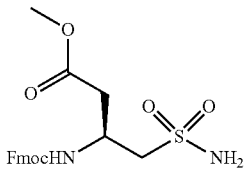

(S)-methyl 3-((((9H-fluoren-9-yl)methoxy)carbonyl)amino)-4-sulfamoylbutanoate:A concentrated aqueous solution of ammonium hydroxyde (0.22 mL, 3.1 mmol, 5.0 equiv.) was added to a solution of (9-methyl 3-((((9H-fluoren-9-yl)methoxy)carbonyl)amino)-4-(chlorosulfonyl)butanoate (275 mg, 0.628 mmol, 1.00 equiv.) in THF (3.1 mL). The reaction mixture was stirred for 2 min and the solvent was evaporated. The crude product was purified by flash chromatography on silica gel using a solution of ethyl acetate in hexanes (5 to 60%) to provide 140 mg (53%) of the title compound as a pale orange solid. m/z (M+H)$^+$=419.1; RT=1.52 min; purity=>95%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.$^1$H NMR (500 MHz, DMSO) δ 2.64-2.58 (m, 1H), 2.80 (dd, J=15.8, 4.7 Hz, 1H), 3.18 (dd, J=14.0, 6.9 Hz, 1H), 3.25 (dd, J=14.0, 6.0 Hz, 1H), 3.58 (s, 3H), 4.31-4.19 (m, 4H), 6.92 (s, 2H), 7.32 (t, J=7.5 Hz, 2H), 7.42 (t, J=7.3 Hz, 2H), 7.49 (d, J=8.2 Hz, 1H), 7.67 (d, J=7.4 Hz, 2H), 7.89 (d, J=7.5 Hz, 2H).

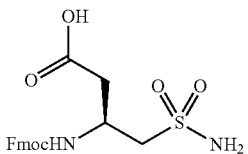

(S)-3-((((9H-fluoren-9-yl)methoxy)carbonyl)amino)-4-sulfamoylbutanoic acid: HCl (conc., 1.1 mL) was added to a solution of (I)-methyl 3-((((9H-fluoren-9-yl)methoxy)carbonyl)amino)-4-sulfamoylbutanoate (140 mg, 0.335 mmol, 1.00 equiv.) in AcOH (11 mL). The reaction mixture was heated at 100° C. for 15 h. The reaction mixture was poured in 70 mL of water and ethyl acetate was added. The phases were separated and the organic layer was dried with sodium sulfate, filtered and evaporated. The crude mixture was co-evaporated with dioxane and DCM to provide 122 mg (90%) of the title compound as a pale yellow solid. m/z (M+H)$^+$=405.2; R$_T$=1.45 min; purity=96.6%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

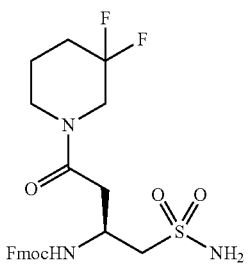

(S)-(9H-fluoren-9-yl)methyl (4-(3,3-difluoropiperidin-1-yl)-4-oxo-1-sulfamoylbutan-2-yl)carbamate: HATU (126 mg, 0.332 mmol, 1.10 equiv.) was added to a solution of (I)-3-((((9H-fluoren-9-yl)methoxy)carbonyl)amino)-4-sulfamoylbutanoic acid (122 mg, 0.302 mmol, 1.00 equiv.), HOAt (41 mg, 0.30 mmol, 1.0 equiv.), 3,3-difluoropiperidine hydrochloride (95 mg, 0.60 mmol, 2.0 equiv.) and diisopropylethylamine (0.16 mL, 0.91 mmol, 3.0 equiv.) in DMF (1.2 mL) at 0° C. The reaction was stirred at rt for 3 days. Water was added, followed by ethyl acetate. The phases were separated and the organic layer was washed with satd. aq. NaHCO$_3$ (3×), dried with sodium sulfate, filtered and evaporated. The crude product was purified by flash chromatography on silica gel using a solution of MeOH in DCM (0 to 5%) to provide 136 mg (89%) of the title compound as a pale orange solid. m/z (M+H)+32 508.2; R$_T$=1.65 min; purity=97.2%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.62-1.53 (m, 1H), 1.70-1.63 (m, 1H), 2.09-1.98 (m, 3H), 2.09-1.98 (m, 3H), 2.77-2.70 (m, 1H), 3.30-3.18 (m, J=7.1 Hz, 3H), 3.46-3.42 (m, 1H), 3.82-3.71 (m, 2H), 4.24-4.18 (m, 1H), 4.32-4.26 (m, 3H), 6.88 (d, J=5.5 Hz, 2H), 7.35-7.30 (m, 3H), 7.41 (t, J=7.2 Hz, 2H), 7.68 (d, J=7.5 Hz, 2H), 7.89 (d, J=7.5 Hz, 2H).

bined and lyophilized to provide 2.2 mg (10%) of the title compound. m/z (M+H)+=592.3; RT=1.76 min; purity=>99%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 8.10 and 8.05 (d, J=8.6 Hz, 1H, NH, rotamers), 1.64-1.45 (m, 4H), 1.73-1.65 (m, 1H),2.10-1.76 (m, 10H), 2.22-2.12 (m, 2H), 2.84-2.73 (m, 1H), 3.02-2.88 (m, 1H), 3.28-3.23 (m, 4H), 3.60-3.37 (m, 3H), 3.91-3.68 (m, 3H), 4.20 (quint, J=7.4 Hz, 1H), 4.70-4.65 (m, 1H), 6.63 (s, 1H), 7.57-7.51 (m, 2H), 7.76 (t, J=7.6 Hz, 1H),7.82 (t, J=7.4 Hz, 1H), 7.93 (d, J=8.0 Hz, 1H).

Scheme 11: Preparation of (S)-N-(1-(N-cyclobutylsulfamoyl)-4-(3,3-difluoropiperidine-1-yl)-4-oxobutan-2-yl)-1-cyclopentyl-5-(2-(trifluoromethyl)phenyl)-1H-pyrazole-3-carboxamide

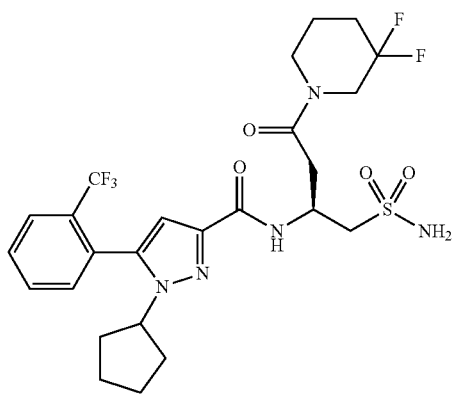 [SMILES: NS(=O)(=O)C[C@H](CC(=O)N1CCCC(F)(F)C1)NC(=O)c1cc(-c2ccccc2C(F)(F)F)n(C2CCCC2)n1]

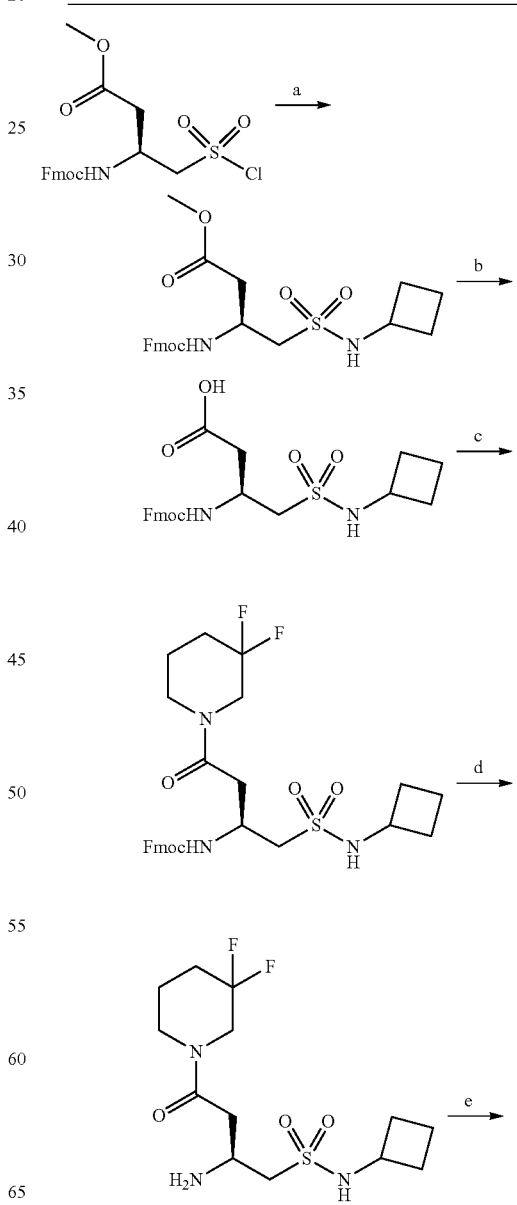

(S)-1-cyclopentyl-N-(4-(3,3-difluoropiperidin-1-yl)-4-oxo-1-sulfamoylbutan-2-yl)-5-(2-(trifluoromethyl)phenyl)-1H-pyrazole-3-carboxamide: Diethylamine (0.28 mL, 2.7 mmol, 10 equiv.) was added to a solution of (S)-(9H-fluoren-9-yl)methyl (4-(3,3-difluoropiperidin-1-yl)-4-oxo-1-sulfamoylbutan-2-yl)carbamate (135 mg, 0.266 mmol, 1.00 equiv.) in acetonitrile (2.7 mL). The reaction was stirred for 1.5 h. The solvent was evaporated and the crude mixture was co-evaporated 2× with DCM to provide 118 mg of the crude amine (64% w/w considering an hypothetic quantitative yield) which was used as is. HATU (16 mg, 0.041 mmol, 1.1 equiv.) was added to a solution of 1-cyclopentyl-5-(2-trifluoromethyl)phenyl)-1H-pyrazole-3-carboxylic acid (12 mg, 0.037 mmol), HOAt (5.0 mg, 0.037 mmol, 1.0 equiv.) and diisopropylethylamine (19 µL, 0.11 mmol, 3.0 equiv.) in DIVIF (0.2 mL). A suspension of the crude amine (16 mg, 0.037 mmol, 1.0 equiv., 64% w/w) in DMF (0.17 mL) was added. The reaction mixture was stirred for 2 h. The reaction was put on top of a C-18 column and was purified by reverse phase chromatography using a solution of MeCN in water (containing 10 mM of ammonium formate, pH=3.8) (5 to 65%). Fractions were combined and lyophilized to give 10 mg of the title compound which was further purified by semi-prep HPLC-MS (column X-Bridge 30×50) using a solution of MeCN in water (containing 10 mM of ammonium formate, pH=3.8) (45 to 65%). Fractions were com- -continued

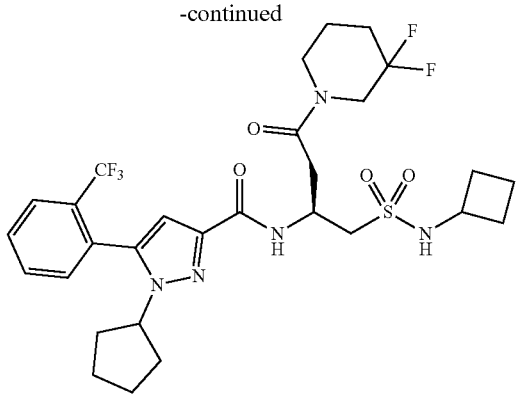

Reagents and conditions:
(a) cyclobutylamine, THF, rt, 10 min;
(b) HCl, AcOH, H₂O, 100° C.;
(c) 3,3-difluoropiperidine hydrochloride, i-PrNEt2, DMF, 0° C., rt, 3 days;
(d) Et₂NH, CH₃CN, 1.5 h
(e) 1-cyclopentyl-5-(2-(trifluoromethyl)phenyl)-1H-pyraole-3-carboxylic acid, HATU, HOAt, iPrNEt₂, DMF, rt, 2 h

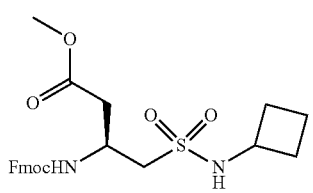

(S)-methyl 3-((((9H-fluoren-9-yl)methoxy)carbonyl)amino)-4-(N-cyclobutylsulfamoyl)butanoate:
Cyclobutylamine (0.13 mL, 1.6 mmol, 2.5 equiv.) was added to a solution of (9-methyl 3-((((9H-fluoren-9-yl)methoxy)carbonyl)amino)-4-(chlorosulfonyl)butanoate (275 mg, 0.628 mmol) in THF (3.1 mL). The reaction mixture was stirred for 10 min and the solvent was evaporated. The crude product was purified by flash chromatography on silica gel using a solution of ethyl acetate in hexanes (5 to 60%) to provide 159 mg (54%) of the title compound as an orange viscous oil. m/z (M+H)⁺=473.1; RT=1.72 min; purity=>95%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.59-1.48 (m, 2H), 1.95-1.84 (m, 2H), 2.20-2.11 (m, 2H), 2.58 (dd, J=15.7, 8.7 Hz, 1H), 2.76 (dd, J=15.7, 4.9 Hz, 1H), 3.10 (dd, J=14.2, 6.5 Hz, 1H), 3.16 (dd, J=14.1, 6.3 Hz, 1H), 3.58 (s, 3H), 3.70 (six, J=8.4 Hz, 1H), 4.25-4.18 (m, 2H), 4.34-4.26 (m, 2H), 7.34-7.30 (m, 2H), 7.41 (t, J=7.4 Hz, 2H), 7.46 (d, J=8.1 Hz, 1H), 7.54 (d, J=8.7 Hz, 1H), 7.68 (d, J=7.5 Hz, 2H), 7.89 (d, J=7.5 Hz, 2H).

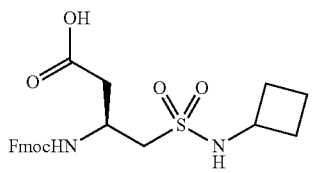

(S)-3-((((9H-fluoren-9-yl)methoxy)carbonyl)amino)-4-(N-cyclobutylsulfamoyl)butanoic acid
HCl (conc., 0.84 mL) was added to a solution of (9-methyl 3-((((9H-fluoren-9-yl)methoxy)carbonyl)amino)-4-(N-cyclobutylsulfamoyl)butanoate (140 mg, 0.335 mmol, 1.00 equiv.) in AcOH (8.4 mL). The reaction mixture was heated at 100° C. for 15 h. The reaction mixture was poured in 70 mL of water and ethyl acetate was added. The phases were separated and the organic layer was dried with sodium sulfate, filtered and evaporated. The crude mixture was co-evaporated with dioxane and DCM to provide 81 mg (70%) of the title compound as a pale brown solid. m/z (M+H)⁺=459.2; R$_T$=1.64 min; purity=98.1%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

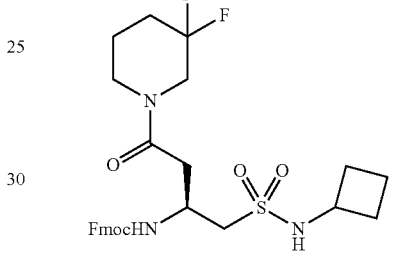

(S)-(9H-fluoren-9-yl)methyl (1-(N-cyclobutylsulfamoyl)-4-(3,3-difluoropiperidin-1-yl)-4-oxobutan-2-yl)carbamate:
HATU (74 mg, 0.19 mmol, 1.10 equiv.) was added to a solution of (S)-3-((((9H-fluoren-9-yl)methoxy)carbonyl)amino)-4-(N-cyclobutylsulfamoyl)butanoic acid (81 mg, 0.18 mmol, 1.0 equiv.), HOAt (24 mg, 0.18 mmol, 1.0 equiv.), 3,3-difluoropiperidine hydrochloride (56 mg, 0.35 mmol, 2.0 equiv.) and diisopropylethylamine (92 μL, 0.53 mmol, 3.0 equiv.) in DMF (0.7 mL) at 0° C. The reaction was stirred at rt for 3 days. Water was added, followed by ethyl acetate. The phases were separated and the organic layer was washed with aq. satd. NaHCO₃ (3×), dried with sodium sulfate, filtered and evaporated. The crude product was purified by flash chromatography on silica gel using a solution of MeOH in DCM (1 to 2%) to provide 73 mg (74%) of the title compound as a pale orange solid. m/z (M+H)⁺=562.3; R$_T$=1.84 min; purity=99.2%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.59-1.48 (m, 3H), 1.70-1.63 (m, 2H), 1.94-1.85 (m, 2H), 2.10-1.99 (m, 3H), 2.19-2.10 (m, 2H), 2.74-2.66 (m, 1H), 3.18-3.12 (m, 1H), 3.47-3.41 (m, 1H), 3.83-3.65 (m, 4H), 4.25-4.19 (m, 2H), 4.31-4.27 (m, 2H), 7.32 (t, J=7.5 Hz, 2H), 7.41 (t, J=7.1 Hz, 2H), 7.51-7.47 (m, 1H), 7.68 (d, J=6.9 Hz, 2H), 7.89 (d, J=7.6 Hz, 2H).

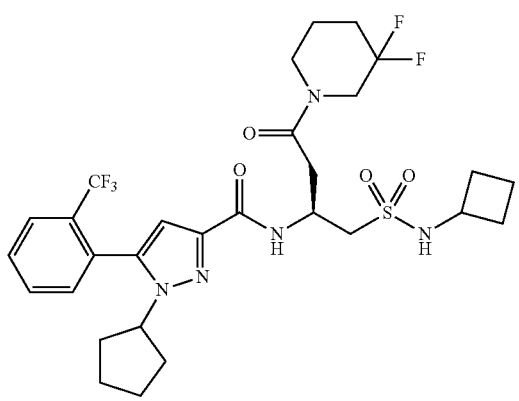 [SMILES: O=C(N[C@@H](CC(=O)N1CCCC(F)(F)C1)CS(=O)(=O)NC1CCC1)c1cc(-c2ccccc2C(F)(F)F)n(C2CCCC2)n1]

(S)—N—(1-(N-cyclobutylsulfamoyl)-4-(3,3-difluoropiperidin-1-yl)-4-oxobutan-2-yl)-1-cyclopentyl-5-(2-(trifluoromethyl)phenyl)-1H-pyrazole-3-carboxamide: Diethylamine (0.13 mL, 1.3 mmol, 10 equiv.) was added to a solution of (S)-(9H-fluoren-9-yl)methyl (1-(N-cyclobutylsulfamoyl)-4-(3,3-difluoropiperidin-1-yl)-4-oxobutan-2-yl)carbamate (73 mg, 0.13 mmol, 1.0 equiv.) in acetonitrile (1.3 mL). The reaction was stirred for 1.5 h. The solvent was evaporated and the crude mixture was co-evaporated 2× with DCM to provide 68 mg of the crude amine (65% w/w considering an hypothetic quantitative yield) which was used as is. HATU (17 mg, 0.046 mmol, 1.1 equiv.) was added to a solution of 1-cyclopentyl-5-(2-(trifluoromethyl)phenyl)-1H-pyrazole-3-carboxylic acid (14 mg, 0.042 mmol), HOAt (5.7 mg, 0.042 mmol, 1.0 equiv.) and diisopropylethylamine (22 µL, 0.13 mmol, 3.0 equiv.) in DMF (0.22 mL). A suspension of the crude amine (22 mg, 0.042 mmol, 1.0 equiv., 65% w/w) in DMF (0.20 mL) was added. The reaction mixture was stirred for 2 h. Water was added, followed by ethyl acetate. The phases were separated and the organic layer was washed 2× with an aqueous saturated solution of sodium bicarbonate, dried with sodium sulfate, filtered and evaporated. The crude product was purified by semi-prep HPLC-MS (column X-Bridge 30×50) using a solution of MeCN in water (containing 10 mM of ammonium formate, pH=3.8) (55 to 75%). Pure fractions were combined and lyophilized to provide 6.7 mg (25%) of the title compound. m/z (M+H)$^+$=646.3; RT=1.93 min; purity=>99%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 8.15 and 8.11 (d, J=8.4 Hz, 1H, NH, rotamers), 1.64-1.47 (m, 2H), 1.73-1.65 (m, 1H), 1.98-1.75 (m, 4H), 2.11-1.99 (m, 2H), 2.89-2.77 (m, 1H), 3.04-2.92 (m, 1H), 3.40-3.34 (m, 4H), 3.61-3.42 (m, 3H), 3.91-3.70 (m, 2H), 4.20 (quint, J=7.2 Hz, 1H), 4.77-4.68 (m, 1H), 6.62 (s, 1H), 6.99-6.94 (m, 2H), 7.54 (d, J=7.8 Hz, 1H), 7.76 (t, J=7.7 Hz, 1H), 7.82 (t, J=7.5 Hz, 1H), 7.93 (d, J=7.5 Hz, 1H).

Scheme 12: Preparation of (R)-3-(1-cyclopentyl-5-(2-(trifluoromethyl)phenyl)-1H-pyrazole-3-carboxamido)-4-(4-fluorophenoxy)butanoic acid

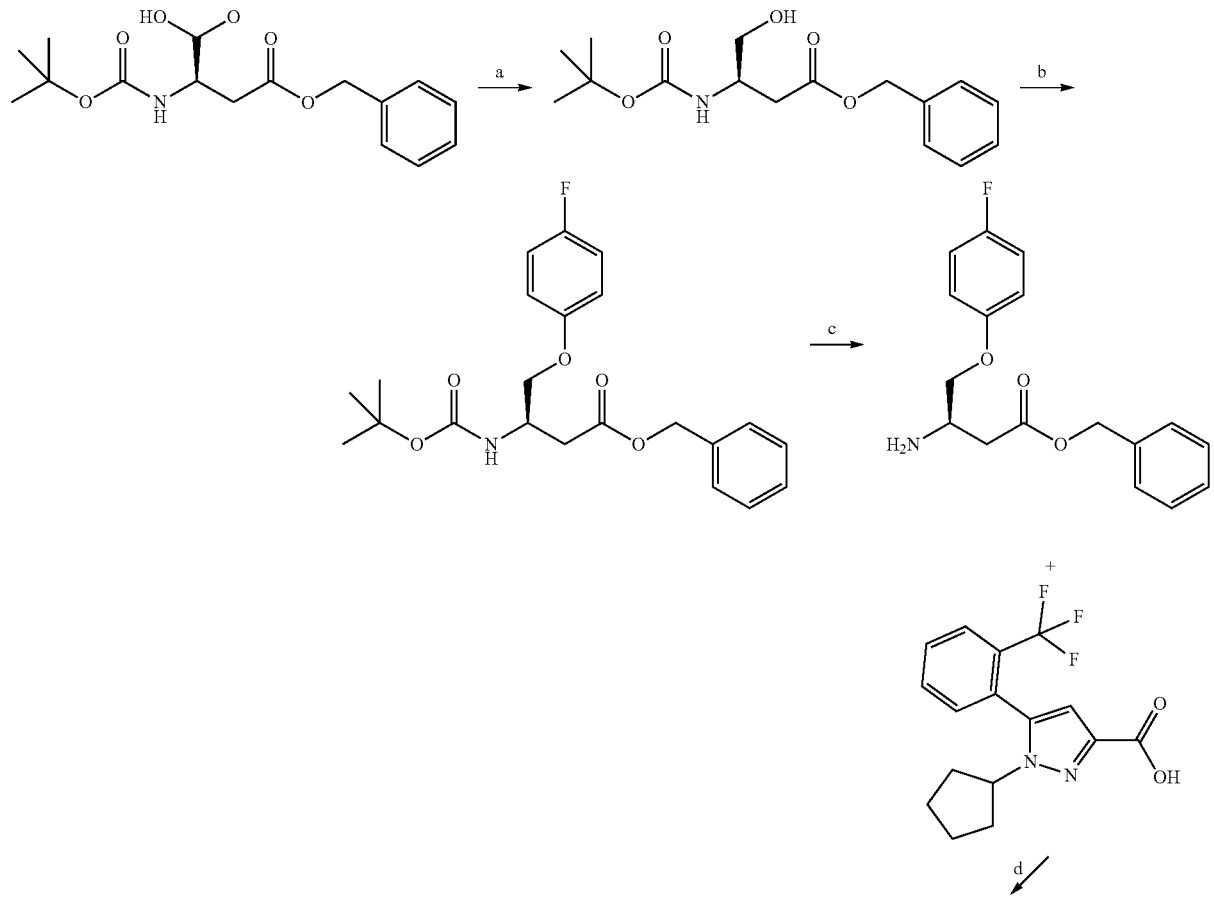

-continued

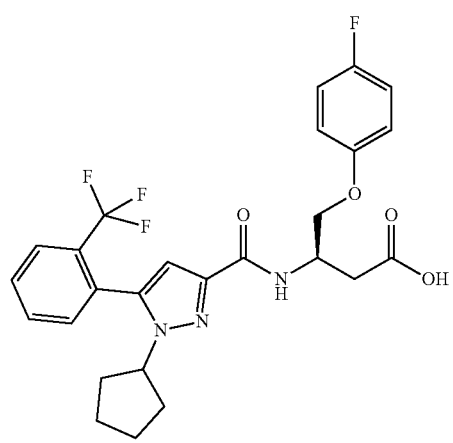 ← e 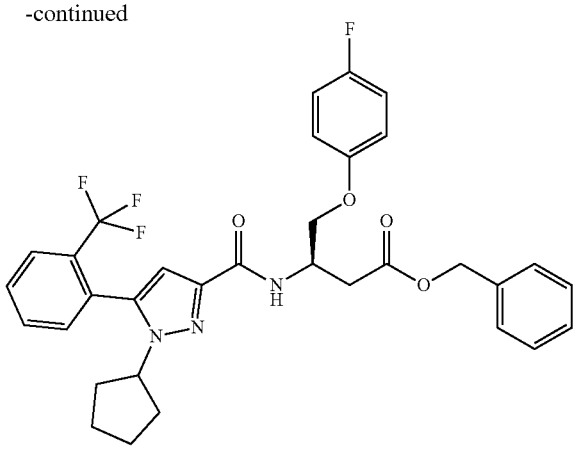

Reagents and conditions: (a) Isobutyl chloroformate, N-methylmorpholine, THF, -20° C., 1 h; NaBH4, MeOH, 1 h; (b) p-fluorophenol, PPh3, diamide, rt, 18 h; (d) 4M HCl in dioxane, rt, 2 h; (d) 1-cyclopentyl-5-(2-(trifluoromethyl)phenyl)-1H-pyrazole-3-carboxylic acid, HATU, HOAt, DIPEA, DMF, rt, 2 h; (e) H2 (balloon), EtOH, 10% Pd/C, 16 h

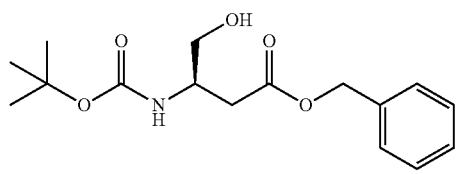 [SMILES: CC(C)(C)OC(=O)N[C@@H](CO)CC(=O)OCc1ccccc1]

(R)-Benzyl-3-((tert-butoxycarbonyl)amino)-4-hydroxybutanoate: To a stirred and cooled (-20° C., CryoCool) THF (150 mL) sol. of Boc-D-Asp(βOBn)—OH (10.00 g, 30.93 mmol, 1.00 equiv.) under nitrogen was added N-methylmorpholine (3.40 mL, 30.93 mmol, 1.00 equiv.). Isobutyl chloroformate (4.01 mL, 30.93 mmol, 1.00 equiv.) was next added over 45 min. (syringe pump). The resulting white suspension was stirred 1 hr. Sodium borohydride (3.51 g, 92.79 mmol, 3.00 equiv.) was added in one portion, mixture stirred in the cold 1 hr. Methanol (50 mL) was added drop-wise over c.a. 30 min. Mixture was stirred 30 min. then 40 mL of aq. 1 M KHSO$_4$ was slowly added (over 30 min.), stirring continued 15 min. then organic solvent was evaporated. Residue was treated with 30 ml of aq. 1M HCl and product was extracted 2×100 mL EtOAc. Organic extracts were pooled, washed with 25 mL aq. 1M HCl, 25 ml sat. aq. NaHCO$_3$, 25 mL water, 25 ml sat. aq. NaCl. Sol. was dried (MgSO$_4$), filtered, filtrate evaporated. Residue was purified CombiFlash®, 100 g column, DCM isocratic 5 min. then to 10% MeOH/DCM in 15 min. Purest fractions were pooled, solvent evaporated, residue dried under high vacuum overnight to yield the title compound, 3.0 g (31%) clear thick oil. m/z (M+H)$^+$-Boc=210.1; R$_T$=1.48 min; purity=80%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.36 (s, 9H), 2.37 (dd, J=15.3, 8.6 Hz, 1H), 2.60 (dd, J=15.2, 5.2 Hz, 1H), 3.25-3.18 (m, 1H), 3.39-3.34 (m, 1H), 3.87-3.77 (m, 1H), 4.77 (t, J=5.7 Hz, 1H), 5.06 (s, 2H), 6.67 (d, J=8.6 Hz, 1H), 7.38-7.30 (m, 5H).

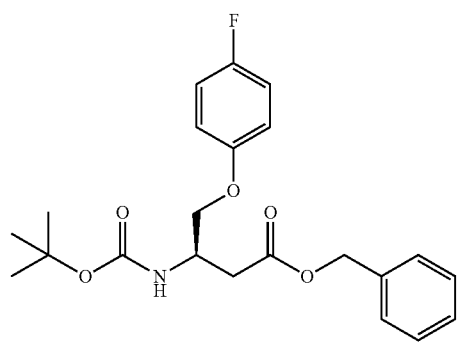 [SMILES: CC(C)(C)OC(=O)N[C@@H](COc1ccc(F)cc1)CC(=O)OCc1ccccc1]

(R)-Benzyl-3-((tert-butoxycarbonyl)amino)-4-(4-fluorophenoxy)butanoate: To a stirred, ice cold toluene (3 mL) solution of (R)-benzyl-3-((tert-butoxycarbonyl)amino)-4-hydroxybutanoate (100 mg, 0.320 mmol, 1.00 equiv.) under nitrogen was added p-fluorophenol (47 mg, 0.420 mmol, 1.30 equiv.), triphenylphosphine (110 mg, 0.420 mmol, 1.30 equiv.) and finally diamide (72 mg, 0.420 mmol, 1.30 equiv.). Suspension was stirred 1 hr in the cold, allowed to warm to RT, stirred overnight. Solvent was evaporated, residue purified CombiFlash®, 4 g column, dry-pack, 10% ethyl acetate/hexane isocratic 3 min. then to 50:50 EtOAc: Hex in 15 min. Fractions containing product were pooled and solvent was evaporated. Residue was still impure. It was re-purified, CombiFlash®, 12 g column, hexane, isocratic 4 min. then to 5% iPrOH/Hex. in 10 min. Purest fractions were pooled, solvent evaporated, residue dried under high vacuum to give the title compound, 62 mg (48%) as a clear oil. $^1$H NMR (500 MHz, DMSO) δ 1.36 (s, 9H), 2.58 (dd, J=14.6, 8.0 Hz, 1H),2.67 (dd, J=15.6, 5.9 Hz, 1H),3.83 (dd, J=9.6, 6.2 Hz, 1H),3.92 (dd, J=9.6, 5.9 Hz, 1H), 5.09 (s, 2H), 4.23-4.12 (m, 1H), 6.95-6.87 (m, 2H), 7.12-7.06 (m, 2H), 7.45-7.30 (m, 6H).

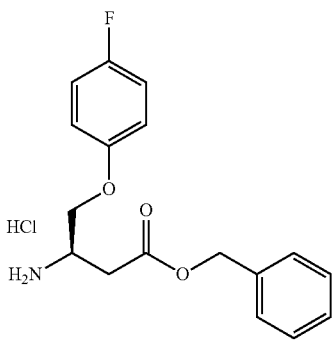 [SMILES: Cl ; N[C@@H](COc1ccc(F)cc1)CC(=O)OCc1ccccc1]

(R)-Benzyl 3-amino-4-(4-fluorophenoxy)butanoate hydrochloride: (R)-benzyl-3-((tert-butoxycarbonyl)amino)-4-(4-fluorophenoxy)butanoate (60 mg, 0.15 mmol, 1.00 equiv.) was dissolved in 3 mL of HCl$_4$N/Dioxane solution. Sol. was stirred at RT 2 hrs; nitrogen was bubbled in the sol. for 1 hr to remove as much HCl as possible. Solvent was evaporated; to the oily residue was added 1 mL diethylether. Product was soluble; hexane (c.a. 0.5 mL) was slowly added to obtain a white precipitate. Suspension was sonicated 5 min. then centrifuged 10 min. at 3000 rpm, supernatant was decanted. Residual solid was re-suspended in 1.5 mL diethylether, sonicated 10 min., centrifuged 10 min at 3000 rpm, supernatant was decanted, solid was dried under high vacuum to give the title compound, 36 mg (71%) as a white solid. m/z (M+H)$^+$=304.0; R$_T$=1.32 min; purity=91.3%. HPLC conditions: Column:) (Bridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.'H NMR (500 MHz, DMSO) δ 2.89 (d, J=6.7 Hz, 2H), 3.90-3.82 (m, 1H), 4.09 (dd, J=10.4, 6.2 Hz, 1H), 4.18 (dd, J=10.4, 3.8 Hz, 1H), 5.16 (s, 2H), 7.01-6.95 (m, 2H), 7.18-7.12 (m, 2H), 7.41-7.32 (m, 5H), 8.36 (s, broad, 3H).

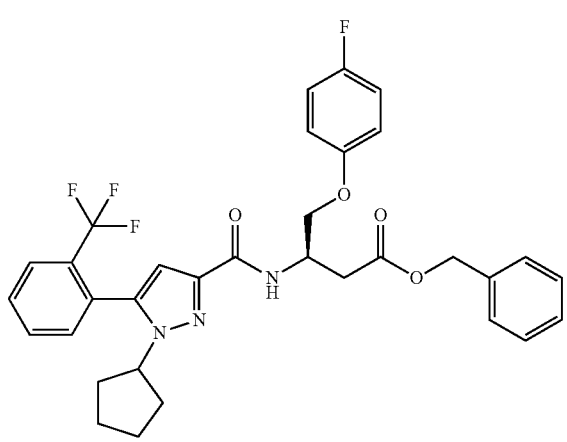 [SMILES: O=C(C[C@H](COc1ccc(F)cc1)NC(=O)c1cc(-c2ccccc2C(F)(F)F)n(C2CCCC2)n1)OCc1ccccc1]

(R)-Benzyl 3-(1-cyclopentyl-5-(2-(trifluoromethyl)phenyl)-1H-pyrazole-3-carboxamido)-4-(4-fluorophenoxy)butanoate: To a stirred DMF (1 mL) sol. of 1-cyclopentyl-5-(2-(trifluoromethyl)phenyl)-1H-pyrazole-3-carboxylic acid (42 mg, 0.130 mmol, 1.25 equiv.) under nitrogen was added HATU (49 mg, 0.130 mmol, 1.25 equiv.), HOAt (18 mg, 0.130 mmol, 1.25 equiv.) and DIPEA (72 0.412 mmol, 4.00 equiv.). Yellow sol. was stirred 10 min. then (R)-benzyl 3-amino-4-(4-fluorophenoxy)butanoate hydrochloride (32 mg, 0.103 mmol, 1.00 equiv.) was added. Sol. was stirred 2 hrs at RT, diluted with EtOAc (20 ml), washed 2×10 ml aq. 0.5N citric acid, 3×10 ml sat. aq. NaHCO$_3$, 10 ml sat. aq. NaCl, dried (MgSO$_4$), filtered, filtrate evaporated. Residue was purified CombiFlash®, 12 g column, 10% EtOAc/Hex isocratic 3 min. then to 50% EtOAc/Hex in 10 min. Purest fractions were pooled, solvent evaporated, residue dried under high vacuum to give the title compound, 34 mg (61%) as a clear amorphous solid. m/z (M+H)$^+$=610.4; R$_T$=2.17 min; purity=87.0%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.58-1.45 (m, 2H), 2.05-1.72 (m, 6H), 2.91-2.83 (m, 2H), 4.03-3.97 (m, 1H), 4.25-4.07 (m, 2H), 4.78-4.68 (m, 1H), 5.11 (s, 2H), 6.66 (s, 1H), 7.00-6.93 (m, 2H), 7.14-7.07 (m, 2H), 7.35-7.25 (m, 5H), 7.54 (d, J=7.8 Hz, 1H), 7.77 (t, J=7.7 Hz, 1H), 7.83 (t, J=7.4 Hz, 1H), 7.94 (d, J=7.6 Hz, 1H), 8.15 (d, J=8.7 Hz, 1H).

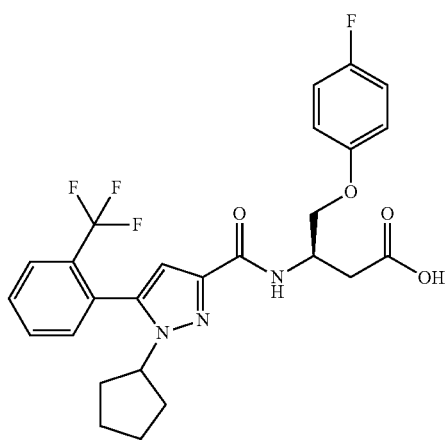 [SMILES: O=C(O)C[C@H](COc1ccc(F)cc1)NC(=O)c1cc(-c2ccccc2C(F)(F)F)n(C2CCCC2)n1]

(R)-3-(1-Cyclopentyl-5-(2-(trifluoromethyl)phenyl)-1H-pyrazole-3-carboxamido)-4-(4-fluorophenoxy)butanoic acid: To a stirred EtOAc (5 mL) sol. of (R)-benzyl 3-(1-cyclopentyl-5-(2-(trifluoromethyl)phenyl)-1H-pyrazole-3-carboxamido)-4-(4-fluorophenoxy)butanoate (30 mg, 0.050 mmol, 1.00 equiv.) under nitrogen was added Pd/C 10% (25 mg). System was purged 3×H$_2$ then hydrogenated (H$_2$ balloon) overnight. Mixture was filtered through Celite®, cake washed 3×10 mL EtOAc, filtrates pooled, solvent evaporated. Residue purified CombiFlash®, 12 g C18 column, 1 min. isocratic aq. 10 mM ammonium bicarbonate then to 50% acetonitrile/aq. 10 mM ammonium bicarbonate in 12 min. Purest fractions were pooled, acetonitrile evaporated, remaining aq. sol. was frozen and lyophilized to give the title compound, 15 mg (58%) as a solid. m/z (M+H)$^+$=520.3; R$_T$=1.85 min; purity=92.2%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, CDCl$_3$) δ 1.60-1.46 (m, 2H), 2.15-1.80 (m, 6H), 2.98-2.88 (m, 2H), 4.21-4.11 (m, 2H), 4.24 (dd, J=9.5, 4.0 Hz, 1H), 4.88-4.78 (m, 1H), 6.77 (s, 1H), 6.94-6.86 (m, 2H), 6.98-6.95 (m, 2H), 7.30 (d, J=7.1 Hz, 1H), 7.65-7.57 (m, 3H), 7.67 (d, J=7.9 Hz, 1H), 7.80 (dd, J=7.4, 1.5 Hz, 1H).

287

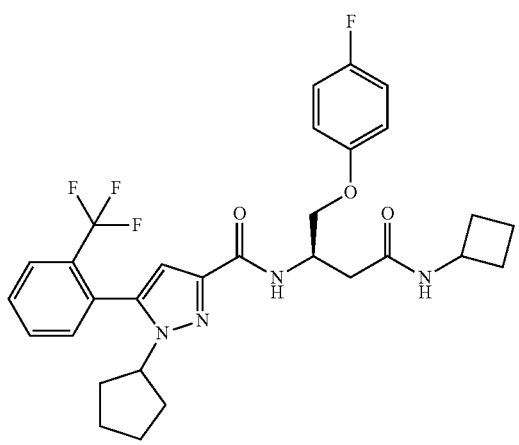 [SMILES: O=C(C[C@H](COc1ccc(F)cc1)NC(=O)c1cc(-c2ccccc2C(F)(F)F)n(C2CCCC2)n1)NC1CCC1]

(R)—N—(4-(Cyclobutylamino)-1-(4-fluorophenoxy)-4-oxobutan-2-yl)-1-cyclopentyl-5-(2-(trifluoromethyl)phenyl)-1H-pyrazole-3-carboxamide: To a stirred DMF (500 µL) sol. of (R)-3-(1-cyclopentyl-5-(2-(trifluoromethyl)phenyl)-1H-pyrazole-3-carboxamido)-4-(4-fluorophenoxy)butanoic acid (12 mg, 0.023 mmol, 1.00 equiv.) under nitrogen was added HATU (13 mg, 0.035 mmol, 1.50 equiv.), HOAt (4.8 mg, 0.035 mmol, 1.50 equiv.) and DIPEA (16 µL, 0.092 mmol, 4.00 equiv.). Yellow sol. was stirred 10 min. then cyclobutylamine (3.3 mg, 0.046 mmol, 2.00 equiv.) was added. Sol. was stirred 4 hrs at RT, diluted with EtOAc (20 ml), washed 2×10 ml aq. 0.5N citric acid, 3×10 ml sat. aq. NaHCO₃, 10 ml sat. aq. NaCl, dried (MgSO₄), filtered, filtrate evaporated. Residue was purified CombiFlash®, 12 g column, DCM isocratic 2 min. to 2% MeOH/DCM in 6 min. Purest fractions were pooled, solvent evaporated, residue dried under high vacuum to give the title compound, 5.2 mg (40%) as a clear amorphous solid. m/z (M+H)=573.4; $R_T$=1.95 min; purity=98.5%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.64-1.47 (m, 4H), 2.02-1.75 (m, 8H), 2.17-2.05 (m, 2H), 2.52-2.45 (m, 1H), 2.55 (dd, J=14.6, 7.0 Hz, 1H), 3.98 (dd, J=9.9, 6.2 Hz, 1H), 4.24-4.07 (m, 3H), 4.62-4.53 (m, 1H), 6.63 (s, 1H), 7.03-6.97 (m, 2H), 7.14-7.08 (m, 2H), 7.53 (d, J=7.5 Hz, 1H), 7.76 (t, J=7.7 Hz, 1H), 7.82 (t, J=7.5 Hz, 1H), 7.93 (d, J=7.3 Hz, 1H), 8.08 (d, J=8.4 Hz, 1H), 8.21 (d, J=7.7 Hz, 1H).

Scheme 13: Preparation of (R)-3-(1-cyclopentyl-5-(2-(trifluoromethyl)phenyl)-1H-pyrazole-3-carboxamido)-4-oxo-4-((tetrahydo-2H-pyran-4-yl)butanoic acid

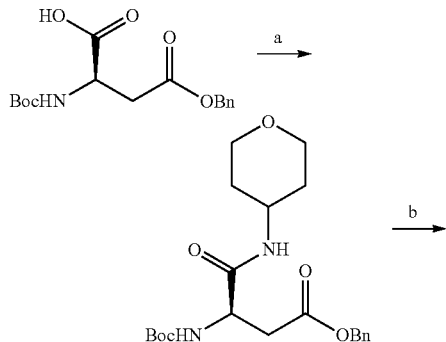

288

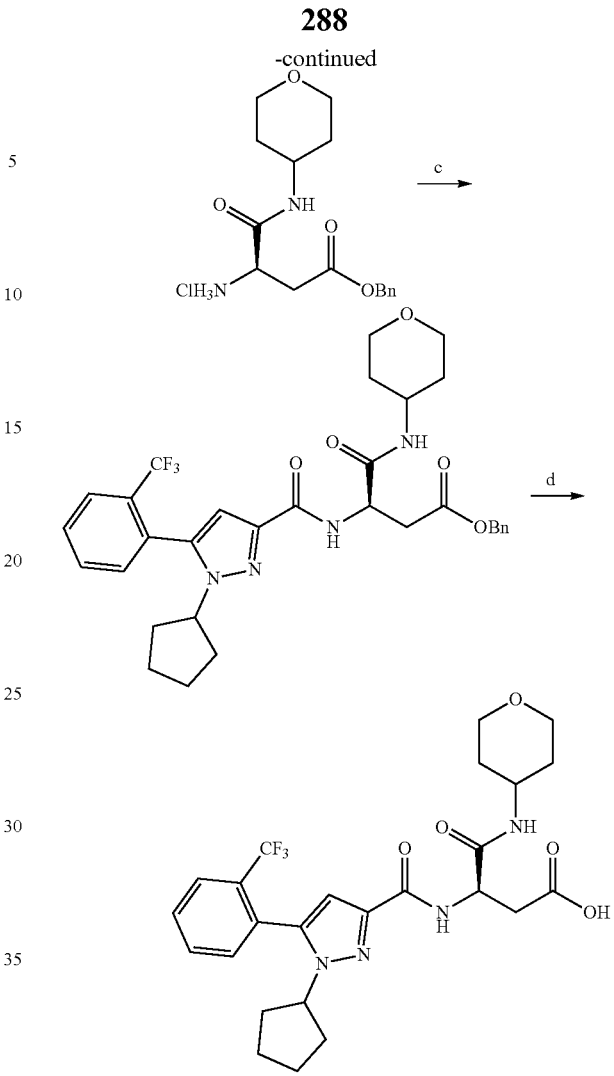

Reagents and conditions: (a) tetrahydro-2H-pyran-4-amine, EDC•HCl, HOBt, N-methylmorpholine, DMF, 0° C. to rt, 15 h; (b) 4M HCl in dioxane, rt, 18 h; (c) 1-cyclopentyl-5-(2-(trifluoromethyl)phenyl)-1H-pyrazole-3-carboxylic acid, HATU, DIPEA, DMF, 2 h; (d) H₂ (balloon), EtOH, 10% Pd/C, 15 h

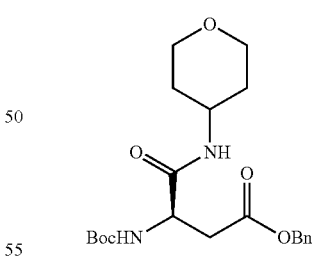

(R)-benzyl 3-((tert-butoxycarbonyl)amino)-4-oxo-4-((tetrahydro-2H-pyran-4-yl)amino)butanoate:

HOBt (240 mg, 1.78 mmol, 1.15 equiv.) was added to a solution of (R)-4-(benzyloxy)-2-((tert-butoxycarbonyl)amino)-4-oxobutanoic acid (500 mg, 1.55 mmol) and tetrahydro-2H-pyran-4-amine (240 mg, 1.55 mmol) in DMF (10 mL). EDC.HCl (296 mg, 1.55 mmol) and N-methylmorpholine (202 mg, 2.00 mmol) were added at 0° C. and the reaction mixture was stirred at rt for 15 h. Ethyl acetate was added and the mixture was washed with an aqueous saturated solution of sodium bicarbonate, with brine (2×), dried with sodium sulfate, filtered and evaporated. The crude product was purified by flash chromatography on silica gel using a solution of ethyl acetate in hexanes (10 to 20%) to provide 488 mg (78%) of the title compound as a white solid. m/z (M+H)$^+$=407.2; R$_T$=1.51 min; purity=>95%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

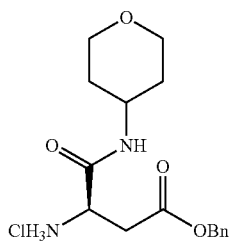

(R)-benzyl 3-amino-4-oxo-4-((tetrahydro-2H-pyran-4-yl) amino)butanoate hydrochloride:

4M HCl in dioxane (3.0 mL, 12 mmol) was added to (R)-benzyl 3-((tert-butoxycarbonyl)amino)-4-oxo-4-((tetrahydro-2H-pyran-4-yl)amino)butanoate (488 mg, 1.20 mmol).The reaction was stirred at rt for 18 h. A saturated aqueous solution of NaHCO$_3$ (25 mL) was added, followed by 6N NaOH until pH=10. The mixture was extracted 4× with a solution of THF in DCM (1:3), the combined organic layers were dried with sodium sulfate, filtered and evaporated to provide 415 mg (quantitative yield) of the title compound as a white foam. m/z (M+H)$^+$=307.2; R$_T$=1.00 min; purity=>95%. HPLC conditions: Column:)(Bridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

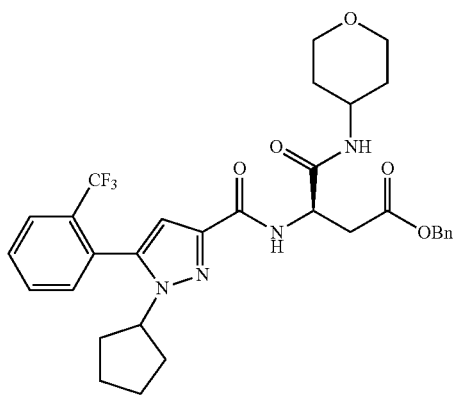 [SMILES: O=C(C[C@@H](NC(=O)c1cc(-c2ccccc2C(F)(F)F)n(C2CCCC2)n1)C(=O)NC1CCOCC1)OCc1ccccc1]

(R)-benzyl 3-(1-cyclopentyl-5-(2-(trifluoromethyl)phenyl)-1H-pyrazole-3-carboxamido)-4-oxo-4-((tetrahydro-2H-pyran-4-yl)amino)butanoate:

HATU (121 mg, 0.31 mmol) was added to a solution of 1-cyclopentyl-5-(2-(trifluoromethyl)phenyl)-1H-pyrazole-3-carboxylic acid (94 mg, 0.19 mmol),HOAt (39 mg, 0.29 mmol) and diisopropylethylamine (150 µL, 0.87 mmol) in DMF (1 mL). The reaction mixture was stirred for 10 min and a solution of (R)-benzyl 3-amino-4-oxo-4-((tetrahydro-2H-pyran-4-yl)amino)butanoate hydrochloride (99 mg, 0.29 mmol) in DMF (0.85 mL) was added. The reaction mixture was stirred at rt for 2 h. Water was added, followed by ethyl acetate. The phases were separated and the organic layer was washed 2× with an aqueous saturated solution of sodium bicarbonate, dried with sodium sulfate, filtered and evaporated. The crude product was purified by flash chromatography on silica gel using a solution of ethyl acetate in hexanes (20 to 40%) to provide 85 mg of the title compound as a colorless viscous oil. m/z (M+H)$^+$=613.4; R$_T$=1.87 min; purity=99.5%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

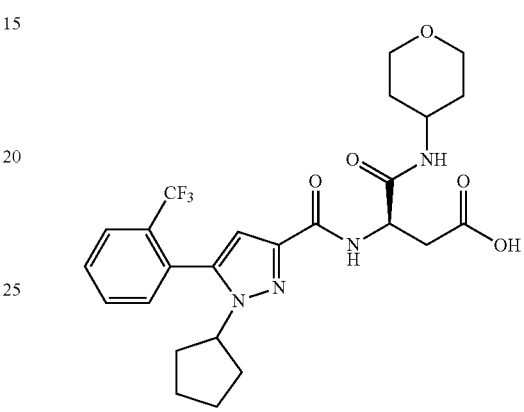

(R)-3-(1-cyclopentyl-5-(2-(trifluoromethyl)phenyl)-1H-pyrazole-3-carboxamido)-4-oxo-4-((tetrahydro-2H-pyran-4-yl)amino)butanoic acid:

10% Pd/C (10 mg) was added to a nitrogen purged flask containing a solution of (R)-benzyl 3-(1-cyclopentyl-5-(2-(trifluoromethyl)phenyl)-1H-pyrazole-3-carboxamido)-4-oxo-4-((tetrahydro-2H-pyran-4-yl)amino)butanoate (85 mg (0.14 mmol) in EtOH (0.5 mL). The flask was put under vacuum for 30 sec and put back under nitrogen. This procedure was done another time. The flask was put back again under vacuum and a balloon of hydrogen was inserted through the septum. The reaction was vigorously stirred for 15 h. The flask was put under vacuum for 30 sec and put back under nitrogen. This procedure was done two other times. The solution was filtered on Celite®, the solid cake was washed with EtOH and the filtrate was evaporated to provide 61 mg (85%) of the title compound as a white solid. Half the compound was dissolved in a mixture of acetonitrile and water and was lyophilized to give 23 mg of a white solid. m/z (M+H)$^+$=523.2; R$_T$=1.51 min; purity=99.1%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.48-1.36 (m, 2H), 1.58-1.48 (m, 2H), 1.71-1.63 (m, 2H), 1.90-1.77 (m, 3H), 2.01-1.90 (m, 3H), 2.78-2.66 (m, 2H), 3.38-3.33 (m, 2H), 3.85-3.70 (m, 3H), 4.21 (quint, J=7.4 Hz, 1H), 4.76-4.69 (m, 1H), 6.66 (s, 1H), 7.54 (d, J=7.5 Hz, 1H), 7.76 (t, J=7.6 Hz, 1H), 7.83 (t, J=7.5 Hz, 1H), 7.94 (d, J=7.6 Hz, 1H), 8.14-8.00 (m, 2H), 12.43-12.22 (m, 1H).

Scheme 14: Preparation of (S)-3-(1-cyclopentyl-5(2-(trifluoromethyl)phenyl)-1H-pyrazole-3-carboxamido-5-(2-oxopiperidin-1-yl)pentanoic acid

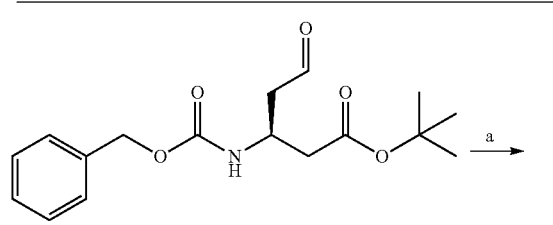

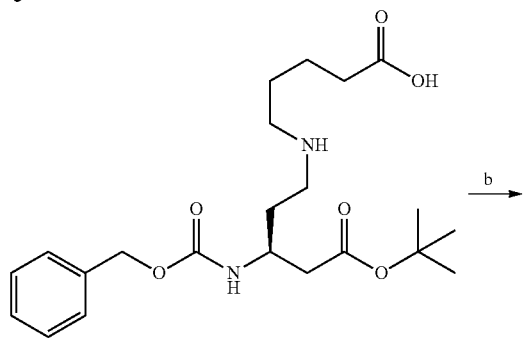

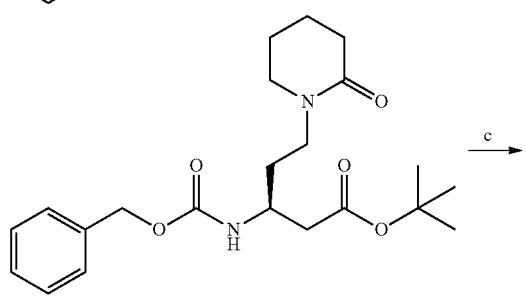

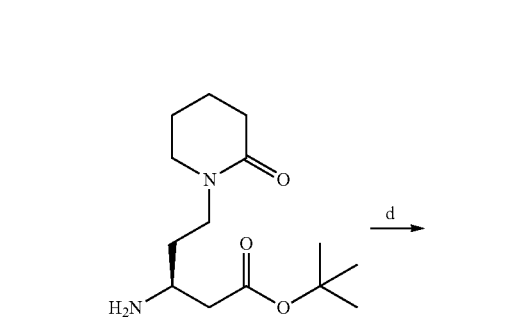

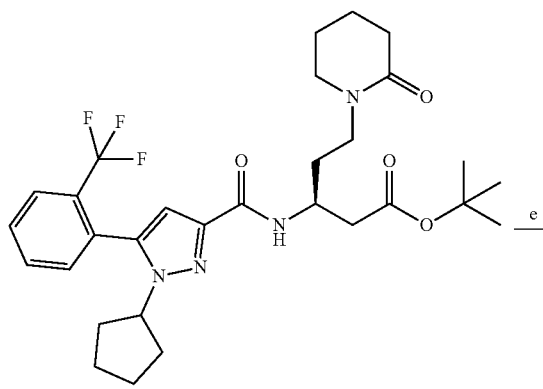

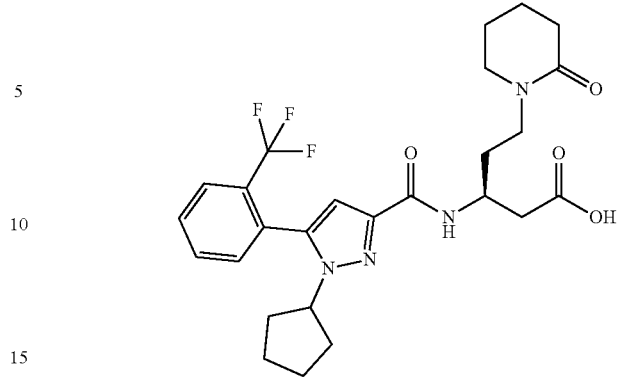

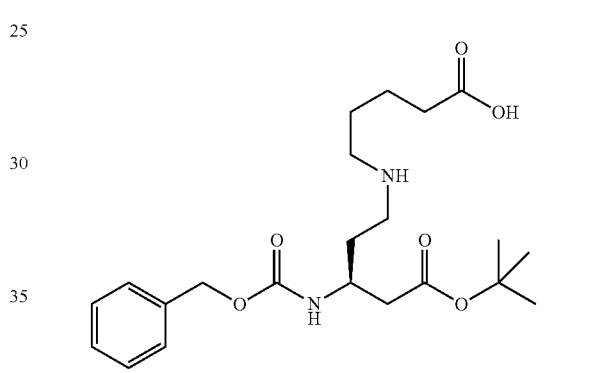

Reagents and conditions:
(a) 5-aminovaleric acid, NaBH(OAc)₃, MeOH, rt, 1 h;
(b) HATU, HOAt, DIPEA, DMF, rt, 1 h;
(c) H₂ (balloon), EtOAc, 10% Pd/C, 4 h;
(d) 1-cyclopentyl-5-(2-(trifluoromethyl)phenyl)-1H-pyrazole-3-carboxylic acid, HATU, HOAt, DIPEA, DMF, rt, 3 h;
(e) 4N HCl in dioxane, rt, 18 h (S)-5-((3-(((benzyloxy)carbonyl)amino)-5-(tert-butoxy)-5-oxopentyl)amino)pentanoic acid: To a stirred methanol (2 mL) sol. of 5-aminovaleric acid (38 mg, 0.372 mmol, 1.20 equiv.) under nitrogen was added (S)-tert-butyl 3-(((benzyloxy)carbonyl)amino)-5-oxopentanoate (100 mg, 0.310 mmol) in 1 mL methanol. Sol. was stirred at RT 1 hr then sodium triacetoxyborohydride (79 mg, 0.372 mmol, 1.2 equiv.) was added. Sol. was stirred a further hour, solvent evaporated, residue purified CombiFlash®, 30 g column (C18), 10 mM aq. ammonium formate isocratic 5 min. then to 50% aq. AF-acetonitrile in 10 min., isocratic 8 min. then to 100% acetonitrile in 10 min. Purest fractions were pooled, solvents evaporated (rotavapor, 45° C., high vacuum), residue re-dissolved in ethanol (30 mL), solvent re-evaporated, residue dried under high vacuum to give the title compound, 59 mg (45%) amorphous solid. m/z (M+H)⁺=423.4; $R_T$=1.28 min; purity=92.7%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.36 (s, 9H), 1.70-1.42 (m, 6H), 2.16 (t, J=6.7 Hz, 2H), 2.40-2.30 (m, 2H), 2.65-2.54 (m, 3H), 4.40-3.20 (m, 4H), 5.05-4.97 (m, 2H), 7.38-7.25 (m, 5H), 8.37 (s, boad, 1H).

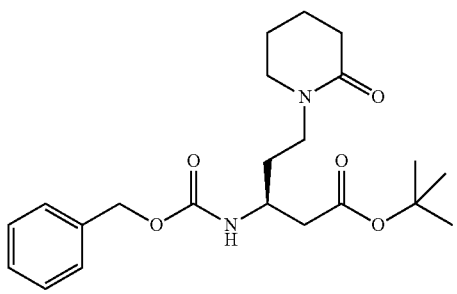 [SMILES: CC(C)(C)OC(=O)C[C@H](CCN1CCCCC1=O)NC(=O)OCc1ccccc1]

(S)-tert-butyl-3-(((benzyloxy)carbonyl)amino)-5-(2-oxopiperidin-1-yl)pentanoate: To a stirred DMF (500 µL) sol. of (S)-5-((3-(((benzyloxy)carbonyl)amino)-5-(tert-butoxy)-5-oxopentyl)amino)pentanoic acid (55 mg, 0.130 mmol, 1.00 equiv.) under nitrogen was added DIPEA (90 µL, 0.520 mmol, 4.00 equiv.) followed by HOAt (28 mg, 0.208 mmol, 1.60 equiv.) and HATU (74 mg, 0.195 mmol, 1.50 equiv.). Yellow sol. was stirred at RT 1 hr, diluted with EtOAc (20 mL), washed 4×10 mL sat. aq. NaHCO$_3$, 2×10 mL sat. aq. NaCl, dried (MgSO$_4$), filtered, filtrate evaporated. Crude material was used as such for next transformation. m/z (M+H)$^+$=405.2; R$_T$=1.57 min; purity: 69%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.36 (s, 9H), 1.73-1.50 (m, 6H), 2.20-2.12 (m, 2H), 2.38-2.27 (m, 2H), 3.31-3.12 (m, 4H), 3.82-3.74 (m, 1H), 5.07-4.95 (m, 2H), 7.24 (d, J=8.8 Hz, 1H), 7.38-7.28 (m, 5H).

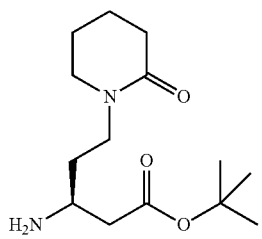 [SMILES: CC(C)(C)OC(=O)C[C@@H](N)CCN1CCCCC1=O]

(S)-tert-butyl-3-amino-5-(2-oxopiperidin-1-yl)pentanoate: To a stirred EtOAc (5 mL) sol. of (S)-tert-butyl-3-(((benzyloxy)carbonyl)amino)-5-(2-oxopiperidin-1-yl)pentanoate (25 mg, 0.062 mmol, 1.00 equiv.) under nitrogen was added Pd/C 10% (50 mg). System was purged 3× with H$_2$ then hydrogenated (balloon) 4 hrs. Mixture was filtered over Celite® (under a nitrogen stream), cake washed 4×10 mL EtOAc, all filtrates pooled, solvent evaporated. Residue dried under high vacuum overnight to give the title compound, 6.8 mg (41%) as a glassy solid. Crude material was used as such for next transformation.

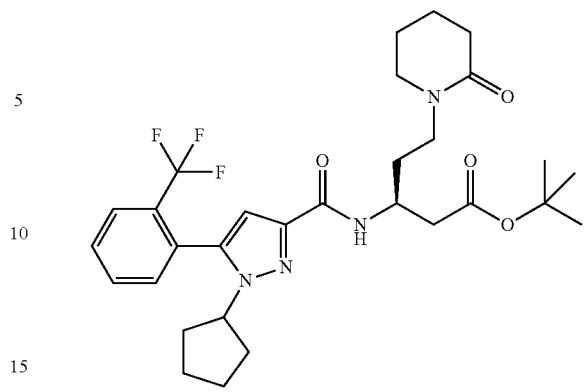

(S)-tert-butyl-3-(1-cyclopentyl-5-(2-(trifluoromethyl)phenyl)-1H-pyrazole-3-carboxamido)-5-(2-oxopiperidin-1-yl)pentanoate: To a stirred DMF (1 mL) sol. of 1-cyclopentyl-5-(2-(trifluoromethyl)phenyl)-1H-pyrazole-3-carboxylic acid (9.4 mg, 0.029 mmol, 1.20 equiv.) under nitrogen was added HATU (11 mg, 0.030 mmol, 1.25 equiv.), HOAt (4 mg, 0.030 mmol, 1.25 equiv.) and DIPEA (17 µL, 0.096 mmol, 4.00 equiv.). Yellow sol. was stirred 5 min. then (S)-tert-butyl 3-amino-5-(2-oxopiperidin-1-yl)pentanoate (6.8 mg, 0.024 mmol, 1.00 equiv.) was added. Sol. was stirred 3 hrs at RT, diluted with EtOAc (20 ml), washed 4×10 ml sat. aq. NaHCO$_3$, 10 ml sat. aq. NaCl, dried (MgSO$_4$), filtered, filtrate evaporated. Residue was purified CombiFlash®, 4 g column, isocratic DCM 1 min. then to 5% MeOH/DCM in 12 min. Purest fractions were pooled, solvent evaporated, residue dried overnight under high vacuum to give the title compound, 9.4 mg (68%) amorphous solid. m/z (M+H)$^+$=577.4; R$_T$=1.90 min; purity: 98%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, CDCl$_3$) δ 1.45 (s, 9H), 2.20-1.65 (m, 12H), 2.40-2.28 (m, 2H), 2.70-2.58 (m, 2H), 3.46-3.17 (m, 3H), 3.77-3.47 (m, 1H), 1.60-1.48 (m, 2H), 4.22-4.10 (m, 1H), 4.43-4.34 (m, 1H), 6.74 (s, 1H), 7.31 (d, J=7.2 Hz, 1H), 7.43-7.37 (m, 1H), 7.66-7.56 (m, 2H), 7.80 (dd, J=7.9, 1.0 Hz, 1H).

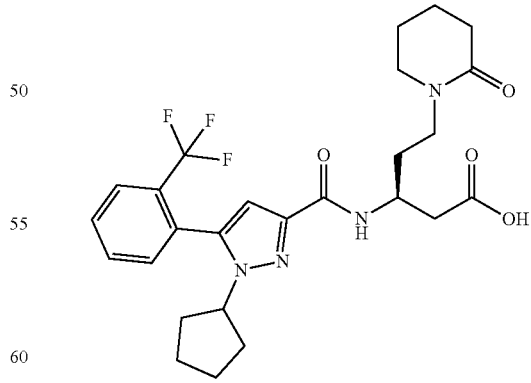

(S)-tert-butyl-3-(1-cyclopentyl-5-(2-(trifluoromethyl)phenyl)-1H-pyrazole-3-carboxamido)-5-(3,5-dimethyl-1H-pyrazol-1-yl)pentanoate: (S)-tert-butyl-3-(1-cyclopentyl-5-(2-(trifluoromethyl)phenyl)-1H-pyrazole-3-carboxamido)-5-(2-oxopiperidin-1-yl)pentanoate (9.0 mg, 0.016 mmol, 1.00 equiv.) was dissolved in 4N HCl/dioxane (2 mL) solution and stirred at RT 3 hrs. Solvent was evaporated, residue dried under high vacuum. Residue was purified CombiFlash®, 12 g C18 column, 1 min. isocratic aq. 10 mM ammonium bicarbonate then to 50% acetonitrile/aq. 10 mM ammonium bicarbonate in 12 min. Purest fractions were pooled, acetonitrile evaporated, remaining aq. sol. was frozen and lyophilized to give the title compound, 8.0 mg (96%).m/z (M+H)$^+$=521.3; R$_T$=1.55 min; purity: 96%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, DMSO) δ 1.53-1.46 (m, 2H), 2.03-1.60 (m, 10H), 2.19-2.13 (m, 2H), 2.63-2.46 (m, 4H), 3.75-3.15 (m, 4H), 4.30-4.15 (m, 2H), 6.62 (s, 1H), 7.55 (d, J=7.5 Hz, 1H), 7.76 (t, J=7.7 Hz, 1H), 7.82 (t, J=7.4 Hz, 1H), 7.93 (d, J=7.5 Hz, 1H), 7.98-7.90 (m, broad, 1H), 12.40-12.00 (s, broad, 1H).

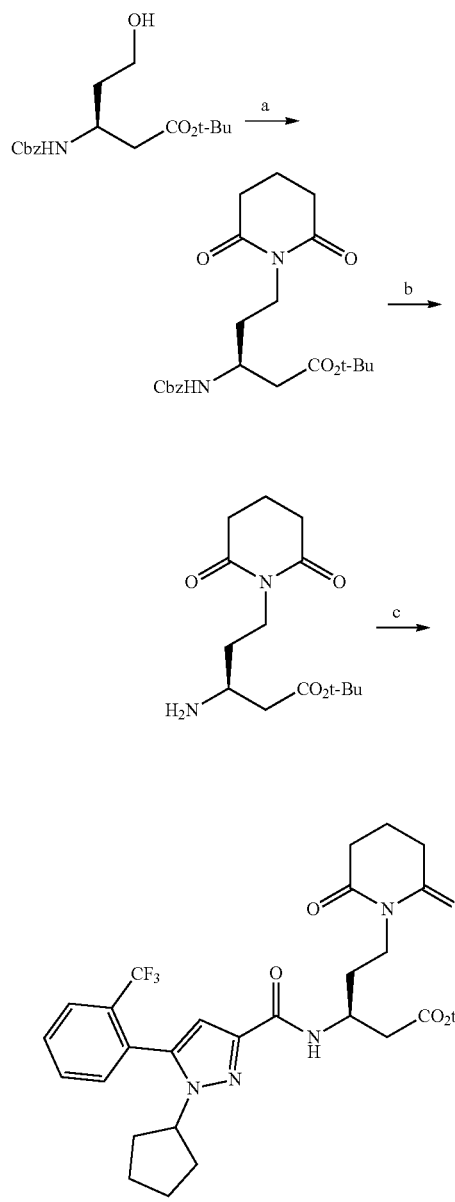

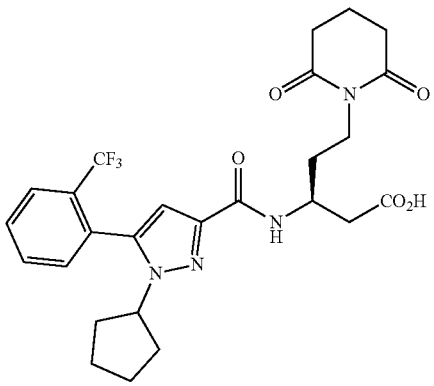

Reagents and conditions:
(a) Glutarimide, ADDP, PBu3, i-PrNEt THF rt, 16 h;
(b) H$_2$ (balloon), EtOAc, 10% Pd/C, rt, 18 h;
(c) 1-cyclopentyl-5-(2-(trifluoromethyl)phenyl)-1H-pyrazole-3-carboxylic acid, HATU, HOAt, DIPEA, DMF, rt, 18 h;
(d) 4N HCl in dioxane, rt, 18 h (S)-tert-butyl 3-(((benzyloxy)carbonyl)amino)-5-(2,6-dioxopiperidin-1-yl)pentanoate

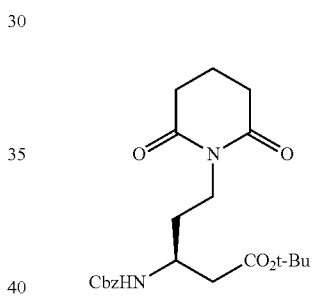

A solution of ADDP (41 mg, 0.16 mmol, 1.3 equiv.) in THF (0.6 mL) was added to a solution of (S)-tert-butyl 3-(((benzyloxy)carbonyl)amino)-5-hydroxypentanoate (40 mg, 0.12 mmol, 1.0 equiv.), glutarimide (14 mg, 0.12 mmol, 1.0 equiv.), diisopropylethylamine (24 μL, 0.14 mmol, 1.1 equiv.) and tributylphosphine (40 μL, 0.16 mmol, 1.3 equiv.) in THF (0.64 mL). The reaction mixture was stirred at rt for 16 h and was filtered in a pipette with a cotton wool. Water was added to the filtrate and the mixture was extracted with ethyl acetate (2x). The combined organic layers were dried with sodium sulfate filtered and evaporated. The crude product was purified by flash chromatography on silica gel using a solution of ethyl acetate in hexanes (30 to 60%) to provide 34 mg (66%) of the title compound as a pale yellow oil. m/z (M+H)$^+$=419.3; R$_T$=1.62 min; purity=>90%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, CDCl$_3$) δ 7.37-7.28 (m, 5H), 5.35 (d, J=8.5 Hz, 1H), 5.15-5.03 (m, 2H), 3.95-3.79 (m, 3H), 2.66-2.57 (m, 4H), 2.51-2.44 (m, 2H), 1.96-1.87 (m, 2H), 1.83-1.71 (m, 2H), 1.43 (s, 9H).

(S)-tert-butyl 3-amino-5-(2,6-dioxopiperidin-1-yl)pentanoate

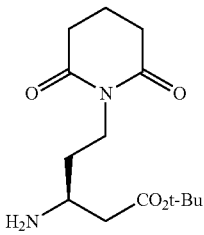 [SMILES: CC(C)(C)OC(=O)C[C@@H](N)CCN1C(=O)CCCC1=O]

10% Pd/C (10 mg) was added to a nitrogen purged flask containing a solution of (S)-tert-butyl 3-(((benzyloxy)carbonyl)amino)-5-(2,6-dioxopiperidin-1-yl)pentanoate (34 mg, 0.081 mmol, 1.00 equiv.) in EtOH (0.27 mL). The flask was put under vacuum for 30 sec and put back under nitrogen. This procedure was done another time. The flask was put back again under vacuum and a balloon of hydrogen was inserted through the septum. The reaction was vigorously stirred for 18 h. The flask was put under vacuum for 30 sec and put back under nitrogen. This procedure was done two other times. The solution was filtered on Celite®, the solid cake was washed with EtOH and the filtrate was evaporated. The obtained product (23 mg) was resubmitted to the above reaction, using ethyl acetate as the solvent this time, to provide 7.5 mg (32%) of the title compound as a colorless oil. m/z (M+H)$^+$=285.3; R$_T$=1.08 min; purity=77.8%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

(S)-tert-butyl 3-(1-cyclopentyl-5-(2-(trifluoromethyl)phenyl)-1H-pyrazole-3-carboxamido)-5-(2,6-dioxopiperidin-1-yl)pentanoate

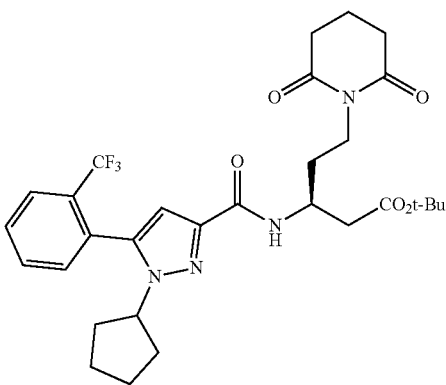 [SMILES: CC(C)(C)OC(=O)C[C@H](CCN1C(=O)CCCC1=O)NC(=O)c1cc(-c2ccccc2C(F)(F)F)n(C2CCCC2)n1]

HATU (7.1 mg, 0.019 mmol, 1.1 equiv.) was added to a solution of 1-cyclopentyl-5-(2-(trifluoromethyl)phenyl)-1H-pyrazole-3-carboxylic acid (5.5 mg, 0.017 mmol, 1.0 equiv.), HOAt (2.3 mg, 0.017 mmol, 1.0 equiv.) and diisopropylethylamine (8.9 μL, 0.051 mmol, 3.0 equiv.) and (S)-tert-butyl 3-amino-5-(2,6-dioxopiperidin-1-yl)pentanoate (7.5 mg, 0.017 mmol, 1.0 equiv.) in DMF (0.17 mL) at 0° C. The reaction mixture was stirred at rt for 18 h. The mixture was dissolved in ethyl acetate and was washed with a saturated aqueous solution of sodium bicarbonate, dried with sodium sulfate, filtered and evaporated to provide 6.5 mg (65%, crude) of the title compound which was used as is. m/z (M+H)$^+$=591.3; R$_T$=1.93 min; purity=hard to say. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile.

(S)-3-(1-cyclopentyl-5-(2-(trifluoromethyl)phenyl)-1H-pyrazole-3-carboxamido)-5-(2,6-dioxopiperidin-1-yl)pentanoic acid

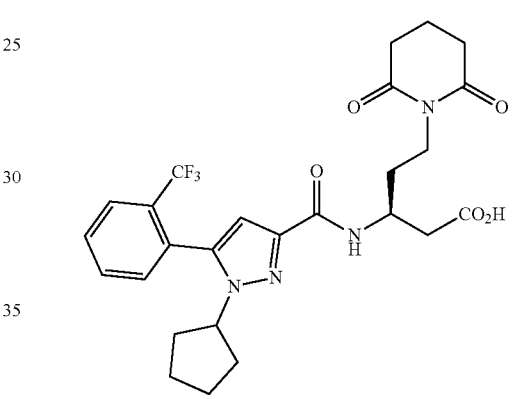

A 4M solution of HCl in dioxane (0.28 mL, 1.1 mmol, 100 equiv.) was added to crude (S)-tert-butyl 3-(1-cyclopentyl-5-(2-(trifluoromethyl)phenyl)-1H-pyrazole-3-carboxamido)-5-(2,6-dioxopiperidin-1-yl)pentanoate (6.5 mg, 0.011 mmol, 1.00 equiv.). The reaction mixture was stirred at rt for 18 h and the solvent was evaporated. The crude product was purified by semi-prep HPLC-MS (column X-Bridge 30×50) using a solution of MeCN in water (containing 10 mM of ammonium formate, pH=3.8) (40 to 60%). Pure fractions were lyophilized to provide 0.65 mg (11%) of the title compound as a white solid. m/z (M+H)$^+$=535.3; R$_T$=1.60 min; purity=>99%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. $^1$H NMR (500 MHz, CD$_3$CN) δ 7.88 (d, J=7.3 Hz, 1H), 7.74 (t, J=7.1 Hz, 1H), 7.69 (t, J=7.4 Hz, 1H), 7.52-7.46 (m, 2H), 6.64 (s, 1H), 4.32-4.22 (m, 2H), 3.80-3.71 (m, 2H), 2.68-2.61 (m, 1H), 2.61-2.51 (m, 1H), 2.54 (t, J=6.7 Hz, 4H), 2.10-2.05 (m, 2H), 1.96-1.92 (m, 2H), 1.88-1.77 (m, 6H), 1.59-1.51 (m, 2H).

Scheme 15: Preparation of (3S)-3-(1-cyclopentyl-5-(2-(trifluoromethyl)phenyl)-1H-pyrazole-3-carboxamide)-5(3,3-difuoropiperdin-1-yl)-2-methylpentanoic acid
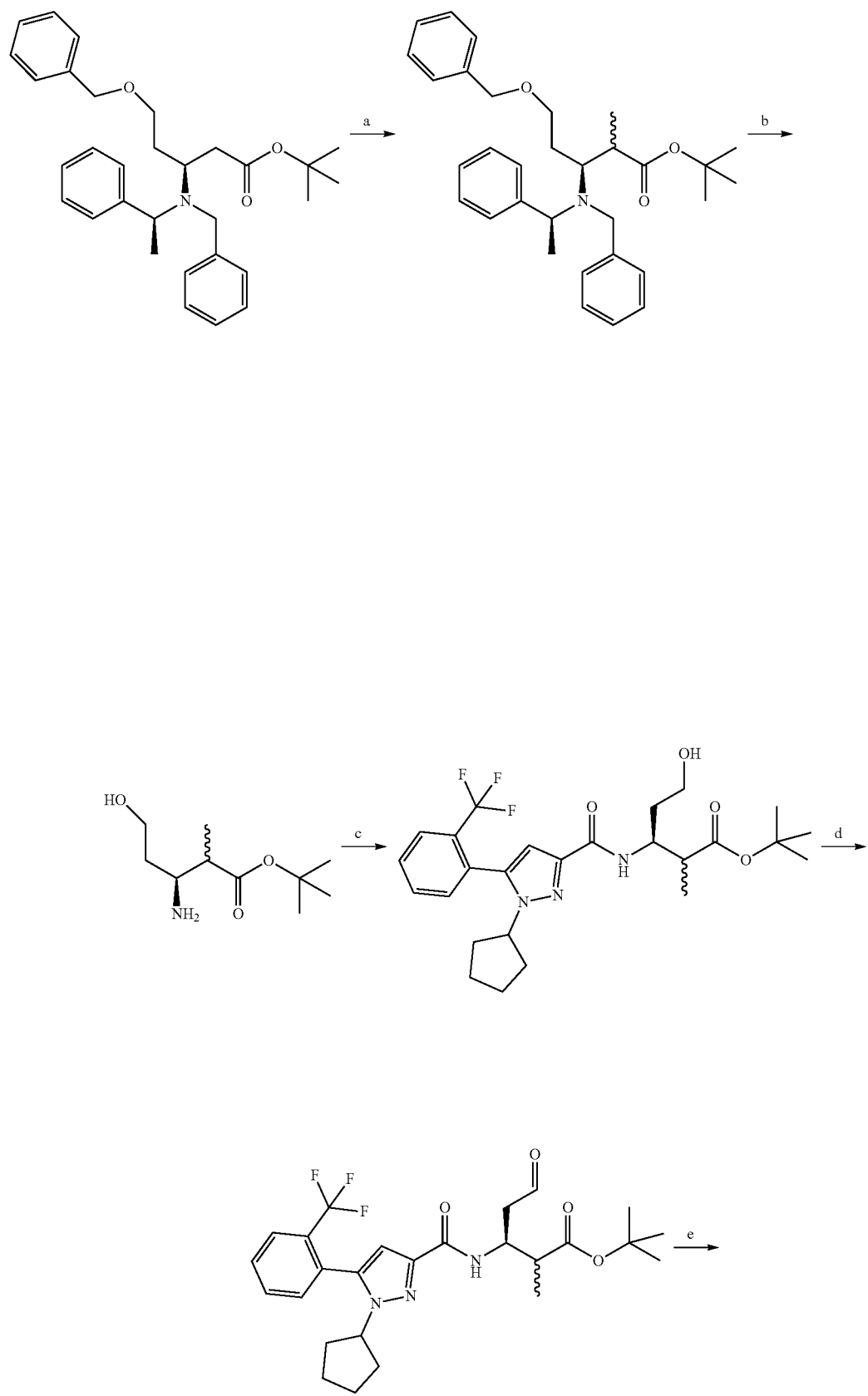

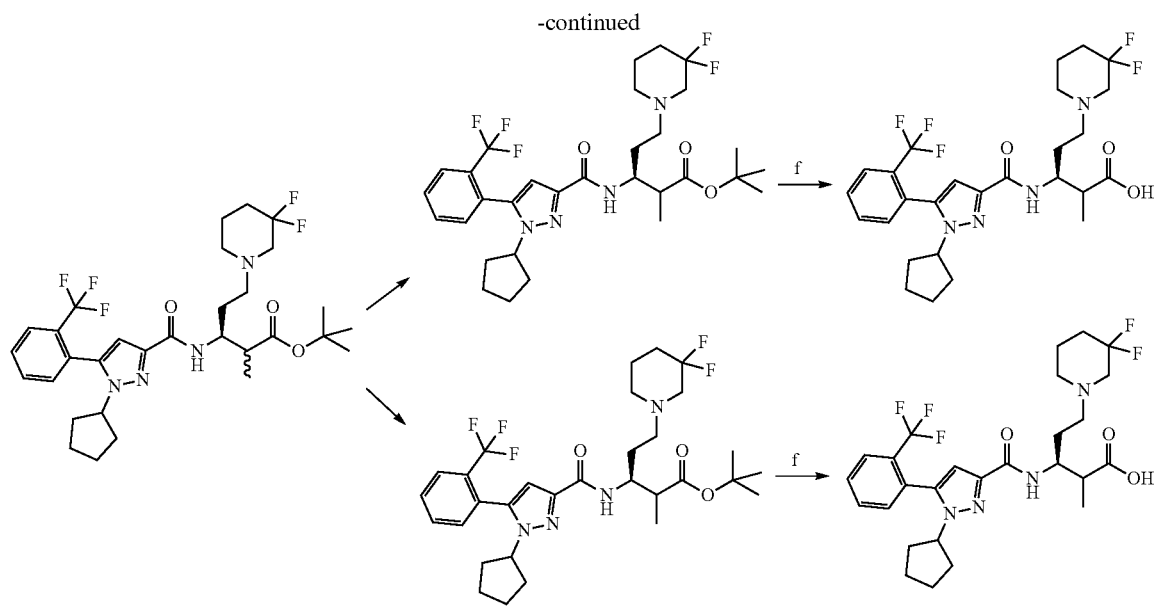

Reagents and conditions:
(a) LDA, -78° C., 1 h; CH₃I, 78° C., 4 h;
(b) H₂, 10% Pd/C, 20% AcOH/EtOH, 50 psi, 30 h;
(c) SOCl₂, refluxed, 4 h, 1-cyclopentyl-5-(2-(trifluoromethyl)phenyl)-1H-pyrazole-3-carboxylic acid, DIPEA, THF, rt, 2 h;
(d) Dess-Martin, DCM, rt, 16 h; (e) 3,3-difluoropyrrolidine hydrochloride, NaBH(OAc)₃, MeOH, rt, 1 h; (f) 4N HCl in dioxane, rt, 4 h

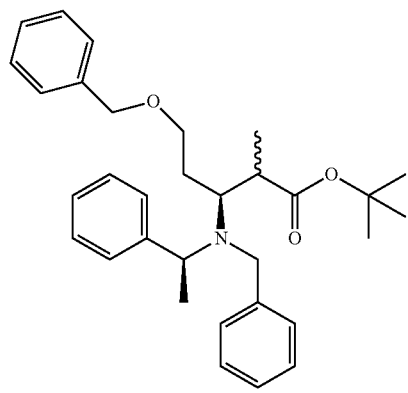 [SMILES: CC(C(=O)OC(C)(C)C)[C@H](CCOCc1ccccc1)N(Cc1ccccc1)[C@@H](C)c1ccccc1]

(3S)-tert-butyl-3-(benzyl((S)-1-phenylethyl)amino)-5-(benzyloxy)-2-methylpentanoate: To a stirred THF (10 mL) sol. of freshly distilled (over CaH2) diisopropylamine (651 µL, 4.64 mmol, 2.20 equiv.) at −78° C. under nitrogen was added drop-wise n-BuLi 2.46 M/Hexane (1.80 mL, 4.43 mmol, 2.10 equiv.). Resulting sol. was stirred 1 hr at −78° C., (S)-tert-butyl 3-(benzyl((S)-1-phenylethyl)amino)-5-(benzyloxy)pentanoate (1.00 g, 2.11 mmol, 1.00 equiv.) dissolved in THF (2 mL) was added drop-wise, sol. was stirred 2 hrs at −78° C. Iodomethane (525 µL, 8.44 mmol, 4.00 equiv.) was added drop-wise, sol.stirred 4 hrs at −78° C., stirring was continued overnight, temperature rose to c.a. −10° C. during this period. Reaction was quenched by the addition of 1 ml sat. aq. NH₄Cl, stirred 15 min, THF was evaporated, residue parted between sat. aq. NaHCO₃ (50 ml) and EtOAc (50 ml). Organic layer was washed 50 ml sat. aq. NaHCO₃, 50 mL sat. aq. NaCl, dried (MgSO₄), filtered, filtrate evaporated, residue dried under high vacuum to give the title compound, 953 mg (92%) thick amber oil.m/z (M+H)⁺=488.3; R$_T$=2.44 min; purity: 93%. HPLC conditions: Column: XBridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO, mixture of conformers/rotamers) δ 7.40-7.15 (m, 15H), 4.47-4.36 (m, 2H), 3.95-3.63 (m, 3H), 3.55-3.35 (m, 2H), 3.27-3.22 (m, 0.5H), 2.88-2.83 (m, 0.5H), 2.36-2.25 (m, 1H), 1.88-1.75 (m, 1H), 1.70-1.60 (m, 1H), 1.31; 1.32 (2s, 9H), 1.25-1.20 (m, 3H), 0.82-0.76 (m, 3H).

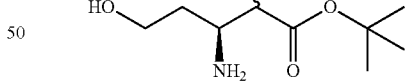

(3S)-tert-butyl-3-amino-5-hydroxy-2-methylpentanoate: In a Parr shaker reactor (3S)-tert-butyl-3-(benzyl((S)-1-phenylethyl)amino)-5-(benzyloxy)-2-methylpentanoate (950 mg, 1.95 mmol, 1.00 equiv.) was dissolved in 20% AcOH/Ethanol (50 ml). Vessel was purged with nitrogen then Pd/C 10% (600 mg) was added. System was evacuated (house vacuum), filled with hydrogen (45 psi), shaken 5 min. System was purged a second time then put under hydrogen pressure (50 psi) and shaken for 30 hrs. System was purged 2× nitrogen, mixture was filtered through a Celite® cake, washed 4×10 ml ethanol, filterate and washings were pooled and evaporated (rotavapor, high vacuum) to give the title compound, 403 mg, which was used as such for the next transformation.

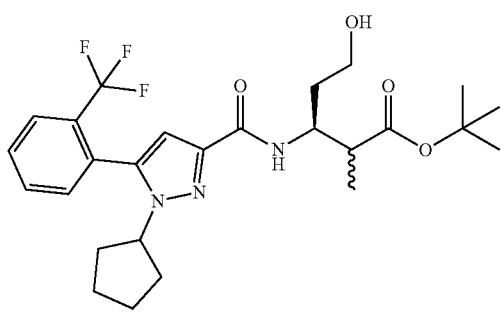 [SMILES: CC(C(=O)OC(C)(C)C)[C@H](CCO)NC(=O)c1cc(-c2ccccc2C(F)(F)F)n(C2CCCC2)n1]

(3S)-tert-butyl 3-(1-cyclopentyl-5-(2-(trifluoromethyl) phenyl)-1H-pyrazole-3-carboxamido)-5-hydroxy-2-methylpentanoate: 1-cyclopentyl-5-(2-(trifluoromethyl)phenyl)-1H-pyrazole-3-carboxylic acid (159 mg, 0.49 mmol) was gently refluxed in thionyl chloride (4 mL) under nitrogen for 4 hrs. Volatiles were evaporated, residue re-dissolved in 4 mL dioxane, solvent evaporated, solid dried under high vacuum 1 hr. This solid was dissolved in THF, DIPEA (257 µL, 1.48 mmol, 3.00 equiv.) was added drop-wise followed by (3S)-tert-butyl 3-amino-5-hydroxy-2-methylpentanoate (100 mg, 0.49 mmol) dissolved-suspended in THF (1 mL). Resulting sol. turned to white suspension shortly after addition. Stirred under nitrogen 2 hrs, diluted with EtOAc (40 ml), washed 3×20 ml sat. aq. NaHCO₃, 20 ml sat. aq. NaCl, dried (MgSO₄), filtered, filtrate evaporated. Product purified CombiFlash®, dry-pack, 10 g column, 20% EtOAc isocratic 2 min. then to 50% EtOAc/Hex. in 6 min, isocratic 2 min. Purest fractions were pooled, solvent evaporated, residue dried under high vacuum to to give the title compound, 83 mg (33%) as an amorphous solid. m/z (M+H)⁺=510.4; $R_T$=1.96 min; purity: 99%. HPLC conditions: Column:) (Bridge® C18, 3.5 µm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: Acetonitrile. ¹H NMR (500 MHz, DMSO) δ 1.09-1.02 (m, 3H), 1.38 (s, 1H), broad (9H), 1.42 (s, 1H), 1.58-1.46 (m, 2H),1.73-1.63 (m, 2H),2.05-1.75 (m, 6H),2.73-2.60 (m, 1H),3.48-3.36 (m, 2H),4.25-4.10 (m, 2H),4.50-4.44 (m, 2H),6.63 (d, J=6.2 Hz, 1H),7.55 (d, J=7.5 Hz, 1H),7.76 (t, J=7.7 Hz, 1H),7.82 (t, J=7.3 Hz, 1H),7.82 (t, J=7.3 Hz, 1H),7.82 (t, J=7.3 Hz, 1H).

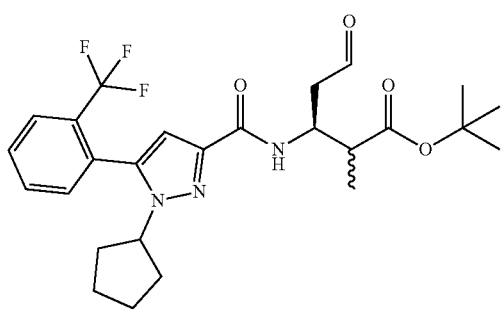 [SMILES: CC(C(=O)OC(C)(C)C)[C@H](CC=O)NC(=O)c1cc(-c2ccccc2C(F)(F)F)n(C2CCCC2)n1]

(3S)-tert-butyl 3-(1-cyclopentyl-5-(2-(trifluoromethyl) phenyl)-1H-pyrazole-3-carboxamido)-2-methyl-5-oxopentanoate: To a stirred, ice cold DCM (2 mL) sol. of (3S)-tert-butyl 3-(1-cyclopentyl-5-(2-(trifluoromethyl)phenyl)-1H-pyrazole-3-carboxamido)-5-hydroxy-2-methylpentanoate (80 mg, 0.157 mmol) under nitrogen was added Dess-Martin periodinane (100 mg, 0.236 mmol, 1.5 equiv.). The white suspension was stirred 15 min. in the cold, allowed to warm to RT and stirred overnight. Mixture was diluted with EtOAc (40 mL) washed 4×25 ml sat. aq. NaHCO₃, 25 ml sat. aq. NaCl, dried (MgSO₄), filtered, filtrate was evaporated, residue dried under high vacuum 1 hr. Crude material was used as such for next transformation.

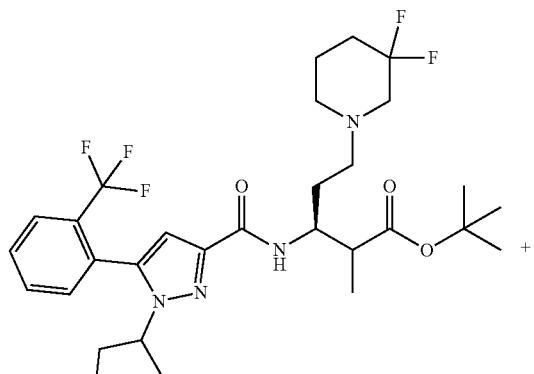

A

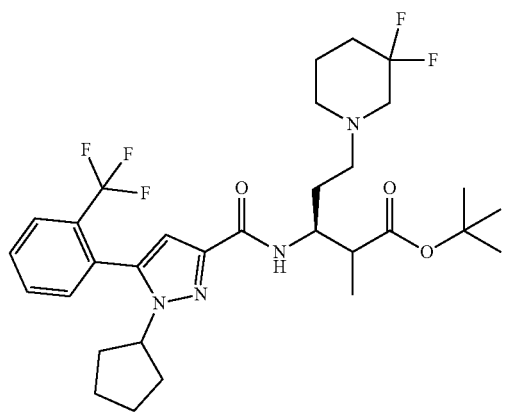

B (3S)-tert-butyl 3-(1-cyclopentyl-5-(2-(trifluoromethyl) phenyl)-1H-pyrazole-3-carboxamido)-5-(3,3-difluoropiperidin-1-yl)-2-methylpentanoate (A and B)

To a stirred methanol (2 mL) sol. of 3,3-difluoropyrrolidine hydrochloride (42 mg, 0.268 mmol, 1.00 equiv.) under nitrogen was added triethylamine (50 µL, 0.358 mmol, 3.00 equiv.). Sol. was stirred min. then (3S)-tert-butyl 3-(1-cyclopentyl-5-(2-(trifluoromethyl)phenyl)-1H-pyrazole-3-carboxamido)-2-methyl-5-oxopentanoate (60 mg, 0.118 mmol, 1.00 equiv.) in 1 mL methanol was added. Sol. was stirred at RT 1 h then sodium triacetoxyborohydride (45 mg, 0.215 mmol, 1.80 equiv.) was added. Solution was stirred a further 3 hrs, solvent was evaporated, residue taken in ethyl acetate (30 mL), washed 3×20 mL sat. aq. NaHCO₃, 20 mL sat. aq. NaCl, dried (MgSO₄), filtered, filtrate evaporated. Residue purified CombiFlash®, 12 g column, DCM isocratic 3 min. then to 1% MeOH/DCM in 6 min. isocratic 5 min. Two products were separated;

(3S)-tert-butyl 3-(1-cyclopentyl-5-(2-(trifluoromethyl)phenyl)-1H-pyrazole-3-carboxamido)-5-(3,3-difluoropiperidin-1-yl)-2-methylpentanoate A (less polar diastereomer), 17.6 mg (24%) amorphous solid [49% based on a 1:1 mixture of diastereoisomers].

m/z (M+H)⁺=614.5; $R_T$=2.12 min; purity: 95%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: CH₃CN. ¹H NMR (500 MHz, CDCl₃) δ 1.21 (d, J=7.1 Hz, 3H), 1.48 (s, 9H),1.58-1.49 (m, 2H),2.20-1.61 (m, 12H),2.79-2.37 (m, 7H),4.16 (p, J=7.6 Hz, 1H), 4.35-4.26 (m, 1H),6.75 (s, 1H),7.28 (d, broad, J=9.8 Hz, 1H),7.32 (d, broad, J=7.1 Hz, 1H),7.65-7.56 (m, 2H),7.80 (dd, J=7.8, 1.0 Hz, 1H).

(3 S)-tert-butyl 3-(1-cyclopentyl-5-(2-(trifluoromethyl)phenyl)-1H-pyrazole-3-carboxamido)-5-(3,3-difluoropiperidin-1-yl)-2-methylpentanoate B (more polar diastereomer), 23.5 mg (33%) amorphous solid [65% based on a 1:1 mixture of diastereoisomers].

m/z (M+H)⁺=614.5; $R_T$=2.12 min; purity: 93%. HPLC conditions: Column: XBridge® C18, 3.5 μm, 4.6×30 mm;Gradient: 5B 0.2 min, 5B-100B 1.8 min, 100B 1 min; 3 mL/min. Eluent A: pH 3.8 10 mM Ammonium Formate in Water;Eluent B: CH₃CN. ¹H NMR (500 MHz, CDCl₃) δ 1.22 (d, J=6.1 Hz, 3H), 1.48 (s, 9H),1.55-1.50 (m, 2H),2.17-1.70 (m, 12H),2.74-2.37 (m, 7H),4.21-4.12 (m, 1H),4.32-4.23 (m, 1H),6.74 (s, 1H),7.32 (d, J=7.2 Hz, 1H),7.56-7.45 (m, 1H),7.65-7.57 (m, 2H),7.80 (d, J=7.2 Hz, 1H).

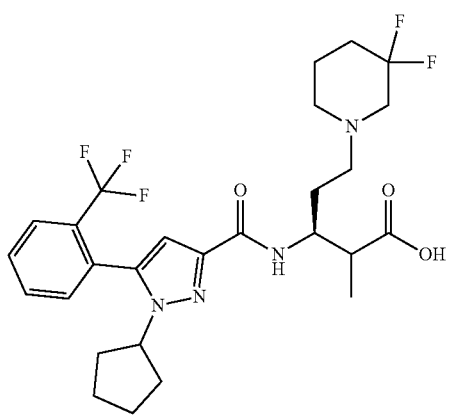

Acid 1

(3S)-3-(1-cyclopentyl-5-(2-(trifluoromethyl)phenyl)-1H-pyrazole-3-carboxamido)-5-(3,3-difluoropiperidin-1-yl)-2-methylpentanoic acid (Acid 1): (3S)-tert-butyl 3-(1-cyclopentyl-5-(2-(trifluoromethyl)phenyl)-1H-pyrazole-3-carboxamido)-5-(3,3-difluoropiperidin-1-yl)-2-methylpentanoate A (16 mg, 0.026 mmol, 1.00 equiv.) was dissolved in 4NHCl/dioxane solution (4 mL). Stirred at RT 4 hrs, volatiles were evaporated, residue purified CombiFlash®, 12 g Biotage KP-C18-HS column, aq. 10 mM ammonium bicarbonate isocratic 1 min., to 50% acetonitrile in 5 min., isocratic 3 min. Purest fractions were pooled, most acetonitrile was evaporated, remaining solution was frozen and lyophilized to give the title compound, 7.5 mg (52%) white solid.m/z (M+H)⁺=557.3; $R_T$=1.54 min; purity: 98%. HPLC conditions: Column: XBridge® C18, 3.5 μm, 4.6×30 mm; Gradient: 5B 0.2 min, 5B-100B 1.8 min, 100B 1 min; 3 mL/min. Eluent A: pH 3.8 10 mM Ammonium Formate in Water; Eluent B: CH₃CN. ¹H NMR (500 MHz, DMSO) δ 1.06 (d, J=7.0 Hz, 3H), 1.56-1.45 (m, 2H),1.73-1.57 (m, 4H),2.05-1.75 (m, 8H),2.44-2.30 (m, 4H),2.65-2.55 (m, 3H), 4.23-4.09 (m, 2H),6.63 (s, 1H),7.56 (d, J=7.5 Hz, 1H),7.76 (t, J=7.7 Hz, 1H),7.82 (t, J=7.4 Hz, 1H),7.88-7.79 (s, broad, 1H),7.93 (d, J=7.4 Hz, 1H), 11.70 (s, broad, 1H).

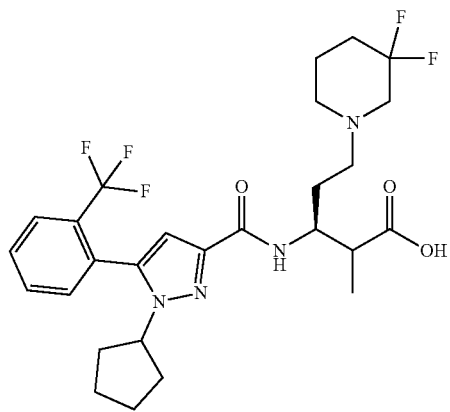

Acid 2

(3S)-3-(1-cyclopentyl-5-(2-(trifluoromethyl)phenyl)-1H-pyrazole-3-carboxamido)-5-(3,3-difluoropiperidin-1-yl)-2-methylpentanoic acid (Acid 2): (3S)-tert-butyl 3-(1-cyclopentyl-5-(2-(trifluoromethyl)phenyl)-1H-pyrazole-3-carboxamido)-5-(3,3-difluoropiperidin-1-yl)-2-methylpentanoate B(22 mg, 0.036 mmol, 1.00 equiv.) was dissolved in 4N HCl/dioxane solution (4 mL). Stirred at RT 4 hrs, volatiles were evaporated, residue purified CombiFlash®, 12 g Biotage KP-C18-HS column, aq. 10 mM ammonium bicarbonate isocratic 1 min., to 40% acetonitrile in 5 min., isocratic 4 min. Purest fractions were pooled, most acetonitrile was evaporated, remaining solution was frozen and lyophilized to give the title compound, 14.6 mg (73%) white solid.m/z (M+H)⁺=557.2; $R_T$=1.56 min; purity: >99%. HPLC conditions: Column: XBridge® C18, 3.5 μm, 4.6×30 mm;Gradient: 5B 0.2 min, 5B-100B 1.8 min, 100B 1 min; 3 mL/min. Eluent A: pH 3.8 10 mM Ammonium Formate in Water; Eluent B: CH₃CN. ¹H NMR (500 MHz, DMSO) δ 13.20-11.80 (s, broad, 1H), 1.09 (d, J=7.1 Hz, 3H), 1.56-1.45 (m, 2H),1.75-1.58 (m, 4H),2.00-1.75 (m, 8H),2.45-2.32 (m, 4H),2.73-2.55 (m, 3H),4.15-4.05 (m, 1H), 4.20 (p, J=7.2 Hz, 1H),6.62 (s, 1H),7.56 (d, J=7.5 Hz, 1H),7.76 (t, J=7.7 Hz, 1H),7.82 (t, J=7.4 Hz, 1H),7.93 (d, J=7.4 Hz, 1H), 8.13-7.92 (s, broad, 1H)

Scheme 16: Preparation of (3S)-3-(1-cyclopentl-5-(2-(trifluoromethyl)phenyl)-1H-pyrazole-3-carboxamido)-5(3,3-difuoropiperidin-1-yl)hexanoic acid
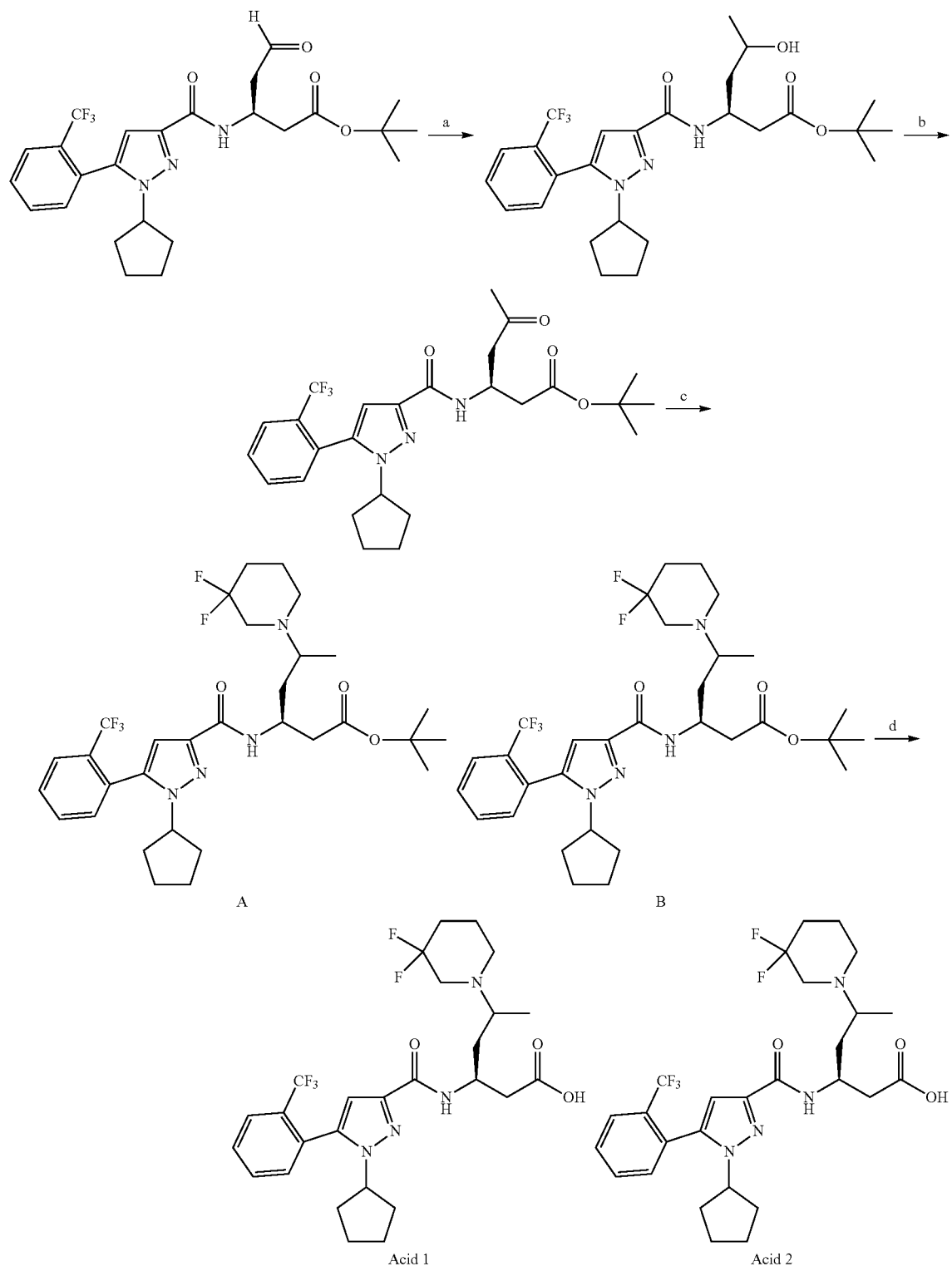
Reagents and conditions:
(a) CH₃MgBr, THF, -78° C., 4 h;
(b) Dess-Martin reagent, DCM, 12 h;
(c) 3,3-difluoropiperidine•HCl, NaBH(OAc)₃, DCE, rt, 12 h;
(d) TFA, DCM, rt, 2 h, 90%.

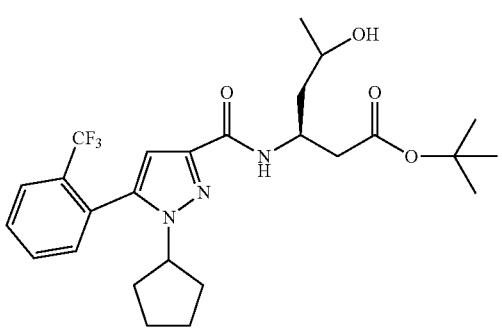 [SMILES: CC(O)C[C@@H](CC(=O)OC(C)(C)C)NC(=O)c1cc(-c2ccccc2C(F)(F)F)n(C2CCCC2)n1]

(3S)-tert-butyl 3-(1-cyclopentyl-5-(2-(trifluoromethyl)phenyl)-1H-pyrazole-3-carboxamido)-5-hydroxyhexanoate: To a solution of (S)-tert-butyl 3-(1-cyclopentyl-5-(2-(trifluoromethyl)phenyl)-1H-pyrazole-3-carboxamido)-5-oxopentanoate(230 mg, 0.466 mmol) in THF (10 mL) at −78° C. was slowly added a solution of $CH_3MgBr$ (0.31 mL, 0.93 mmol, 3.0 M in $Et_2O$). The mixture was allowed to stir at −78° C. for 30 min. Then the solution was warmed to rt and stirring for 4 h. The reaction was quenched with water (2 mL). Then the solution was extracted with $Et_2O$ (3×15 mL), the combined organic layers were dried over $MgSO_4$, concentrated in vacuo and purified by chromatography over silica gel, eluting with 0-40% EtOAc/Hexanes to give known (3S)-tert-butyl 3-(1-cyclopentyl-5-(2-(trifluoromethyl)phenyl)-1H-pyrazole-3-carboxamido)-5-hydroxyhexanoate, yield 85% colorless oil. $^1$H NMR (300 MHz, $CDCl_3$) δ 1.23-1.29 (m, 3H), 1.39-1.61 (m, 11H), 1.80-2.16 (m, 8H), 2.58-2.74 (m, 2H), 3.91-4.05 (m, 1H),4.08-4.25 (m, 1H), 4.43-4.68 (m, 1H), 6.73-6.79 (m, 1H), 7.29p-7.37 (m, 1H), 7.49-7.70 (m, 3H), 7.76-7.87 (m, 1H).LC-MS (ESI): m/z [M+H]510.5.

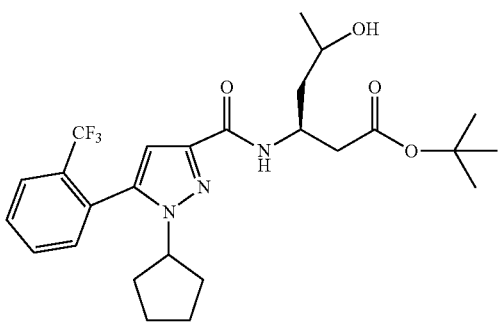 [SMILES: CC(O)C[C@@H](CC(=O)OC(C)(C)C)NC(=O)c1cc(-c2ccccc2C(F)(F)F)n(C2CCCC2)n1]

(S)-tert-butyl 3-(1-cyclopentyl-5-(2-(trifluoromethyl)phenyl)-1H-pyrazole-3-carboxamido)-5-oxohexanoate: To a solution of crude (3S)-tert-butyl 3-(1-cyclopentyl-5-(2-(trifluoromethyl)phenyl)-1H-pyrazole-3-carboxamido)-5-hydroxyhexanoate (100 mg 0.196 mmol) in DCM (6 mL) was added sodium bicarbonate (33 mg, 0.39 mmol) followed by Dess Martins reagent (166 mg, 0.39 mmol). The mixture was allowed to stir for overnight before the reaction was quenched with 10% aqueous sodium bicarbonate (2 mL). Then the solution was extracted with $Et_2O$ (3×15 mL), the combined organic layers were dried over $MgSO_4$, concentrated in vacuo and purified by chromatography over silica gel, eluting with 0-40% EtOAc/Hexanes to give known ketone (S)-tert-butyl 3-(1-cyclopentyl-5-(2-(trifluoromethyl)phenyl)-1H-pyrazole-3-carboxamido)-5-oxohexanoate, yield 85% colorless oil. $^1$H NMR (300 MHz, $CDCl_3$) δ 1.45 (s, 9H), 1.78-2.04 (m, 8H), 1.50-1.61 (m, 2H), 2.20 (s, 3H), 2.66-2.76 (m, 2H), 2.90-3.10 (m, 2H), 4.08-4.23 (m, 1H), 4.65-4.82 (m, 1H), 6.74 (s, 1H), 7.28-7.36 (m, 1H), 7.51-7.67 (m, 3H), 7.76-7.84 (m, 1H).LC-MS (ESI): m/z [M+M$^+$]508.5.

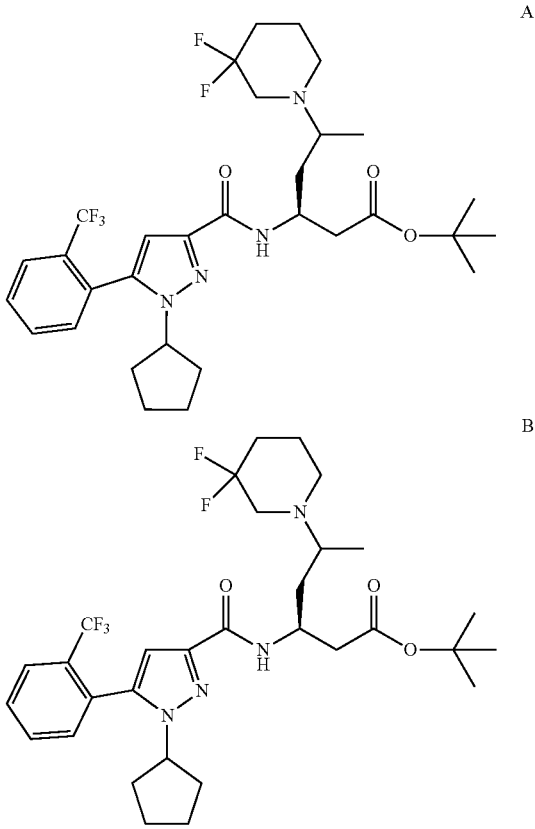

(3S)-3-(1-cyclopentyl-5-(2-(trifluoromethyl)phenyl)-1H-pyrazole-3-carboxamido)-5-(3,3-difluoropiperidin-1-yl) hexanoic acid (A and B): A solution of the ketone (S)-tert-butyl 3-(1-cyclopentyl-5-(2-(trifluoromethyl)phenyl)-1H-pyrazole-3-carboxamido)-5-oxohexanoate(75 mg, 0.147 mmol), 3,3 difluoro piperidine hydrochloride (28 mg, 0.177 mmol), crushed 4 A molecular sieves in dichloroethane (10 mL) was treated with sodium triacetoxyborohydride (63 mg0.294 mmol) and the resulting mixture was stirred at ambient temperature overnight. The sieves were filtered off through a plug of Celite®, the filtrate was washed with a saturated solution of sodium bicarbonate, water and brine. The combined aqueous solutions were back extracted with dichloromethane, the combined organic extracts were dried with anhydrous sodium sulfate, and the solvent was evaporated in vacuo and purified by chromatography over silica gel, eluting with 0-35% EtOAc/Hexanes to give the two diastereoisomers (A and B).

(3S)-3-(1-cyclopentyl-5-(2-(trifluoromethyl)phenyl)-1H-pyrazole-3-carboxamido)-5-(3,3-difluoropiperidin-1-yl) hexanoic acid(A, less polar diastereomer), yield 20 mg (30%) colorless oil. $^1$H NMR (300 MHz, $CDCl_3$) δ 1.02 (d, J=6.59 Hz, 3H), 1.47 (s., 9H), 1.50-1.61 (m, 2H), 1.69-2.05 (m, 12H), 2.31-2.46 (m, 1H), 2.55-2.71 (m, 4H), 2.72-2.92 (m, 2H), 4.10-4.23 (m, 1H), 4.45-4.60 (m, 1H), 6.75 (s, 1H), 7.30-7.43 (m, 1H), 7.56-7.67 (m, 3H), 7.77-7.83 (m, 1H).LC-MS (ESI): m/z [M+H$^+$]613.7.

(3S)-3-(1-cyclopentyl-5-(2-(trifluoromethyl)phenyl)-1H-pyrazole-3-carboxamido)-5-(3,3-difluoropiperidin-1-yl)hexanoic acid (B, more polar diastereomer), yield 6.5 mg (10%) colorless oil. $^1$H NMR (300 MHz, CDCl$_3$) δ 0.98 (d, J=6.59 Hz, 3H), 1.45 (s, 9H), 1.50-1.61 (m, 2H),1.67-2.18 (m, 12H),2.31-2.46 (m, 1H),2.61-2.95 (m, 6H),4.04-4.22 (m, 1H),4.44-4.58 (m, 1H),6.75 (s, 1H),7.28-7.35 (m, 1H), 7.51-7.68 (m, 3H), 7.77-7.84 (m, 1H). LC-MS (ESI): m/z [M-H$^+$] 613.8.

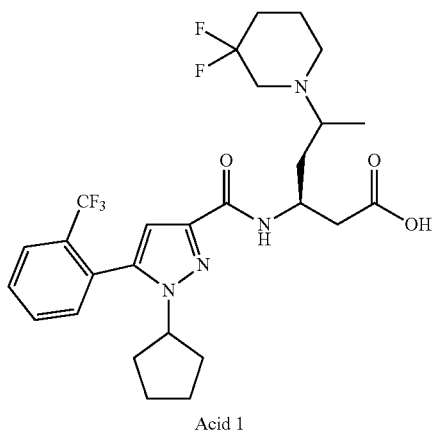 [SMILES: CC(C[C@@H](CC(=O)O)NC(=O)c1cc(-c2ccccc2C(F)(F)F)n(C2CCCC2)n1)N1CCCC(F)(F)C1]

Acid 1

(3S)-3-(1-cyclopentyl-5-(2-(trifluoromethyl)phenyl)-1H-pyrazole-3-carboxamido)-5-(3,3-difluoropiperidin-1-yl)hexanoic acid (Acid 1):To a solution of (3S)-3-(1-cyclopentyl-5-(2-(trifluoromethyl)phenyl)-1H-pyrazole-3-carboxamido)-5-(3,3-difluoropiperidin-1-yl)hexanoic acid (A)(20 mg) in DCM:TFA (1:1, 1 mL) and stirred at rt for 2 h. Solvent was removed in vacuo and diluted with CHCl$_3$. Solvent was removed to provide 90% (3S)-3-(1-cyclopentyl-5-(2-(trifluoromethyl)phenyl)-1H-pyrazole-3-carboxamido)-5-(3,3-difluoropiperidin-1-yl)hexanoic acid (Acid 1) as a white solid, $^1$H NMR (300 MHz, CDCl$_3$) δ 1.40-1.56 (m, 6H), 1.77-2.21 (m, 12H), 2.43-2.63 (m, 1H), 2.70-2.81 (m, 2H), 3.2-3.93 (m, 4H), 4.07-4.24 (m, 1H), 4.45-4.65 (m, 1H), 6.74 (s, 1H), 7.37-7.28 (m, 1H), 7.62 (t, J=6.40 Hz, 2H), 7.81 (d, J=8.48 Hz, 1H), 7.85-7.98 (m, 1H).LC-MS (ESI): m/z[M+H$^+$] 557.9, [M–H$^+$]556.0.

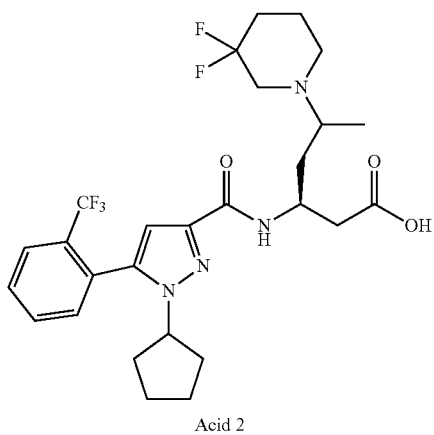 [SMILES: CC(C[C@@H](CC(=O)O)NC(=O)c1cc(-c2ccccc2C(F)(F)F)n(C2CCCC2)n1)N1CCCC(F)(F)C1]

Acid 2

(3S)-3-(1-cyclopentyl-5-(2-(trifluoromethyl)phenyl)-1H-pyrazole-3-carboxamido)-5-(3,3-difluoropiperidin-1-yl)hexanoic acid (Acid 2): To a solution of (3S)-3-(1-cyclopentyl-5-(2-(trifluoromethyl)phenyl)-1H-pyrazole-3-carboxamido)-5-(3,3-difluoropiperidin-1-yl)hexanoic acid (B)(6 mg) in DCM:TFA (1:1, 1 mL) and stirred at rt for 2 h. Solvent was removed in vacuo and diluted with CH$_2$Cl$_2$. Solvent was removed to provide 90% of (3S)-3-(1-cyclopentyl-5-(2-(trifluoromethyl)phenyl)-1H-pyrazole-3-carboxamido)-5-(3,3-difluoropiperidin-1-yl)hexanoic acid (Acid 2) as a white solid. $^1$H NMR (300 MHz, CDCl$_3$) δ 1.32-1.58 (m, 6H), 1.78-2.43 (m, 12H), 2.80-2.95 (m, 2H), 3.04-3.61 (m, 4H), 4.16 (d, J=6.97 Hz, 1H), 4.25-4.44 (m, 1H), 6.74 (br. s., 1H), 7.28-7.37 (m, 1H), 7.63 (t, J=6.12 Hz, 2H), 7.81 (d, J=7.91 Hz, 1H), 8.02-8.23 (m, 1H).LC-MS (ESI): m/z [M+H$^+$] 557.9, [M--H$^+$]556.1.

Scheme 17: Preparation of (S)-N-(1-(cyclobutylamino)-5-(3,3-difluoropiperidin-1-yl)-1-oxopentan-3-yl)-1-cyclopentyl-5-(3-(trifluoromethyl)pyridin-2-yl)-1H-pyrazole-3-carboxamide

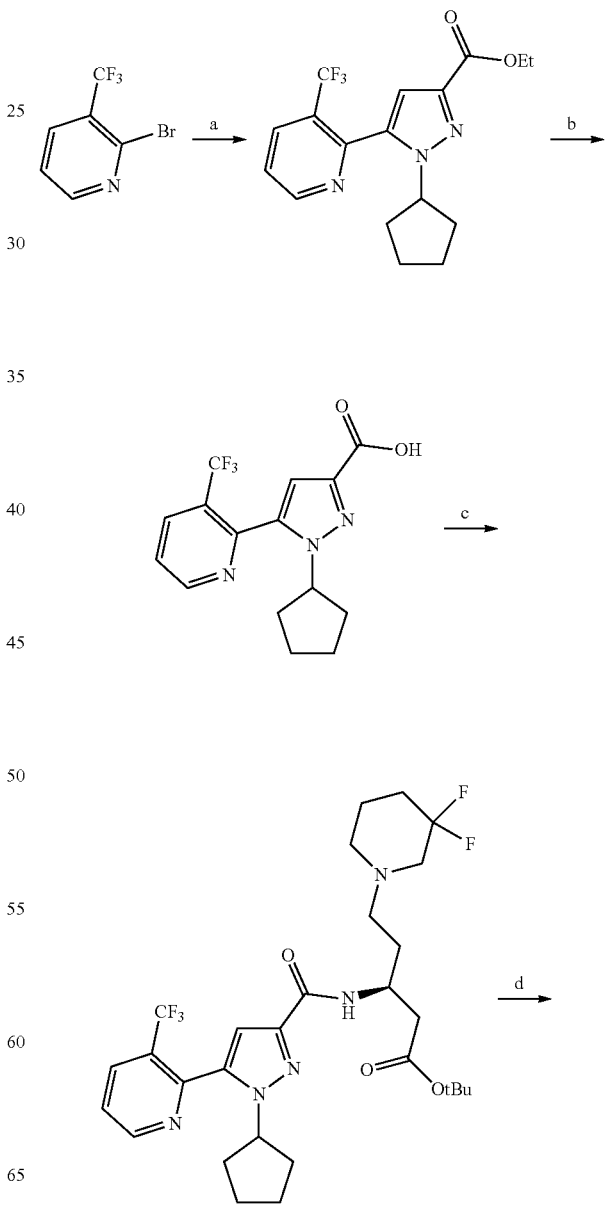

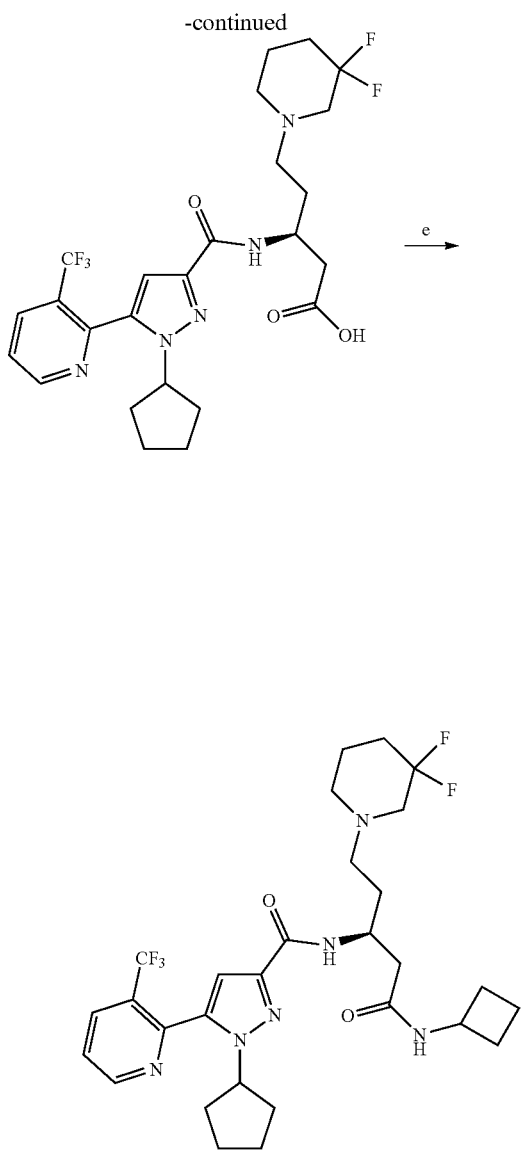

Ethyl 1-cyclopentyl-5-(3-(trifluoromethyl)pyridin-2-yl)-1H-pyrazole-3-carboxylate: To a solution of 85 (0.90 g, 4.0 mmol) in Et₂O (40 ml) at −78° C. was added dropwise of nBuLi (1.9 ml, 2.5 M in hexanes, 4.8 mmol). After addition the mixture was stirred at −78° C. for 1 h, followed by dropwise addition of Bu₃SnCl (1.20 ml, 4.4 mmol). Stirring was continued at this temperature for 1 h and then slowly warmed to rt. The solution was quenched with ammonium chloride (sat., 20 ml) and extracted with hexanes (20 ml). The extract was dried (Na₂SO₄) and concentrated. The concentrate was triturated with hexanes, filtered and concentrated to give a brown oil (1.51 g).

To a mixture of the above oil (0.79 g), bromopyrazole (0.43 g, 1.5 mmol) and toluene (15 ml) in a sealed tube was added Pd(PPh₃)₂Cl₂ (53 mg, 0.075 mmol) under N₂. The mixture was heated at 120° C. for 40 h. Then it was concentrated and purified using EA in hexanes to give the desired product 86 (50 mg) as a yellow oil; ¹H NMR (200 MHz, CDCl₃): δ=1.39 (t, 3H, J=7.4 Hz), 1.40-1.70 (m, 2H), 1.80-2.30 (m, 6H), 4.30-4.50 (m, 3H), 6.91 (s, 1H), 7.40-7.60 (m, 1H), 8.17 (d, 1H, J=8.0 Hz), 8.93 (d, 1H, J=4.6 Hz); LC-MS (ESI): m/z calculated for C₁₇H₂₀F₃N₃O₂ [M+H⁺]: 354, Found: 354.0.

1-Cyclopentyl-5-(3-(trifluoromethyl)pyridin-2-yl)-1H-pyrazole-3-carboxylic acid:To a solution of ethyl 1-cyclopentyl-5-(3-(trifluoromethyl)pyridin-2-yl)-1H-pyrazole-3-carboxylate (50 mg, 0. 141 mmol) in THF (5 ml) and H₂O (1 ml) was added LiOH (10 mg). The mixture was stirred at rt for 20 h, acidified to PH 4, and extracted with EtOAc. The EtOAc extract was dried (Na₂SO₄), concentrated and purified (if necessary) to give title compound (45 mg) as a brown solid; ¹H NMR (200 MHz, CDCl₃): δ=1.40-1.70 (m, 2H), 1.80-2.30 (m, 6H), 4.40-4.60 (m, 1H), 6.99 (s, 1H), 7.50-7.60 (m, 1H), 8.17 (d, 1H, J=8.0 Hz),8.93 (d, 1H, J=4.4 Hz); LC-MS (ESI): m/z calculated for C₁₅H₁₆F₃N₃O₂ [M⁺]: 326, Found: 325.9.

(S)-Tert-butyl 3-(1-cyclopentyl-5-(3-(trifluoromethyl)pyridin-2-yl)-1H-pyrazole-3-carboxamido)-5-(3,3-difluoropiperidin-1-yl)pentanoate:A mixture of 1-cyclopentyl-5-(3-(trifluoromethyl)pyridin-2-yl)-1H-pyrazole-3-carboxylic acid(42 mg, 0.15 mmol), (S)-tert-butyl 3-amino-5-(3,3-difluoropiperidin-1-yl)pentanoate(67 mg, 0.23 mmol), Et₃N (0.060 ml, 0.60 mmol) and TBTU (72 mg, 0.22) in MeCN (5 ml) was stirred at rt for 15 h. The mixture was diluted with EtOAc and washed with NaHCO₃. The organic layer was dried (Na₂SO₄), concentrated, and purified using 0-10% MeOH in DCM (with 1% NH₃) to give the title compound (58 mg) as a colorless oil; ¹H NMR (200 MHz, CDCl₃): δ=1.40 (s, 9H), 1.50-2.20 (m, 14H), 2.30-2.80 (m, 8H), 4.30-4.60 (m, 2H), 6.61 (d, 1H, J=9.8 Hz), 6.89 (s, 1H), 7.40-7.60 (m, 1H), 8.13 (d, 1H, J=8.0 Hz),8.91 (d, 1H, J=4.0 Hz); LC-MS (ESI): m/z calculated for C₂₉H₃₉F₅N₅O₃ [M+H⁺]: 600, Found: 599.8.

(S)-3-(1-Cyclopentyl-5-(3-(trifluoromethyl)pyridin-2-yl)-1H-pyrazole-3-carboxamido)-5-(3,3-difluoropiperidin-1-yl)pentanoic acid: To a solution of (S)-tert-butyl 3-(1-cyclopentyl-5-(3-(trifluoromethyl)pyridin-2-yl)-1H-pyrazole-3-carboxamido)-5-(3,3-difluoropiperidin-1-yl) pentanoate (50 mg) in DCM (2 ml) was added HCl (4 M in dioxane, 0.1 ml). The mixture was stirred at rt for 15 h and concentrated to dryness to give the acid as the HCl salt. (40 mg). LC-MS (ESI): m/z calculated for C₂₅H₃₁F₅N₅O₃ [M+H⁺]: 544, Found: 543.7.

(S)—N—(1-(Cyclobutylamino)-5-(3,3-difluoropiperidin-1-yl)-1-oxopentan-3-yl)-1-cyclopentyl-5-(3-(trifluoromethyl)pyridin-2-yl)-1H-pyrazole-3-carboxamide:A mixture of (S)-3-(1-cyclopentyl-5-(3-(trifluoromethyl)pyridin-2-yl)-1H-pyrazole-3-carboxamido)-5-(3,3-difluoropiperidin-1-yl) pentanoic acid hydrochloride (40 mg, 0.073 mmol), cyclobutylamine (10 mg, 0.10 mmol), Et₃N (0.030 ml, 0.29 mmol) and TBTU (24 mg, 0.10) in MeCN (5 ml) was stirred at rt for 15 h. The mixture was diluted with EtOAc and washed with NaHCO₃. The organic layer was dried (Na₂SO₄), concentrated, and purified using 0-10% MeOH in DCM (with 1% NH₃) to give the title product (34 mg) as a white solid; ¹H NMR (200 MHz, CDCl₃): δ=1.40-2.80 (m, 28H), 4.30-4.50 (m, 3H), 6.42 (d, 1H, J=8.4 Hz), 6.90 (s, 1H), 7.50-7.70 (m, 1H), 8.14 (d, 1H, J=8.2 Hz),8.91 (d, 1H, J=4.0 Hz); LC-MS (ESI): m/z calculated for C₂₉H₃₈F₅N₆O₂ [M+H⁺]: 597, Found: 596.8; LC purity: 96.4%.

Scheme 18: Preparation of (S)-tert-butyl 3-amino-5-cyclohexylpentanoate

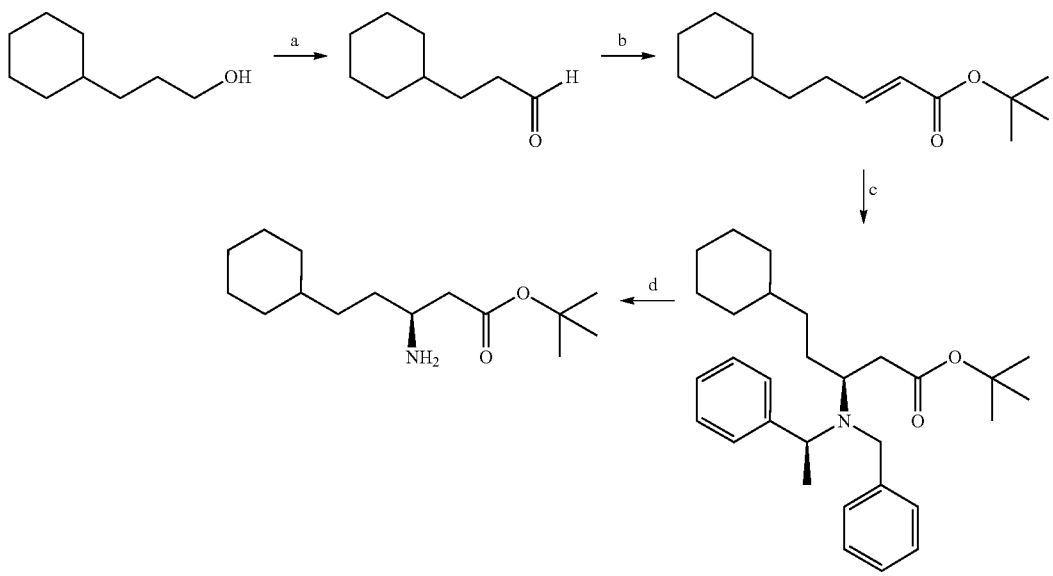

Reagents and conditions: a) PCC, DCM, rt, 3 h, 100% b) (EtO)₂POCH₂CO₂ᵗBiu,BuLi, THF, -78° C. to rt, 1 h c) (S)-N-benzyl-N-α-methyl-benzylamine, BuLi, THF, -78° C., 3 h d) 10% Pd/C, H₂, 45 psi, 20% AcOH/EtOH, rt, 24 h

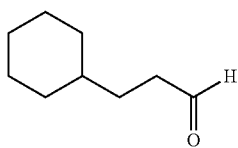

3-Cyclohexylpropanal To a solution of commercially available 3-cyclohexylpropanol (45.5 g, 0.32 mol) in CH₂Cl₂ (1000 mL) was added PCC (103.5 g, 0.48 mol), Celite® 545 (50 g) and stirred at room temperature for 3 h. The reaction mixture was diluted with ethyl ether (1000 mL), stirred at rt for 1 h, before it was filtered through Celite® and silica gel (1:1) pad. The filtrate was concentrated to give crude residue. Crude product was purified by silica gel flash chromatography (0-30% EtOAc/hexanes) to give the title compound as oil (50.7 g), which contained residual hexanes as judged by NMR analysis. ¹H NMR (300 MHz, CDCl₃) δ 0.83-0.98 (m, 3H), 1.15-1.31 (m, 4H), 1.49-1.56 (m, 2H), 1.61-1.73 (m, 4H), 2.41-2.46 (m, 2H), 9.77 (s, 1H).

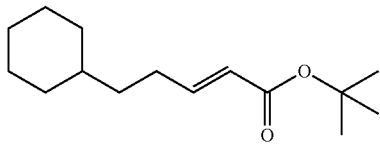 [SMILES: CC(C)(C)OC(=O)/C=C/CCC1CCCCC1]

(E)-Tent-butyl 5-cyclohexylpent-2-enoate To a stirred solution of tert-butyl diethylphosphonoacetate (82.67 mL, 0.352 mol) in THF (500 mL) was slowly added n-BuLi (2.5 M in hexanes) (141 mL, 0.352 mol) dropwise with cooling at -78° C. After stirring for 30 minutes at -78° C., a solution of 3-cyclohexylpropanal (50.7 g, 0.32 mol) in 250 mL of THF also cooled at -78° C. was transferred via cannula. The resulting solution was stirred at -78° C. for 40 minutes before being allowed to warm at rt and then stirred at 40 minutes. The solution was subsequently cooled to -78° C. and quenched with sat. aqs. NH₄Cl (250 mL). The layers were separated and the aqueous layer was extracted in DCM (3×200 mL) and the combined organics were dried over Na₂SO₄, filtered and the solvent was evaporated in vacuo to give the crude residue. Crude product was purified by silica gel flash chromatography (0-2% EtOAc/hexanes) to give the title compound as oil (59.8 g, 78%). ¹H NMR (300 MHz, CDCl₃) δ 0.82-0.94 (m, 3H), 1.11-1.37 (m, 3H), 1.48 (s, 9 H), 1.63-1.87 (m, 3H), 2.14-2.21(m, 2H), 3.73-3.77 (m, 1H), 4.12-4.22 (m, 2H), 5.73 (dt, J=15.45, 1.51 Hz, 1H), 6.86 (m, 1H).

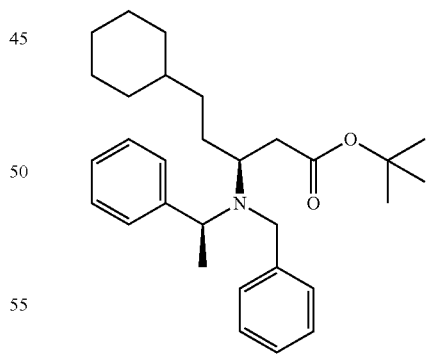

(S)-Tert-butyl 3-(benzyh(S)-1-phenylethyl)amino)-5-cyclohexylpentanoate: To a stirred solution of (S)—N-benzyl-N-a-methylbenzylamine (84.86 g, 0.402 mol) in THF (312 mL) was slowly added n-BuLi (2.5 M in hexanes) (161 mL, 0.402 mol) with cooling at -78° C. After 30 minutes, a solution of (E)-tert-butyl 5-cyclohexylpent-2-enoate (59.81 g, 0.251 mol) in 100 mL of THF also at -78° C. was transferred via cannula. The resulting solution was stirred at -78° C. for 3 h before quenching with sat. aqs. NH₄Cl (200 mL). Upon warming to rt, THF was removed and the aqueous layer was extracted in DCM (3×200 mL). The combined organic layers were washed with 10% aqs. citric acid (3×50 mL) to remove the excess amine. The organic layer was then washed with aqs. NaHCO3 (50 mL), brine (50 mL), dried with Na$_2$SO$_4$ and the solvent was removed in vacuo to give the crude product. Crude product was purified by silica gel flash chromatography (0-2% EtOAc/hexanes) to give the title compound as oil (97.3 g, 86%). $^1$H NMR (300 MHz, CDCl$_3$) δ 0.80-0.90 (m, 4H), 1.04-1.33 (m, 9 H), 1.39 (m, 9 H), 1.60-1.74 (m, 4H), 1.82-1.99 (m, 2H), 3.21-3.29 (m, 1H), 3.47 (d, J=14.69 Hz, 1H), 3.76-3.84 (m, 2H), 7.20-7.43 (m, 10H)

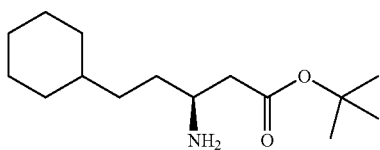 [SMILES: CC(C)(C)OC(=O)C[C@@H](N)CCC1CCCCC1]

(S)-Tert-butyl 3-amino-5-cyclohexylpentanoate

A mixture of (S)-tert-butyl 3-(benzyl((S)-1-phenylethyl)amino)-5-cyclohexylpentanoate (50 g, 0.111 mol) and 10% Pd/C (7.44 g) in 20% AcOH/EtOH (500 mL) was hydrogenated at 45 psi for 24 h. The mixture was filtered through Celite® pad and concentrated. The residue was dissolved in DCM (500 mL), basified with sat. sodium bicarbonate. The layers were separated and the aqueous layer was extracted with DCM (3×200 mL). The combined DCM extracts were dried with Na$_2$SO$_4$, filtered and solvent was removed in vacuo to obtain crude product (28.3 g, 100%) as clear oil. $^1$H NMR (300 MHz, CDCl$_3$) δ 0.85-0.95 (m, 3H), 1.11-1.27 (m, 6H), 1.46 (s, 9 H), 1.62-1.75 (m, 6H), 2.128-2.22 (m, 1H), 2.34-2.40 (m, 1H), 3.05-3.14 (m, 1H)

Scheme 19: Preparation of (S)-N-(1-(cyclobutylamino)-5-cyclohexyl-1-oxopentan-3-yl)-1-cyclopentyl-5-(2,6-dimethoxyphenyl)-1H-pyrazole-3-carboxamide

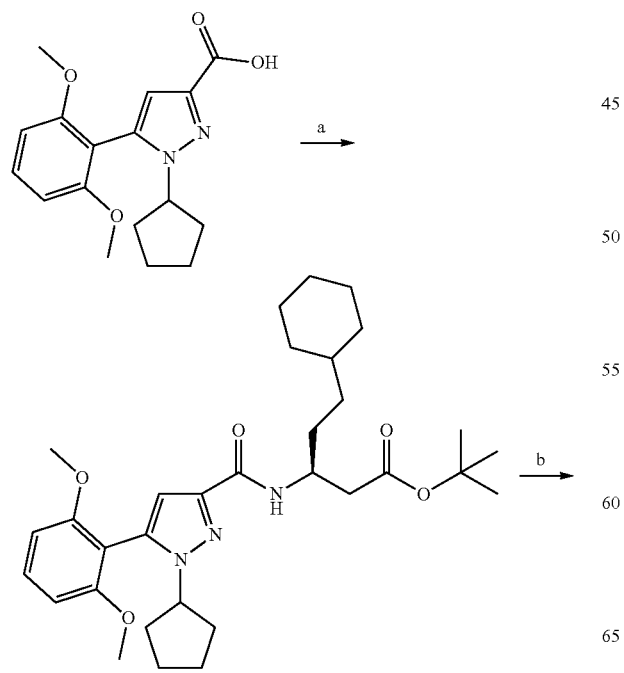

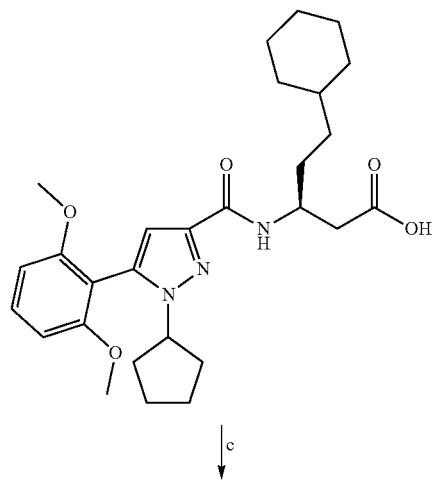

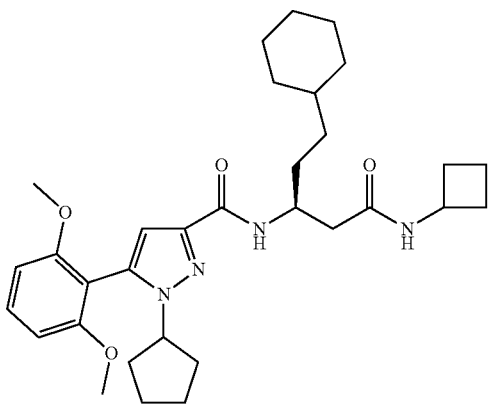

Reagents and conditions: a) tert-butyl (S)-3-amino-5-cyclohexylpentanoate, BOP, Et$_3$N, THF, rt, 1.5 h; b) TFA, DCM, rt, 1.5 h; c) cyclobutylamine, BOP, Et$_3$N, THF, rt, 3 h.

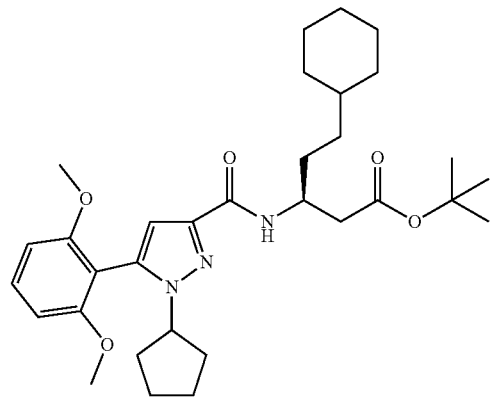 [SMILES: COc1cccc(OC)c1-c1cc(C(=O)N[C@@H](CCC2CCCCC2)CC(=O)OC(C)(C)C)nn1C1CCCC1]

(S)-Tert-butyl 5-cyclohexyl-3-(1-cyclopentyl-5-(2,6-dimethoxyphenyl)-1H-pyrazole-3-carboxamido)pentanoate 1-cyclopentyl-5-(2,6-dimethoxyphenyl)-1H-pyrazole-3-carboxylic acid (100 mg, 0.316 mmol) was dissolved in THF (5 mL). To the solution was added benzotriazol-1-yl-oxy-tris(dimethylamino)phosphonium hexafluorophosphate (BOP) (184 mg, 0.416 mmol) and triethylamine (0.130 mL, 0.948 mmol). The resulting mixture was stirred at room temperature for 15 minutes. tert-butyl (S)-3-amino-5-cyclohexylpentanoate (89 mg, 0.347 mmol) in 0.4 mL of THF was added dropwise, and stirred at room temperature for 3 h. THF was evaporated in vacuo, water was added to the residue and the aqueous layer was extracted with $CH_2Cl_2$ (3×15 mL). The combined organic layers were washed with water, brine and then dried with $Na_2SO_4$, followed by filtration. The solvent was evaporated in vacuo. The residue was purified by silica gel flash chromatography (EtOAc: Hex) to give the title compound as oil (152 mg, 87%). $^1$H NMR ($CDCl_3$, 300 MHz) δ 0.81-0.96 (m, 2H), 1.10-1.38 (m, 8 H), 1.48 (s, 9 H), 1.59-1.77 (m, 8 H), 1.81-1.96 (m, 4H), 2.00-2.16 (m, 2H), 2.55 (d, J=5.46 Hz, 2H), 3.73 (s, 3H), 3.74 (s, 3H), 4.21-4.30 (m, 1H), 4.30-4.43 (m, 1H), 6.62 (d, J=8.48 Hz, 2H), 6.67 (s, 1H), 7.25 (br. s., 1H), 7.37 (t, J=8.38 Hz, 1H). MS m/z: Calcd. for $C_{32}H_{47}N_3O_5$ 553.73 [M]$^+$, found 555.0 [M+H]$^+$,

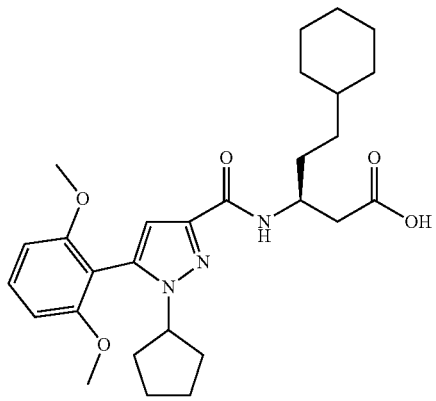 [SMILES: COc1cccc(OC)c1-c1cc(C(=O)N[C@@H](CCC2CCCCC2)CC(=O)O)nn1C1CCCC1]

(S)-5-cyclohexyl-3-(1-cyclopentyl-5-(2,6-dimethoxyphenyl)-1H-pyrazole-3-carboxamido)pentanoic acid To a solution of (S)-tert-butyl 5-cyclohexyl-3-(1-cyclopentyl-5-(2,6-dimethoxyphenyl)-1H-pyrazole-3-carboxamido)pentanoate (150 mg) in DCM (2 ml) was added HCl (4 M in dioxane, 0.7 ml). The mixture was stirred at rt for 15 h and concentrated to dryness to give the acid as the HCl salt (120 mg). $^1$H NMR ($CDCl_3$, 300 MHz) δ ppm 0.78-1.00 (m, 3H), 1.09-1.40 (m, 6H), 1.49-1.77 (m, 4H), 1.71 (t, J=7.44 Hz, 4H), 1.82-1.98 (m, 4H), 1.99-2.13 (m, 2H), 2.65-2.80 (m, 2H), 3.73 (s, 3H), 3.74 (s, 3H), 4.21-4.33 (m, 2H), 6.63 (d, J=8.48 Hz, 2H), 6.68 (s, 1H), 7.29 (s, 1H), 7.38 (t, J=8.38 Hz, 1H). MS (ESI) m/z: Calcd. for $C_{28}H_{39}N_3O_5$ 497.63 [M]$^+$, found 496.7[M−H]$^−$

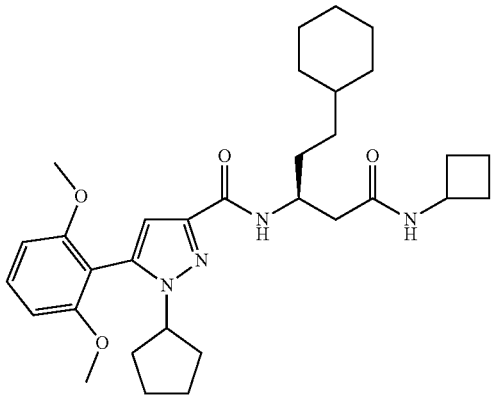 [SMILES: COc1cccc(OC)c1-c1cc(C(=O)N[C@@H](CCC2CCCCC2)CC(=O)NC2CCC2)nn1C1CCCC1]

(S)—N—(1-(cyclobutylamino)-5-cyclohexyl-1-oxopentan-3-yl)-1-cyclopentyl-5-(2,6-dimethoxyphenyl)-1H-pyrazole-3-carboxamide (S)-5-cyclohexyl-3-(1-cyclopentyl-5-(2,6-dimethoxyphenyl)-1H-pyrazole-3-carboxamido)pentanoic acid (97 mg, 0.195 mmol) was dissolved in THF (5 mL). To the solution was added benzotriazol-1-yl-oxy-tris(dimethylamino)phosphonium hexafluorophosphate (BOP) (95 mg, 0.214 mmol) and triethylamine (0.080 mL, 0.585 mmol). The resulting mixture was stirred at room temperature for 15 minutes. Cyclobutylamine (33 mg, 0.389 mmol) in 0.4 mL of THF was added dropwise, and stirred at room temperature for 3 h. THF was evaporated in vacuo, water was added to the residue and the aqueous layer was extracted with $CH_2Cl_2$ (3×15 mL). The combined organic layers were washed with water, brine and then dried with $Na_2SO_4$, followed by filtration. The solvent was evaporated in vacuo. The residue was purified by silica gel flash chromatography (EtOAc: Hex) to give the title compound as white solid (80 mg, 75%). $^1$H NMR ($CDCl_3$, 300 MHz) δ ppm 0.88 (d, J=11.30 Hz, 2H), 1.12-1.39 (m, 6H), 1.60-1.77 (m, 9 H), 1.80-1.97 (m, 6H), 2.00-2.13 (m, 2H), 2.18-2.32 (m, 2H), 2.24 (d, J=7.16 Hz, 2H), 2.53 (d, J=6.40 Hz, 2H), 3.74 (s, 3H), 3.73 (s, 3H), 4.15-4.46 (m, 3H), 6.63 (d, J=8.29 Hz, 2H), 6.67 (s, 1H), 6.75 (d, J=8.29 Hz, 1H), 7.06 (d, J=9.04 Hz, 1H), 7.38 (t, J=8.38 Hz, 1H). MS (ESI) m/z: Calcd. for $C_{32}H_{46}N_4O_4$ 550.73 [M]$^+$, found 551.6 [M+H]

Characterization of the Apelin Agonist Activity of the Compounds

The compounds above were studied for their in vitro activity as apelin agonists using the methods described by Giddings et al. Giddings et al., 2010 Int J High Thro Screen. 1:39-47, the contents of which are hereby incorporated by reference in its entirety. Using the methods described in Giddings et al. and Apelin-13 as a positive control.

TABLE 2

| ID# | IUPAC Name | $EC_{50}$ (nM) Ave |
|---|---|---|
| 253 | (3S)-N-cyclobutyl-3-{[1-cyclopentyl-5-(2,6-dimethoxyphenyl)-1H-pyrazol-3-yl]formamido}-5-(piperidin-1-yl)pentanamide | 382 nM |
| 296 | (3S)-N-cyclobutyl-3-{[5-(2,6-dimethoxyphenyl)-1-(2-methylpropyl)-1H-pyrazol-3-yl]formamido}-5-phenylpentanamide | 83 |
| 297 | (3S)-3-{[5-(2,6-dimethoxyphenyl)-1-(2-methylpropyl)-1H-pyrazol-3-yl]formamido}-4-phenylbutanoic acid | >10000 |

TABLE 2-continued

| ID# | IUPAC Name | EC$_{50}$ (nM) Ave |
|---|---|---|
| 298 | (3S)-5-cyclohexyl-3-{[5-(2,6-dimethoxyphenyl)-1-(4-fluorophenyl)-1H-pyrazol-3-yl]formamidolpentanoic acid | 589 |
| 299 | (3S)-3-{[5-(2,6-dimethoxyphenyl)-1-(4-fluorophenyl)-1H-pyrazol-3-yl]formamido}-5-phenylpentanoic acid | 2906 |
| 300 | (3R)-3-{[5-(2,6-dimethoxyphenyl)-1-(2-methylpropyl)-1H-pyrazol-3-yl]formamido}-3-phenylpropanoic acid | >10000 |
| 301 | (3S)-6-cyclohexyl-3-{[5-(2,6-dimethoxyphenyl)-1-(2-methylpropyl)-1H-pyrazol-3-yl]formamido}hexanoic acid | 2593 |
| 302 | (2S)-N-cyclobutyl-2-{[5-(2,6-dimethoxyphenyl)-1-(2-methylpropyl)-1H-pyrazol-3-yl]formamido}-3-phenylpropanamide | >10000 |
| 303 | tert-butyl (3S)-3-{[1-cyclopentyl-5-(2,6-dimethoxyphenyl)-1H-pyrazol-3-yl]formamido}-5-(morpholin-4-yl)pentanoate | >10000 |
| 304 | tert-butyl (3S)-3-{[1-cyclopentyl-5-(2,6-dimethoxyphenyl)-1H-pyrazol-3-yl]formamido}-5-(4-methylpiperazin-1-yl)pentanoate | >10000 |
| 305 | tert-butyl (3S)-3-{[1-cyclopentyl-5-(2,6-dimethoxyphenyl)-1H-pyrazol-3-yl]formamido}-5-(diethylamino)pentanoate | >10000 |
| 306 | tert-butyl (3S)-3-{[1-cyclopentyl-5-(2,6-dimethoxyphenyl)-1H-pyrazol-3-yl]formamido}-5-[(pyridin-4-ylmethyl)amino]pentanoate | >10000 |
| 307 | (3S)-3-{[1-cyclopentyl-5-(2,6-dimethoxyphenyl)-1H-pyrazol-3-yl]formamido}-5-(morpholin-4-yl)pentanoic acid | 6010 |
| 308 | (3S)-3-{[1-cyclopentyl-5-(2,6-dimethoxyphenyl)-1H-pyrazol-3-yl]formamido}-5-(4-methylpiperazin-1-yl)pentanoic acid | >10000 |
| 309 | (3S)-3-{[1-cyclopentyl-5-(2,6-dimethoxyphenyl)-1H-pyrazol-3-yl]formamido}-5-(diethylamino)pentanoic acid | >10000 |
| 310 | (3S)-3-{[1-cyclopentyl-5-(2,6-dimethoxyphenyl)-1H-pyrazol-3-yl]formamido}-5-[(pyridin-4-ylmethyl)amino]pentanoic acid | >10000 |
| 311 | (2S)-2-{[5-(2,6-dimethoxyphenyl)-1-(2-methylpropyl)-1H-pyrazol-3-yl]formamido}-4-phenylbutanoic acid | >10000 |
| 312 | (3S)-N-cyclobutyl-3-{[1-cyclopentyl-5-(2,6-dimethoxyphenyl)-1H-pyrazol-3-yl]formamido}-5-(morpholin-4-yl)pentanamide | 343 |
| 313 | (3S)-N-cyclobutyl-3-{[1-cyclopentyl-5-(2,6-dime thoxyphenyl)-1H-pyrazol-3-yl]formamido}-5-(4-methylpiperazin-1-yl)pentanamide | >10000 |
| 314 | (3S)-N-cyclobutyl-3-{[1-cyclopentyl-5-(2,6-dimethoxyphenyl)-1H-pyrazol-3-yl]formamido}-5-(diethylamino)pentanamide | 1845 |
| 315 | 1-cyclopentyl-5-(2,6-dimethoxyphenyl)-N-[(4S)-2-oxo-1-(pyridin-4-ylmethyl)piperidin-4-yl]-1H-pyrazole-3-carboxamide | >10000 |
| 316 | tert-butyl (3S)-3-{[1-cyclopentyl-5-(2,6-dimethoxyphenyl)-1H-pyrazol-3-yl]formamido}-5-(pyrrolidin-1-yl)pentanoate | >10000 |
| 317 | (3S)-3-{[1-cyclopentyl-5-(2,6-dimethoxyphenyl)-1H-pyrazol-3-yl]formamido}-5-(pyrrolidin-1-yl)pentanoic acid hydrochloride | 9350 |
| 318 | (3S)-N-cyclobutyl-3-{[1-cyclopentyl-5-(2,6-dimethoxyphenyl)-1H-pyrazol-3-yl]formamido}-5-(pyrrolidin-1-yl)pentanamide | 996 |
| 319 | tert-butyl (3S)-5-(azepan-1-yl)-3-{[1-cyclopentyl-5-(2,6-dimethoxyphenyl)-1H-pyrazol-3-yl]formamido}pentanoate | 3510 |
| 320 | tert-butyl (3S)-5-{7-azabicyclo[2.2.]heptan-7-yl}-3-{[1-cyclopentyl-5-(2,6-dimethoxyphenyl)-1H-pyrazol-3-yl]formamido}pentanoate | >10000 |
| 321 | (3S)-N-cyclobutyl-3-{[5-(2,6-dimethoxyphenyl)-1-(2-methylpropyl)-1H-pyrazol-3-yl]formamido}-4-phenylbutanamide | 114 |
| 322 | (3S)-5-(azepan-1-yl)-3-{[1-cyclopentyl-5-(2,6-dimethoxyphenyl)-1H-pyrazol-3-yl]formamido}pentanoic acid | 1441 |
| 323 | (3S)-5-{7-azabicyclo[2.2.1]heptan-7-yl}-3-{[1-cyclopentyl-5-(2,6-dimethoxyphenyl)-1H-pyrazol-3-yl]formamido}pentanoic acid | >10000 |
| 324 | (3S)-5-(azepan-1-yl)-N-cyclobutyl-3-{[1-cyclopentyl-5-(2,6-dimethoxyphenyl)-1H-pyrazol-3-yl]formamido}pentanamide | 107 |
| 325 | (3S)-5-{7-azabicyclo[2.2.1]heptan-7-yl}-N-cyclobutyl-3-{[1-cyclopentyl-5-(2,6-dimethoxyphenyl)-1H-pyrazol-3-yl]formamido}pentanamide | 3578 |
| 326 | (3S)-3-{[1-cyclopentyl-5-(2,6-dimethoxyphenyl)-1H-pyrazol-3-yl]formamido}-N-(1-methylcyclobutyl)-5-(piperidin-1-yl)pentanamide | 1041 |
| 327 | (3S)-3-{[1-cyclopentyl-5-(2,6-dimethoxyphenyl)-1H-pyrazol-3-yl]formamido}-N-(3-methyloxetan-3-yl)-5-(piperidin-1-yl)pentanamide | 675 |
| 328 | (3S)-3-{[1-cyclopentyl-5-(2,6-dimethoxyphenyl)-1H-pyrazol-3-yl]formamido}-N-(1-methylcyclopropyl)-5-(piperidin-1-yl)pentanamide | ia |
| 329 | (3S)-N-cyclobutyl-3-{[1-cyclopentyl-5-(2,6-dimethoxyphenyl)-1H-pyrazol-3-yl]formamido}-5-(2,6-dimethylpiperidin-1-yl)pentanamide | 170 |
| 330 | (3S)-3-{[1-cyclopentyl-5-(2,6-dimethoxyphenyl)-1H-pyrazol-3-yl]formamido}-5-(2,6-dimethylpiperidin-1-yl)pentanoic acid | 5165 |
| 331 | (3S)-N-cyclobutyl-3-{[1-cyclopentyl-5-(2,6-dimethoxyphenyl)-1H-pyrazol-3-yl]formamido}-N-methyl-5-(piperidin-1-yl)pentanamide | 353 |
| 332 | (3S)-3-{[1-cyclopentyl-5-(2,6-dimethoxyphenyl)-1H-pyrazol-3-yl]formamido}-N-(oxan-4-yl)-5-(piperidin-1-yl)pentanamide | 391 |
| 333 | (3S)-N-tert-butyl-3-{[1-cyclopentyl-5-(2,6-dimethoxyphenyl)-1H-pyrazol-3-yl]formamido}-5-(piperidin-1-yl)pentanamide | 2533 |
| 334 | (3S)-3-{[1-cyclopentyl-5-(2,6-dimethoxyphenyl)-1H-pyrazol-3-yl]formamido}-N-(2-methoxyethyl)-N-methyl-5-(piperidin-1-yl)pentanamide | 6574 |
| 335 | (3S)-N-cyclobutyl-3-{[1-cyclopentyl-5-(2,6-dimethoxyphenyl)-1H-pyrazol-3-yl]formamido}-5-(4,4-difluoropiperidin-1-yl)pentanamide | 63 |

TABLE 2-continued

| ID# | IUPAC Name | EC$_{50}$ (nM) Ave |
|---|---|---|
| 336 | (3S)-3-{[1-cyclopentyl-5-(2,6-dimethoxyphenyl)-1H-pyrazol-3-yl]formamido}-N-(2-methoxyethyl)-5-(piperidin-1-yl)pentanamide | 4738 |
| 337 | 1-cyclopentyl-5-(2,6-dimethoxyphenyl)-N-[(3S)-1-{2-oxa-6-azaspiro[3.3]heptan-6-yl}-1-oxo-5-(piperidin-1-yl)pentan-3-yl]-1H-pyrazole-3-carboxamide | >10000 |
| 338 | (3S)-3-{[1-cyclopentyl-5-(2,6-dimethoxyphenyl)-1H-pyrazol-3-yl]formamido}-5-(piperidin-1-yl)-N-(1,3-thiazol-2-yl)pentanamide | 12 |
| 339 | (3S)-3-{[1-cyclopentyl-5-(2,6-dimethoxyphenyl)-1H-pyrazol-3-yl]formamido}-N-(1,3-oxazol-2-yl)-5-(piperidin-1-yl)pentanamide | 31 |
| 340 | (3S)-3-{[1-cyclopentyl-5-(2,6-dimethoxyphenyl)-1H-pyrazol-3-yl]formamido}-N-(1,3-oxazol-2-ylmethyl)-5-(piperidin-1-yl)pentanamide | 543 |
| 341 | cyclobutyl (3S)-3-{[1-cyclopentyl-5-(2,6-dimethoxyphenyl)-1H-pyrazol-3-yl]formamido}-5-(piperidin-1-yl)pentanoate | 997 |
| 342 | (3S)-3-(1-{5-[2,6-bis(2,2,2-trifluoroethoxy)phenyl]-1-cyclopentyl-1H-pyrazol-3-yl}-N-ethylformamido)-N-cyclobutyl-5-(piperidin-1-yl)pentanamide | >10000 |
| 343 | 1-cyclopentyl-5-(2,6-dimethoxyphenyl)-N-[(2S)-1-(5-methyl-1,3,4-oxadiazol-2-yl)-4-(piperidin-1-yl)butan-2-yl]-1H-pyrazole-3-carboxamide | 1534 |
| 344 | (3S)-N-cyclobutyl-3-(1-{1-cyclopentyl-5-[2-(trifluoromethoxy)phenyl]-1H-pyrazol-3-yl}-N-ethylformamido)-5-(piperidin-1-yl)pentanamide | 2374 |
| 345 | (3S)-N-cyclobutyl-3-{1-[1-cyclopentyl-5-(2-fluoro-6-methoxyphenyl)-1H-pyrazol-3-yl]-N-ethylformamido}-5-(piperidin-1-yl)pentanamide | >10000 |
| 346 | (3S)-N-cyclobutyl-3-{1-[5-(2,6-dimethoxyphenyl)-1-(pentan-3-yl)-1H-pyrazol-3-yl]-N-ethylformamido}-5-(piperidin-1-yl)pentanamide | >10000 |
| 347 | (3S)-N-cyclobutyl-3-{1-[1-cyclopentyl-5-(thiophen-2-yl)-1H-pyrazol-3-yl1-N-ethylformamido}-5-(piperidin-1-yl)pentanamide | >10000 |
| 348 | (3S)-N-cyclobutyl-3-{[1-cyclopentyl-5-(2,6-dimethoxyphenyl)-1H-pyrazol-3-yl]formamido}-5-(3,3-difluoropiperidin-1-yl)pentanamide | 15 |
| 349 | (3S)-5-{2-azaspiro [3 .3 ]heptan-2-yl}-N-cyclobutyl-3-{[1-cyclopentyl-5-(2,6-dimethoxyphenyl)-1H-pyrazol-3-yl]formamido}pentanamide | 197 |
| 350 | (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-yl)pentanamide | 720 |
| 351 | (3S)-3-{[1-cyclopentyl-5-(2,6-dimethoxyphenyl)-1H-pyrazol-3-yl]formamido}-N-methyl-5-(piperidin-1-yl)-N-(1,3-thiazol-2-yl)pentanamide | 73 |
| 352 | (3S)-3-{[1-cyclopentyl-5-(2,6-dimethoxyphenyl)-1H-pyrazol-3-yl]formamido}-5-(piperidin-1-yl)pentanamide | >10000 |
| 353 | (3S)-3-({5-[,6-bis(2,2,2-trifluoroethoxy)phenyl1-1-cyclopentyl-1H-pyrazol-3-yl }formamido)-N-cyclobutyl-5-(piperidin-1-yl)pentanamide | >10000 |
| 354 | (3S)-N-cyclobutyl-3-{[1-cyclopentyl-5-(2,4,6-trifluorophenyl)-1H-pyrazol-3-yl]formamido}-5-(piperidin-1-yl)pentanamide | >10000 |
| 355 | (3S)-N-cyclobutyl-3-{[1-cyclopentyl-5-(4-ethoxy-2,6-difluorophenyl)-1H-pyrazol-3-yl]formamido}-5-(pipe ridin-1-yl)pentanamide | 5085 |
| 356 | (3S)-N-cyclobutyl-3-{[5-(2,6-dimethoxyphenyl)-1-(2-methylcyclohexyl)-1H-pyrazol-3-yl]formamido}-5-(piperidin-1-yl)pentanamide | >10000 |
| 357 | (3S)-N-cyclobutyl-3-{[5-(2,6-dimethoxyphenyl)-1-(pentan-3-yl)-1H-pyrazol-3-yl]formamido}-5-(piperidin-1-yl)pentanamide | >10000 |
| 358 | 1-cyclopentyl-5-(2,6-dimethoxyphenyl)-N-R3S)-1-hydroxy-5-(piperidin-1-yl)pentan-3-yl]-1H-pyrazole-3-carboxamide | >10000 |
| 359 | (3S)-N-cyclobutyl-3-({1-cyclopentyl-5-[2-(trifluoromethoxy)phenyl]-1H-pyrazol-3-yl}formamido)-5-(pipe ridin-1-yl)pentanamide | 271 |
| 360 | (3S)-N-cyclobutyl-3-({1-cyclopentyl-5-[2-(methylsulfanyl)phenyl]-1H-pyrazol-3-yl}formamido)-5-(pipe ridin-1-yl)pentanamide | 376 |
| 361 | (3S)-N-cyclobutyl-3-{[1-cyclopentyl-5-(2-methoxyphenyl)-1H-pyrazol-3-yl]formamido}-5-(piperidin-1-yl)pentanamide | 234 |
| 362 | (3S)-N-cyclobutyl-3-{[1-cyclopentyl-5-(thiophen-2-yl)-1H-pyrazol-3-yl]formamido}-5-(piperidin-1-yl)pentanamide | 5856 |
| 363 | (3S)-N-cyclobutyl-3-{[1-cyclopentyl-5-(2-ethylphenyl)-1H-pyrazol-3-yl]formamido}-5-(piperidin-1-yl)pentanamide | 44 |
| 364 | 1-cyclopentyl-5-(2,6-dimethoxyphenyl)-N-[(2S)-4-(piperidin-1-yl)-1-(1H-1,2,3,4-tetrazol-5-yl)butan-2-yl]-1H-pyrazole-3-carboxamide | 235 |
| 365 | (3S)-N-cyclobutyl-3-[(1-cyclopentyl-5-phenyl-1H-pyrazol-3-yl)formamido]-5-(piperidin-1-yl)pentanamide | >10000 |
| 366 | (3S)-N-cyclobutyl-3-({1-cyclopentyl-5[4-fluoro-2-(2,2,2-trifluoroethoxy)phenyl]-1H-pyrazol-3-yl}formamido)-5-(piperidin-1-yl)pentanamide | >10000 |
| 367 | (3S)-N-cyclobutyl-3-{[1-cyclopentyl-5-(2-methanesulfonylphenyl)-1H-pyrazol-3-yl]formamido}-5-(piperidin-1-yl)pentanamide | 2966 |
| 368 | (3S)-N-cyclobutyl-3-{[1-cyclopentyl-5-(pyrimidin-5-yl)-1H-pyrazol-3-yl]formamido}-5-(piperidin-1-yl)pentanamide | >10000 |
| 369 | (3S)-N-cyclobu tyl-3-{[1-cyclopentyl-5-(dimethyl-1,2-oxazol-4-yl)-1H-pyrazol-3-yl]formamido}-5-(piperidin-1-yl)pentanamide | >10000 |
| 370 | (3S)-3-{[5-(2-chloro-6-methoxyphenyl)-1-cyclopentyl-1H-pyrazol-3-yl]formamido}-N-cyclobutyl-5-(piperidin-1-yl)pentanamide | 1028 |
| 371 | (3S)-N-cyclobutyl-3-{[1-cyclopentyl-5-(2,6-dimethylphenyl)-1H-pyrazol-3-yl]formamido}-5-(piperidin-1-yl)pentanamide | 3841 |
| 372 | (3S)-N-cyclobutyl-3-{[1-cyclopentyl-5-(2-fluoro-6-methoxyphenyl)-1H-pyrazol-3-yl]formamido}-5-(piperidin-1-yl)pentanamide | 90 |
| 373 | (3S)-3-{[1-cyclopentyl-5-(2,6-dimethoxyphenyl)-1H-pyrazol-3-yl]formamido}-5-(piperidin-1-yl)-N-[2-(1H-1,2,3,4-tetrazol-5-yl)ethyl]pentanamide | >10000 |

TABLE 2-continued

| ID# | IUPAC Name | EC$_{50}$ (nM) Ave |
|---|---|---|
| 374 | 2-(3-{[(2S)-1-(cyclobutylcarbamoyl)-4-(piperidin-1-yl)butan-2-yl]carbamoyl}-1-cyclopentyl-1H-pyrazol-5-yl)pyridin-1-ium-1-olate | >10000 |
| 375 | (3S)-N-cyclobutyl-3-{[1-cyclopentyl-5-(pyridin-2-yl)-1H-pyrazol-3-yl]formamido}-5-(piperidin-1-yl)pentanamide | >10000 |
| 376 | (2S)-N-cyclobutyl-2-{[1-cyclopentyl-5-(2,6-dimethoxyphenyl)-1H-pyrazol-3-yl]formamido}-3-cyclopropylpropanamide | >10000 |
| 377 | (2S)-N,3-dicyclobutyl-2-{[1-cyclopentyl-5-(2,6-dimethoxyphenyl)-1H-pyrazol-3-yl]formamido}propanamide | >10000 |
| 378 | (3S)-N-cyclobutyl-3-{[1-cyclopentyl-5-(1,3-thiazol-4-yl)-1H-pyrazol-3-yl]formamido}-5-(piperidin-1-yl)pentanamide | 9386 |
| 379 | (3S)-3-{[1-cyclopentyl-5-(2,6-dimethoxyphenyl)-1H-pyrazol-3-yl]formamido}-5-(piperidin-1-yl)-N-(1H-1,2,3,4-tetrazol-5-ylmethyl)pentanamide | 1407 |
| 380 | (3S)-3-{[1-cyclopentyl-5-(2,6-dimethoxyphenyl)-1H-pyrazol-3-yl]formamido}-5-phenyl-N-(1,3-thiazol-2-yl)pentanamide | 94 |
| 381 | (3S)-3-{[1-cyclopentyl-5-(2,6-dimethoxyphenyl)-1H-pyrazol-3-yl]formamido}-5-phenyl-N-(1H-1,2,3,4-tetrazol-5-yl)pentanamide | 647 |
| 382 | (3S)-3-{[1-cyclopentyl-5-(2,6-dimethoxyphenyl)-1H-pyrazol-3-yl]formamido}-5-phenyl-N-(1,3-thiazol-2-ylmethyl)pentanamide | 3441 |
| 383 | (3S)-3-{[1-cyclopentyl-5-(2,6-dimethoxyphenyl)-1H-pyrazol-3-yl]formamido}-5-phenyl-N-(1H-1,2,3,4-tetrazol-5-ylmethyl)pentanamide | 5177 |
| 384 | (3S)-3-{[1-cyclopentyl-5-(2,6-dimethoxyphenyl)-1H-pyrazol-3-yl]formamido}-5-(3,3-difluoropiperidin-1-yl)-N-(1,3-thiazol-2-yl)pentanamide | 15 |
| 385 | (2S)-2-{[1-cyclopentyl-5-(2,6-dimethoxyphenyl)-1H-pyrazol-3-yl]formamido}-3-cyclopropylpropanoic acid | >10000 |
| 386 | (2S)-3-cyclobutyl-2-{[1-cyclopentyl-5-(2,6-dimethoxyphenyl)-1H-pyrazol-3-yl]formamido}propanoic acid | 6170 |
| 387 | (2S)-2-{[1-cyclopentyl-5-(2,6-dimethoxyphenyl)-1H-pyrazol-3-yl]formamido}-4-phenyl-N-(1H-1,2,3,4-tetrazol-5-ylmethyl)butanamide | 8716 |
| 388 | (2S)-2-{[1-cyclopentyl-5-(2,6-dimethoxyphenyl)-1H-pyrazol-3-yl]formamido}-4-phenyl-N-(1,3- thiazol-2-ylmethyl)butanamide | 399 |
| 389 | (2S)-2-{[1-cyclopentyl-5-(2,6-dimethoxyphenyl)-1H-pyrazol-3-yl]formamido}-4-phenylbutanoic acid | >10000 |
| 390 | 1-cyclopentyl-5-(2,6-dimethoxyphenyl)-N-[(2S)-4-phenyl-1-(1H-1,2,3,4-tetrazol-5-yl)butan-2-yl]-1H-pyrazole-3-carboxamide | 429 |
| 391 | N-[(2S)-1-cyano-4-phenylbutan-2-yl]-1-cyclopentyl-5-(2,6-dimethoxyphenyl)-1H-pyrazole-3-carboxamide | 6344 |
| 392 | (3S)-3-{[1-cyclopentyl-5-(2,6-dimethoxyphenyl)-1H-pyrazol-3-yl]formamido}-5-phenylpentanamide | >10000 |
| 393 | (2S)-3-cyclopentyl-2-{[1-cyclopentyl-5-(2,6-dimethoxyphenyl)-1H-pyrazol-3-yl]formamido}propanoic acid | 424 |
| 395 | (2S)-2-{[1-cyclopentyl-5-(2,6-dimethoxyphenyl)-1H-pyrazol-3-yl]formamido}-4-phenyl-N-(1H-1,2,3,4-tetrazol-5-yl)butanamide | >10000 |
| 396 | (2S)-2-{[1-cyclopentyl-5-(2,6-dimethoxyphenyl)-1H-pyrazol-3-yl]formamido}-4-phenyl-N-(1,3-thiazol-2-yl)butanamide | >10000 |
| 397 | (3S)-N-cyclobutyl-3-({1-cyclopentyl-5-[2-(propan-2-yl)phenyl]-1H-pyrazol-3-yl}formamido)-5-(piperidin-1-yl)pentanamide | 140 |
| 398 | N-[(3R)-1-(cyclobutylamino)-5-(piperidin-1-yl)pentan-3-yl]-1-cyclopentyl-5-(2,6-dimethoxyphenyl)-1H-pyrazole-3-carboxamide | >10000 |
| 399 | (3S)-N-cyclobutyl-3-{[1-cyclopentyl-5-(2-ethyl-4-fluorophenyl)-1H-pyrazol-3-yl]formamido}-5-(piperidin-1-yl)pentanamide | 264 |
| 400 | (3S)-N-cyclobutyl-3-({1-cyclopentyl-5-[2-(1,1-difluoroethyl)phenyl]-1H-pyrazol-3-yl]formamido)-5-(pipe ridin-1-yl)pentanamide | 46 |
| 401 | (3S)-3-{[1-cyclopentyl-5-(2,6-dimethoxyphenyl)-1H-pyrazol-3-yl]formamido}-4-phenylbutanoic acid | >10000 |
| 402 | (3S)-3-{[1-cyclopentyl-5-(2,6-dimethoxyphenyl)-1H-pyrazol-3-yl]formamido}-4-phenyl-N-(1,3-thiazol-2-yl)butanamide | 203 |
| 403 | (3S)-3-{[1-cyclopentyl-5-(2-ethylphenyl)-1H-pyrazol-3-yl]formamido}-5-(piperidin-1-yl)pentanoic acid hydrochloride | 42 |
| 404 | (3S)-3-{[1-cyclopentyl-5-(2-ethylphenyl)-1H-pyrazol-3-yl]formamido}-5-(3,3-difluoropiperidin-1-yl)pentanoic acid | 65 |
| 405 | (3S)-3-{[1-cyclopentyl-5-(2-ethylphenyl)-1H-pyrazol-3-yl]formamido}-5-(4,4-difluoropiperidin-1-yl)pentanoic acid | 227 |
| 406 | (3S)-3-{[1-cyclopentyl-5-(2-ethylphenyl)-1H-pyrazol-3-yl]formamido}-5-(piperidin-1-yl)-N-(1,3-thiazol-2-yl)pentanamide | 22 |
| 407 | (3S)-3-{[5-(2-chlorophenyl)-1-cyclopentyl-1H-pyrazol-3-yl]formamido}-N-cyclobutyl-5-(piperidin-1-yl)pentanamide | 162 |
| 408 | (3S)-N-cyclobutyl-3-({1-cyclopentyl-5-[2-(trifluoromethyl)phenyl]-1H-pyrazol-3-yl]formamido)-5-(piperidin-1-yl)pentanamide | 64 |
| 409 | (3S)-3-{[1-cyclopentyl-5-(2-ethylphenyl)-1H-pyrazol-3-yl]formamido}-5-(4,4-difluoropiperidin-1-yl)-N-(1,3-thiazol-2-yl)pentanamide | 12.5 |
| 410 | (3S)-3-{[1-cyclopentyl-5-(2-ethylphenyl)-1H-pyrazol-3-yl]formamido}-5-(3,3-difluoropiperidin-1-yl)-N-(1,3-thiazol-2-yl)pentanamide | 7 |
| 411 | (3S)-N-cyclobutyl-3-{[1-cyclopentyl-5-(2-ethylphenyl)-1H-pyrazol-3-yl]formamido}-5-(4,4-difluoropiperidin-1-yl)pentanamide | 14.5 |
| 412 | (3S)-N-cyclobutyl-3-{[1-cyclopentyl-5-(2-ethylphenyl)-1H-pyrazol-3-yl]formamido}-5-(3,3-difluoropiperidin-1-yl)pentanamide | 5 |

TABLE 2-continued

| ID# | IUPAC Name | EC$_{50}$ (nM) Ave |
|---|---|---|
| 413 | (3S)-N-cyclobutyl-3-{[1-cyclopentyl-5-(2-cyclopropylphenyl)-1H-pyrazol-3-yl]formamido}-5-(piperidin-1-yl)pentanamide | 49 |
| 414 | 1-cyclopentyl-5-(2,6-dimethoxyphenyl)-N-R2S)-4-(piperidin-1-yl)-1-(4H-1,2,4-triazol-3-yl)butan-2-yl1-1H-pyrazole-3-carboxamide | 200 |
| 415 | (3R,4E)-N-cyclobutyl-3-{[1-cyclopentyl-5-(2,6-dimethoxyphenyl)-1H-pyrazol-3-yl]formamido}-5-(4-fluorophenyl)pent-4-enamide | 292 |
| 416 | (3S)-N-cyclobutyl-3-{[1-cyclopentyl-5-(2,6-dimethoxyphenyl)-1H-pyrazol-3-yl]formamido}-5-(4-fluorophenyl)pentanamide | 606 |
| 417 | (3S)-3-{[1-cyclopentyl-5-(2,6-dimethoxyphenyl)-1H-pyrazol-3-yl]formamido}-5-(4-fluorophenyl)-N-(1,3-thiazol-2-yl)pentanamide | 36 |
| 418 | (3R,4E)-N-cyclobutyl-3-{[1-cyclopentyl-5-(2,6-dimethoxyphenyl)-1H-pyrazol-3-yl]formamido}-5-(pyridin-3-yl)pent-4-enamide | 664 |
| 419 | (3R,4E)-N-cyclobutyl-3-{[1-cyclopentyl-5-(2,6-dimethoxyphenyl)-1H-pyrazol-3-yl]formamido}-5-(pyridin-4-yl)pent-4-enamide | >10000 |
| 420 | (3S)-N-cyclobutyl-3-{[1-cyclopentyl-5-(2,6-dimethoxyphenyl)-1H-pyrazol-3-yl]formamido}-5-(pyridin-3-yl)pentanamide | 883 |
| 421 | (3S)-N-cyclobutyl-3-{[1-cyclopentyl-5-(2,6-dimethoxyphenyl)-1H-pyrazol-3-yl]formamido}-5-(1-methylpiperidin-4-yl)pentanamide | 3312 |
| 422 | 1-cyclopentyl-5-(2,6-dimethoxyphenyl)-N-[(2S)-1-(1,3,4-oxadiazol-2-yl)-4-(piperidin-1-yl)butan-2-yl]-1H-pyrazole-3-carboxamide | 1422 |
| 423 | (3S)-3-({1-cyclopentyl-5-[2-(trifluoromethyl)phenyl]-1H-pyrazol-3-yl}formamido)-5-(3,3-difluoropiperidin-1-yl)pentanoic acid | 35 |
| 424 | (3S)-3-({1-cyclopentyl-5-[2-(trifluoromethyl)phenyl]-1H-pyrazol-3-yl}formamido)-5-(4,4-difluoropiperidin-1-yl)pentanoic acid | 110 |
| 425 | (3S)-N-cyclobutyl-3-({1-cyclopentyl-5-[2-(trifluoromethyl)phenyl]-1H-pyrazol-3-yl}formamido)-5-(3,3-difluoropiperidin-1-yl)pentanamide | 10.9 |
| 426 | (3S)-3-({1-cyclopentyl-5-[2-(trifluoromethyl)phenyl]-1H-pyrazol-3-yl}formamido)-5-(3,3-difluoropiperidin-1-yl)-N-(1,3-thiazol-2-yl)pentanamide | 10.6 |
| 427 | (3S)-3-({1-cyclopentyl-5-[2-(trifluoromethyl)phenyl]-1H-pyrazol-3-yl}formamido)-5-(3,3-difluoropiperidin-1-yl)-N-(1,3-oxazol-2-yl)pentanamide | 8.5 |
| 428 | (3S)-3-({1-cyclopentyl-5-[2-(1,1-difluoroethyl)phenyl]-1H-pyrazol-3-yl}formamido)-5-(3,3-difluoropiperidin-1-yl)-N-(1,3-thiazol-2-yl)pentanamide | 7.5 |
| 429 | (3S)-3-{[5-(2-chlorophenyl)-1-cyclopentyl-1H-pyrazol-3-yl]formamido}-5-(3,3-difluoropiperidin-1-yl)-N-(1,3-thiazol-2-yl)pentanamide | 6.1 |
| 430 | (3S)-3-({1-cyclopentyl-5-[2-(trifluoromethyl)phenyl]-1H-pyrazol-3-yl}formamido)-5-(4,4-difluoropiperidin-1-yl)-N-(1,3-thiazol-2-yl)pentanamide | 17.5 |
| 431 | (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-thiazol-2-yl)pentanamide | 22.5 |
| 432 | (3S)-3-({1-cyclopentyl-5-[2-(1,1-difluoroethyl)phenyl]-1H-pyrazol-3-yl}formamido)-5-(3,3-difluoropiperidin-1-yl)pentanoic acid | 16 |
| 433 | (3S)-3-{[5-(2-chlorophenyl)-1-cyclopentyl-1H-pyrazol-3-yl]formamido}-5-(3,3-difluoropiperidin-1-yl)pentanoic acid | 151 |
| 434 | (3S)-N-cyclobutyl-3-({1-cyclopentyl-5-[2-(trifluoromethypthiophen-3-yl]-1H-pyrazol-3-yl]formamido)-5-(piperidin-1-yl)pentanamide | 641 |
| 435 | (3R,4E)-N-cyclobutyl-3-{[1-cyclopentyl-5-(2,6-dimethoxyphenyl)-1H-pyrazol-3-yl]formamido}-5-(pyridin-2-yl)pent-4-enamide | 9211 |
| 436 | (3S)-3-({1-cyclopentyl-5-[2-(trifluoromethyl)phenyl]-1H-pyrazol-3-yl}formamido)-5-(4,4-difluoropiperidin-1-yl)-N-(5-methyl-1,3-thiazol-2-yl)pentanamide | 58 |
| 437 | 1-cyclopentyl-N-[(2S)-4-(3,3-difluoropiperidin-1-yl)-1-(4H-1,2,4-triazol-3-yl)butan-2-yl]-5-[2-(trifluoromethyl)phenyl]-1H-pyrazole-3-carboxamide | 21 |
| 438 | (3S)-N-cyclobutyl-3-{[1-cyclopentyl-5-(2-ethynylphenyl)-1H-pyrazol-3-yl]formamido}-5-(piperidin-1-yl)pentanamide | 290 |
| 439 | (3S)-N-benzyl-3-({1-cyclopentyl-5-[2-(trifluoromethyl)phenyl]-1H-pyrazol-3-yl}formamido)-5-(4,4-difluoropiperidin-1-yl)pentanamide | 920 |
| 440 | (3S)-N-(cyclohexylmethyl)-3-({1-cyclopentyl-5-[2-(trifluoromethyl)phenyl]-1H-pyrazol-3-yl]formamido)-5-(4,4-difluoropiperidin-1-yl)pentanamide | 301 |
| 441 | (3S)-N-benzyl-3-({1-cyclopentyl-5-[2-(trifluoromethyl)phenyl]-1H-pyrazol-3-yl}formamido)-5-methylhexanamide | >10,000 |
| 442 | N-benzyl-3-({1-cyclopentyl-5-[2-(trifluoromethyl)phenyl]-1H-pyrazol-3-yl}formamido)propanamide | >10,000 |
| 443 | (3S)-3-{[1-cyclopentyl-5-(2,6-dimethoxyphenyl)-1H-pyrazol-3-yl]formamidol-N-(3,3-difluorocyclobutyl)-5-(piperidin-1-yl)pentanamide | 73 |
| 445 | 1-cyclopentyl-5-(2,6-dimethoxyphenyl)-N-[(2S)-1-(1-methyl-1H-1,2,3,4-tetrazol-5-yl)-4-(piperidin-1-yl)butan-2-yl]-1H-pyrazole-3-carboxamide | 2835 |
| 447 | (3S)-3-{[5-(2-chlorophenyl)-1-cyclopentyl-1H-pyrazol-3-yl]formamido}-5-(3,3-difluoropiperidin-1-yl)-N-methyl-N-(1,3-thiazol-2-yl)pentanamide | 84 |
| 448 | 1-cyclopentyl-5-(2,6-dimethoxyphenyl)-N-[(2S)-4-(piperidin-1-yl)-1-(1,3-thiazol-2-yl)butan-2-yl]-1H-pyrazole-3-carboxamide | 1338 |
| 449 | 3-({1-cyclopentyl-5-[2-(trifluoromethyl)phenyl]-1H-pyrazol-3-yl}formamido)-N-(1,3-thiazol-2-yl)propanamide | 12670 |
| 450 | 5-(2-chlorophenyl)-1-cyclopentyl-N-[(2S)-4-(3,3-difluoropiperidin-1-yl)-1-(4H-1,2,4-triazol-3-yl)butan-2-yl]-1H-pyrazole-3-carboxamide | 30 |

TABLE 2-continued

| ID# | IUPAC Name | EC$_{50}$ (nM) Ave |
|---|---|---|
| 451 | (3S)-3-({1-cyclopentyl-5-[2-(trifluoromethyl)phenyl]-1H-pyrazol-3-yl}formamido)-5-(3,3-difluoropiperidin-1-yl)-N-methyl-N-(1,3-oxazol-2-yl)pentanamide | 27 |
| 452 | (3S)-3-{[5-(2-chlorophenyl)-1-cyclopentyl-1H-pyrazol-3-yl]formamido}-5-(3,3-difluoropiperidin-1-yl)-N-methyl-N-(1,3-oxazol-2-yl)pentanamide | 70 |
| 457 | (3S)-3-{[5-(3-chloropyridin-4-yl)-1-cyclopentyl-1H-pyrazol-3-yl]formamido}-N-cyclobutyl-5-(3,3-difluoropiperidin-1-yl)pentanamide | 1324 |
| 458 | 5-(2-chlorophenyl)-1-cyclopentyl-N-[(2S)-4-(3,3-difluoropiperidin-1-yl)-1-(5-methyl-4H-1,2,4-triazol-3-yl)butan-2-yl]-1H-pyrazole-3-carboxamide | 261 |
| 459 | 5-(2-chlorophenyl)-1-cyclopentyl-N-[(2S)-4-(3,3-difluoropiperidin-1-yl)-145-(trifluoromethyl)-4H-1,2,4-triazol-3-yl]butan-2-yl]-1H-pyrazole-3-carboxamide | 243 |
| 460 | (3S)-N-cyclobutyl-3-( f 1-cyclopentyl-544-(trifluoromethyppyridin-3-yl1-1H-pyrazol-3-yl}formamido)-5-(3,3-difluoropiperidin-1-yl)pentanamide | 23 |
| 463 | (3S)-3-( f 1-cyclopentyl-5-[2-(trifluoromethyl)phenyl]-1H-pyrazol-3-yl}formamido)-5-(4-fluorophenyl)pentanoic acid | 1236 |
| 464 | 1-cyclopentyl-N- [(2S)-4-(4-fluorophenyl)-1-(hydrazinecarbonyl)butan-2-yl]-5-[2-(trifluoromethyl)phenyl1-1H-pyrazole-3-carboxamide | 1036 |
| 465 | 5-(2-chlorophenyl)-1-cyclopentyl-N-[(2S)-4-(3,3-difluoropiperidin-1-yl)-1-(hydrazinecarbonyl)butan-2-yl]-1H-pyrazole-3-carboxamide | 191 |
| 466 | (3S)-3-{[5-(4-chloropyridin-3-yl)-1-cyclopentyl-1H-pyrazol-3-yl]formamido}-N-cyclobutyl-5-(3,3-difluoropiperidin-1-yl)pentanamide | 1217 |
| 467 | (3S)-3-{[5-(4-chloropyridin-3-yl)-1-cyclopentyl-1H-pyrazol-3-yl]formamido}-5-(3,3-difluoropiperidin-1-yl)pentanoic acid | >10,000 |
| 468 | (3S)-3-{[5-(2-chloropyridin-3-yl)-1-cyclopentyl-1H-pyrazol-3-yl]formamido1-5-(3,3-difluoropiperidin-1-yl)pentanoic acid | 1674 |
| 469 | (3S)-3-{[5-(2-chloropyridin-3-yl)-1-cyclopentyl-1H-pyrazol-3-yl]formamido}-N-cyclobutyl-5-(3,3-difluoropiperidin-1-yl)pentanamide | 133 |
| 470 | 1-cyclopentyl-N-[(2S)-4-(4-fluorophenyl)-1-(4H-1,2,4-triazol-3-yl)butan-2-yl]-5-[2-(trifluoromethyl)phenyl]-1H-pyrazole-3-carboxamide | 435 |
| 471 | 1-cyclopentyl-N-[(2S)-4-(4-fluorophenyl)-1-(5-methyl-4H-1,2,4-triazol-3-yl)butan-2-yl]-5-[2-(trifluoromethyl)phenyl]-1H-pyrazole-3-carboxamide | 1144 |
| 475 | 1-cyclopentyl-N-[(2S)-4-(4-fluorophenyl)-1-[5-(trifluoromethyl)-1,3,4-oxadiazol-2-yl]butan-2-yl]-5-[2-(trifluoromethyl)phenyl]-1H-pyrazole-3-carboxamide | 146 |
| 479 | (3S)-N-cyclobutyl-3-({1-cyclopentyl-5-[3-(trifluoromethyl)pyridin-2-yl]-1H-pyrazol-3-yl}formamido)-5-(3,3-difluoropiperidin-1-yl)pentanamide | 0.86 |
| 480 | (3S)-N-cyclobutyl-3-({1-cyclopentyl-5-[2-(trifluoromethyl)phenyl]-1H-pyrazol-3-yl}formamido)-5-(3,3-difluoropyrrolidin-1-yl)pentanamide | 2.76 |
| 481 | (3S)-5-(3-cyanopyrrolidin-1-yl)-N-cyclobutyl-3-({1-cyclopentyl-5-[2-(trifluoromethyl)phenyl]-1H-pyrazol-3-yl}formamido)pentanamide | 1.96 |
| 482 | (3S)-3-({1-cyclopentyl-5-[2-(trifluoromethyl)phenyl]-1H-pyrazol-3-yl}formamido)-5-(4-fluorophenyl)-N-(1-methylazetidin-3-yl)pentanamide | 474 |
| 483 | (3S)-N-cyclobutyl-5- [cyclohexyl(methyl)amino]-3-({1-cyclopentyl-5-[2-(trifluoromethyl)phenyl1-1H-pyrazol-3-yl}formamido)pentanamide | 14 |
| 484 | (3S)-5-cyclohexyl-3-({1-cyclopentyl-5-[2-(trifluoromethyl)phenyl]-1H-pyrazol-3-yl }formamido)pentanoic acid | 1518 |
| 485 | (3S)-3-({1-cyclopentyl-5-[2-(trifluoromethyl)phenyl]-1H-pyrazol-3-yl}formamido)-5-(3,3-difluoropyrrolidin-1-yl)pentanoic acid | 110 |
| 486 | (3S)-3-({1-cyclopentyl-5-[2-(trifluoromethyl)phenyl]-1H-pyrazol-3-yl}formamido)-5-(morpholin-4-yl)pentanoic acid | 931 |
| 487 | (3S)-3-({1-cyclopentyl-5-[2-(trifluoromethyl)phenyl]-1H-pyrazol-3-yl}formamido)-5-[(2S)-2-(trifluoromethyl)piperidin-1-yl]pentanoic acid | 277 |
| 488 | (3S)-3-({1-cyclopentyl-5-[2-(trifluoromethyl)phenyl]-1H-pyrazol-3-yl }formamido)-5-[(2R)-2-(trifluoromethyl)piperidin-1-yl]pentanoic acid | 1342 |
| 489 | (3S)-3-({1-cyclopentyl-5-[2-(trifluoromethyl)phenyl]-1H-pyrazol-3-yl}formamido)-N-methyl-N-(1,3-thiazol-2-yl)-5-[(2R)-2-(trifluoromethyl)piperidin-1-yl]pentanamide | 161 |
| 490 | (3S)-N-cyclobutyl-5-[cyclopentyl(methyl)amino]-3-({1-cyclopentyl-5-[2-(trifluoromethyl)phenyl]-1H-pyrazol-3-yl}formamido)pentanamide | 10.3 |
| 491 | (3S)-N-cyclobutyl-3-({1-cyclopentyl-5-[2-(trifluoromethyl)phenyl]-1H-pyrazol-3-yl}formamido)-5-(morpholin-4-yl)pentanamide | 68 |
| 492 | (3S)-N-cyclobutyl-3-({1-cyclopentyl-5-[2-(trifluoromethyl)phenyl]-1H-pyrazol-3-yl}formamido)-5-(dipropylamino)pentanamide | 36 |
| 493 | (3S)-N-cyclobutyl-3-({1-cyclopentyl-5-[2-(trifluoromethyl)phenyl]-1H-pyrazol-3-yl}formamido)-5-[methyl(2-methylpropyl)amino]pentanamide | 24 |
| 494 | (3S)-3-({1-cyclopentyl-5-[2-(trifluoromethyl)phenyl]-1H-pyrazol-3-yl}formamido)-5-(piperidin-1-yl)pentanoic acid | 215 |
| 495 | (3S)-3-({1-cyclopentyl-5-[2-(trifluoromethyl)phenyl]-1H-pyrazol-3-yl}formamido)-N-methyl-5-(morpholin-4-yl)-N-(1,3-thiazol-2-yl)pentanamide | 165 |
| 496 | (3S)-N-cyclobutyl-3-({1-cyclopentyl-5-[2-(trifluoromethyl)phenyl]-1H-pyrazol-3-yl}formamido)-5-[(2S)-2-(trifluoromethyl)piperidin-1-yl]pentanamide | 30 |
| 497 | (3S)-N-cyclobutyl-3-({1-cyclopentyl-5-[2-(trifluoromethyl)phenyl]-1H-pyrazol-3-yl}formamido)-5-(4-fluorophenyl)pentanamide | 103 |
| 498 | (3S)-5-{8-azabicyclo[3.2.1]octan-8-yl}-N-cyclobutyl-3-({1-cyclopentyl-5-[2-(trifluoromethyl)phenyl]-1H-pyrazol-3-yl}formamido)pentanamide | 105 |
| 499 | (3S)-3-({1-cyclopentyl-5-[2-(trifluoromethyl)phenyl]-1H-pyrazol-3-yl}formamido)-5-(pyrrolidin-1-yl)pentanoic acid | 548 |

TABLE 2-continued

| ID# | IUPAC Name | EC$_{50}$ (nM) Ave |
|---|---|---|
| 500 | (3S)-3-({1-cyclopentyl-5-[2-(trifluoromethyl)phenyl]-1H-pyrazol-3-yl}formamido)-N-methyl-5-(4-methyl-1H-pyrazol-1-yl)-N-(1,3-thiazol-2-yl)pentanamide | 79 |
| 501 | (3S)-N-cyclobutyl-3-({1-cyclopentyl-5-[2-(trifluoromethyl)phenyl]-1H-pyrazol-3-yl}formamido)-5-(4-methyl-1H-pyrazol-1-yl)pentanamide | 26 |
| 502 | (3S)-3-({1-cyclopentyl-5-[2-(trifluoromethyl)phenyl]-1H-pyrazol-3-yl}formamido)-5-(3,5-dimethyl-1H-pyrazol-1-yl)-N-methyl-N-(1,3-thiazol-2-yl)pentanamide | 77 |
| 503 | (3S)-N-cyclobutyl-3-({1-cyclopentyl-5-[2-(trifluoromethyl)phenyl]-1H-pyrazol-3-yl}formamido)-5-(3,5-dimethyl-1H-pyrazol-1-yl)pentanamide | 157 |
| 504 | (3S)-N-cyclobutyl-3-({1-cyclopentyl-5-[2-(trifluoromethyl)phenyl]-1H-pyrazol-3-yl}formamido)-5-(pyrrolidin-1-yl)pentanamide | 59 |
| 505 | (3S)-5-(azepan-1-yl)-N-cyclobutyl-3-({1-cyclopentyl-5-[2-(trifluoromethyl)phenyl]-1H-pyrazol-3-yl}formamido)pentanamide | 34 |
| 506 | (3S)-N-cyclobutyl-5-[cyclobutyl(methyl)amino]-3-({1-cyclopentyl-5-[2-(trifluoromethyl)phenyl]-1H-pyrazol-3-yl}formamido)pentanamide | 32 |
| 507 | (3S)-N-cyclobutyl-3-({1-cyclopentyl-5-[2-(trifluoromethyl)phenyl]-1H-pyrazol-3-yl}formamido)-5-{2-oxa-6-azaspiro[3.3]heptan-6-yl}pentanamide | 162 |
| 508 | (3S)-3-({1-cyclopentyl-5-[2-(trifluoromethyl)phenyl]-1H-pyrazol-3-yl}formamido)-5-oxo-5-(piperidin-1-yl)pentanoic acid | 475 |
| 509 | (3S)-3-({1-cyclopentyl-5-[2-(trifluoromethyl)phenyl]-1H-pyrazol-3-yl}formamido)-5-(3,3-difluoropiperidin-1-yl)-5-oxopentanoic acid | 1065 |
| 510 | (3S)-3-({1-cyclopentyl-5-[2-(trifluoromethyl)phenyl]-1H-pyrazol-3-yl}formamido)-5-(4-fluorophenyl)-N-(pyrrolidin-1-yl)pentanamide | 2192 |
| 511 | (3S)-N-cyclobutyl-3-({1-cyclopentyl-5-[2-(trifluoromethyl)phenyl]-1H-pyrazol-3-yl}formamido)-5-[methyl(1-methylcyclopentyl)amino]pentanamide | 35 |
| 514 | (3R)-N-cyclobutyl-3-({1-cyclopentyl-5-[2-(trifluoromethyl)phenyl]-1H-pyrazol-3-yl}formamido)-5-oxo-5-(piperidin-1-yl)pentanamide | 79 |
| 515 | (3R)-N-cyclobutyl-3-({1-cyclopentyl-5-[2-(trifluoromethyl)phenyl]-1H-pyrazol-3-yl}formamido)-5-(3,3-difluoropiperidin-1-yl)-5-oxopentanamide | 47 |
| 516 | (3S)-N-cyclobutyl-3-({1-cyclopentyl-5-[2-(trifluoromethyl)phenyl]-1H-pyrazol-3-yl}formamido)-5-(dimethylamino)pentanamide | 834 |
| 517 | (3S)-N-cyclobutyl-3-({1-cyclopentyl-5-[2-(trifluoromethyl)phenyl]-1H-pyrazol-3-yl}formamido)-5-(2,2-dimethylpiperidin-1-yl)pentanamide | 261 |
| 518 | (3R)-3-({1-cyclopentyl-5-[2-(trifluoromethyl)phenyl]-1H-pyrazol-3-yl}formamido)-4-(3,3-difluoropyrrolidin-1-yl)butanoic acid | >10,000 |
| 519 | (3R)-3-({1-cyclopentyl-5-[2-(trifluoromethyl)phenyl]-1H-pyrazol-3-yl}formamido)-4-(3,3-difluoropiperidin-1-yl)butanoic acid | >10,000 |
| 520 | (3S)-3-({1-cyclopentyl-5-[2-(trifluoromethyl)phenyl]-1H-pyrazol-3-yl}formamido)-N-(3,3-difluorocyclobutyl)-5-(piperidin-1-yl)pentanamide | 45 |
| 521 | (3S)-5-{2-azabicyclo[2.2.21octan-2-yl]-N-cyclobutyl-3-({1-cyclopentyl-5-[2(trifluoromethyl)phenyl+-1H-pyrazol-3-yl}formamido)pentanamide | 100 |
| 522 | (3S)-N-cyclobutyl-3-({1-cyclopentyl-5-[2-(trifluoromethyl)phenyl]-1H-pyrazol-3-yl}formamido)-5-{2-oxa-5-azaspiro[3.51nonan-5-yl}pentanamide | 64 |
| 523 | (3R)-N-cyclobutyl-3-({1-cyclopentyl-5-[2-(trifluoromethyl)phenyl]-1H-pyrazol-3-yl}formamido)-4-(3,3-difluoropyrrolidin-1-yl)butanamide | 1207 |
| 524 | (3R)-N-cyclobutyl-3-({1-cyclopentyl-5-[2-(trifluoromethyl)phenyl]-1H-pyrazol-3-yl}formamido)-4-(3,3-difluoropiperidin-1-yl)butanamide | 910 |
| 525 | (3S)-3-({1-cyclopentyl-5-[2-(trifluoromethyppyridin-3-yl]-1H-1,2,4-triazol-3-yl]formamido)-5-(3,3-difluoropiperidin-1-yppentanoic acid | >10,000 |
| 526 | (2S)-3-cyclopentyl-2-({1-cyclopentyl-5-[2-(trifluoromethyl)phenyl]-1H-pyrazol-3-yl}formamido)propanoic acid | 1717 |
| 527 | (2S)-2-({1-cyclopentyl-5-[2-(trifluoromethyl)phenyl]-1H-pyrazol-3-yl}formamido)-4-methylpentanoic acid | >10,000 |
| 528 | (2S)-2-({1-cyclopentyl-5-[2-(trifluoromethyl)phenyl]-1H-pyrazol-3-yl}formamido)-3-methylbutanoic acid | >10,000 |
| 529 | (3S)-3-({1-cyclopentyl-5-[2-(trifluoromethyl)phenyl]-1H-pyrazol-3-yl}formamido)-5-(3,3-difluoropiperidin-1-yl)-N-(trifluoromethane)sulfonylpentanamide | 134 |
| 533 | (3R)-4-[cyclohexyl(methy)amino1]-3-({1-cyclopentyl-5-[2-(trifluoromethyl)phenyl]-1H-pyrazol-3-yl}formamido)butanoic acid | 822 |
| 534 | (3S)-3-({1-cyclopentyl-5-[2-(trifluoromethyl)phenyl]-1H-pyrazol-3-yl}formamido)-5-(3,3-difluoroazetidin-1-yl)pentanoic acid | 388 |
| 535 | (3S)-N-cyclobutyl-3-({1-cyclopentyl-5-[2-(trifluoromethyl)phenyl]-1H-pyrazol-3-yl}formamido)-5-(3,3-difluoroazetidin-1-yl)pentanamide | 32 |
| 536 | (3S)-N-cyclobutyl-3-({1-cyclopentyl-5-[2-(trifluoromethyl)phenyl]-1H-pyrazol-3-yl}formamido)-5-(cyclopentylformamido)pentanamide | 39 |
| 537 | (3S)-3-({1-cyclopentyl-5-[2-(1,1-difluoroethyl)phenyl]-1H-pyrazol-3-yl}formamido)-5-(3,3-difluoropyrrolidin-1-yl)pentanoic acid | 16 |
| 538 | (3S)-3-({1-cyclopentyl-5-[2-(trifluoromethyl)phenyl]-1H-pyrazol-3-yl}formamido)-5-(cyclopentylformamido)pentanoic acid | 544 |
| 539 | (3S)-N-cyclobutyl-3-({1-cyclopentyl-5-[2-(trifluoromethyl)phenyl]-1H-pyrazol-3-yl}formamido)-5-(oxetan-3-ylformamido)pentanamide | 176 |
| 540 | 1-cyclopentyl-N-[(2S)-4-(3,3-difluoropiperidin-1-yl)-4-oxo-1-sulfamoylbutan-2-yl]-5-[2-(trifluoromethyl)phenyl]-1H-pyrazole-3-carboxamide | 1382 |

TABLE 2-continued

| ID# | IUPAC Name | EC$_{50}$ (nM) Ave |
|---|---|---|
| 541 | N-[(2S)-1-(cyclobutylsulfamoyl)-4-(3,3-difluoropiperidin-1-yl)-4-oxobutan-2-yl]-1-cyclopentyl-5-[2-(trifluoromethyl)phenyl]-1H-pyrazole-3-carboxamide | 1058 |
| 542 | (2S)-2-({1-cyclopentyl-5-[2-(trifluoromethyl)phenyl]-1H-pyrazol-3-yl}formamido)-N-(2-methoxyethyl)-N-methyl-4-phenylbutanamide | 105 |
| 544 | (3R)-3-(cyclohexylcarbamoyl)-3-({1-cyclopentyl-5-[2-(trifluoromethyl)phenyl]-1H-pyrazol-3-yl]formamido)propanoic acid | 205 |
| 545 | (3R)-3-({1-cyclopentyl-5-[2-(trifluoromethyl)phenyl]-1H-pyrazol-3-yl}formamido)-4-(4-fluorophenoxy)butanoic acid | 1233 |
| 546 | (3R)-N-cyclobutyl-3-({1-cyclopentyl-5-[2-(trifluoromethyl)phenyl]-1H-pyrazol-3-yl}formamido)-4-(4-fluorophenoxy)butanamide | 114 |
| 547 | (3R)-N-cyclobutyl-44cyclohexyl(methyl)amino]-3-({1-cyclopentyl-5-[2-(trifluoromethyl)phenyl]-1H-pyrazol-3-yl]formamido)butanamide | 5125 |
| 548 | (3S)-3-({1-cyclopentyl-5-[2-(trifluoromethyl)phenyl]-1H-pyrazol-3-yl}formamido)-5-[(3,3-difluorocyclobutyl)amino]pentanoic acid | 255 |
| 549 | (2R)-N-cyclobutyl-N'-cyclohexyl-2-({1-cyclopentyl-5-[2-(trifluoromethyl)phenyl]-1H-pyrazol-3-yl}formamido)butanediamide | 152 |
| 550 | (3R)-3-({1-cyclopentyl-5-[2-(trifluoromethyl)phenyl]-1H-pyrazol-3-yl}formamido)-N-(3-methyloxetan-3-yl)-5-oxo-5-(piperidin-1-yl)pentanamide | 8679 |
| 551 | 1-cyclopentyl-N-[(2S)-4-(3,3-difluoropiperidin-1-yl)-1-(1H-1,2,3,4-tetrazol-5-yl)butan-2-yl]-5{2-(trifluoromethyl)phenyl]-1H-pyrazole-3-carboxamide | 25 |
| 552 | (3S)-3-({1-cyclobutyl-5-[2-(trifluoromethyl)phenyl]-1H-pyrazol-3-yl}formamido)-5-(3,3-difluoropiperidin-1-yl)pentanoic acid | 167 |
| 553 | (3S)-5-(3,3-difluoropiperidin-1-yl)-3-{[1-(oxan-4-yl)-5-[2-(trifluoromethyl)phenyl]-1H-pyrazol-3-yl]formamido}pentanoic acid | 1482 |
| 554 | (3S)-3-({1-cyclopentyl-544-fluoro-2-(trifluoromethyl)phenyl]-1H-pyrazol-3-yl}formamido)-5-(3,3-difluoropiperidin-1-yl)pentanoic acid | 126 |
| 555 | (3S)-3-({5-[4-chloro-2-(trifluoromethyl)phenyl]-1-cyclopentyl-1H-pyrazol-3-yl}formamido)-5-(3,3-difluoropiperidin-1-yl)pentanoic acid | 1573 |
| 556 | (3S)-3-({-[2-chloro-6-(trifluoromethyl)phenyl]-1-cyclopentyl-1H-pyrazol-3-yl}formamido)-5-(3,3-difluoropiperidin-1-yl)pentanoic acid | >10 |
| 557 | (3S)-3-{[1-(cyclopropylmethyl)-5-[2-(trifluoromethyl)phenyl]-1H-pyrazol-3-yl]formamido}-5-(3,3-difluoropiperidin-1-yl)pentanoic acid | 401 |
| 558 | (3R)-3-[cyclohexyl(methyl)carbamoyl]-3-({1-cyclopentyl-5-[2-(trifluoromethyl)phenyl]-1H-pyrazol-3-yl}formamido)propanoic acid | 1172 |
| 559 | (3R)-3-({1-cyclopentyl-5-[2-(trifluoromethyl)phenyl]-1H-pyrazol-3-yl}formamido)-3-[(oxan-4-yl)carbamoyl]propanoic acid | 596 |
| 560 | (3R)-3-({1-cyclopentyl-5-[2-(trifluoromethyl)phenyl]-1H-pyrazol-3-yl}formamido)-3-[(4-fluorophenyl)carbamoyl]propanoic acid | 738 |
| 561 | (2R)-N-cyclobutyl-N'-cyclohexyl-2-({1-cyclopentyl-5-[2-(trifluoromethyl)phenyl]-1H-pyrazol-3-yl}formamido)-N'-methylbutanediamide | 879 |
| 562 | (2R)-N-cyclobutyl-2-({1-cyclopentyl-5-[2-(trifluoromethyl)phenyl]-1H-pyrazol-3-yl}formamido)-N'-(oxan-4-yl)butanediamide | 169 |
| 563 | 1-cyclopentyl-N-[(3R)-1-(4-fluorophenyl)-2,5-dioxopyrrolidin-3-yl]-5-[2-(trifluoromethyl)phenyl]-1H-pyrazole-3-carboxamide | >10,000 |
| 564 | (2S)-2-({1-cyclopentyl-5-[3-(trifluoromethyppyridin-2-yl]-1H-1,2,4-triazol-3-yl}formamido)-N-(2-methoxyethyl)-N-methyl-4-phenylbutanamide | 982 |
| 565 | (3S)-5-(3,3-difluoropiperidin-1-yl)-3-{[1-(2-methylpropyl)-5-[2-(trifluoromethyl)phenyl]-1H-pyrazol-3-yl]formamido}pentanoic acid | 544 |
| 566 | (3S)-3-({1-cyclopentyl-5-[2-(trifluoromethyl)phenyl]-1H-pyrazol-3-yl}formamido)-5-(3,3,4,4,5,5-hexafluoropiperidin-1-yl)pentanoic acid | 3051 |
| 567 | (3S)-3-({1-cyclopentyl-5-[2-(trifluoromethyl)phenyl]-1H-pyrazol-3-yl}formamido)-5-(3,3-difluoropyrrolidin-1-yl)hexanoic acid | 648 |
| 568 | (3S)-5-(3,3-difluoropipe ridin-1-yl)-3-{[1-(2,2-dimethylpropyl)-5-[2-(trifluoromethyl)phenyl]-1H-pyrazol-3-yl]formamido}pentanoic acid | >10,000 |
| 570 | (2S)-2-({1-cyclopentyl-5-[2-(trifluoromethyl)phenyl]-1H-pyrazol-3-yl}formamido)-N-(2-methoxyethyl)-N-methyl-3-phenoxypropanamide | 4250 |
| 571 | (3S)-3-{[1-(cyclobutylmethyl)-5-[2-(trifluoromethyl)phenyl]-1H-pyrazol-3-yl]formamido}-5-(3,3-difluoropiperidin-1-yl)pentanoic acid | 130 |
| 572 | (3S,5S)-3-({1-cyclopentyl-5-[2-(trifluoromethyl)phenyl]-1H-pyrazol-3-yl}formamido)-5-(3,3-difluoropyrrolidin-1-yl)hexanoic acid | 124 |
| 573 | (3S)-N-cyclobutyl-3-({1-cyclopentyl-5-[2-(trifluoromethyl)phenyl]-1H-pyrazol-3-yl}formamido)-5-(3,3-difluoropyrrolidin-1-yl)hexanamide | 299 |
| 574 | (3S)-3-({1-cyclopentyl-5-[2-(trifluoromethyl)phenyl]-1H-pyrazol-3-yl}formamido)-5-(3,3,4,4-tetrafluoropyrrolidin-1-yl)pentanoic acid | 981 |
| 575 | (3S,5R)-3-({1-cyclopentyl-5-[2-(trifluoromethyl)phenyl]-1H-pyrazol-3-yl}formamido)-5-(3,3-difluoropiperidin-1-yl)hexanoic acid | 91 |
| 576 | (3S,5S)-3-({1-cyclopentyl-5-[2-(trifluoromethyl)phenyl]-1H-pyrazol-3-yl}formamido)-5-(3,3-difluoropiperidin-1-yl)hexanoic acid | 1374 |
| 577 | (2S)-3-cyclohexyl-2-({1-cyclopentyl-5-[2-(trifluoromethyl)phenyl]-1H-pyrazol-3-yl}formamido)propanoic acid | 1026 |
| 578 | (3S)-3-({1-cyclopentyl-5-[2-(trifluoromethyl)phenyl]-1H-pyrazol-3-yl}formamido)-5-[3-(trifluoromethyl)pyrrolidin-1-yl]pentanoic acid | 78 |
| 579 | (3R)-3-({1-cyclopentyl-5-[2-(trifluoromethyl)phenyl]-1H-pyrazol-3-yl}formamido)-5-(3,3-difluoropiperidin-1-yl)pentanoic acid | 1874 |
| 580 | (3S)-5-(3,3-difluoropiperidin-1-yl)-3-({1-propyl-5-[2-(trifluoromethyl)phenyl]-1H-pyrazol-3-yl}formamido)pentanoic acid | 718 |

TABLE 2-continued

| ID# | IUPAC Name | EC$_{50}$ (nM) Ave |
|---|---|---|
| 581 | (3S)-3-({1-cyclopentyl-5-[2-(trifluoromethyl)phenyl]-1H-pyrazol-3-yl}formamido)-5-[(3R,4S)-3,4-difluoropyrrolidin-1-yl]pentanoic acid | 215 |
| 582 | (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid | 109 |
| 583 | (3S)-3-({1-cyclopentyl-5-[2-(trifluoromethyl)phenyl]-1H-pyrazol-3-yl}formamido)-5-[(3S)-3-fluoropiperidin-1-yl]pentanoic acid | 302 |
| 584 | (3S)-3-({1-cyclopentyl-5-[2-(trifluoromethyl)phenyl]-1H-pyrazol-3-yl}formamido)-5-[(3R)-3-fluoropiperidin-1-yl]pentanoic acid | 184 |
| 585 | (3S)-3-({1-cyclopentyl-5-[2-(trifluoromethyl)phenyl]-1H-pyrazol-3-yl}formamido)-5-[(3S)-3-fluoropyrrolidin-1-yl]pentanoic acid | 654 |
| 587 | (3S)-3-({1-cyclopentyl-5-[2-(trifluoromethyl)phenyl]-1H-pyrazol-3-yl}formamido)-5-(2-oxopiperidin-1-yl)pentanoic acid | 355 |
| 588 | (3S)-3-({1-cyclopentyl-5-[2-(trifluoromethyl)phenyl]-1H-pyrazol-3-yl}formamido)-5-(3,3-dime thylazetidin-1-yl)pentanoic acid | 502 |
| 589 | (3S)-3-({1-cyclopentyl-5-[2-(1,1-difluoroethyl)phenyl]-1H-pyrazol-3-yl}formamido)-5-(3,3-difluoroazetidin-1-yl)pentanoic acid | 171 |
| 590 | (3S)-3-({1-cyclopentyl-5-[2-(trifluoromethyl)phenyl]-1H-pyrazol-3-yl}formamido)-5-[(3R)-3-fluoropyrrolidin-1-yl]pentanoic acid | 1159 |
| 591 | (3S)-3-({1-cyclopentyl-5-[2-(trifluoromethyl)phenyl]-1H-pyrazol-3-yl}formamido)-5-{5,5-difluoro-2-azaspiro[3.3]heptan-2-yl}pentanoic acid | 528 |
| 592 | (2S)-3-(tert-butoxy)-2-({1-cyclopentyl-5-[2-(trifluoromethyl)phenyl]-1H-pyrazol-3-yl}formamido)-N-(2-methoxyethyl)-N-methylpropanamide | 5549 |
| 593 | (3S)-3-({1-cyclopentyl-5-[2-(1,1-difluoroethyl)phenyl]-1H-pyrazol-3-yl}formamido)-5-[(3R)-3-fluoropiperidin-1-yl]pentanoic acid | 79 |
| 594 | (3S)-3-({1-cyclopentyl-5-[2-(1,1-difluoroethyl)phenyl]-1H-pyrazol-3-yl}formamido)-5-[trans-3,4-difluoropyrrolidin-1-yl]pentanoic acid | 44 |
| 595 | (3S)-3-({1-cyclopentyl-5-[2-(1,1-difluoroethyl)phenyl]-1H-pyrazol-3-yl}formamido)-5-[trans-3,4-dimethylpyrrolidin-1-yl]hexanoic acid | 140 |
| 596 | (2S,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid | 88 |
| 597 | (2R,3S)-3-({1-cyclopentyl-5-[2-(trifluoromethyl)phenyl]-1H-pyrazol-3-yl}formamido)-5-(3,3-difluoropiperidin-1-yl)-2-methylpentanoic acid | 23 |
| 598 | (3S)-3-({1-cyclopentyl-5-[2-(1,1-difluoroethyl)phenyl]-1H-pyrazol-3-yl}formamido)-5-[cis-3,4-difluoropyrrolidin-1-yl]pentanoic acid | 103 |
| 599 | (3S,5R)-3-({1-cyclopentyl-5-[2-(1,1-difluoroethyl)phenyl]-1H-pyrazol-3-yl}formamido)-5-[trans-3,4-difluoropyrrolidin-1-yl]hexanoic acid | 24 |
| 600 | (3S,5S)-3-({1-cyclopentyl-5-[2-(1,1-difluoroethyl)phenyl]-1H-pyrazol-3-yl}formamido)-5-(3,3-difluoropyrrolidin-1-yl)hexanoic acid | 67 |
| 601 | (3S)-3-({1-cyclopentyl-5-[2-(trifluoromethyl)phenyl]-1H-pyrazol-3-yl]formamido)-543-(trifluoromethypazetidin-1-yl)pentanoic acid | 128 |
| 602 | (3S)-3-({1-cyclopentyl-5-[2-(trifluoromethyl)phenyl]-1H-pyrazol-3-yl}formamido)-5-{3,3-difluoro-8-azabicyclo[3.2.1]octan-8-yl}pentanoic acid | 346 |
| 603 | (3S)-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}pentanoic acid | 46 |
| 604 | (3S)-3-({1-cyclopentyl-5-[2-(trifluoromethyl)phenyl]-1H-pyrazol-3-yl}formamido)-5-(2,6-dioxopiperidin-1-yl)pentanoic acid | 55 |
| 605 | (3S)-3-({1-cyclopentyl-5-[2-(1,1-difluoroethyl)phenyl]-1H-pyrazol-3-yl}formamido)-5-[(2R)-4,4-difluoro-2-methylpyrrolidin-1-yl]pentanoic acid | 11 |
| 606 | (3S)-3-({1-cyclopentyl-5-[2-(trifluoromethyl)phenyl]-1H-pyrazol-3-yl}formamido)-5-{8,8-difluoro-3-azabicyclo[3.2.1]octan-3-yl}pentanoic acid | 310 |
| 607 | (3S)-3-({1-cyclopentyl-5-[2-(1,1-difluoroethyl)phenyl]-1H-pyrazol-3-yl}formamido)-5-(5,5-difluoro-2-methylpiperidin-1-yl)pentanoic acid | 69 |
| 608 | (3S)-3-({1-cyclopentyl-5-[2-(trifluoromethyl)phenyl]-1H-pyrazol-3-yl}formamido)-5-(2,2-dimethyl-4-oxopyrrolidin-1-yl)pentanoic acid | 1074 |
| 609 | (3S)-3-({1-cyclopentyl-5-[2-(trifluoromethyl)phenyl]-1H-pyrazol-3-yl}formamido)-5-(3-fluoro-3-methylpyrrolidin-1-yl)pentanoic acid | 98 |
| 610 | (3S)-3-({1-cyclopentyl-5-[2-(trifluoromethyl)phenyl]-1H-pyrazol-3-yl]formamido)-54(3S,4R)-3,4-difluoropiperidin-1-yl]pentanoic acid | 43 |
| 611 | (3S)-3-({1-cyclopentyl-5-[2-(1,1-difluoroethyl)phenyl]-1H-pyrazol-3-yl}formamido)-5-(2,2-dimethyl-4-oxopiperidin-1-yl)pentanoic acid | 509 |
| 612 | (3S)-3-({1-cyclopentyl-5-[2-(trifluoromethyl)phenyl]-1H-pyrazol-3-yl}formamido)-5-(4,4-difluoro-2,2-dimethylpyrrolidin-1-yl)pentanoic acid | 231 |
| 613 | (3S)-3-({1-cyclopentyl-5-[2-(trifluoromethyl)phenyl]-1H-pyrazol-3-yl}formamido)-5-(3-fluoro-3-methylpiperidin-1-yl)pentanoic acid trifluoroacetate | 104 |
| 614 | (3S)-3-({1-cyclopentyl-5-[2-(trifluoromethyl)phenyl]-1H-pyrazol-3-yl}formamido)-5-[(3S)-3-fluoro-3-methylpiperidin-1-yl]pentanoic acid | 41 |
| 615 | (3S)-3-({1-cyclopentyl-5-[2-(trifluoromethyl)phenyl]-1H-pyrazol-3-yl}formamido)-5-{[1-(trifluoromethyl)cyclopentyl]amino}pentanoic acid trifluoroacetate | 353 |
| 618 | (3S)-N-cyclobutyl-5-cyclohexyl-3-{[5-(2,6-dimethoxyphenyl)-1-(4-fluorophenyl)-1H-pyrazol-3-yl]formamido]pentanamide | 425 |
| 621 | (3S)-5-cyclohexyl-3-{[1-cyclopentyl-5-(2,6-dimethoxyphenyl)-1H-pyrazol-3-yl]formamido}pentanoic acid | 424 |
| 622 | (3S)-5-cyclohexyl-3-{[1-cyclohexyl-5-(2,6-dimethoxyphenyl)-1H-pyrazol-3-yl]formamido}pentanoic acid | 380 |

TABLE 2-continued

| ID# | IUPAC Name | EC$_{50}$ (nM) Ave |
|---|---|---|
| 623 | (3S)-5-cyclohexyl-3-{[5-(2,6-dimethoxyphenyl)-1-propyl-1H-pyrazol-3-yl]formamido}pentanoic acid | 416 |
| 624 | (3S)-N-cyclobutyl-5-cyclohexyl-3-{[1-cyclopentyl-5-(2,6-dimethoxyphenyl)-1H-pyrazol-3-yl]formamido}pentanamide | 70 |
| 625 | (3S)-N-cyclobutyl-5-cyclohexyl-3-{[111-cyclohexyl-5-(2,6-dimethoxyphenyl)-1H-pyrazol-3-yl]formamido}pentanamide | 101 |
| 626 | (3S)-N-cyclobutyl-5-cyclohexyl-3-{[5-(2,6-dimethoxyphenyl)-1-propyl-1H-pyrazol-3-yl]formamido}pentanamide | 49 |
| 628 | 1-cyclopentyl-N-[(2S)-4-{6,6-difluoro-3-azabicyclo[3.1.0]hexan-3-yl}-1-(1H-1,2,3,4-tetrazol-5-yl)butan-2-yl]-5-[2-(trifluoromethyl)phenyl]-1H-pyrazole-3-carboxamide | 61 |
| 629 | (3S)-3-({1-cyclopentyl-5-[2-(trifluoromethyl)phenyl]-1H-pyrazol-3-yl}formamido)-5-[(3S,4S)-3,4-difluoropyrrolidin-1-yl]pentanoic acid | 77 |
| 630 | 1-cyclopentyl-N-[(2S)-4-(3S,4S)-3,4-difluoropyrrolidin-1-yl]-1-(1H-1,2,3,4-tetrazol-5-yl)butan-2-yl]-5-[2-(trifluoromethyl)phenyl]-1H-pyrazole-3-carboxamide | 24 |
| 631 | (3S)-3-({1-cyclopentyl-5-[2-(trifluoromethyl)phenyl]-1H-pyrazol-3-yl}formamido)-5-[(3R,4R)-3,4-difluoropyrrolidin-1-yl]pentanoic acid | 75 |
| 634 | (2S,3S)-3-({1-cyclopentyl-5-[2-(trifluoromethyl)phenyl]-1H-pyrazol-3-yl}formamido)-5-{6,6-difluoro-3-azabicyclo[13.1.0]hexan-3-yl}-2-methylpentanoic acid | 87 |
| 635 | (2R,3S)-3-({1-cyclopentyl-5-[2-(trifluoromethyl)phenyl]-1H-pyrazol-3-yl}formamido)-5-{6,6-difluoro-3-azabicyclo[13.1.0]hexan-3-yl}-2-methylpentanoic acid | 13 |
| 636 | (3S)-N-cyclobutyl-3-({1-cyclopentyl-5-[2-(trifluoromethyl)phenyl]-1H-pyrazol-3-yl}formamido)-5-{6,6-difluoro-3-azabicyclo[3.1.0]hexan-3-yl}-2-methylpentanamide | 158 |
| 637 | 1-cyclopentyl-N-[(3S)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide | 21 |
| 638 | 1-cyclopentyl-N-[(3S,4R)-1-{6,6-difluoro-3-azabicyclo[3.1.0]hexan-3-yl}-4-(1H-1,2,3,4-tetrazol-5-yl)pentan-3-yl]-5-[2-(trifluoromethyl)phenyl]-1H-pyrazole-3-carboxamide | 14 |
| 639 | (3S)-3-({1-cyclopentyl-5-[2-(trifluoromethyl)phenyl]-1H-pyrazol-3-yl}formamido)-5-(3,5-difluoropiperidin-1-yl)pentanoic acid | 40 |
| 641 | 1-cyclopentyl-N-[2S)-4-(3,3-difluoropiperidin-1-yl)-1-(1H-1,2,3,4-tetrazol-5-yl)butan-2-yl]-5-[3-(trifluoromethyl)pyridin-2-yl]-1H-pyrazole-3-carboxamide | 27 |
| 643 | (3S)-3-({1-cyclopentyl-5-[2-(trifluoromethyl)phenyl]-1H-pyrazol-3-yl}formamido)-5-(2,5-dioxopyrrolidin-1-yl)pentanoic acid | 182 |
| 646 | (3S)-5-cyclohexyl-3-{[5-(2,6-dimethoxyphenyl)-1-methyl-1H-pyrazol-3-yl]formamido}pentanoic acid | 1476 |
| 647 | (3S)-5-cyclohexyl-3-{[1-cyclooctyl-5-(2,6-dimethoxyphenyl)-1H-pyrazol-3-yl]formamido}pentanoic acid | >10000 |
| 648 | (3S)-5-cyclohexyl-3-{[1-(cyclohexylmethyl)-5-(2,6-dimethoxyphenyl)-1H-pyrazol-3-yl]formamidolpentanoic acid | >10000 |
| 649 | (3S)-5-cyclohexyl-3-{[5-(2,6-dimethoxyphenyl)-1-(pentan-3-yl)-1H-pyrazol-3-yl]formamido}pentanoic acid | >10000 |
| 655 | 1-cyclopentyl-N-[(2S)-4-(2,6-dioxopiperidin-1-yl)-1-(1H-1,2,3,4-tetrazol-5-yl)butan-2-yl]-5-[2-(trifluoromethyl)phenyl]-1H-pyrazole-3-carboxamide | 66 |

5.3. Cellular Uptake Assay

Caco-2 cells (clone C2BBe1) were obtained from American Type Culture Collection (Manassas, Va,). Cell monolayers were grown to confluence on collagen-coated, microporous, polycarbonate membranes in 12-well Costar Transwell plates. Details of the plates and their certification are shown below. The permeability assay buffer was Hanks' balanced salt solution (HBSS) containing 10 mM HEPES and 15 mM glucose at a pH of 7.4. The buffer in the receiver chamber also contained 1% bovine serum albumin. The dosing solution concentration was 5 µM for each test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. After the experiment, all assay buffers were removed from the inserts. Cell monolayers were dosed with blank 500 µM lucifer yellow on the A-to-B side and blank HBSS on the B-to-A side and incubated at 37° C. Samples were taken from the B-to-A side at 60 minutes. The flux of lucifer yellow was measured for each monolayer to ensure no damage was inflicted to the cell monolayers during the flux period. All samples were analyzed by LC-MS/MS using electrospray ionization. The apparent permeability ($P_{app}$) and percent recovery were calculated as follows:

$$P_{app} = (dCr/dt) \times Vr/(A \times C_A) \quad (1)$$

$$\text{Percent Recovery} = 100 \times ((Vr \times C_r^{final}) + (V_d \times C_d^{final}))/(V_d \times C_N) \quad (2)$$

Where, $dC_r/dt$ is the slope of the cumulative concentration in the receiver compartment versus time in µM s$^{-1}$;

$V_r$ is the volume of the receiver compartment in cm$^3$;

$V_d$ is the volume of the donor compartment in cm$^3$;

A is the area of the insert (1.13 cm$^2$ for 12-well Transwell);

$C_A$ is the average of the nominal dosing concentration and the measured 120-minute donor concentration in µM;

$C_N$ is the nominal concentration of the dosing solution in µM;

$C_r^{final}$ is the cumulative receiver concentration in µM at the end of the incubation period;

$C_d^{final}$ is the concentration of the donor in µM at the end of the incubation period.

Efflux ratio (ER) is defined as $P_{app}$ (B-to-A)/$P_{app}$ (A-to-B).

Absorption Potential Classification:

$P_{app}$ (A-to-B) <1.0×10$^{-6}$ cm/s: Low $P_{app}$ (A-to-B) ≥1.0×10$^{-6}$ cm/s: High Significant Efflux is defined as: ER ≥2.0 and $P_{app}$ (B-to-A) ≥1.0×10$^{-6}$ cm/

TABLE 3

Cellular Uptake Results

| ID # | EC50 (nM) | Efflux ratio |
|---|---|---|
| 253 | 382 | 34 |
| 348 | 15 | 2.1 |
| 335 | 63 | 1 |
| 363 | 44 | 3.6 |
| 384 | 15 | 1.7 |
| 410 | 7 | 1 |

In Vivo Blood Pressure Lowering Activity of the Compounds

Select compounds were evaluated for their effects upon oral administration on hemodynamic changes, including blood pressure reduction, in conscious, telemetered male Sprague-Dawley rats. Apelin peptides are known to lower blood pressure, e.g., Tatemoto, K., et.al. Regul. Pept. 2001, 99, 87-92.

Animals were approximately 7-9 weeks of age and weighed between 247 g to 263 g just prior to surgery. Dose levels administered were 7.5, 15 or 30 mg/kg, dose volumes were 10 mL/kg, and dose route of administration was oral gavage. Animals were assigned to a crossover experimental treatment schedule as shown below.

| Animal No. | Compound (mg/kg) | | | |
|---|---|---|---|---|
| | Treatment 1 | Treatment 2 | Treatment 3 | Treatment 4 |
| 1 | 30 | 15 | 7.5 | 0 (vehicle) |
| 2 | 15 | 7.5 | 0 (vehicle) | 30 |
| 3 | 7.5 | 0 (vehicle) | 30 | 15 |
| 4 | 0 (vehicle) | 30 | 15 | 7.5 |
| 5 | 30 | 15 | 7.5 | 0 (vehicle) |
| 6 | 15 | 7.5 | 0 (vehicle) | 30 |
| 7 | 7.5 | 0 (vehicle) | 30 | 15 |
| 8 | 0 (vehicle) | 30 | 15 | 7.5 |

Collected data included systolic, diastolic, and mean arterial blood pressure (MAP). Data collection time points were for pre-dose baseline approximately 48 h (prior to treatment 1) or approximately 24 h (prior to treatment 2-4) for 10 sec every 2 min. Data collection post-dose was collected through approximately 24 h (data collected for 10 sec every 2 min) per treatment. Resulting data is presented below as the 2-5 h mean change from baseline in mmHg.

| | Compound 423 | | | Compound 551 | | |
|---|---|---|---|---|---|---|
| | Systolic | Diastolic | MAP | Systolic | Diastolic | MAP |
| Vehicle (0 mg/kg) | −3.7 | −3.2 | −4.7 | −2.6 | −2.1 | −2.4 |
| 7.5 mg/kg | −13.0 | −9.9 | −10.0 | −6.6 | −4.3 | −4.5 |
| 15 mg/kg | −9.8 | −7.3 | −8.4 | −9.6 | −7.3 | −8.5 |
| 30 mg/kg | −10.7 | −8.3 | −9.3 | −11.3 | −8.4 | −9.8 |

Compound 423 treatment via oral gavage to male Sprague-Dawley rats resulted in a mild sustained decrease in blood pressure, and compound 551 treatment resulted in a dose-dependent, mild sustained decrease in blood pressure.

It is to be understood that, while the disclosure has been described in conjunction with the detailed description, thereof, the foregoing description is intended to illustrate and not limit the scope of the disclosure. Other aspects, advantages, and modifications of the disclosure are within the scope of the claims set forth below. All publications, patents, and patent applications cited in this specification are herein incorporated by reference as if each individual publication or patent application was specifically and individually indicated to be incorporated by reference.

What is claimed is:

1. A method of therapeutically treating one or more of acute decompensated heart failure (ADHF), amyotrophic lateral sclerosis, arrhythmia, asthma, atherosclerosis, atrial fibrillation, Brugada syndrome, burn injuries, sunburn, cancer, cardiac fibrosis, cardiomyopathy, cerebrovascular accidents, ischemic heart failure, diabetes, gestational diabetes, dyslipidemia, HIV neurodegeneration, hypertension, pulmonary arterial hypertension, inflammation, ischemic cardiovascular diseases, liver disease, alcoholic liver disease, toxicant-induced liver disease, viral-induced liver disease, metabolic disorder, neurodegenerative disease, obesity, peripheral arterial disease, preeclampsia, pulmonary hypertension, renal dysfunction, polycystic kidney disease, restenosis, transient ischemic attacks, traumatic brain injuries, vein-related disorders, pulmonary veno-occlusive disease, angioma, venous insufficiency, stasis, thrombosis, ventricular tachycardia, and water retention in a patient in need thereof, comprising administering a therapeutically effective amount of a compound represented by the Formula IV:

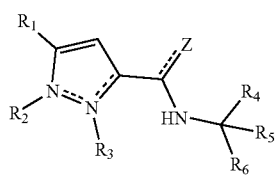

IV or a pharmaceutically acceptable salt thereof, a prodrug thereof, or a salt of a prodrug thereof, wherein $R_1$ is represented by the formula:

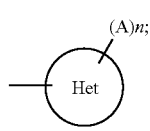

wherein

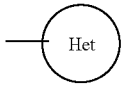

is a monocyclic aryl or heteroaryl group;

each A is independently fluoro substituted $C_1$-$C_3$ alkoxy, or fluoro substituted $C_1$-$C_3$ alkyl;

n is 1 or 2;

$R_2$ is optionally substituted $C_{3-8}$ alkyl, optionally substituted $C_{1-8}$ alkyl ($C_{3-8}$ cycloalkyl), optionally substituted $C_{3-8}$ cycloalkyl, or optionally substituted heteroaryl;

$R_3$ is absent;

$R_4$ is optionally substituted $C_{1-8}$ alkyl, $C_{2-8}$ alkenyl, $C_{3-8}$ cycloalkyl, $C_{2-8}$ alkyl(aryl), $C_{1-8}$ alkyl($C_{3-8}$ cycloalkyl), $C_{1-8}$ alkyl(heteroaryl), or $(CH_2)_xNR_7R_8$;

$R_5$ is optionally substituted adamantanyl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl($C_{3-8}$ cycloalkyl), $C_{1-8}$ alkyl($C_{3-8}$ cycloalkyl)-$CO_2R_7$, $C_{1-8}$ alkyl(guanidinyl), $C_{1-8}$ alkyl(heteroaryl), $C_{1-8}$ alkyl(tetrazol-5-one), $C_{2-4}$ alkyl(heterocycloalkyl), $C_{1-8}$ alkyl(thioether), $C_{1-8}$ alkyl(thiol), $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $(CH_2)_xNR_7R_8$, $(CH_2)_xOR_7$, $(CH_2)_xNR_9COR_7$, $(CH_2)_xNR_9SO_2R_7$, $(CH_2)_xNR_9CO_2R_7$, $(CH_2)_xNHCOR_7$, $(CH_2)_xNHSO_2R_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xSO_2NR_7(CH_2)_yR_9$, $CHR_7COR_9$, $CHR_7CONHCHR_8COR_9$, $CONR_7R_8$, $CONR_7(CH_2)_xCO_2R_8$, $CONR_7CHR_8CO_2R_9$, $NHCO_2R_7$, $(CH_2)_x SO_2NR_7R_8$, or $(CH_2)_{xx}CO_2R_7$;

R6 is H; or $R_4$ and $R_5$ together make a 5-8 member nitrogen-containing ring with one or more carbonyl groups;

$R_7$ and $R_8$ each are independently H, $C_{1-8}$ alkoxy, aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, 01-8 alkyl thiol, $C_{2-8}$ alkenyl, $C_{3-8}$ alkynyl, $C_{3-8}$ cycloalkyl, $(CH_2)_xCONHR_9$, $(CH_2)_xCOR_9$, $(CH_2)_xCO_2R_9$, or heteroaryl; or $R_7$ and $R_8$ together make a 3-9 member ring which may contain one or more heteroatoms; or $R_7$ and $R_8$ together make a 5-8 member nitrogen-containing ring with one or more carbonyl groups;

$R_9$ is H, $C_{1-8}$ alkoxy, $C_{1-8}$ alkyl, $C_{1-8}$ alkyl(aryl), $C_{3-8}$ cycloalkyl, aryl, heteroaryl, or hydroxyl;

each x is independently 0, 1, 2, 3, 4, 5, 6, 7, or 8;

each xx is independently 1, 2, 3, 4, 5, 6, 7, or 8;

each y is independently 1, 2, 3, 4, 5, 6, 7, or 8; and

Z is =O.

2. The method of claim 1, wherein the method treats one or more of asthma, atherosclerosis, cancer, cardiomyopathy, diabetes, dyslipidemia, hypertension, inflammation, liver disease, metabolic disorder, neurodegenerative disease, obesity, and preeclampsia.

3. The method of claim 1, wherein the method further comprises administering one or more of an α-blocker, an angiotensin converting enzyme (ACE) inhibitor, an angiotensin-receptor blocker (ARB), a 6-blocker, a calcium channel blocker, and/or a diuretic.

4. The method of claim 1, wherein $R_5$ is optionally substituted adamantanyl, $C_{1-8}$ alkyl, $C_{1-8}$ alkyl alcohol, $C_{1-8}$ alkyl amino, $C_{1-8}$ alkyl amido, C2-8 alkyl(aryl), $C_{1-8}$ alkyl ($C_{3-8}$ cycloalkyl), $C_{1-8}$ alkyl($C_{3-8}$ cycloalkyl)-$CO_2R_7$, $C_{1-8}$ alkyl(guanidinyl), $C_{1-8}$ alkyl(heteroaryl), $C_{1-8}$ alkyl(tetrazol-5-one), $C_{2-4}$ alkyl(heterocycloalkyl), $C_{1-8}$ alkyl(thioether), $C_{1-8}$ alkyl(thiol), $C_{2-8}$ alkenyl, $C_{2-8}$ alkenyl(aryl), $C_{2-8}$ alkenyl(heteroaryl), $C_{3-8}$ alkynyl, $C_{3-8}$ cycloalkyl, $C_{3-8}$ cycloalkyl-$CO_2R_7$, $(CH_2)_xNR_7R_8$, $(CH_2)_xOR_7$, $(CH_2)_xNR_9COR_7$, $(CH_2)_xNR_9SO_2R_7$, $(CH_2)_xNR_9CO_2R_7$, $(CH_2)_xNHCOR_7$, $(CH_2)_xNHSO_2R_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yR_8$, $(CH_2)_xCONR_7(CH_2)_yR_9$, $(CH_2)_xCOR_7$, $(CH_2)_xSO_2NR_7(CH_2)_yR_9$, $CHR_7COR_9$, $CHR_7CONHCHR_8COR_3$, $CONR_7R_8$, $CONR_7(CH_2)_xCO_2R_8$, $CONR_7CHR_8CO_2R_3$, $NHCO2R_7$, $(CH_2)_xSO_2NR_7R_8$, or $(CH_2)_{xx}CO_2R_7$.

5. The compound of claim 1, wherein

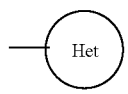

is phenyl, pyridyl, or pyrimidinyl.

6. The compound of claim 1, wherein

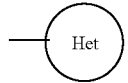

is phenyl.

7. The compound of claim 1, wherein

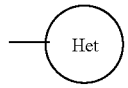

is pyridyl.

8. The compound of claim 6, wherein:
n is 2 and each A is $CF_3$, respectively;
or
n is 1 and A is $CF_3$.

9. The compound of claim 1, wherein $R_2$ is optionally substituted $C_{3-8}$ alkyl.

10. The compound of claim 1, wherein $R_2$ is optionally substituted $C_{1-8}$ alkyl($C_{3-8}$ cycloalkyl).

11. The compound of claim 1, wherein $R_2$ is optionally substituted $C_{3-8}$ cycloalkyl.

12. The compound of claim 1, wherein $R_2$ is optionally substituted cyclopentyl.

13. The compound of claim 1, wherein $R_2$ is optionally substituted heteroaryl.

14. The compound of claim 6, wherein $R_4$ is optionally substituted $C_{1-8}$ alkyl, $C_{2-8}$ alkenyl, $C_{3-8}$ cycloalkyl, $C_{2-8}$ alkyl(aryl), $C_{1-8}$ alkyl($C_{3-8}$ cycloalkyl), $C_{1-8}$ alkyl(heteroaryl), or $(CH_2)_xNR_7R_8$;

$R_5$ is optionally substituted adamantanyl, $C_{1-8}$ alkyl, $C_{1-8}$ alkyl alcohol, $C_{1-8}$ alkyl amino, $C_{1-8}$ alkyl amido, $C_{2-8}$ alkyl(aryl), $C_{1-8}$ alkyl($C_{3-8}$ cycloalkyl), $C_{1-8}$ alkyl($C_{3-8}$ cycloalkyl)-$CO_2R_7$, $C_{1-8}$ alkyl(guanidinyl), $C_{1-8}$ alkyl (heteroaryl), $C_{1-8}$ alkyl(tetrazol-5-one), $C_{2-4}$ alkyl(heterocycloalkyl), $C_{1-8}$ alkyl(thioether), $C_{1-8}$ alkyl(thiol), $C_{2-8}$ alkenyl, $C_{2-8}$ alkenyl(aryl), C2-8 alkenyl(heteroaryl), $C_{3-8}$ alkynyl, $C_{3-8}$ cycloalkyl, $C_{3-8}$ cycloalkyl-$CO_2R_7$, $(CH_2)_xNR_7R_8$, $(CH_2)_xOR_7$, $(CH_2)_xNR_9COR_7$, $(CH_2)_xNR_9SO_2R_7$, $(CH_2)_xNR_9CO_2OR_7$, $(CH_2)_xNHCOR_7$, $(CH_2)_xNHSO_2R_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$, $(CH_2)_xCONR_7(CH_2)_yR_9$, $(CH_2)_xCOR_7$, $(CH_2)_xSO_2NR_7(CH_2)_yR_9$, $CHR_7COR_9$, $CHR_7CONHCHR_8COR_9$, $CONR_7R_8$, $CONR_7(CH_2)_xCO_2R_8$, $CONR_7CHR_8CO_2R_9$, $NHCO_2R_7$, $(CH_2)_xSO_2NR_7R_8$, or $(CH_2)_{xx}CO_2R_7$; and $R_6$ is H.

15. The compound of claim 14, wherein $R_4$ is optionally substituted $C_{1-8}$ alkyl(heteroaryl).

16. The compound of claim 14, wherein $R_5$ is optionally substituted $C_{1-8}$ alkyl, $C_{1-8}$ alkyl(aryl), $C_{1-8}$ alkyl(C3-8 cycloalkyl), $C_{1-8}$ alkyl(heteroaryl), $C_{3-8}$ cycloalkyl, $(CH_2)_xNR_7R_8$, $(CH_2)_xNHCOR_7$, $(CH_2)_xNHCO_2R_7$, $(CH_2)_xCONR_7R_8$, $(CH_2)_xCONR_7(CH_2)_yCO_2R_9$, $(CH_2)_xCONR_7(CH_2)_yCONR_7R_8$,$(CH_2)_xCONR_7(CH_2)_yR_9$, $(CH_2)_x{}^xCOR_7$, $CHR_7COR_9$, $CHR_7CONHCHR_8COR_9$, $CONR_7R_8$, or $(CH_2)_{xx}CO_2R_7$.

17. The compound of claim 14, wherein $R_7$ and $R_8$ each are independently H, $C_{1-8}$ alkoxy, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl tetrazol-5-one, $C_{1-8}$ alkyl guanidinyl, $C_{1-8}$ alkyl heteroaryl, $C_{1-8}$ alkyl thioether, $C_{1-8}$ alkyl thiol, $C_{2-8}$ alkenyl, $C_{3-8}$ alkynyl, $C_{3-8}$ cycloalkyl, $(CH_2)_xCONHR_9$, $(CH_2)_xCOR_9$, $(CH_2)_xCO_2R_9$, or heteroaryl.

\* \* \* \* \*

UNITED STATES PATENT AND TRADEMARK OFFICE
CERTIFICATE OF CORRECTION

PATENT NO. : 11,535,630 B2
APPLICATION NO. : 17/082650
DATED : December 27, 2022
INVENTOR(S) : Scott P. Runyon It is certified that error appears in the above-identified patent and that said Letters Patent is hereby corrected as shown below:

In the Claims

Column 342, Line 14, Claim 4 delete "$CHR_7CONHCHR_8COR_3$" and insert therefore --$CHR_7CONHCHR_8COR_9$--; and Column 342, Line 15, Claim 4 delete "$CONR_7CHR_8CO_2R_3$" and insert therefore --$CONR_7CHR_8CO_2R_9$--.

Signed and Sealed this
Fourteenth Day of March, 2023

*Katherine Kelly Vidal*
Katherine Kelly Vidal
*Director of the United States Patent and Trademark Office*